US010837016B2

(12) United States Patent
Hung et al.

(10) Patent No.: US 10,837,016 B2
(45) Date of Patent: Nov. 17, 2020

(54) MODULATION OF HUNTINGTIN EXPRESSION

(71) Applicant: Ionis Pharmaceuticals, Inc., Carlsbad, CA (US)

(72) Inventors: Gene Hung, Carlsbad, CA (US); C. Frank Bennett, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/801,431

(22) Filed: Feb. 26, 2020

(65) Prior Publication Data

US 2020/0270608 A1    Aug. 27, 2020

Related U.S. Application Data

(60) Division of application No. 16/270,983, filed on Feb. 8, 2019, now Pat. No. 10,619,158, which is a continuation of application No. 15/596,249, filed on May 16, 2017, now Pat. No. 10,202,603, which is a continuation of application No. 15/005,712, filed on Jan. 25, 2016, now Pat. No. 9,683,236, which is a continuation of application No. 14/528,656, filed on Oct. 30, 2014, now Pat. No. 9,273,315, which is a continuation of application No. 13/395,188, filed as application No. PCT/US2010/048532 on Sep. 10, 2010, now Pat. No. 8,906,873.

(60) Provisional application No. 61/241,853, filed on Sep. 11, 2009.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/113* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| 5,595,756 | A | 1/1997 | Bally et al. |
|---|---|---|---|
| 5,686,288 | A | 11/1997 | MacDonald et al. |
| 5,700,922 | A | 12/1997 | Cook |
| 5,801,154 | A | 9/1998 | Baracchini et al. |
| 5,998,148 | A | 12/1999 | Bennett et al. |
| 6,043,060 | A | 3/2000 | Imanishi |
| 6,147,200 | A | 11/2000 | Manoharan et al. |
| 6,582,908 | B2 | 6/2003 | Fodor et al. |
| 6,670,461 | B1 | 12/2003 | Wengel et al. |
| 7,320,965 | B2 | 1/2008 | Sah et al. |
| 7,374,927 | B2 | 5/2008 | Palma et al. |
| 2001/0053519 | A1 | 12/2001 | Fodor et al. |
| 2003/0109476 | A1 | 6/2003 | Kmiec |
| 2003/0144242 | A1 | 7/2003 | Ward et al. |
| 2003/0228597 | A1 | 12/2003 | Cowsert et al. |
| 2004/0092465 | A1 | 5/2004 | Dobie |
| 2004/0096880 | A1 | 5/2004 | Kmiec |
| 2004/0137471 | A1 | 7/2004 | Vickers et al. |
| 2004/0146902 | A1 | 7/2004 | Ecker et al. |
| 2005/0042646 | A1 | 2/2005 | Davidson |
| 2005/0096284 | A1 | 5/2005 | McSwiggen |
| 2005/0101013 | A1 | 5/2005 | Freier et al. |
| 2005/0191638 | A1 | 9/2005 | McSwiggen |
| 2005/0245475 | A1 | 11/2005 | Khvorova et al. |
| 2005/0255086 | A1 | 11/2005 | Davidson |
| 2005/0255487 | A1 | 11/2005 | Khvorova et al. |
| 2006/0051769 | A1 | 3/2006 | Barts |
| 2007/0031844 | A1 | 2/2007 | Khvorova et al. |
| 2007/0099860 | A1 | 5/2007 | Sah |
| 2007/0299027 | A1 | 12/2007 | Hung et al. |
| 2008/0015158 | A1 | 1/2008 | Ichiro |
| 2008/0039415 | A1 | 2/2008 | Stewart et al. |
| 2008/0039418 | A1 | 2/2008 | Freier |
| 2008/0274989 | A1 | 11/2008 | Davidson et al. |
| 2009/0092981 | A1 | 4/2009 | Swayze et al. |

FOREIGN PATENT DOCUMENTS

| CA | 2526893 | 11/2004 |
|---|---|---|
| JP | 2009-513144 | 4/2009 |
| JP | 2009-524431 | 7/2009 |

(Continued)

OTHER PUBLICATIONS

Anderson et al., "An Overview of Psychiatric Symptoms in Huntington's Disease" Current Psychiatry Reports (2001) 3:379-388.

(Continued)

*Primary Examiner* — Kimberly Chong
(74) *Attorney, Agent, or Firm* — McDonnell Boehnen Hulbert & Berghoff LLP

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

16 Claims, 10 Drawing Sheets

Specification includes a Sequence Listing.

(56) References Cited

FOREIGN PATENT DOCUMENTS

| | | |
|---|---|---|
| RU | 2297833 | 4/2007 |
| WO | WO 1994/026764 | 11/1994 |
| WO | WO 1999/050409 | 10/1999 |
| WO | WO 2000/003720 | 1/2000 |
| WO | WO 2001/079283 | 10/2001 |
| WO | WO 2003/013437 | 2/2003 |
| WO | WO 2003/009835 | 8/2003 |
| WO | WO 2003/064625 | 8/2003 |
| WO | WO 2004/044123 | 4/2004 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/083436 | 9/2005 |
| WO | WO 2005/105995 | 11/2005 |
| WO | WO 2005/116204 | 12/2005 |
| WO | WO 2006/128141 | 11/2006 |
| WO | WO 2007/022470 | 2/2007 |
| WO | WO 2007/051045 | 5/2007 |
| WO | WO 2007/120883 | 10/2007 |
| WO | WO 2007089584 | 11/2007 |
| WO | WO 2008/005562 | 1/2008 |
| WO | WO 2008/018795 | 2/2008 |
| WO | WO 2009/008725 | 1/2009 |
| WO | WO 2011/097388 | 8/2011 |

OTHER PUBLICATIONS

Bennett et al., "Antisense oligonucleoties as a tool for gene functionalization and target validation" Biochimica Biophysica Acta (1999) 1489:19-30.

Boado et al., "Antisense-mediated down-regulation of the human huntington gene" Journal of Pharmacology and Experimental Therapeutics (2000) 295:239-243.

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" Proc. Natl. Acad. Sci. USA (2005) 102:11023-11028.

Branch et al., "A good antisense molecule is hard to find," TIBS (1998) 23:45-50.

Caplen et al., "Rescue of polyglutamine-mediated cytotoxicity by double-stranded RNA-mediated RNA interference" Human Molecular Genetics (2002) II (2): 175-184.

Chang et al., "Structural Analysis of Complementary DNA and Amino Acid Sequences of Human and Rat Androgen Receptors" PNAS (1988) 85:7211-7215.

Chin "On the Preparation and Utilization of Isolated and Purififed Oligonucleotides." Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Davidson et al., "Molecular medicine for the brain: silencing of disease genes with RNA interference" Lancet Neural. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" J Neurosci(2005) 25:9773-9781.

Drouet et al., "Sustained effects of nonallele-specific Huntingtin silencing" Ann Neural. (2009) 65(3): 276-285.

Eder et al., "Inhibition of LNCaP Prostate Cancer Cells by Means of Androgen Receptor Antisense Oligonucleotides" Cancer Gene Therapy (2000) 7(7):997-1007.

Gagnon et al., "HD Therapeutics—CHDI Fifth Annual Conference" IDrugs 13( 4): 219-223 (2010).

Gonzalez-Alegre et al., "Technology Insight: therapeutic RNA interference- how far from the neurology clinic?" Nature Clinical Practice 3:394-404, 2007.

Gryaznov et al., "Oligodeoxyribonucleotide N3'->P5' Phosphoramidates Synthesis and Hybridization Properties" J Am. Chem. Soc. (1994) 116:3143-3144.

Haque et al., "Antisense gene therapy for neurodegenerative disease" Experimental Neurology (1997) 144:139-146.

Harper et al., "Ten years of presymptomatic testing for Huntington's disease: the experience of the UK Huntington's Disease Prediction Consortium" J. Med. Genet. 37:567-571, 2000.

Harper et al., RNA interference improves motor and neuropathological abnormalities in a Huntington's disease mouse model PNAS (2005) 102:5820-5825.

Hasholt et al., "Antisense downregulation of mutant huntingtin in a cell model" Journal of Gene Medicine (2003) 5:528-538.

Hersch et al., "Translating Therapies for Huntington's Disease from Genetic Animal Models to Clinical Trials" NeuroRX (2004) 1:298-306.

Hersch et al., "Neuroprotection for Huntington's disease: Ready, set, slow" Neurotherapeutics (2008) 5(2):226-236.

Liu et al., "Specific inhibition of Huntington's disease gene expression by siRNAs in cultures cells" Proceedings of the Japan Academy. Series B, Physical and Biological Sciences (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" Biochem. Biophys. Res. Commun. (2006) 343:190-197.

MacMillan et al., "Molecular analysis and clinical correlations of the Huntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.

Martin et al., "38. Ein neuer Zugang zu 2'-0-Alkylribonucleosiden and Eigenschaften deren Oligonucleotide" Helv. Chim. Acta (1995) 78:486-504.

Nellemann et al., "Inhibition of Huntington synthesis by antisense oligonucleotides" Molecular and Cellular Neurosciences (2000) 16:313-323.

New England BioLabs, Inc. Catalogue (1998): 121, 284.

Nguyen et al., "Clioquinol down-regulates mutant huntingtin expression in vitro and mitigates pathology in a Huntington's disease mouse model" PNAS (2005) 102:11840-11845.

Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.

Pakula et al., "Genetic analysis of protein stability and function" Annual review of genetics 23: 289-310 (1989).

Reynolds et al., "Rational siRNA design for RNA interference" Nature Biotechnology (2004) 22:326-330.

Sanghvi et al., "Heterocyclic Base Modifications in Nucleic Acids and Their Applications in Antisense Oligonucleotides" Antisense Research and Applications (1993) pp. 273-288.

Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.

Sheehan et al., "Biochemical properties of phosphonoacetate and thiophosphonoacetate oligodeoxyribonucleotides" Nucleic Acids Research (2003) 31:4109-4118.

Uhlmann et al., "Antisense oligonucleotides: a new therapeutic principle" Chemical Reviews (1990) 90:543-584.

Vickers et al., "Efficient Reduction of Target RNAs by Small Interfering RNA and Rnase H-dependent Antisense Agents. A comparative analysis." J Bioi. Chem. (2003) 278:7108-7118.

Wang et al., "Clinico-pathological rescue of a model mouse of Huntington's disease by siRNA" Neurosci. Res. (2005) 53:241-249.

Woolf et al., "Specificity of antisense oligonucleotides in vivo" Proc. Natl. Acad. Sci. USA (1992) 89:7305-7309.

(56) References Cited

OTHER PUBLICATIONS

Yen et al., "Sequence-specific cleavage of Huntingtin mRNA by catalytic DNA" Annals of Neurology (1999) 46 (3)366-373.
International Search Report for Application No. PCT/US2007/002215 dated Nov. 16, 2017.
International Search Report for Application No. PCT/US2007/002171 dated Sep. 26, 2007.
International Search Report for Application # PCT/US2010/048532 dated Jan. 26, 2011.

MODULATION OF HUNTINGTIN EXPRESSION

SEQUENCE LISTING

The present application is being filed along with a Sequence Listing in electronic format. The Sequence Listing is provided as a file entitled BIOL0113USC3SEQ_ST25.txt created May 15, 2017, which is 488 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 1:
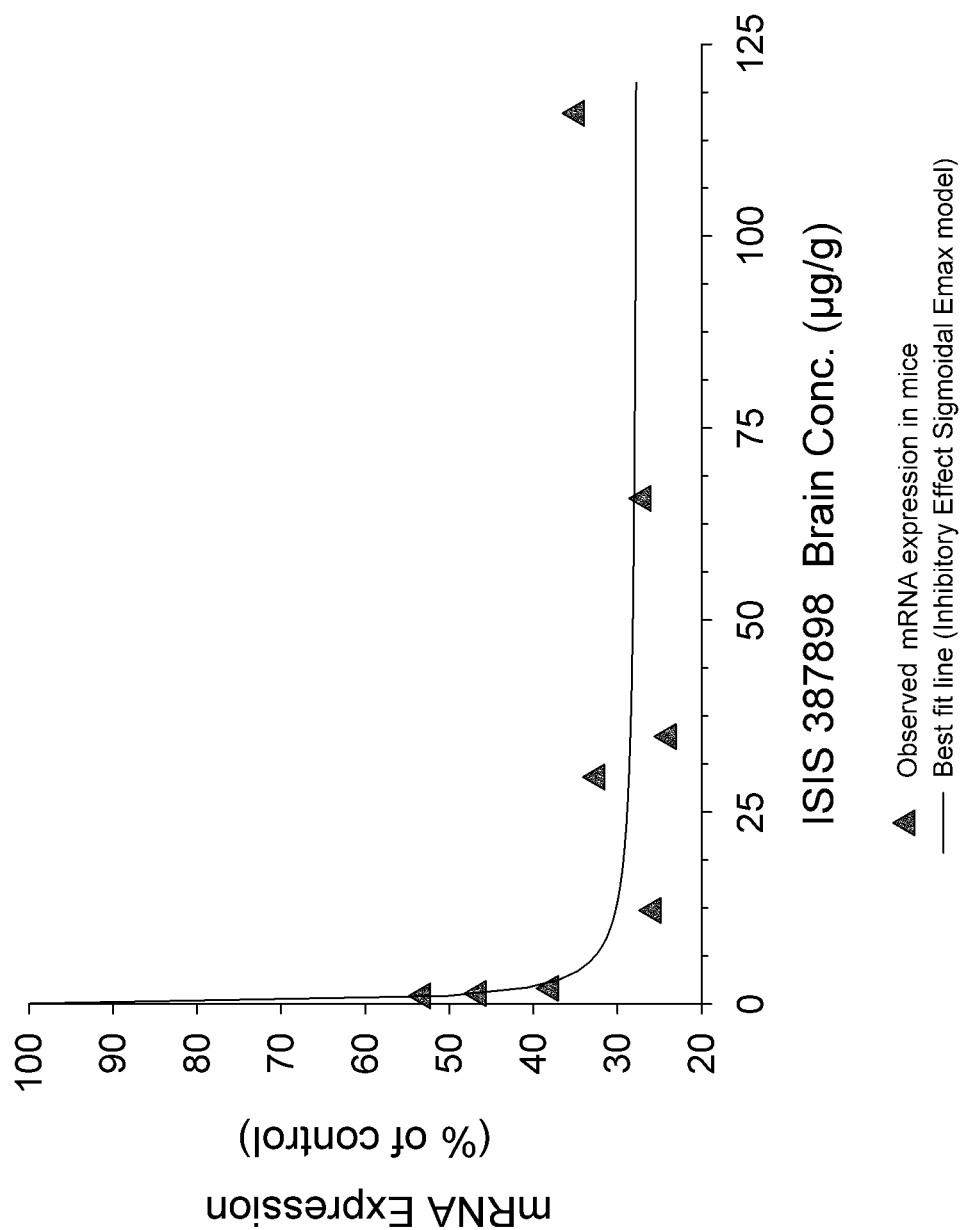
FIG. 1.

The PK/PD relationship of huntingtin mRNA expression in intrastriatal tissue with ISIS 387898 concentration in mouse brain. C57/BL6 mice were administered a single bolus of 50 µg of ISIS 387898 and huntingtin mRNA expression as well as the concentration of the antisense oligonucleotide in the tissue were measured. The $EC_{50}$ of ISIS 387898 was also calculated.

FIG. 2:

Comparison of huntingtin mRNA expression in intrastriatal tissue and ISIS 387898 concentrations at various time points. C57/BL6 mice were administered a single bolus of 50 µg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

FIG. 3:

The PK/PD relationship of huntingtin mRNA expression in the anterior cortex tissue with ISIS 387898 concentration in mouse brain. BACHD mice were administered an intracerebroventricular infusion of 75 µg of ISIS 387898 for 2 weeks and huntingtin mRNA expression as well as the concentration of the antisense oligonucleotide in the tissue were measured. The $EC_{50}$ of ISIS 387898 was also calculated.

FIG. 4:

Comparison of huntingtin mRNA expression in anterior cortex tissue and ISIS 387898 concentrations at various time points. BACHD mice were administered intracerebroventricular infusion of 75 µg of ISIS 387898 for 2 weeks, and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

FIG. 5:

Comparison of huntingtin mRNA expression in posterior cortex tissue and ISIS 388241 concentrations at various time points. BACHD mice were administered intracerebroventricular infusion of 50 µg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

FIG. 6:

Comparison of huntingtin mRNA expression in posterior cortex tissue and ISIS 443139 concentrations at various time points. BACHD mice were administered intracerebroventricular infusion of 50 µg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

FIG. 7.

Effect of antisense oligonucleotide treatment on the motor performance of BACHD mice using the Rotarod assay. BACHD mice were treated with 50 µg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

FIG. 8.

Effect of antisense oligonucleotide treatment on brain weight of R6/2 mice. Six-month old R6/2 mice were treated with 50 µg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

FIG. 9

Behavioral characterization of antisense oligonucleotide-treated YAC128 mice using the Open Field assay. Five month old YAC128 mice were treated with 50 µg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

FIG. 10

Behavioral characterization of antisense oligonucleotide-treated YAC128 mice using the Elevated Plus Maze assay. Five month old YAC128 mice were treated with 50 µg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. 3-D-ribonucleosides) or a DNA nucleotide (i.e. 3-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM_002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM_010414.1 (incorporated herein as SEQ ID NO: 3), the complement of GENBANK Accession No. NW_001109716.1 truncated at nucleotides 698000 to 866000 (incorporated herein as SEQ ID NO: 4), and GENBANK Accession No. NM_024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5.

In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH$_3$)—O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

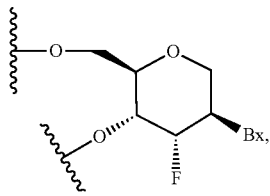

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of six linked nucleosides;
(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:
(i) a compound as described herein; and alternatively
(ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include 3-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif.

In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences Nucleotide sequences that encode huntingtin include, without limitation, the following: GENBANK Accession No. NM_002111.6, first deposited with GEN-BANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM_010414.1, first deposited with GENBANK® on Mar. 23, 2004, incorporated herein as SEQ ID NO: 3; the complement of GENBANK Accession No. NW 001109716.1 truncated at nucleotides 698000 to 866000, first deposited with GEN-BANK® on Jun. 14, 2006, incorporated herein as SEQ ID NO: 4, and GENBANK Accession No. NM_024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression. Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—$C_1$-$C_{10}$ alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2'; 4'-(CH2)-O-2' (LNA); 4'-(CH2)2-O-2' (ENA); 4'-C(CH3)2-O-2' (see PCT/US2008/068922); 4'-CH(CH3)-O-2' and 4'-C—H(CH2OCH3)-O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

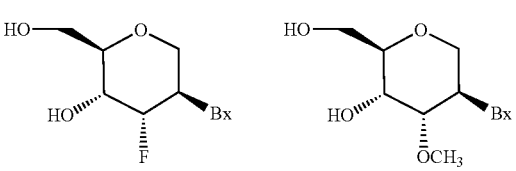

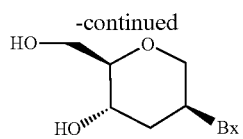

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro IC50 of less than 7 uM, less than 6 uM, less than 5, uM, less than 4 uM, less than 3 uM, less than 2 uM, less than 1 uM when delivered to a human fibroblast cell line as described herein or an ED50 of less than 10 µg, less than 9 µg, less than 8 µg, less than 7.5 µg, less than 7.4 µg, less than 7.0 µg, less than 6 µg, less than 5 µg, less than 4 µg, less than 3 µg, or less than 2 µg by bolus injection. As described herein, ICV infusion can result in 3 to 4 fold higher ED50 values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 µg/g. The $EC_{50}$ after ICV administration was determined to be 26.4 µg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; anti-depressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference
While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeted to Human Huntingtin Gene Sequences About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P=S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT_006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |
| 4617 | 4636 | 1 | 444615 | TGGAATGATTGCCTCTGATT | 5-10-5 | 14 |
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |
| 4868 | 4887 | 1 | 436684 | ATGAGTCTCAGTAACATTGA | 5-10-5 | 23 |

TABLE 1-continued

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the mouse mRNA sequence.

TABLE 2

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |

TABLE 2-continued

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |

TABLE 3-continued

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having phosphorothioate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 1 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCTGAACTG | 5-10-5 | 10 |
| 4608 | 4627 | 1 | 444659 | TGCCTCTGATTCCCTGAACT | 5-10-5 | 11 |
| 4609 | 4628 | 1 | 444660 | TTGCCTCTGATTCCCTGAAC | 5-10-5 | 12 |
| 4610 | 4629 | 1 | 444661 | ATTGCCTCTGATTCCCTGAA | 5-10-5 | 13 |

TABLE 5-continued

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4813 | 4832 | 1 | 444663 | CTGCATCAGCTTTATTTGTT | 5-10-5 | 18 |
| 4862 | 4881 | 1 | 443139 | CTCAGTAACATTGACACCAC | 5-10-5 | 22 |
| 5809 | 5828 | 1 | 444652 | TTTCTCTATTGCACATTCCA | 5-10-5 | 32 |
| 4928 | 4947 | 1 | 451541 | TTCTCCTTGTGGCACTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No. NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2: Dose-Dependent Antisense Inhibition of Human Huntingtin mRNA In Vitro About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence CTC-CGTCCGGTAGACATGCT, designated herein as SEQ ID NO: 37; reverse sequence GGAAATCAGAACCCT-CAAAATGG, designated herein as SEQ ID NO: 38; probe sequence TGAGCACTGTTCAACTGTGGA-TATCGGGAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in μM.

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in μM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in μM.

TABLE 11

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 12 expressed in μM.

TABLE 12

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 13 expressed in μM.

TABLE 13

Dose dependent reduction of huntingtin mRNA in GM04281 fibroblasts

| ISIS No. | 250 nM | 500 nM | 1000 Nm | 2000 nM | 4000 nM | 8000 nM | $IC_{50}$ (μM) |
|---|---|---|---|---|---|---|---|
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 14 expressed in μM.

TABLE 14

Dose dependent reduction of huntingtin mRNA in GM04281 fibroblasts

| ISIS No | 156.25 nM | 312.5 Nm | 625 nM | 1250 nM | 2500 nM | $IC_{50}$ (μM) |
|---|---|---|---|---|---|---|
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |

TABLE 14-continued

Dose dependent reduction of huntingtin mRNA in GM04281 fibroblasts

| ISIS No | 156.25 nM | 312.5 Nm | 625 nM | 1250 nM | 2500 nM | $IC_{50}$ (μM) |
|---|---|---|---|---|---|---|
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15 expressed in μM.

TABLE 15

Dose dependent reduction of huntingtin mRNA in GM04281 fibroblasts

| ISIS No. | 13.6719 nM | 27.3438 nM | 54.6875 nM | 109.375 nM | 218.75 nM | 437.5 nM | 875 nM | 1750 nM | 3500 nM | 7000 nM | $IC_{50}$ (μM) |
|---|---|---|---|---|---|---|---|---|---|---|---|
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.1 expressed in M.

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.2 expressed in M.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.3 expressed in μM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | $IC_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 17 expressed in μM.

TABLE 17

Dose dependent reduction of huntingtin mRNA in A549 cells

| ISIS No. | 250 nM | 500 nM | 1000 nM | 2000 nM | 4000 nM | 8000 nM | $IC_{50}$ (μM) |
|---|---|---|---|---|---|---|---|
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 Cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGT-CAA, designated herein as SEQ ID NO: 40; reverse sequence AAGGGATGCTGGGCTCTGT, designated herein as SEQ ID NO: 41; probe sequence AGCAAAGCT-TGGTGTCTTGGCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 18 expressed in μM.

TABLE 18

Dose dependent reduction of huntingtin mRNA in LLC-MK2 cells

| ISIS No. | 625 nM | 1250 nM | 2500 nM | 5000 nM | 10000 nM | 20000 nM | $IC_{50}$ (μM) |
|---|---|---|---|---|---|---|---|
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 19 expressed in μM.

TABLE 19

Dose dependent reduction of huntingtin mRNA in LLC-MK2 cells

| ISIS No. | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 | n.d. = $IC_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 20 expressed in μM.

TABLE 20

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 35 | 44 | 68 | 74 | 90 | 96 | 1.35 |
| 388241 | 23 | 37 | 54 | 56 | 68 | 89 | 2.64 |
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

Dose dependent reduction of huntingtin mRNA in LLC-MK2 cells

| ISIS No. | 6.25 nM | 12.5 nM | 25.0 nM | 50.0 nM | 100.0 nM | 200.0 nM | IC$_{50}$ |
|---|---|---|---|---|---|---|---|
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 22 expressed in nM.

TABLE 22

Dose dependent reduction of huntingtin mRNA in LLC-MK2 cells

| ISIS No | 6.25 nM | 12.5 nM | 25 nM | 50 nM | 100 nM | 200 nM | IC$_{50}$ (nM) |
|---|---|---|---|---|---|---|---|
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 23 expressed in nM.

TABLE 23

Dose dependent reduction of huntingtin mRNA in LLC-MK2 cells

| ISIS No. | 4.6875 nM | 9.375 nM | 18.75 nM | 37.5 nM | 75.0 nM | 150.0 nM | IC$_{50}$ (nM) |
|---|---|---|---|---|---|---|---|
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The IC$_{50}$ of each antisense oligonucleotide is also presented in Table 24 expressed in nM.

TABLE 24

Dose dependent reduction of huntingtin mRNA in BACHD transgenic murine hepatocytes

| ISIS No. | 7.4074 nM | 22.222 nM | 66.667 nM | 200.00 nM | IC$_{50}$ (nM) |
|---|---|---|---|---|---|
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 25 expressed in nM.

TABLE 25

Dose dependent reduction of huntingtin mRNA
in BACHD transgenic murine hepatocytes

| ISIS No. | 12.5 nM | 25 nM | 50 Nm | 100 nM | 200 nM | $IC_{50}$ (nM) |
|---|---|---|---|---|---|---|
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 26 expressed in nM.

TABLE 26

Dose dependent reduction of huntingtin mRNA in
BACHD transgenic murine hepatocytes

| ISIS No. | 12.5 nM | 25 nM | 50 nM | 100 nM | 200 nM | $IC_{50}$ (nM) |
|---|---|---|---|---|---|---|
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGTCAACCG-TATCC, designated herein as SEQ ID NO: 43; reverse sequence GGCTTAAACAGGGAGCCAAAA, designated herein as SEQ ID NO: 44; probe sequence ACTTCATGAT-GAGCTCGGAGTTCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 27 expressed in nM.

TABLE 27

Dose dependent reduction of huntingtin mRNA
in BACHD transgenic murine hepatocytes

| ISIS No. | 6.667 nM | 20 nM | 60 nM | 180 nM | $IC_{50}$ (nM) |
|---|---|---|---|---|---|
| 387916 | 15 | 15 | 68 | 94 | 37 |
| 419640 | 4 | 39 | 73 | 94 | 32 |
| 419641 | 16 | 45 | 81 | 96 | 24 |
| 419642 | 23 | 39 | 75 | 93 | 25 |

Example 3: Systemic Administration of Antisense Oligonucleotides Against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.

Study 1.
Treatment

Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

Percent inhibition of human
huntingtin mRNA in BACHD mice

| ISIS No. | % inhibition |
|---|---|
| 387916 | 82 |
| 388241 | 52 |
| 419629 | 80 |
| 419637 | 83 |

TABLE 28-continued

Percent inhibition of human huntingtin mRNA in BACHD mice

| ISIS No. | % inhibition |
|---|---|
| 436684 | 55 |
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |

TABLE 30-continued

Percent change in organ weight of BACHD mice after antisense oligonucleotide treatment

| ISIS No. | Liver | Spleen | Kidney |
|---|---|---|---|
| 444658 | −1 | 0 | −16 |
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 31.

TABLE 31

Effect of antisense oligonucleotide treatment on markers of liver function

| | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

Percent inhibition of human huntingtin mRNA in BACHD mice

| ISIS No. | Dose (mg/kg) | % inhibition |
|---|---|---|
| 387916 | 12.5 | 71 |
| 419581 | 12.5 | 54 |
|  | 50 | 68 |
| 419602 | 12.5 | 72 |
|  | 50 | 77 |
| 419628 | 12.5 | 65 |
|  | 50 | 76 |
| 419629 | 12.5 | 87 |
|  | 50 | 93 |
| 419640 | 12.5 | 69 |
|  | 50 | 79 |
| 419641 | 12.5 | 61 |
|  | 50 | 80 |
| 419642 | 12.5 | 76 |
|  | 50 | 83 |

TABLE 33

Percent inhibition of murine huntingtin mRNA in BACHD mice

| ISIS No. | Dose (mg/kg) | % inhibition |
|---|---|---|
| 387916 | 12.5 | 70 |
| 419581 | 12.5 | 42 |
|  | 50 | 86 |
| 419602 | 12.5 | 77 |
|  | 50 | 85 |
| 419628 | 12.5 | 67 |
|  | 50 | 86 |
| 419629 | 12.5 | 90 |
|  | 50 | 93 |
| 419640 | 12.5 | 63 |
|  | 50 | 84 |
| 419641 | 12.5 | 52 |
|  | 50 | 81 |
| 419642 | 12.5 | 56 |
|  | 50 | 83 |

Organ Weight Measurements

Liver, spleen and kidney weights were measured at the end of the study, and are presented in Table 34 as a percent of the saline control normalized to body weight.

TABLE 34

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | −9 | 3 | −4 |
| 419581 | 12.5 | −2 | −6 | −1 |
|  | 50 | 14 | −1 | −11 |
| 419602 | 12.5 | 10 | 1 | −2 |
|  | 50 | 28 | 9 | −3 |
| 419628 | 12.5 | −2 | −7 | −2 |
|  | 50 | −3 | 7 | −9 |
| 419629 | 12.5 | −7 | −5 | −10 |
|  | 50 | 16 | 0 | −8 |
| 419640 | 12.5 | −5 | −2 | −8 |
|  | 50 | 1 | −20 | −4 |
| 419641 | 12.5 | −7 | −10 | −11 |
|  | 50 | −2 | −13 | −9 |
| 419642 | 12.5 | −11 | −21 | −19 |
|  | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L and the results are presented in Table 35.

TABLE 35

Effect of antisense oligonucleotide treatment on markers of liver function

|  | Dose (mg/kg) | ALT | AST |
|---|---|---|---|
| PBS |  | 44 | 80 |
| 387916 | 12.5 | 44 | 75 |
| 419581 | 12.5 | 56 | 101 |
|  | 50 | 390 | 281 |
| 419602 | 12.5 | 86 | 108 |
|  | 50 | 240 | 229 |
| 419628 | 12.5 | 52 | 110 |
|  | 50 | 51 | 73 |
| 419629 | 12.5 | 104 | 118 |
|  | 50 | 1262 | 1150 |
| 419640 | 12.5 | 36 | 65 |
|  | 50 | 38 | 55 |
| 419641 | 12.5 | 56 | 103 |
|  | 50 | 57 | 172 |
| 419642 | 12.5 | 40 | 64 |
|  | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

Percent inhibition of human huntingtin mRNA in BACHD mice

| ISIS No. | Dose (mg/kg) | % inhibition |
|---|---|---|
| 388241 | 12.5 | 32 |
| 388250 | 12.5 | 21 |
|  | 50 | 45 |
| 388251 | 12.5 | 30 |
|  | 50 | 34 |
| 388263 | 12.5 | 29 |
|  | 50 | 35 |
| 388264 | 12.5 | 35 |
|  | 50 | 42 |
| 419641 | 12.5 | 71 |
|  | 50 | 73 |
| 436645 | 12.5 | 43 |
|  | 50 | 48 |
| 436649 | 12.5 | 40 |
|  | 50 | 38 |
| 436668 | 12.5 | 45 |
|  | 50 | 69 |
| 436689 | 12.5 | 62 |
|  | 50 | 78 |

TABLE 37

Percent inhibition of murine huntingtin mRNA in BACHD mice

| ISIS No. | Dose (mg/kg) | % inhibition |
|---|---|---|
| 419641 | 12.5 | 68 |
|  | 50 | 77 |
| 436668 | 12.5 | 41 |
|  | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

Percent change in organ weight of BACHD mice after antisense oligonucleotide treatment

| ISIS No. | Dose (mg/kg) | Liver | Spleen | Kidney |
|---|---|---|---|---|
| 388241 | 12.5 | 1 | 6 | 9 |
| 388250 | 12.5 | 2 | 1 | -2 |
|  | 50 | 1 | 30 | 3 |
| 388251 | 12.5 | 4 | -8 | 1 |
|  | 50 | 19 | 19 | 2 |
| 388263 | 12.5 | 4 | 8 | 9 |
|  | 50 | 23 | 52 | 1 |
| 388264 | 12.5 | 2 | -2 | 3 |
|  | 50 | 12 | 9 | 6 |
| 419641 | 12.5 | -1 | -9 | 3 |
|  | 50 | 2 | -4 | 3 |
| 436645 | 12.5 | 8 | 6 | 5 |
|  | 50 | 26 | 25 | 9 |
| 436649 | 12.5 | 1 | 0 | 6 |
|  | 50 | 0 | 1 | 3 |
| 436668 | 12.5 | 1 | 5 | 10 |
|  | 50 | -2 | 3 | 11 |
| 436689 | 12.5 | -3 | -5 | 4 |
|  | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 39.

TABLE 39

Effect of antisense oligonucleotide treatment on markers of liver function

| | Dose (mg/kg) | ALT | AST |
|---|---|---|---|
| PBS |  | 43 | 76 |
| 388241 | 12.5 | 43 | 88 |
| 388250 | 12.5 | 37 | 55 |
|  | 50 | 44 | 89 |
| 388251 | 12.5 | 42 | 98 |
|  | 50 | 67 | 91 |
| 388263 | 12.5 | 51 | 90 |
|  | 50 | 55 | 93 |
| 388264 | 12.5 | 31 | 59 |
|  | 50 | 65 | 90 |
| 419641 | 12.5 | 39 | 70 |
|  | 50 | 42 | 83 |
| 436645 | 12.5 | 43 | 82 |
|  | 50 | 179 | 143 |
| 436649 | 12.5 | 35 | 47 |
|  | 50 | 38 | 76 |
| 436668 | 12.5 | 36 | 73 |
|  | 50 | 28 | 57 |
| 436689 | 12.5 | 31 | 52 |
|  | 50 | 49 | 164 |

Study 4

Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

Percent inhibition of human huntingtin mRNA in BACHD mice

| ISIS No. | Dose (mg/kg) | % inhibition |
|---|---|---|
| 387916 | 12.5 | 51 |
| 388241 | 12.5 | 47 |
|  | 50 | 67 |
| 437123 | 12.5 | 0 |
|  | 50 | 21 |
| 437132 | 12.5 | 31 |
|  | 50 | 33 |
| 437140 | 12.5 | 7 |
|  | 50 | 32 |
| 437442 | 12.5 | 42 |
|  | 50 | 85 |
| 437446 | 12.5 | 39 |
|  | 50 | 70 |
| 437477 | 12.5 | 52 |
|  | 50 | 75 |
| 437478 | 12.5 | 54 |
|  | 50 | 78 |
| 437490 | 12.5 | 42 |
|  | 50 | 44 |

TABLE 41

Percent inhibition of murine huntingtin mRNA in BACHD mice

| ISIS No. | Dose (mg/kg) | % inhibition |
|---|---|---|
| 387916 | 12.5 | 48 |
| 437442 | 12.5 | 27 |
|  | 50 | 76 |
| 437446 | 12.5 | 38 |
|  | 50 | 71 |
| 437477 | 12.5 | 63 |
|  | 50 | 87 |
| 437478 | 12.5 | 60 |
|  | 50 | 89 |

Organ Weight Measurements

Liver, spleen and kidney weights were measured at the end of the study, and are presented in Table 42 as a percent of the saline control normalized to body weight.

TABLE 42

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | 1 | 6 | 12 |
| 388241 | 12.5 | −3 | 16 | −2 |
|  | 50 | −6 | 10 | 0 |
| 437123 | 12.5 | −4 | 0 | 4 |
|  | 50 | 4 | 0 | −4 |
| 437132 | 12.5 | −2 | −3 | −5 |
|  | 50 | 2 | −6 | −2 |
| 437140 | 12.5 | −4 | 11 | −3 |
|  | 50 | 4 | 5 | −5 |
| 437442 | 12.5 | −10 | 9 | 3 |
|  | 50 | −3 | −20 | −10 |
| 437446 | 12.5 | −6 | 7 | 2 |
|  | 50 | −4 | 1 | −1 |
| 437477 | 12.5 | 1 | −2 | 0 |
|  | 50 | 25 | −9 | −6 |
| 437478 | 12.5 | −7 | −4 | −9 |
|  | 50 | 22 | 4 | 3 |
| 437490 | 12.5 | −5 | 0 | −5 |
|  | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 43.

TABLE 43

Effect of antisense oligonucleotide treatment on markers of liver function

|  | Dose (mg/kg) | ALT | AST |
|---|---|---|---|
| PBS |  | 32 | 58 |
| 387916 | 12.5 | 40 | 122 |
| 388241 | 12.5 | 39 | 93 |
|  | 50 | 28 | 62 |
| 437123 | 12.5 | 38 | 88 |
|  | 50 | 34 | 66 |
| 437132 | 12.5 | 34 | 52 |
|  | 50 | 30 | 52 |
| 437140 | 12.5 | 30 | 62 |
|  | 50 | 40 | 63 |
| 437442 | 12.5 | 40 | 106 |
|  | 50 | 63 | 119 |
| 437446 | 12.5 | 35 | 119 |
|  | 50 | 35 | 89 |
| 437477 | 12.5 | 39 | 68 |
|  | 50 | 52 | 162 |
| 437478 | 12.5 | 37 | 53 |
|  | 50 | 55 | 71 |
| 437490 | 12.5 | 48 | 71 |
|  | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control. All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

Percent inhibition of human huntingtin mRNA in BACHD mice

| ISIS No. | % inhibition |
|---|---|
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

Percent inhibition of murine huntingtin mRNA in BACHD mice

| ISIS No. | % inhibition |
|---|---|
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

Percent change in body weight of BACHD mice after antisense oligonucleotide treatment

| | day 4 | day 7 | day 10 | day 12 |
|---|---|---|---|---|
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

Percent change in organ weight of BACHD mice after antisense oligonucleotide treatment

| ISIS No. | Liver | Spleen | Kidney |
|---|---|---|---|
| 388241 | +2 | +13 | −7 |
| 419640 | −2 | +12 | −12 |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L. Plasma levels of bilirubin and albumin were also measured using the same clinical chemistry analyzer and expressed in g/dL. The results are presented in Table 48.

TABLE 48

Effect of antisense oligonucleotide treatment on markers of liver function

| | ALT | AST | Bilirubin | Albumin |
|---|---|---|---|---|
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, N.Y.). Results are presented in Table 49 expressed in mg/dL.

TABLE 49

Effect of antisense oligonucleotide treatment on markers of kidney function

| | BUN | Creatinine |
|---|---|---|
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |
| ISIS 437507 | 19.9 | 0.16 |
| ISIS 443139 | 23.3 | 0.16 |

TABLE 49-continued

Effect of antisense oligonucleotide treatment on markers of kidney function

|  | BUN | Creatinine |
|---|---|---|
| ISIS 444591 | 23.5 | 0.18 |
| ISIS 444661 | 25.4 | 0.18 |

Measurement of Other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, N.Y.). Results are presented in Table 50 expressed in mg/dL and demonstrate that treatment with these oligonucleotides did not cause any adverse changes in the levels of these metabolic markers between the control and treatment groups.

TABLE 50

Effect of antisense oligonucleotide treatment on metabolic markers

|  | Glucose | Cholesterol | Triglycerides |
|---|---|---|---|
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4: Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.

Treatment and Surgery

Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 µg, 10 µg or 25 µg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.

RNA Analysis

RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (µg) for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |
| 436689 | 27 | 63 | 81 | 7.0 |
| 436754 | 31 | 54 | 61 | 10.5 |
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |
| 444618 | 57 | 64 | 83 | 4.0 |
| 444627 | 47 | 70 | 61 | 5.0 |

TABLE 51-continued

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels in vivo and $ED_{50}$ of the antisense oligonucleotides

| ISIS No. | 3 mg | 10 mg | 25 mg | $ED_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED50 over ISIS 388241.

Example 5: Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity.

Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 pg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCA-GAA, designated herein as SEQ ID NO: 46; reverse sequence CAATTAGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |
| 436668 | 447 |
| 436671 | 239 |
| 436684 | 700 |
| 436689 | 149 |
| 436754 | 125 |
| 437168 | 130 |
| 437175 | 131 |
| 437441 | 158 |
| 437442 | 157 |
| 437507 | 133 |
| 437527 | 184 |
| 443139 | 143 |
| 444578 | 352 |
| 444584 | 317 |
| 444591 | 194 |
| 444607 | 362 |
| 444608 | 476 |
| 444615 | 645 |
| 444618 | 547 |
| 444627 | 377 |
| 444652 | 336 |

TABLE 53-continued

Percent expression of AIF1 mRNA levels in vivo as a measure of neurotoxicity

| ISIS No. | % expression |
|---|---|
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343 (forward sequence CAGAGCTGGTGAAC-CGTATCC, designated herein as SEQ ID NO: 49; reverse sequence GGCTTAAGCAGGGAGCCAAAA, designated herein as SEQ ID NO: 50; probe sequence ACTTCATGAT-GAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

Percent reduction of rat huntingtin mRNA levels in rats

| ISIS No. | % reduction |
|---|---|
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437527 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6: Intracerebroventricular Administration of Antisense Oligonucleotides Against Huntingtin mRNA-Tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 µg/day delivered ICV with Alzet 2002 pumps at the rate of 12 µL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

Percent reduction of human huntingtin mRNA levels in BACHD mice via ICV administration of antisense oligonucleotides

| ISIS No. | Number of mice | Anterior cortex | Posterior cortex |
|---|---|---|---|
| 388241 | 3 | 82 | 70 |
| 419640 | 1 | 60 | 46 |
| 419641 | 2 | 75 | 66 |

TABLE 56-continued

Percent reduction of human huntingtin mRNA levels in BACHD mice via ICV administration of antisense oligonucleotides

| ISIS No. | Number of mice | Anterior cortex | Posterior cortex |
|---|---|---|---|
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

Percent reduction of murine huntingtin mRNA levels in BACHD mice via ICV administration of antisense oligonucleotides

| ISIS No. | Number of mice | Anterior cortex | Posterior cortex |
|---|---|---|---|
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

Percent change in body weight of BACHD mice during antisense oligonucleotide treatment

| | week 1 | week 2 | week 3 | week 4 |
|---|---|---|---|---|
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

Number of survivals during antisense oligonucleotide treatment

| | week 1 | week 2 | week 3 | week 4 |
|---|---|---|---|---|
| PBS | 5 | 5 | 5 | 5 |
| ISIS 388241 | 4 | 3 | 3 | 3 |
| ISIS 437507 | 5 | 5 | 4 | 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7: Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC 3' (SEQ ID NO: 52), start site 5263 of SEQ ID NO: 3) at 50 pg/day delivered ICV with Alzet 2002 pumps at the rate of 0.5 µL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI #Mm01213820_m1 (Applied Biosystems) and normalized to peptidylprolyl isomerase A mRNA levels. Protein lysates were prepared from mouse brain slabs as described previously (Li S. H. and Li X. J., Methods in Molecular Biology (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software.

The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

|  | day 7 | day 14 |
|---|---|---|
| mRNA | 66 | 68 |
| protein | 21 | 49 |

Example 8: Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression.

Treatment and Surgery

Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of Htt mRNA

RNA was extracted from the anterior caudate, posterior caudate, temporal cortex, parietal cortex, hypothalamus, mid-brain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| | Dose (mg/day) | | | |
|---|---|---|---|---|
| Tissue | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. | n.d. = no data

Example 9: Measurement of Half-Life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTTC 3' (SEQ ID NO: 53); start position 4042 of SEQ ID NO: 1 and start position 4001 of SEQ ID NO: 3) delivered as a single bolus of 50 pg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
|  | 7 | 74 |
|  | 14 | 68 |
|  | 21 | 77 |
|  | 28 | 75 |
|  | 50 | 63 |
|  | 73 | 55 |
|  | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel eletrophoresis electrokinetic injection. A P/ACE MDQ capillary electrophoresis instrument (Beckman Coulter, Fullerton, Calif.) was used for gel-filled capillary electrophoretic analysis. Oligonucleotide peaks were detected by UV absorbance at 260 nm.

Figure 2:
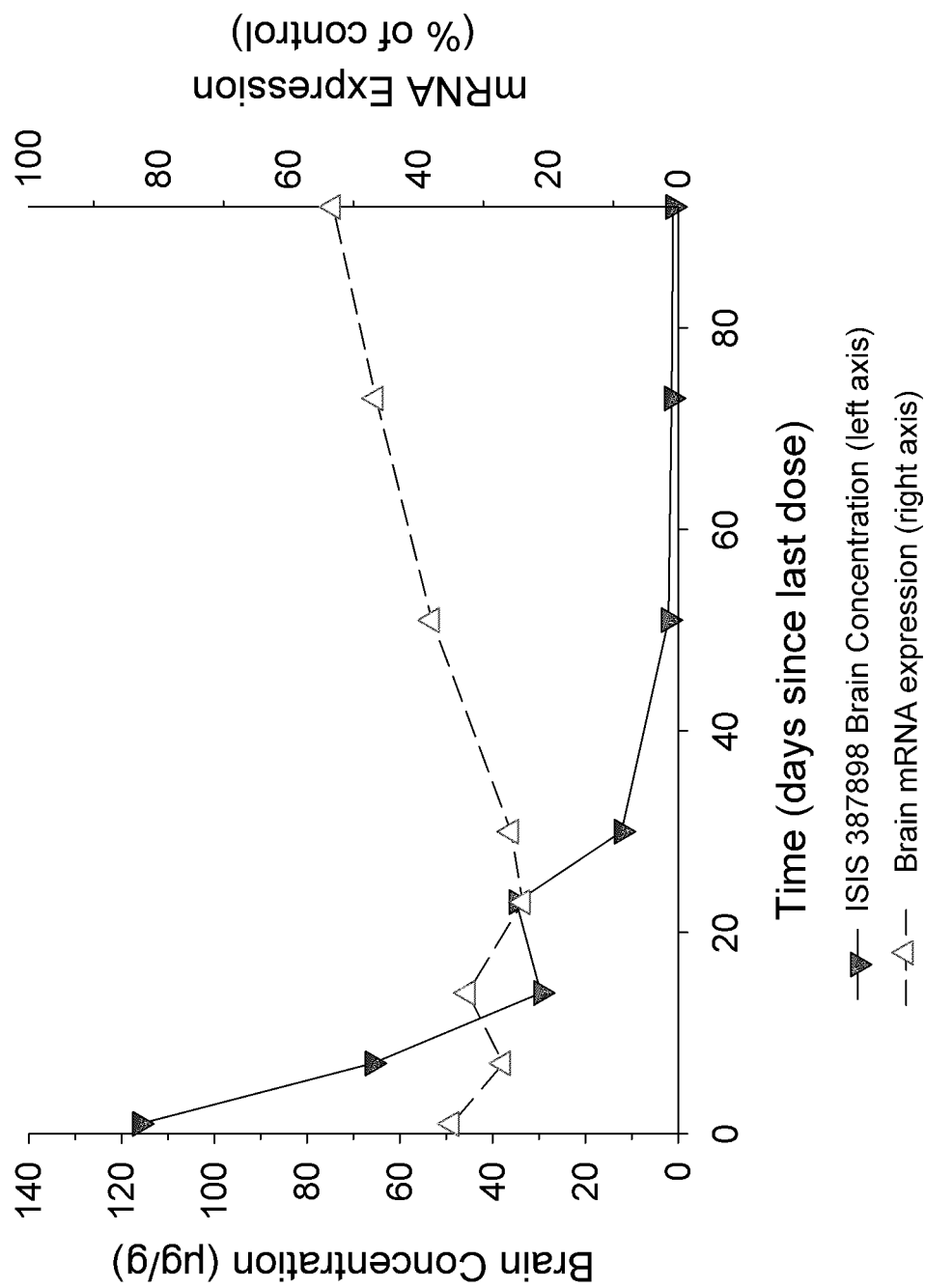

The concentration of ISIS 387898 in the brain (μg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 μg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (μg/g) | % mRNA expression |
|---|---|
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (μg/g) | mRNA % expression |
|---|---|---|
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10: Measurement of Half-Life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 μg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
|---|---|---|---|
| ISIS 387898 | 14 | 74 | 65 |
|  | 28 | 67 | 61 |
|  | 42 | 70 | 61 |
|  | 56 | 57 | 52 |
|  | 70 | 57 | 43 |
|  | 91 | 41 | 61 |
|  | 127 | 28 | 16 |
| PBS | 14 | 0 | 0 |
|  | 28 | 0 | 0 |
|  | 42 | 1 | 0 |
|  | 56 | 9 | 10 |
|  | 70 | 13 | 10 |
|  | 91 | 13 | 25 |
|  | 127 | 11 | 0 |

TABLE 66

Effect of ISIS 387898 administered ICV on murine huntingtin mRNA expression at various time points

| Treatment | Days after dosage | anterior | posterior |
|---|---|---|---|
| ISIS 387898 | 14 | 85 | 81 |
|  | 28 | 81 | 69 |
|  | 42 | 86 | 79 |
|  | 56 | 74 | 69 |
|  | 70 | 73 | 58 |
|  | 91 | 39 | 63 |
|  | 127 | 39 | 0 |
| PBS | 14 | 0 | 0 |
|  | 28 | 0 | 0 |
|  | 42 | 0 | 0 |
|  | 56 | 17 | 14 |
|  | 70 | 5 | 24 |
|  | 91 | 9 | 17 |
|  | 127 | 32 | 0 |

Analysis of Antisense Oligonucleotide Concentration in the Brain.

Figure 3:
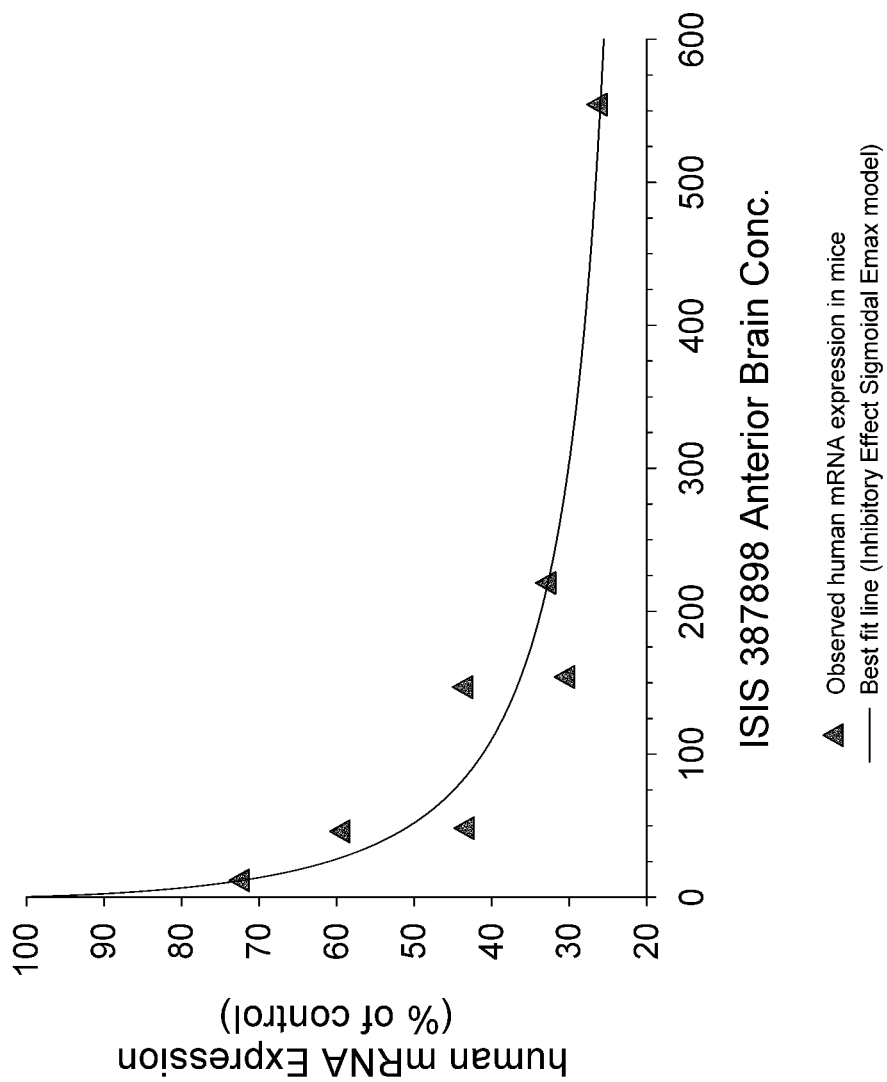
Figure 4:
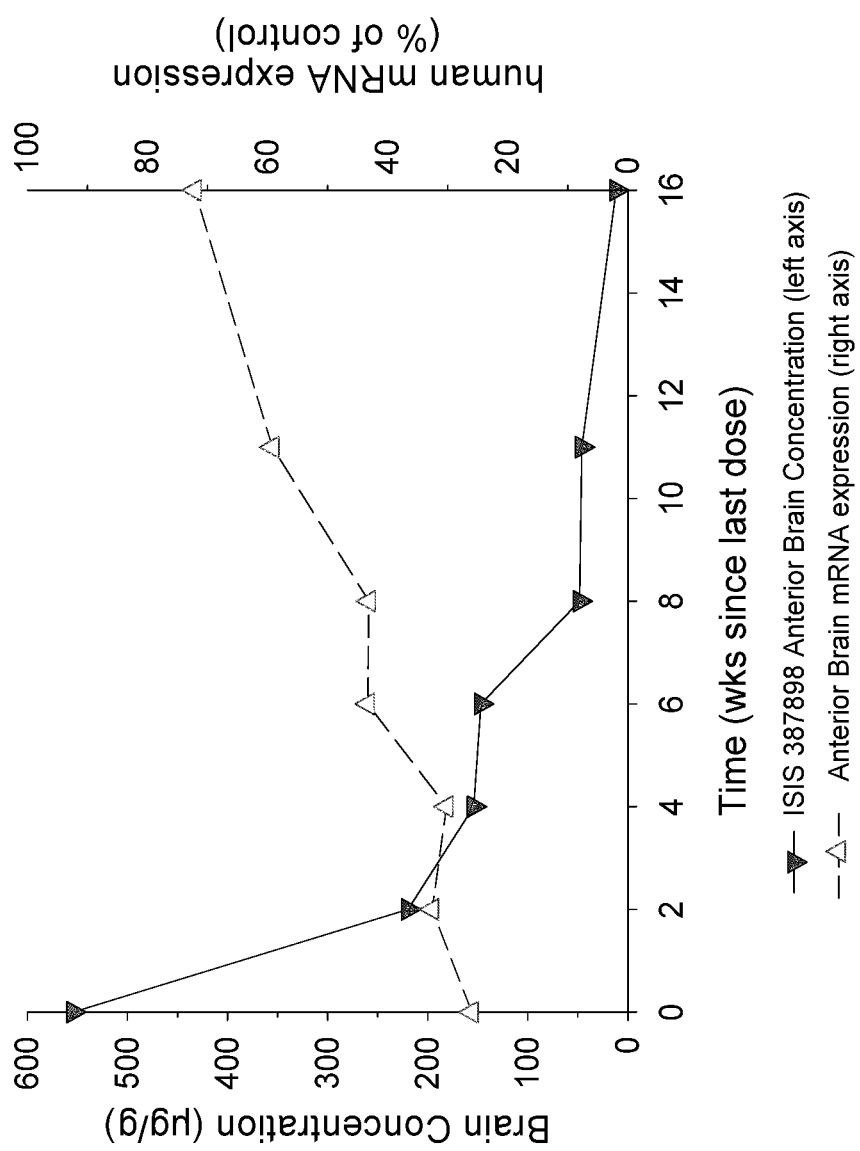

Brain tissue was processed in a procedure similar to that described in Example 9. The concentration of ISIS 387898 in the anterior cortex of the brain (μg/g) was plotted against the inhibition of human huntingtin as a percentage of the PBS control (Table 67 and FIG. 3), and the $EC_{50}$ was calculated to be 26.4 µg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (µg/g) | % mRNA expression |
|---|---|
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
|---|---|---|
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11: Measurement of Half-Life of ISIS 388241 and ISIS 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.

Treatment

Twenty BACHD mice were treated with ISIS 38241 delivered by ICV administration at 50 µg/day for 2 weeks in a procedure similar to that described in Example 9. Twenty BACHD mice were treated with ISIS 443139 delivered by ICV administration at 50 µg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
|---|---|---|---|
| ISIS 388241 | 0 | 63 | 64 |
|  | 4 | 79 | 56 |
|  | 8 | 67 | 51 |
|  | 12 | 76 | 68 |
|  | 16 | 35 | 34 |
| ISIS 443139 | 0 | 35 | 55 |
|  | 4 | 20 | 62 |
|  | 8 | 61 | 59 |
|  | 12 | 67 | 53 |
|  | 16 | 46 | 37 |
| PBS | 0 | 15 | 10 |
|  | 4 | 0 | 2 |
|  | 8 | 5 | 0 |
|  | 12 | 32 | 4 |
|  | 16 | 6 | 2 |

Figure 5:
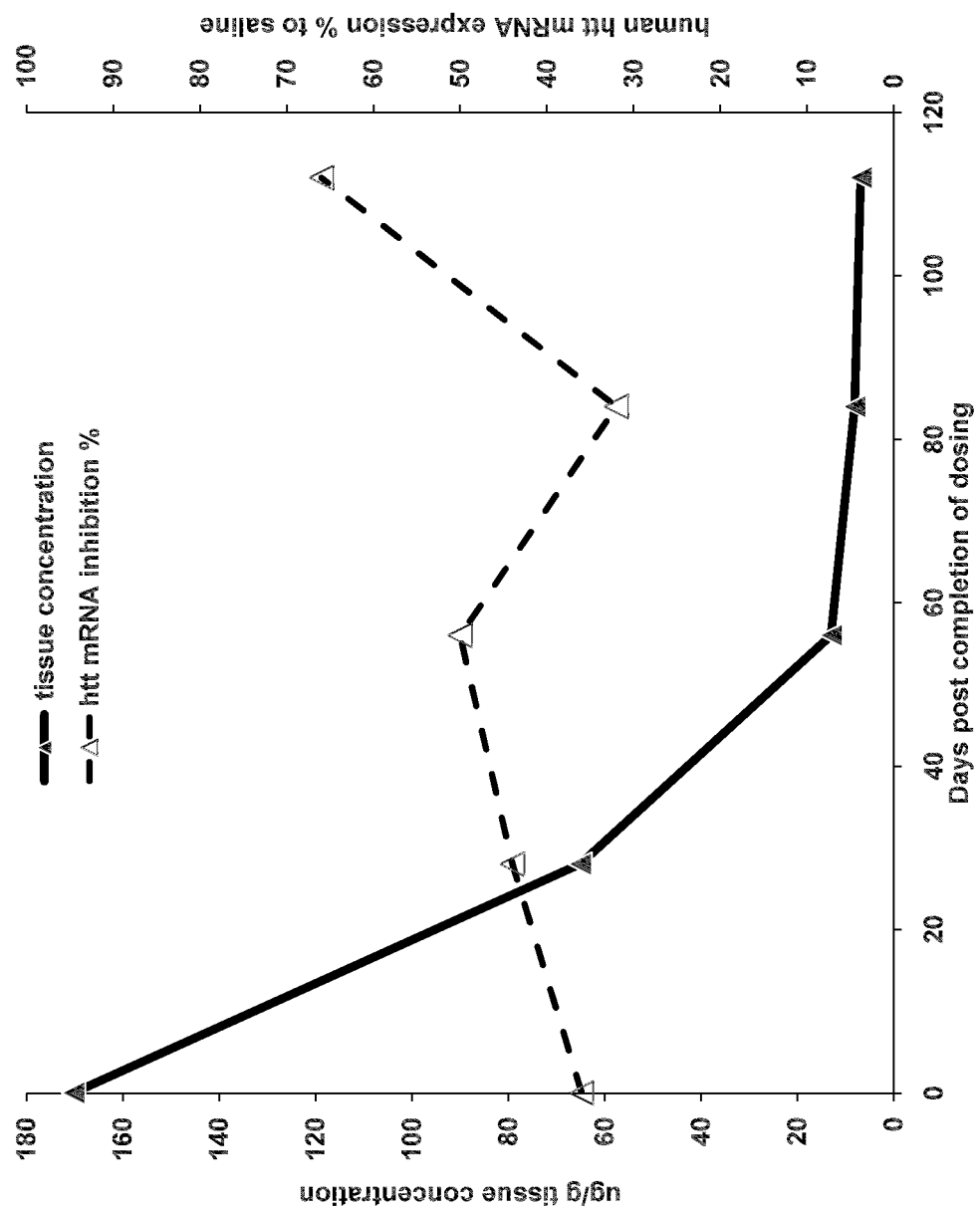
Figure 6:
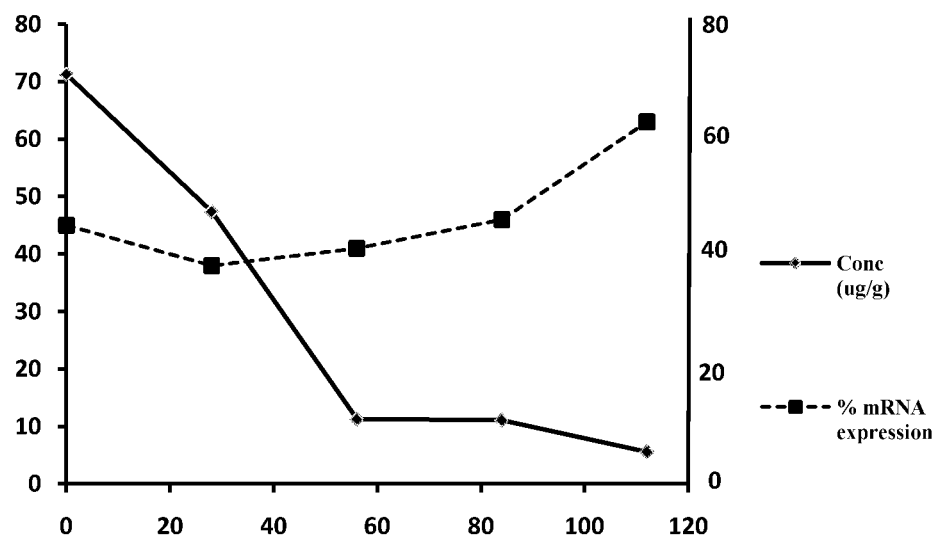

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and its effect on htt mRNA expression as a percentage of the control

| Days after last dose | Conc (ug/g) | % mRNA expression |
|---|---|---|
| 0 | 170.3 | 36 |
| 28 | 65.2 | 43 |
| 56 | 13 | 49 |
| 84 | 8.2 | 32 |
| 112 | 6.9 | 66 |

TABLE 71

Concentration of ISIS 443139 in brain tissue and its effect on htt mRNA expression as a percentage of the control

| Days after last dose | Conc (ug/g) | % mRNA expression |
|---|---|---|
| 0 | 71.3 | 45 |
| 28 | 47.4 | 38 |
| 56 | 11.3 | 41 |

TABLE 71-continued

Concentration of ISIS 443139 in brain tissue and its effect on htt mRNA expression as a percentage of the control

| Days after last dose | Conc (ug/g) | % mRNA expression |
|---|---|---|
| 84 | 11.1 | 46 |
| 112 | 5.6 | 63 |

Example 12: Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 µg/day delivered ICV with Alzet 2002 pumps at the rate of 12 µL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

Figure 7:
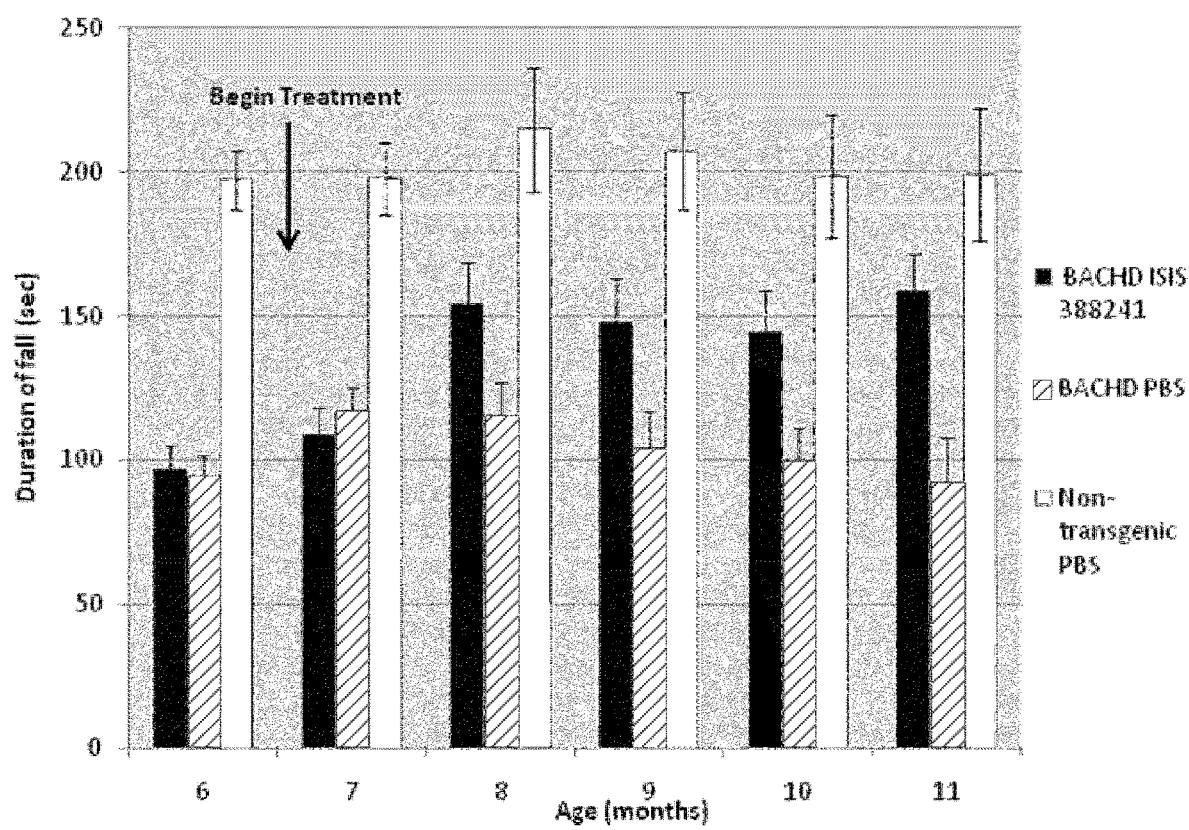

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

Effect of antisense inhibition of mutant huntingtin mRNA on duration to fall (sec)

| | 6 months | 7 month | 8 months | 9 months | 10 months | 11 months |
|---|---|---|---|---|---|---|
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13: Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 µg/day, ISIS 408737 at 75 µg/day, or ISIS 387898 at 75 µg/day, delivered ICV with Alzet 2002 pumps at the rate of 0.5 L/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

TABLE 73

Effect of antisense inhibition of huntingtin mRNA on duration to fall (sec)

|  | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14: Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioServ Product #K3323), a Petite Green Gumabone (BioServ Product #K3214) and a nestlet (Hockley et al., Ann Neurol. 2002, 51: 235-242). Food and water were available ad libitum to the mice in their home cages.

A group of ten six month old R6/2 mice was administered 50 µg/day of ISIS 388817 delivered ICV with Alzet 1004 pumps at the rate of 0.12 µl/hr for 4 weeks. A group of two non-transgenic littermates was administered 50 Gg/day of ISIS 388817 delivered in a similar manner. A control group of five R6/2 mice was administered 50 Gg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Figure 8:
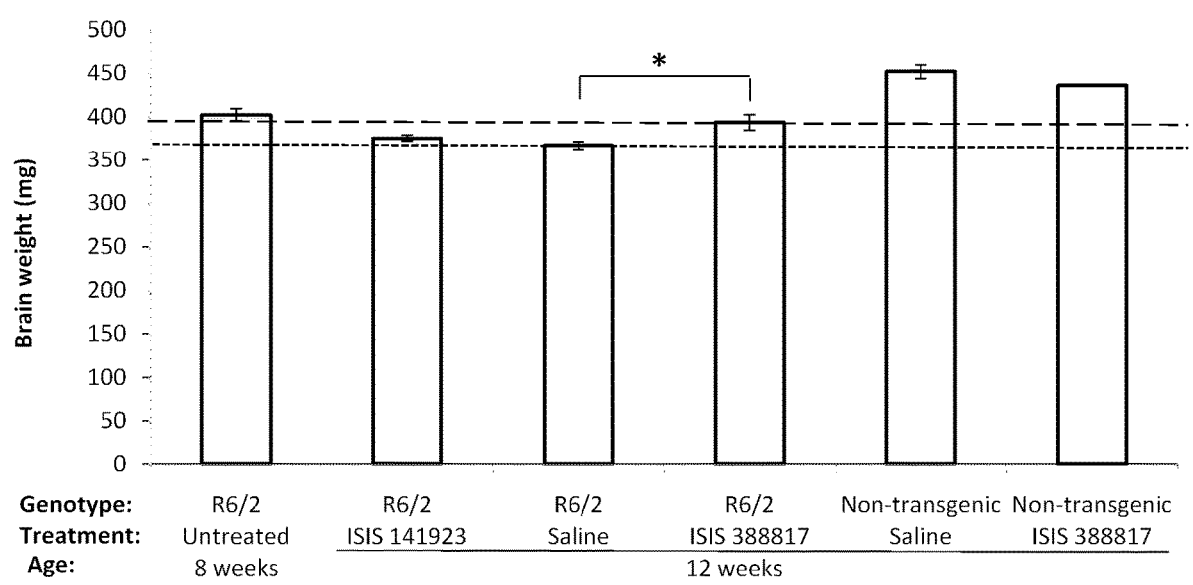

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 74

Effect of antisense inhibition of mutant huntingtin mRNA on brain weight (mg)

| Mouse model | Treatment | Brain weight |
|---|---|---|
| R6/2 | PBS | 367 |
|  | ISIS 141923 | 375 |
|  | ISIS 388817 | 394 |
| R6/2 (8 weeks old) | None | 402 |
| Non-transgenic | ISIS 141923 | 452 |
|  | ISIS 388817 | 436 |

Example 15: Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 µg/day of ISIS 388241 delivered ICV with Alzet 1004 pumps at the rate of 0.5 µl/hr for 14 days. A control group of four YAC128 mice were similarly treated with PBS. A control group of eight non-transgenic FVB/NJ littermates was included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Figure 9:
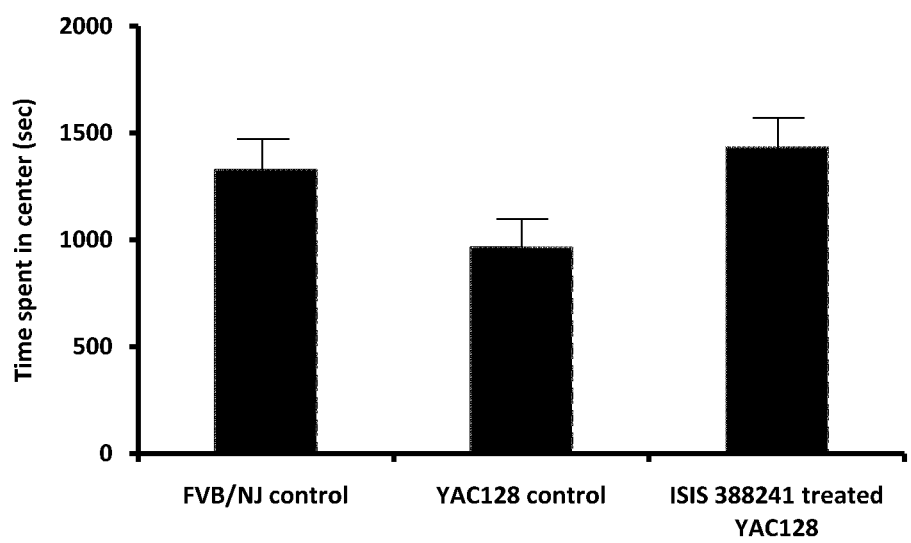

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA on open field performance of YAC128 mice

| Mice model | Time in center (sec) |
|---|---|
| FVB control | 1326 |
| YAC128 control | 964 |
| ISIS 388241 treated YAC128 | 1433 |

Elevated Plus Maze Assay

Figure 10:
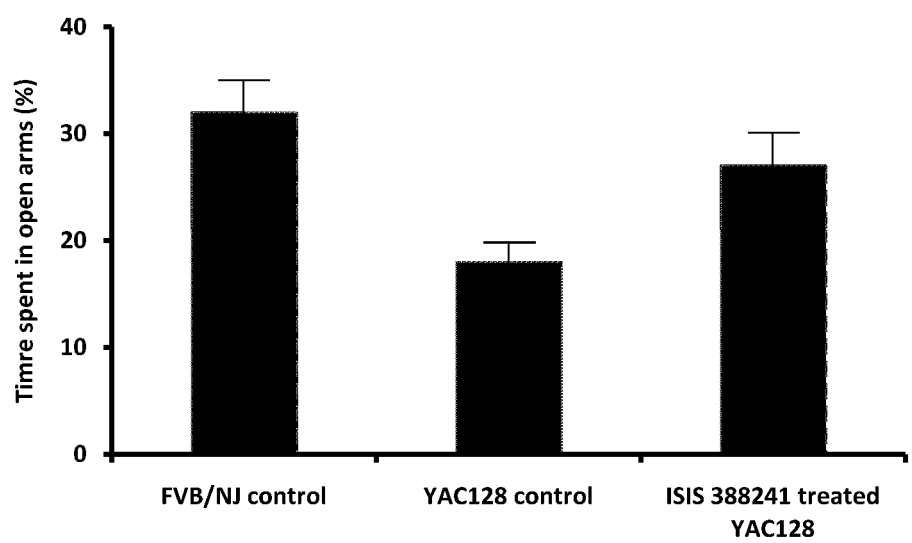

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA on elevated plus maze performance of YAC128 mice

| Mice model | % time in open arms |
|---|---|
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., Methods in Molecular Biology (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

| | % inhibition |
|---|---|
| mRNA | 85 |
| protein | 86 |

Example 16: Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 μg/day delivered ICV with Alzet 2002 pumps at the rate of 0.5 μL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGC-CAAGA, designated herein as SEQ ID NO: 54; reverse sequence CCCACCGTGTGACATCCA, designated herein as SEQ ID NO: 55; probe sequence AGCTATCTC-CGAGCTGCCCTGATTGG, designated herein as SEQ ID NO: 56). The results are presented in Table 79 and indicate that the tested ISIS oligonucleotides did not induce an inflammatory response.

TABLE 79

Percent increase in AIF1 mRNA expression compared to the control in C57/BL6 mice

| ISIS No | anterior | posterior |
|---------|----------|-----------|
| 387916  | 159      | 67        |
| 437527  | 102      | 77        |
| 444578  | 22       | 7         |
| 444584  | 33       | 37        |
| 444607  | 34       | 58        |
| 444608  | 29       | 1         |
| 444627  | 46       | 22        |
| 444652  | 59       | 50        |
| 444660  | -3       | 11        |
| 444661  | 67       | 62        |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

TABLE 80

Body weights of C57/BL6 mice after antisense oligonucleotide treatment

|            | Day 0 | Day 4 | Day 8 | Day 12 | Day 16 | Day 19 | Day 23 | Day 26 | Day 28 |
|------------|-------|-------|-------|--------|--------|--------|--------|--------|--------|
| PBS        | 105   | 108   | 111   | 114    | 111    | 111    | 113    | 114    | 112    |
| ISIS 387916| 107   | 108   | 106   | 111    | 106    | 104    | 101    | 101    | 97     |
| ISIS 437527| 105   | 116   | 116   | 120    | 111    | 112    | 112    | 108    | 108    |
| ISIS 444578| 105   | 116   | 112   | 115    | 103    | 98     | 83     | 81     | 87     |
| ISIS 444584| 105   | 117   | 115   | 111    | 105    | 105    | 103    | 104    | 102    |
| ISIS 444607| 105   | 115   | 112   | 110    | 101    | 98     | 106    | 109    | 106    |
| ISIS 444608| 102   | 111   | 112   | 112    | 97     | 91     | 78     | 75     | 87     |
| ISIS 444627| 105   | 116   | 124   | 126    | 105    | 104    | 93     | 94     | 91     |
| ISIS 444652| 106   | 122   | 124   | 126    | 119    | 113    | 111    | 111    | 108    |
| ISIS 444659| 105   | 118   | 123   | 116    | 92     | 89     | 68     | n/a    | n/a    |
| ISIS 444660| 104   | 115   | 120   | 118    | 103    | 93     | 89     | 84     | 90     |
| ISIS 444661| 107   | 125   | 120   | 106    | 76     | 86     | 89     | 86     | 91     |

TABLE 78

Percent inhibition of murine huntingtin mRNA compared to the control in C57/BL6 mice

| ISIS No | anterior | posterior |
|---------|----------|-----------|
| 387916  | 72       | 74        |
| 437527  | 59       | 62        |
| 444578  | 69       | 69        |
| 444584  | 0        | 9         |
| 444607  | 59       | 79        |
| 444608  | 41       | 66        |
| 444627  | 41       | 45        |
| 444652  | 61       | 64        |
| 444660  | 35       | 33        |
| 444661  | 72       | 69        |

Example 17: Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 pg, 50 pg, 75 pg, or 100 pg. A group of 4 rats were similarly treated with ISIS 387916, delivered as a single bolus at 10 pg, 25 pg, 50 pg, or 75 pg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 81

Percent expression of AIF1 mRNA levels in vivo as a measure of neurotoxicity

| ISIS No | Dose (µg) | % increase |
|---------|-----------|------------|
| 387916  | 10        | 145        |
|         | 25        | 157        |
|         | 50        | 247        |
|         | 75        | 316        |
| 388241  | 25        | 29         |
|         | 50        | 12         |
|         | 75        | 30         |
|         | 100       | 41         |
| 436671  | 25        | 37         |
|         | 50        | 2          |
|         | 75        | 13         |
|         | 100       | 50         |
| 443139  | 25        | 0          |
|         | 50        | 7          |
|         | 75        | 167        |
|         | 100       | 26         |
| 444591  | 25        | 18         |
|         | 50        | 80         |
|         | 75        | 50         |
|         | 100       | 207        |
| 437527  | 25        | 98         |
|         | 50        | 45         |
|         | 75        | 23         |
|         | 100       | 126        |
| 444584  | 25        | −1         |
|         | 50        | 10         |
|         | 75        | 35         |
|         | 100       | 31         |
| 444652  | 25        | 17         |
|         | 50        | 46         |
|         | 75        | 39         |
|         | 100       | 48         |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (µg) | % inhibition |
|---------|-----------|--------------|
| 387916  | 10        | 6            |
|         | 25        | 39           |
|         | 50        | 55           |
|         | 75        | 60           |
| 388241  | 25        | 8            |
|         | 50        | 23           |
|         | 75        | 27           |
|         | 100       | 19           |
| 436671  | 25        | 52           |
|         | 50        | 57           |
|         | 75        | 57           |
|         | 100       | 70           |
| 443139  | 25        | 35           |
|         | 50        | 29           |
|         | 75        | 28           |
|         | 100       | 27           |
| 444591  | 25        | 26           |
|         | 50        | 57           |
|         | 75        | 68           |
|         | 100       | 69           |
| 437527  | 25        | 40           |
|         | 50        | 55           |
|         | 75        | 60           |
|         | 100       | 74           |
| 444584  | 25        | 43           |
|         | 50        | 38           |
|         | 75        | 38           |
|         | 100       | 41           |
| 444652  | 25        | 49           |
|         | 50        | 70           |
|         | 75        | 55           |
|         | 100       | 59           |

Example 18: Dose-Dependent Antisense Inhibition of Huntingtin mRNA in Cynomolgous Primary Hepatocytes ISIS 437527, ISIS 444584, and ISIS 444652 were tested in cynomolgus primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower $IC_{50}$ values than the benchmark oligonucleotide, ISIS 387916.

TABLE 83

Dose-dependent antisense inhibition of huntingtin mRNA in cynomolgous primary hepatocytes

|  | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |
| 10000.0 nM | 82 | 80 | 68 | 77 | 91 | 0 |
| 20000.0 nM | 84 | 75 | 70 | 69 | 92 | 0 |
| $IC_{50}$ (μM) | 1.4 | 5.4 | 2.0 | 4.0 | 0.8 | >20 |

Example 19: Measurement of Half-Life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 μg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin mRNA expression at various time points

| ISIS No | Time (weeks) | Posterior | Anterior |
|---|---|---|---|
| 388241 | 1 | 72 | 91 |
|  | 5 | 65 | 86 |
|  | 10 | 52 | 73 |
|  | 15 | 26 | 56 |
|  | 20 | 14 | 53 |
| 436671 | 1 | 82 | 92 |
|  | 5 | 78 | 89 |
|  | 10 | 68 | 82 |
|  | 15 | 61 | 77 |
|  | 20 | 30 | 77 |
| 444591 | 1 | 60 | 85 |
|  | 5 | 58 | 76 |
|  | 10 | 48 | 60 |
|  | 15 | 27 | 43 |
|  | 20 | 27 | 36 |
| 436689 | 1 | 72 | 83 |
|  | 5 | 72 | 87 |
|  | 10 | 60 | 74 |
|  | 15 | 50 | 74 |
|  | 20 | 44 | 59 |

TABLE 85

Percent inhibition of mouse huntingtin mRNA expression at various time points

| ISIS No | Time (weeks) | Posterior | Anterior |
|---|---|---|---|
| 388241 | 1 | 1 | 12 |
|  | 5 | 22 | 36 |
|  | 10 | 17 | 14 |
|  | 15 | 7 | 18 |
|  | 20 | 9 | 38 |
| 436671 | 1 | 84 | 96 |
|  | 5 | 77 | 80 |
|  | 10 | 64 | 86 |
|  | 15 | 51 | 78 |
|  | 20 | 19 | 75 |
| 444591 | 1 | 74 | 95 |
|  | 5 | 70 | 90 |
|  | 10 | 57 | 67 |
|  | 15 | 34 | 47 |
|  | 20 | 33 | 38 |
| 436689 | 1 | 40 | 32 |
|  | 5 | 47 | 40 |
|  | 10 | 35 | 18 |
|  | 15 | 34 | 22 |
|  | 20 | 36 | 5 |

TABLE 86

Half-life of ISIS oligonucleotides in the anterior section of the brain in BACHD mice after intrastriatal bolus injection

| ISIS No | Half-life (days) |
|---|---|
| 436671 | 46.6 |
| 436689 | 39.4 |
| 444591 | 24.3 |
| 388241 | 25.8 |

Body Weight Measurements

Body weights were measured at regular intervals, and are presented in Table 87 as a percent of the weight of the mice at the start of the study. These weights were utilized as an indicator of tolerability. There were no adverse changes in body weight in any of the mice treated with ISIS oligonucleotides.

TABLE 87

Percent change in body weight of BACHD mice after antisense oligonucleotide treatment

|  | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20: Effect of Intrathecal Administration of ISIS 437527 in Sprague Dawley Rats Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 µg of ISIS 437527 delivered intrathecally. Another group of 5 Sprague Dawley rats was administered bolus injections of 120 µg of ISIS 437527 delivered intrathecally three times over the course of 1 week. Another group of 5 Sprague Dawley rats was administered bolus injections of 350 µg of ISIS 437527 delivered intrathecally three times over the course of 1 week. Another group of 5 Sprague Dawley rats was administered 50 Gg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
|---|---|---|---|
| Frontal Cortex | IT Infusion | 50 µg/day | 11 |
|  | Single IT Bolus | 350 µg | 28 |
|  | Repeated IT Bolus | 120 µg × 3 | 21 |
|  | Repeated IT Bolus | 350 µg × 3 | 0 |
| Temporal Cortex | IT Infusion | 50 µg /day | 0 |
|  | Single IT Bolus | 350 µg | 34 |
|  | Repeated IT Bolus | 120 µg × 3 | 44 |
|  | Repeated IT Bolus | 350 µg × 3 | 48 |
| Cervical Cord | IT Infusion | 50 µg /day | 22 |
|  | Single IT Bolus | 350 µg | 45 |
|  | Repeated IT Bolus | 120 µg × 3 | 58 |
|  | Repeated IT Bolus | 350 µg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
|---|---|---|---|
| Frontal Cortex | IT Infusion | 50 µg/day | −36 |
|  | Single IT Bolus | 350 µg | −4 |
|  | Repeated IT Bolus | 120 µg × 3 | 41 |
|  | Repeated IT Bolus | 350 µg × 3 | −7 |
| Temporal Cortex | IT Infusion | 50 µg /day | 15 |
|  | Single IT Bolus | 350 µg | 22 |
|  | Repeated IT Bolus | 120 µg × 3 | 25 |
|  | Repeated IT Bolus | 350 µg × 3 | 76 |
| Cervical Cord | IT Infusion | 50 µg /day | 108 |
|  | Single IT Bolus | 350 µg | 72 |
|  | Repeated IT Bolus | 120 µg × 3 | 473 |
|  | Repeated IT Bolus | 350 µg × 3 | 268 |

Example 21: Measurement of Half-Life of ISIS 436689 in the CNS Tissues of Cynomolgous Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period.

Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RNAlater RNA stabilization solution (Qiagen, Calif.), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

TABLE 90

Effect of ISIS 436689 administered IT on huntingtin mRNA expression in the spinal cord at various time points

| Recovery period | Lumbar spinal cord | Thoracic spinal cord | Cervical spinal cord |
|---|---|---|---|
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 91

Effect of ISIS 436689 administered IT on huntingtin mRNA expression in various brain tissues at various time points

| Recovery period | Frontal cortex | Occipital cortex | Cerebellar cortex | Caudate | Hippocampus | Middle brain | Pons |
|---|---|---|---|---|---|---|---|
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5'end and a C18 spacer and BioTEG at the 3'end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
|---|---|---|---|---|
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 93

Half-life of ISIS 436689 administered IT on huntingtin mRNA expression in various tissues

| Organ | Half-life |
|---|---|
| Cervical cord | 4.0 |
| Thoracic cord | 15.1 |
| Lumbar cord | 18.7 |
| Liver | 7.6 |

The invention claimed is:

1. A single-stranded modified oligonucleotide consisting of 18 linked nucleosides and having:
- a gap segment consisting of eight linked deoxynucleosides;
- a 5' wing segment consisting of five linked nucleosides; and
- a 3' wing segment consisting of five linked nucleosides;
- wherein the gap segment is positioned between the 5' wing segment and the 3' wing segment;
- wherein each nucleoside of each wing segment comprises a 2'O-methoxyethyl sugar; and
- wherein the nucleobase sequence of the oligonucleotide consists of the sequence recited in SEQ ID NO: 35, or a pharmaceutically acceptable salt thereof.

2. The single-stranded modified oligonucleotide of claim 1, wherein at least one nucleoside comprises a modified nucleobase.

3. The single-stranded modified oligonucleotide of claim 2, wherein the modified nucleobase is a 5-methylcytosine.

4. The single-stranded modified oligonucleotide of claim 1, wherein each cytosine is a 5-methylcytosine.

5. The single-stranded modified oligonucleotide of claim 1, wherein at least one internucleoside linkage is a modified internucleoside linkage.

6. The single-stranded modified oligonucleotide of claim 1, wherein each internucleoside linkage is a phosphorothioate internucleoside linkage.

7. The single-stranded modified oligonucleotide of claim 4, wherein at least one internucleoside linkage is a modified internucleoside linkage.

8. The single-stranded modified oligonucleotide of claim 4, wherein each internucleoside linkage is a phosphorothioate internucleoside linkage.

9. A composition comprising the single-stranded modified oligonucleotide or pharmaceutically acceptable salt thereof of claim 1 and at least one pharmaceutically acceptable carrier or diluent.

10. A composition comprising the single-stranded modified oligonucleotide or pharmaceutically acceptable salt thereof of claim 4 and at least one pharmaceutically acceptable carrier or diluent.

11. A composition comprising the single-stranded modified oligonucleotide or pharmaceutically acceptable salt thereof of claim 6 and at least one pharmaceutically acceptable carrier or diluent.

12. A composition comprising the single-stranded modified oligonucleotide or pharmaceutically acceptable salt thereof of claim 8 and at least one pharmaceutically acceptable carrier or diluent.

13. The single-stranded modified oligonucleotide of claim 1, which is capable of inhibiting huntingtin expression.

14. The single-stranded modified oligonucleotide of claim 4, which is capable of inhibiting huntingtin expression.

15. The single-stranded modified oligonucleotide of claim 6, which is capable of inhibiting huntingtin expression.

16. The single-stranded modified oligonucleotide of claim 8, which is capable of inhibiting huntingtin expression.

* * * * *

SEQUENCE LISTING

<160> NUMBER OF SEQ ID NOS: 56

<210> SEQ ID NO 1
<211> LENGTH: 13481
<212> TYPE: DNA
<213> ORGANISM: Homo sapiens

<400> SEQUENCE: 1

```
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgcccccgcc     360 gccgccccg ccgccacccg gccggctgt ggctgaggag ccgctgcacc gaccaaagaa      420
agaactttca gctaccaaga agaccgtgt gaatcattgt ctgacaatat gtgaaaacat      480
agtggcacag tctgtcagaa attctccaga atttcagaaa cttctgggca tcgctatgga     540 acttttctg ctgtgcagtg atgacgcaga gtcagatgtc aggatggtgg ctgacgaatg      600
cctcaacaaa gttatcaaag ctttgatgga ttctaatctt ccaaggttac agctcgagct     660
ctataaggaa attaaaaaga atggtgcccc tcggagtttg cgtgctgccc tgtgggaggtt     720 tgctgagctg gctcacctgg ttcggcctca gaaatgcagg ccttacctgg tgaaccttct     780
gccgtgcctg actcgaacaa gcaagagacc cgaagaatca gtccaggaga ccttggctgc     840
agctgttccc aaaattatgg cttcttttgg caattttgca aatgacaatg aaattaaggt     900
tttgttaaag gccttcatag cgaacctgaa gtcaagctcc ccaccattc ggcggacagc      960 ggctggatca gcagtgagca tctgccagca ctcaagaagg acacaatatt tctatagttg     1020
gctactaaat gtgctcttag gcttactcgt tcctgtcgag gatgaacact ccactctgct     1080
gattcttggc gtgctgctca ccctgaggta tttggtgccc ttgctgcagc agcaggtcaa     1140
ggacacaagc ctgaaaggca gcttcggagt gacaaggaaa gaaatggaag tctctccttc     1200
tgcagagcag cttgtccagg tttatgaact gacgttacat catacacagc accaagacca     1260
caatgttgtg accggagccc tggagctgtt gcagcagctc ttcagaacgc ctccacccga     1320
gcttctgcaa accctgaccg cagtcggggg cattgggcag ctcaccgctg ctaaggagga     1380
gtctggtggc cgaagccgta gtgggagtat tgtgaaactt atagctggag ggggttcctc     1440
atgcagccct gtcctttcaa gaaaacaaaa aggcaaagtg ctcttaggag aagaagaagc     1500
cttggaggat gactctgaat cgagatcgga tgtcagcagc tctgccttaa cagcctcagt     1560
gaaggatgag atcagtggag agctggctgc ttcttcaggg gtttccactc cagggtcagc     1620
```

```
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat tgtgtgttgag   2100 agatgaagct actgaaccgg gtgatcaaga aaacaagcct tgccgcatca aggtgacat    2160 tggacagtcc actgatgatg actctgcacc tcttgtccat tgtgtccgcc ttttatctgc    2220 ttcgttttg ctaacagggg gaaaaaatgt gctggttccg gacagggatg tgagggtcag     2280
cgtgaaggcc ctggccctca gctgtgtggg agcagctgtg ccctccacc cggaatcttt    2340 cttcagcaaa ctctataaag ttcctcttga caccacggaa taccctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760 aaccccttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taacctttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aacccccctt ctctaagtcc catccgacga aggggaagg agaaagaacc     3720 aggagaacaa gcatcgtgta cgttgagtcc caagaaggc agtgaggcca gtgcagcttc     3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggttc tccgctcagc    3960 cttggatgtt cttttctcaga tactagagct ggccacactg caggacattg ggaagtgtgt    4020
```

```
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aacccagca agtcacaagg ccgagcacag cgccttggct cctccagtgt    4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga aacagtttga atacattgaa gtgggccagt tcagggaatc    4620
agaggcaatc attccaaaca tcttttctt cttggtatta ctatcttatg aacgctatca     4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct    4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct cctcctcc gtccggtaga     5100 catgcttta cggagtatgt tcgtcactcc aaacacaatg gcgtccgtga gcactgttca     5160
actgtggata tcgggaattc tggccatttt gagggttctg atttcccagt caactgaaga   5220
tattgttctt tctcgtattc aggagctctc cttctctccg tatttaatct cctgtacagt    5280
aattaatagg ttaagagatg gggacagtac ttcaacgcta gaagaacaca gtgaagggaa  5340
acaaataaag aatttgccag aagaaacatt ttcaaggttt ctattacaac tggttggtat    5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtg ctgctctggt gtcagatact gctgcttgtc aaccacaccg actaccgctg   5700
gtgggcagag gtgcagcaga ccccgaaaag acacagtctg tccagcacaa agttacttag   5760
tccccagatg tctggagaag aggaggattc tgacttggca gccaaacttg gaatgtgcaa  5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
gaagaaaact cttcagtgct tggagggggat ccatctcagc cagtcgggag ctgtgctcac  6120
gctgtatgtg acaggcttc tgtgcacccc tttccgtgtg ctggctcgca tggtcgacat     6180
ccttgcttgt cgccgggtag aaatgcttct ggctgcaaat ttacagagca gcatggccca   6240
gttgccaatg gaagaactca acagaatcca ggaataccct cagagcagcg ggctcgctca   6300
gagacaccaa aggctctatt ccctgctgga caggtttcgt ctctccacca tgcaagactc   6360
```

-continued

```
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc cttttgaag cagcccgtga    6660 ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg ccctggcac agtacctggt    6840 ggtggtctcc aaactgccca gtcatttgca ccttcctcct gagaaagaga aggacattgt   6900
gaaattcgtg gtggcaaccc ttgaggcccc gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca ataccccaa aagccatcag cgaggaggag gaggaagtag atccaaacac    7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga gcttggatg gtcacccaaa ccgggagggg attttggcac     7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct ggagcagca    7740 gccccggaac aagcctctga agctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
```

-continued

```
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc    9000 agtgattgtt gctatggagc gggtatctgt tcttttgat aggatcagga aaggctttcc    9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180 gttcatggcc accgtggtgt ataaggtgtt tcagactctg cacagcaccg ggcagtcgtc    9240
catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga cgccatggt gggagagact    9600 gtgaggcggc agctggggcc ggagcctttg gaagtctgcg cccttgtgcc ctgcctccac    9660
cgagccagct tggtccctat ggcttccgc acatgccgcg gcggccagg caacgtgcgt    9720 gtctctgcca tgtggcagaa gtgctctttg tggcagtggc caggcaggga gtgtctgcag    9780
tcctggtggg gctgagcctg aggccttcca gaaagcagga gcagctgtgc tgcaccccat    9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg   10020
ggtgtgcatg ccacgccccg tgtctggatg cacagatgcc atggcctgtg ctgggccagt   10080 ggctggggt gctagacacc cggcaccatt ctcccttctc tcttttcttc tcaggattta   10140
aaatttaatt atatcagtaa agagattaat tttaacgtaa ctctttctat gcccgtgtaa   10200
agtatgtgaa tcgcaaggcc tgtgctgcat gcgacacgt ccggggtggt ggacagggcc   10260
cccggccacg ctccctctcc tgtagccact ggcatagccc tcctgagcac ccgctgacat   10320
ttccgttgta catgttcctg tttatgcatt cacaaggtga ctgggatgta gagaggcgtt   10380
agtgggcagg tggccacagc aggactgagg acaggccccc attatcctag ggtgcgctc    10440 acctgcagcc cctcctcctc gggcacagac gactgtcgtt ctccacccac cagtcaggga   10500
cagcagcctc cctgtcactc agctgagaag gccagccctc cctggctgtg agcagcctcc   10560
actgtgtcca gagacatggg cctcccactc ctgttccttg ctagccctgg ggtggcgtct   10620
gcctaggagc tggctggcag gtgttgggac ctgctgctcc atggatgcat gccctaagag   10680
tgtcactgag ctgtgttttg tctgagcctc tctcggtcaa cagcaaagct tggtgtcttg   10740
gcactgttag tgacagagcc cagcatccct tctgcccccg ttccagctga catcttgcac   10800 ggtgaccct tttagtcagg agagtgcaga tctgtgctca tcggagactg ccccacggcc   10860
ctgtcagagc cgccactcct atccccaggc caggtccctg accagcctc ctgtttgcag    10920 gcccagagga gccaagtcat taaaatggaa gtggattctg gatggccggg ctgctgctga   10980
tgtaggagct ggatttggga gctctgcttg ccgactggct gtgagacgag gcaggggctc   11040
tgcttcctca gccctagagg cgagccaggc aaggttggcg actgtcatgt ggcttggttt   11100
```

-continued

```
ggtcatgccc gtcgatgttt tgggtattga atgtggtaag tggaggaaat gttggaactc    11160
tgtgcaggtg ctgccttgag accccccaagc ttccacctgt ccctctccta tgtggcagct    11220
ggggagcagc tgagatgtgg acttgtatgc tgcccacata cgtgaggggg agctgaaagg    11280
gagcccctcc tctgagcagc ctctgccagg cctgtatgag gcttttccca ccagctccca    11340
acagaggcct cccccagcca ggaccacctc gtcctcgtgg cggggcagca ggagcggtag    11400
aaaggggtcc gatgtttgag gaggccctta agggaagcta ctgaattata acacgtaaga    11460
aaatcaccat tccgtattgg ttgggggctc ctgtttctca tcctagcttt ttcctggaaa    11520
gcccgctaga aggtttggga acgaggggaa agttctcaga actgttggct gctccccacc    11580
cgcctcccgc ctcccccgca ggttatgtca gcagctctga gacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820
tgtcccccac ccccaaagac ctgcctgtgt gctccggaga tgaatatgag ctcattagta    11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatctgtg gcaagcaccc atcgtattat ccaaattttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaaccccct ccagacaccc agaatgtagc atctgagaag    12540
gccctgtgcc ctaaaggaca ccctcgcccc ccatcttcat ggaggggtc atttcagagc    12600 cctcggagcc aatgaacagc tcctcctctt ggagctgaga tgagccccac gtggagctcg    12660
ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tcccccgctt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaaggaac gccttcccct    13140
cagttgtttc taagagcaga gtctcccgct gcaatctggg tggtaactgc cagccttgga    13200
ggatcgtggc caacgtggac ctgcctacgg agggtgggct ctgacccaag tggggcctcc    13260
ttgtccaggt ctcactgctt tgcaccgtgg tcagagggac tgtcagctga gcttgagctc    13320
ccctggagcc agcagggctg tgatgggcga gtcccggagc cccacccaga cctgaatgct    13380
tctgagagca aagggaagga ctgacgagag atgtatattt aattttttaa ctgctgcaaa    13440
cattgtacat ccaaattaaa ggaaaaaaat ggaaaccatc a                         13481
```

<210> SEQ ID NO 2
<211> LENGTH: 172001
<212> TYPE: DNA
<213> ORGANISM: Homo sapiens

<400> SEQUENCE: 2

```
cctgcagggg cctctccagc tcactggggg tggggtgggg gtcacacttg gggtcctcag      60
gtcgtgccga ccacgcgcat tctctgcgct ctgcgcagga gctcgcccac cctctccccg     120
tgcagagagc cccgcagctg ctccccgca gggctgtccg ggtgagtatg gctctggcca     180
cgggccagtg tggcgggagg gcaaacccca aggccacctc ggctcagagt ccacggccgg     240
ctgtcgcccc gctccaggcg tcggcggggg atcctttccg catgggcctg cgcccgcgct     300
cggcgccccc tccacggccc cgcccgtcc atggccccgt ccttcatggg cgagcccctc     360
catggccctg ccctccgcg ccccaccct cctcgcccc acctctcacc ttcctgcccc     420
gcccccagcc tccccaaccc tcaccggcca gtccctccc ctatcccgtc cgcccctcag     480
ccgccccgcc cctcagccgg cctgcctaat gtcccgtcc ccagcatcgc cccgccccgc     540
ccccgtctcg ccccgcccct caggcggcct ccctgctgtg ccccgccccg gcctcgccac     600
gcccctacct caccacgccc cccgcatcgc cacgccccc gcatcgccac gcctccctta     660
ccatgcagtc ccgccccgtc ccttcctcgt cccgcctcgc cgcgacactt cacacacagc     720
ttcgcctcac cccattacag tctcaccacg ccccgtcccc tctccgttga gccccgcgcc     780
ttcgcccggg tggggcgctg cgctgtcagc ggccttgctg tgtgaggcag aacctgcggg     840
ggcaggggcg ggctggttcc ctggccagcc attggcagag tccgcaggct agggctgtca     900
atcatgctgg ccggcgtggc cccgcctccg ccggcgcggc cccgcctccg ccggcgcagc     960
gtctgggacg caaggcgccg tggggctgc cgggacgggt ccaagatgga cggccgctca    1020
ggttctgctt ttacctgcgg cccagagccc cattcattgc cccggtgctg agcggcgccg    1080
cgagtcggcc cgaggcctcc ggggactgcc gtgccgggcg ggagaccgcc atggcgaccc    1140
tggaaaagct gatgaaggcc ttcgagtccc tcaagtcctt ccagcagcag cagcagcagc    1200
agcagcagca gcagcagcag cagcagcagc agcagcagca acagccgcca ccgccgccgc    1260
cgccgccgcc gcctcctcag cttcctcagc cgccgccgca ggcacagccg ctgctgcctc    1320
agccgcagcc gccccgccg ccgccccgc cgccacccgg cccggctgtg ctgaggagc    1380
cgctgcaccg accgtgagtt tgggcccgct gcagctccct gtcccggcgg gtcccaggct    1440
acggcgggga tggcggtaac cctgcagcct gcgggccggc gacacgaacc cccggccccg    1500
cagagacaga gtgacccagc aacccagagc ccatgaggga cacccgcccc ctcctggggc    1560
gaggccttcc cccacttcag cccgctccc tcacttgggg cttcccttgt cctctcgcga    1620
ggggaggcag agccttgttg gggcctgtcc tgaattcacc gaggggagtc acggcctcag    1680
ccctctcgcc cttcgcagga tgcgaagagt tggggcgaga acttgtttct ttttatttgc    1740
gagaaaccag ggcgggggtt cttttaactg cgttgtgaag agaacttgga ggagccgaga    1800
tttgctcagt gccacttccc tcttctagtc tgagagggaa gagggctggg ggcgcgggac    1860
acttcgagag gaggcgggt ttggagctgg agagatgtgg gggcagtgga tgacataatg    1920
cttttaggac gcctcggcgg gagtggcggg gcagggggg ggcggggagt gagggcgcgt    1980
ccaatgggaa atttctttc ctagtggcac ttaaaacagc ctgagatttg aggctcttcc    2040
tacattgtca ggacatttca tttagttcat gatcacggtg gtagtaacac gattttaagc    2100
```

```
accacctaag agatctgctc atctaagcct aagttggtct gcaggcgttt gaatgagttg    2160
tggttgccaa gtaaagtggt gaacttacgt ggtgattaat gaaattatct taaatattag    2220
gaagagttga ttgaagtttt ttgcctatgt gtgttgggaa taaaaccaac acgttgctga    2280
tggggaggtt aattgccgag ggatgaatga ggtgtacatt ttaccagtat tccagtcagg    2340
cttgccagaa tacgggggt ccgcagactc cgtgggcatc tcagatgtgc cagtgaaagg    2400
gtttctgttt gcttcattgc tgacagcttg ttacttttg gaagctaggg gtttctgttg    2460
cttgttcttg gggagaattt ttgaaacagg aaaagagaga ccattaaaac atctagcgga    2520
accccaggac tttccctgga agtctgtgtg tcgagtgtac agtaggagtt aggaagtact    2580
ctggtgcagt tcaggccttt ctcttacctc tcagtattct atttccgatc tggatgtgtc    2640
ccagatggca tttggtaaga atatctctgt taagactgat taatttttag taatatttct    2700
tgttctttgt ttctgttatg atccttgtct cgtcttcaaa gtttaattag aaaatgattc    2760
ggagagcagt gttagcttat ttgttggaat aaaatttagg aataaattat tctaaaggat    2820
ggaaaaactt tttggatatt tggagaaatt ttaaaacaat ttggcttatc tcttcagtaa    2880
gtaatttctc atccagaaat ttactgtagt gcttttctag gaggtaggtg tcataaaagt    2940
tcacacattg catgtatctt gtgtaaacac taaacagggc tcctgatggg aaggaagacc    3000
tttctgctgg gctgcttcag acacttgatc attctaaaaa tatgccttct ctttcttatg    3060
ctgatttgac agaacctgca tttgcttatc ttcaaaatat gggtatcaag aaatttcctt    3120
tgctgccttg acaaggaga tagattttgt ttcattactt taaggtaata tatgattacc    3180
ttatttaaaa aatttaatca ggactggcaa ggtggcttac acctttaatc cgagcacttt    3240
gggaggccta ggtggacgaa tcacctgagg tcaggagttt gagaccagcc tggctaacat    3300
ggtgaaaccc tgtctctact aaaaatacaa aaattagctg gtcatggtgg cacgtgcctg    3360
taatccaagc tacctgggag gctgaggcag gaaaatcgct tgaacccggg aggcagagtc    3420
tgcagtgagt tgagatcacg ccactgcact ccagcctggg tgacagagcg agactctatc    3480
tcaaaaaaaa tttttttaa tgtattattt ttgcataagt aatacattga catgatacaa    3540
attctgtaat tacaaaaggg caataattaa aatatcttcc ttccacccct ttcctctgag    3600
tacctaactt tgtccccaag aacaagcact atttcagttc ctcatgtatc ctgccagata    3660
taacctgttc atattgtaag atagatttaa aatgctctaa aaacaaaagt agtttagaat    3720
aatatatatc tatatatttt ttgagatgta gtctcacatt gtcacccagg ctggagtgca    3780
gtgatacaat ctcggctcac tgcagtctct gcctcccagg ttcaaatgct tctcctgcct    3840
cagccttctg agtagctggg attacaggcg cccaccacca tgtccagcta ttttttgtat    3900
ttttagtaga gatggggttt caccatgttg gccaggctgg tcttgaactc ctgaccttgt    3960
gatctgtcca cctcggcctc ccaaagtgct gggattacag gtgtgagcca ccatgcctgg    4020
ctagaataat aacttttaaa ggttcttagc atgctctgaa atcaactgca ttaggtttat    4080
ttatagtttt atagttattt taaataaaat gcatatttgt catatttctc tgtatttgc     4140 tgttgagaaa ggaggtattc actaattttg agtaacaaac actgctcaca agtttggat     4200 tttggcagtt ctgttcacgt gcttcagcca aaaaatcctc ttctcaaagt aagattgatg    4260
aaagcaattt agaaagtatc tgttctgttt ttatggctct tgctctttgg tgtggaactg    4320
tggtgtcacg ccatgcatgg gcctcagttt atgagtgttt gtgctctgct cagcatacag    4380
gatgcaggag ttccttatgg ggctggctgc aggctcagca atctagcat gcttgggagg     4440 gtcctcacag taattaggag gcaattaata cttgcttctg gcagtttctt attctccttc    4500
```

```
agattcctat ctggtgtttc cctgacttta ttcattcatc agtaaatatt tactaaacat    4560
gtactatgtg cctggcactg ttataggtgc agggctcagc agtgagcaga caaagctctg    4620
ccctcgtgaa gctttcattc taatgaagga catagacagt aagcaagata gataagtaaa    4680
atatacagta cgttaatacg tggaggaact tcaaagcagg gaaggggata gggaaatgtc    4740
agggttaatc gagtgttaac ttattttat ttttaaaaaa attgttaagg ctttccagc     4800 aaacccaga aagcctgcta gacaaattcc aaaagagctg tagcactaag tgttgacatt    4860 tttatttat tttgttttgt tttgtttttt ttgagacagt tcttgctcta tcagccaggc    4920
tggagtgcac tagtgtgatc ttggctcact gcaacctctg cctcttgggt tcaagtgatt    4980
ctcatgcctc agcctcctgt ttagctggga ttatagacat gcactgccat gcctgggtaa    5040 ttttttttt ttcccccgag acggagtctt gctctgtcgc ccaggctgga gtgcagtggc     5100
gcgatctcag ctcactgcaa gctccgcttc ccgagttcac gccattctcc tgcctcagtc    5160
tcccaagtag ctgggactac aggcgcctgc caccacgtcc agctaatttt tttgtatttt    5220
taatagagac ggggtttcac cgtgttagcc aggatgatct tgatctcctg acctcgtcat    5280
ccgccgacct tgtgatccgc ccacctcggc ctcccaaagt gctgggatta caggcatgag    5340
ccactgtgcc cggccacgcc tgggtaattt ttgtatttt agtagagatg gggttttgcc    5400
atgatgagca ggctggtctc gaactcccgg cctcatgtga tctgcctgcc ttggcctccc    5460
aaagtgctag gattacaggc atgagccacc atacctggcc agtgttgata ttttaaatac    5520
ggtgttcagg gaaggtccac tgagaagaca gcttttttt ttttttttt tggggttggg     5580 gggcaaggtc ttgctctta acccaggctg gaatgcagta tcactatcgt agctcacttc    5640
agccttgaac tctgggctc aagtgatcct cccacctcaa cctcacaatg tgttgggact     5700
ataggtgtga gccatcacac ctggccagat gatggctttt gagtaaagac ctcaagcgag    5760
ttaagagtct agtgtaaggg tgtatgaagt agtggtattc cagatggggg gaacaggtcc    5820
aaaatcttcc tgtttcagga atagcaagga tgtcatttta gttgggtgaa ttgagtgagg    5880
gggacatttg tagtaagaag taaggtccaa gaggtcaagg gagtgccata tcagaccaat    5940
actacttgcc ttgtagatgg aataaagata ttggcattta tgtgagtgag atgggatgtc    6000
actggaggat tagagcagag gagtagcatg atctgaattt caatcttaag tgaactctgg    6060
ctgacaacag agtgaagggg aacaccggca aaagcagaaa ccagttagga agccactgca    6120
gtgctcagat aagcatggtg ggttctgtca gggtaccggc tgtcggctgt gggcagtgtg    6180
aggaatgact gactggattt tgaatgcgga accaactgca cttgttgaac tctgctaagt    6240
ataacaattt agcagtagct tgcgttatca ggtttgtatt cagctgcaag taacagaaaa    6300
tcctgctgca atagcttaaa ctggtaacaa gcaagagctt atcagaagac aaaaataagt    6360
ctggggaaat tcaacaataa gttaaggaac ccaggctctt tcttttttt tttttgaaa      6420 cggagtttcg ctcttgtcac ccgggctgga gtgcaatgat gtgatctcag ctcactaaaa    6480
cctctacctc ctgggttcaa gtgattcttc tgcctcagcc tcccaagtaa ctgggattac    6540
aggcgtatac caccatgccc agctaatttt tgtgtttta gtagagatgg ggtttcacca    6600
tgttggccag gctggtctcg aacttctgac ctcaggtgat ccactcgcct cagcctgcca    6660
aagtgctggg attacaggtt tgggccactg cacccggtca gaacccaggc tctttcttat    6720
acttaccttg caaaccctg ttctcatttt ttccctttgt attttattg ttgaattgta      6780 atagttcttt atatattctg gatactggat tcttatcaga tagatgattt gtaaaaactc    6840
```

```
tcccttcctt tggattgtct ttttactttc ttgatagtgt cttttgaagt gtaaaagttt      6900
ttaattttga tgaagtcgag tttatctatt ttgtctttgg ttgctgtgct tcaagtgtca      6960
tatctaagaa atcattgtct aatccaaagt caaaaaggtt tactcctatg ttttcttcta      7020
agaattttag agtttacat ttaagtctga tccattttga gttaattttt atatatggtt       7080
caggtagaag tccaacttta ttcttttcca tgtggttatt cagttgtccc agcactgttt      7140
gttgaagaga ctattctttc cccatggaat tatcttagta cccttgttga aaattaatcg      7200
tccttaattg tataaattta tttctagact gtcagttcta cctgttggtc tttatgtcga      7260
tcctgtgcca gtaccataca gtcttgatta ctgaagtttg tgtcacagtt taaattcatg      7320
aaatgtgagt tctccaactt tgttccttttt caagattgat ttggccatgc tgggtccctt     7380
gcatttccgt acgaattgta ggatcagctt gtcagtttca acaaagaagc caagtaggat      7440
tctgagaggg attgtgttga atctgtagat caacttgggg agtattcgca tcttaacaat      7500
attgtcttcc acctatgaac atgggcaaac tttgtgtaaa tggtcagatt gtaagtattt      7560
cgggctgtgt gggcacagtg tctctgtcac agctacgcgg ctctgccatt gtagcatgaa      7620
agtagccata agcaatatgt atgagtgtct gtgttccaat agaattttat taatgacaag      7680
gaagtttgaa tttcatataa ttttcacctg tcatgagata gtatttgatt attttggtca      7740
accatttaaa aatgtaaaaa catttcttag cttgtgaact agccaaaaat atgcaggtta      7800
tagttttccc actcctaggt taaaatatga taggaccaca tttggaaagc atttcttttt      7860
tttttttttt tttttttttt gagacggagt ttcactcttg ttgcccaggc tggagtgcag      7920
tggcgcgatc tcggctcact gcaacctctg cctcccaggt tcaagacatt ctcctgcacg      7980
gcctccctag tagctgggat tacaggcatg cgccaccaca cccagctaat tttgtatttt      8040
tagtagagac ggggtttctc catgttggtc aggctggtct tgaactcctg acctcaggtg      8100
atccacccgc ctcagcctcc caaagtgctg ggattacagg gtgtgagcca ccacaccctg      8160
ctggaaagca tttctttttt ggctgttttt gttttttttt taaactagtt ttgaaaatta      8220
taaaagttac acatatacat tataaaaata tcttcaagca gcacagatga aaaacaaagc      8280
ccttcttgca agtctgtcat cttttgtctaa cttcctaaga acaaaagtgt tcttgtgtc      8340 ttcttcccag attttaatat gcatatacaa gcatttaaat gtgtcatttt ttgtttgctt      8400
gactgagatc acattacata tgtatttttt tacttaacaa tgtgtcatag atattgttcc      8460
atagcagtac ctgtaattct tattaattgc tatgtaatat tttagaattt cttttttaaaa     8520 gaggactttt ggagatgtaa aggcaaaggt ctcacatttt tgtggctgta gaatgtgctg      8580
gtgacatatt ctctctacct tgagaagtcc ccatcccat cacctccatt tcctgtaaat       8640
aagtcaacca cttgataaac tacctttgaa tggatccaca ctcaaaacat ttagtcttat      8700
tcagacaaca aggaggaaaa ataaaatacc ttataaagca ctgtttaata ttgtattaaa      8760
ttggatcaat ttgggggcta gaatgtatgt tagagacatg atatgtccat aggtccttgc      8820
tatcacagtg aggtctcagg gacagtcgtt tggtatcatt tgggatctca taagcagact      8880
ctctctgctt gacctgacaa atcagagtct gtgttttaac aggttcagtg agtgacttac      8940
atgcacattg gagtttggga agctccactg taggtgctta gaccttacct tgttgttgc       9000 taataacaat gcaagcattt gggaggaaga cctgtgttgc tcatatgtgt ccaggtgtag      9060
ctgaggtggc cttgcttatc tgctgtaggg ccgttgagca tttctgtagc tgtgatgagt      9120
gagctgaggt gagcctgcgg agagctccca gccattggta gtgggactcg cttagatgaa      9180
ctggaaggac cctttcatct gagcagccac tatggagaaa aacaaccgaa tgaggggaga      9240
```

```
gacaatgtgc aattttattt agggcacaaa ggagagctgt ggttagaagg tgacatttga   9300
gtggaaaggg ggcaagccat gtgtatagcg ggagaagaga ggtccaggca gagttaacag   9360
aaggcagaaa tgcttccat gtttgagaac cagtaaggag gccagtggct gaagtaaggt    9420
gaagggcaga ataaggatg aggctgcgag agatgagagg ttagagacga gcgtcttgtg    9480
caccaagata agcttgtgtg gtcaaaacaa gtagtttaat ttatgttttt aaaagatcat   9540
tttggctggg cacaatggtt catgcctgta ataccagtag tttgagacgg tgtggtggga   9600
ggattgcctg aggccagacg accagcatag ccaacatagc agcacctata aggtctctac   9660 aaaaaactt aaaaaattag ctgggcatag tggtgtgtgc ctgtagtccc agctactcag    9720
gaggctgagg aggctggagg attgcttgag tccaggagtt tgaggctgca gtgagctatg   9780
attatgccac tacactacaa cctgggcaag agagtgagac cctgtctcta aatatacaca   9840
cacacacaca cacacacaca cacacacaca cacacacaca cacacacaca catatatatg   9900
tatatatatg catttagatg aaagatcac tttgacaata ccacatgctg gtgaggattt    9960
agaaaaacta ggtcacttat tgctggtggg aatataatat agtacggcca ctctggaaaa  10020
cagtttggca gtttgtcata aaactgaaca taccgttagt atacagccca gcagcaacta  10080
caatcctggg cattaatcct agagaaatga aaccttaatg ttcacataaa aacctatact  10140
caagtatgca tagcagcttt acccataata tctaagaact ggaatcagct cagatgtcct  10200
tcaacaggtg aatggttaaa ctactcagta ataaaaagga atgagctact gatagcatgc  10260
aacagtttag gtgaagttat gctaatgaaa aaagccaatc ccaaaaggtt atacatactg  10320
tatgattcta tgttttttg caatggcaca gttttaggga tggagaatag attagtggtt   10380
gcctggggtt agagatgggg tagtagagta ggttagtggt ggcagaggag agaaaagaga  10440
gggaggtgaa tgtggttata aaaggacaac acaggggaat acttgtaatg gaaatgcttt  10500
gtcttttttt tttttttttt tttttggcg acagagtctt gctctgttgc ccaggctgga   10560
gtgcagtggc atgatctttt ctcactgcaa cctctgcctc ctgggttcaa gtgatacttg   10620
tgtctcagtc tcccatgttc agagtgaaac aaaccagagg taatgttcat ccaaataatc   10680
caacacacat gacattaaaa catcaagatc aggtcggacg tggtggctca tgcctgtaat   10740
cccagcactt tgggaggcc aaggtgggca gatcacttga ggtcaggagt tcgagaccag    10800
ccgggccaac atgatgaaac cccatcttga ctaaaaatac aaaaattagc cgggcatggt   10860
ggtgtgcacc tgtagtccca gctacttggg aggctgaggc aagagaactg cttgaacccg   10920
aggggcagag gttgcagtga gctgagagtg cgccattgca cttcagcctg tgtgacagag   10980
taagactcca tctccaaaaa aaaaaaacca agatcaatta aaatacagca ttactgggcc   11040
gggtgtggtg gctcacacct gtaatcccag cactttggga ggccgagatg ggcagatcac   11100
gaggtcagga gatccagacc atcccggcta acacggtgaa accccgtctc tactaaaaaa   11160
tacaaaaaat tagccgggta tagtggtggg tgcctgtagt cccagctact tgggaggctg   11220
aagcaggaga atggtgtgaa cccgggaggc agagctggca gtgagctgag atcgcgccac   11280
tgcactccag cctgggcgac agagcaagac tccgtctcgg gggaaaaaaa aaataaata   11340 aatagaatgc tgtagtgtcc ttgagtttac atgcccctcc ttacgcttgt gtgcccgtgc   11400
agattgcttg attacacaat tagaggaggc tggcggagga ttgttttaat tttttttttt   11460
ttgagacagt ctggctctgt tccccaggct agagtgcaat ggcgcaatct tggtgcactg   11520
caacctctgc ctcctgggtt caagcagttc ttctgccgca gcctcccgag tagctgggat   11580
```

```
tataggcgcc cgccaccacg cccaactatt ttttgtattt ttagtagagc agcgtttcac   11640
catgctggcc aggctggtct cgaactcctg acctcagatg atctgctgcc ccagcctccc   11700
aaagtgctgg gattacaggc gtgagccaca cctggccgtt tgttttaatt ttgaaggtga   11760
agtgaaagtg actacattta ccaaaagtga ttgaaaagcc aggactgttc ttaccctgtt   11820
tttccagttc ttgctcagag caaggtggtt tcttttttcac ttaatcacca tacttacttt   11880
tcatgtagaa caagtcagtt tgagttatca gttcatcatc ttaactaaat tccatggggg   11940
aaggaattag ttttagtttc ttaaacttcc aggtttgctt attggacaaa atgagatagc   12000
aaggcagtgt ttttaagtta gatttttttat ttctttggta atacaattt ctcagaaact   12060 tagtagtctt ttagtttagt tgttttttagt tggtcctatg ttttggatca ccctctcta   12120 ctttattttg atagtgccaa ctgtgaagac atctgaagcc ataggttggg atgggaagga   12180 ggcatctta gcctgatcat cttcgccagg ctgtttatct ccttttgctt ggctgagaag   12240
tcttaatagg aggcttattc ccagctattt ggggacatag aagcagttag ccattgctta   12300
tattttactg aggtctgtgt ggtatgttga ttgtagtcag ttaacgattt tgagaactga   12360
aggcagcctg gtatatatag agtaggtatt agactgtgtt tcttctaatt gaatttccca   12420
tctcttgtaa tctatgccat catcttctgt actgctgaga aagaaagaaa gtttctaatc   12480
aaactatacc actggttgta agatgcagtt tggctttagt gatgttaaca catgattcaa   12540
acgtgaaatt gattgagtat tggtgaaata cagaggagat ttaaagccag aagacctggg   12600
tttaaatgct ggctgtatga cttcatatct gtgtgatctt gggcatgtca tggttggcac   12660
ttcaatttct tctctctata atgggggaag tgaggccagt catggtggct catacctata   12720
atcccagtgc tttgggaggc caagatggga agatcgcttg aggccaggag tttgagcaat   12780
tgggcaacat cgtgaggccc cgtctctaca aaatattttg aaaaaattag ccaggcccag   12840
tggtgcgtgc ctgtggtccg cgccactcag gaggctgaga cgggaggatc ctttcagcct   12900
aggagtttaa ggctaaagtg agccatgatt gtgctatcgt actccagcct gggcagcaga   12960
gcaagatcct gactctaaaa aaaagtaaaa taaagtaaaa tgggggaaat gaactgcttt   13020
agtaacatca tctgtttttt ctgtgagcag cgtagcttga cagccattgg tgaactcgtg   13080
ccctgtgctt ccctgtccag atccccattc tgcccgcaac atggagtata acggtttatt   13140
catagtagtc gagaaacact cactgaatga atgaatgagg tgtagaacta agtggagtgg   13200
gtaattcaac acatattaat ttccttcttt tttttatttt tagaaagaaa gaactttcag   13260
ctaccaagaa agaccgtgtg aatcattgtc tgacaatatg tgaaaacata gtggcacagt   13320
ctgtcaggta attgcacttt gaactgtcta gagaaaataa gaactttgta tattttcagt   13380
cttaatgggc tagaatattc tttgtgtccc agctatttta aatggattca gaaatccatt   13440
taagatgaag aaggacccctt tcccatatt tctggctata tacaaggata tccagacact   13500
gaaatgaata atgttcccctt tttgtaatct tttatgcaaa aattaaaacc attatggtaa   13560
ttgaacaaca tgtttatgtt tagttaacac ccttagcaac tatagttatt ttaaaaccat   13620
ctatggtttg atattttgc atttgttgca atagtaggaa cagcacaaga cagttcagtt   13680
tgtctctctt atttgctttt tcttggcagt ttgctgtcct attgtacctc tgctcctagc   13740
agtggctgga gcccactcct ctgtgcttcg ggattagtgg ggatcgtggg gcattgactg   13800
taggtcagct ttccttgctt gatctttctc actgggatga actagcagca ccttcttttg   13860
tagctgcttt gcttttgact atctttctga ccgttgttcc tagtagctgt agatggtaaa   13920
tatatttagg cctgttttcca atggctcagt aggagacata ttcacctatg atatctgaat   13980
```

```
tctgttaccc acatgggcat gcgtgaaata gttgccttgc cttactttcc cttggaataa    14040
ataattcatg ttattctcct ggtagaagct agaaaaagcc tttatagtca gtcagaaaaa    14100
aatttttaga caaataatct tgattttagt actgacaaaa acgtgtggtg attcttttt     14160
taattttttt ttgagacgga gtttcactct tgttgcccag gctggagtgc aatggcgtga    14220
tctcggctca ctgcaacctc tgcctcctgg gttcaagtga ttctcctgcc tcagcctccc    14280
aagtagctgg agttacaggc atgtgctact gtgcccagct aattttgtat ttttagtaga    14340
gatgttggtc aggctgatct cgaactccca accttaggtg atctgcccgc ctcagcctcc    14400
caaagtgctg ggattacagg cgtgagccag gcgcccggt  gattcatttg ttttttcaaa    14460
aaatttcctc ttggccattg cttttcactt ttgtttttttt tttttttttg agacggagtc   14520
acgatctgtc acccaggctg gagtgcagtg gcatgatctt ggcttactgc aagctctgcc    14580
tcccaggttc acgccattct cctgcttcag cctggcgagt agctgggact acaggtgctc    14640
gccaccacac ccggctaatt ttttgtattt ttagtagaga tggggtttca ccgtggtctt    14700
gatctcctga cctcatgacc cgctcaactc agcctcccaa agtgctggga ttacaggcgt    14760
gagccaccgc gcccggccct ctcttgtctt tttattgtgg taaatgcac  ataaaattga    14820
ctgtcttaac cattttttagg ggtacagttc agtatatata ttcgtaatgt tgtacagcca    14880
tcactgccat ctacttcata agttttttctt ctgtcaaaac tgaacatctg tcttcattaa   14940
actccctatc atccattctt tcctgtagtc cctttctact ttctgtctgt atgagtgtaa    15000
ctgctctgga gacctcatgt aagtggattc ctacaggatt tgtgtttttt ttttggtgat    15060
ctgcttattt ttaatgcctc tgtgcatttg tattatatac tttcaaagtg atttcacaaa    15120
accgtttcat tttaggttaa ctcatttctg ttgtttgtga atactgtgt  atgattctgt    15180
tctgtttctg tctaatttgt ggaaatgttg tgggaagaaa atgaaataac aaatgagcat    15240
atgtcctgaa aataaaaata taaaaattct aagttagcat gctattgtag aatacaacgc    15300
tatgataaaa gtaggaaaaa aaaaggtttg aattctatct ctgctacctg tgtaagctgg    15360
gtgactttag ataagctgta acgtgtttga gccttactgg ctcatttttg aaatgtaatc    15420
cctagttaca cagttcttgt gggatcagat ggtacatgtg aaacactgtg aaaaagcaac    15480
tgcatagata tgttcattag ccacctgagc gggaagcgta tcccattgcg atgcccatca    15540
tccaaagcta tatgttatct ttactttttt tttttgaga  cagagtcttg ctctgttgcc    15600
caggctagag tgcagtggtg caatctcagc tcactgcaag ctccacctcc cgggttcacg    15660
ctattctcct gccccagcct cccaagtagc tgggactaca gcacccgcc  accatgcctg    15720
gctaaatttt tgtatttta  gtagagatgg ggtttcaccg tgttagccag gatggtcttg    15780
atctcctgac ctcgtgatcc gcccgcctcg gcctcccaaa gtgctgggat tacaggcgtg    15840
agccactgcc cctggccatc tttactttt  ttgtgaaatg actttaaata cttggcaaac    15900
atttggtcat tgttcatctg atctccacca tccaggtctc agagaacata atttctctct    15960
gaaagcttat tgacccagga aataagatct ctttcaatct gagtgcgtca ggctttattc    16020
ttgtcatttt gtcttttgat aattttcaaa tggaattcat ggaatgttgg cttatattca    16080
tatattagta aagtatgttg agacatctta agattgattt gtggttctat atgccatatt    16140
aaatcaaaat aatagctgtt aatggttttc acattagtct gtctcttgtt tttatggagt    16200
aatgctgaga gttcattatg cttgttctac agaagagcat gttaaaagga gttttggag    16260
tcagagaggt tattcttggt ttcataggat acactctata ctttttaggg atttcagagt    16320
```

```
atatagctga aggtgatatt ttatgtaaat atgttttatg gaaacttatt gctcatcgct   16380
gtttcctgtt aactctccta aaatataatt aaacttttgg aacttttta tagcttttgt   16440 gctagactaa tttttgtctc taatgaggtt atataaatgg cagcttctga cgttttcaat   16500
gtaggaagtc atttaaaact tcatgtatat tgtgaaaatg tagtctgctt taagctctct   16560
aaagtggtct aagttactgg ttcctaagta tggatgagca tcaaaatcat ctggaaaatt   16620
tgttaaaaat acagtaatga aggcacctca ctgtccttt tcccaaacat acttctgcat   16680
tctgtttgag taggtaggga ctacacattt ttcacaagta tcctcttggg aatacccagg   16740
aatgcttact tgagcaacct cttactaata tgtaccttga taaggtggct aggtaaacat   16800
aaatatacaa aaatccatag atctcccata tattagcata aatcagctag aaaatataac   16860
gtttaaagat ctagttcaca gtagcaccaa tatatcgaac tctaaggaat cgataaatat   16920
gcaaaaactt tataaaaact tctgttaatg tttctgaaag atataggtga ccactttcta   16980
gataggaaga ttttatatta ctaagttgaa ttttctctaa attaacacag aaatttaaaa   17040
taatcttgat caaaattcta gtagaggtat ttttgaactt gttcactgca agaataaata   17100
cataattgca aagaatatct caaaatcatc accaggcctg gtgtggtggc ccatgcctgt   17160
aatcccagca ctttgggagg ctgaggcagg cagatcacct gaggtcaaga gtttgagacc   17220
agctggacca gtgcggtgaa acactgcctc tactaaaaat acaaaaatta gctgggtgtg   17280
gtggtgcatg cctgtagtcc cagctacttg ggaggctgag gcaggagaat tgcttgaacc   17340
caggaggtac aggttgcggt gagcctagat cgcaccactg cattccagcc tgggcgacaa   17400
gagcaaaatt ctgtctcaag aaaaaagaga aaaagaaaa agaaatcaac actaatatgg   17460
tgagacttaa tgtatgtgac attaaaatag tgattggatg ttaaaacagg tatagaacag   17520
aaagaagagt gtatgtgtgt atctgtatga atttatgatg ggtgtaacat atatgtatta   17580
gggaaatgag ggaaatgata catttctctg actttgggag aacattatat ctctacctca   17640
tattgcaaac aaacataaag ttcagattaa ttacctaaat gtgaaaaaat gaaataattt   17700
ctttaaaaaa tgtaatctta gtttgaggaa ggttaacatt ataaggaaa aaactgtttt   17760 gagtggaata tagttcaata tgtcaaaatc caccttcaac aaaattgaaa gtaaattgaa   17820
cttggggaaa gtattgacag catatagatc aaaggttact agcctgtgta aagagcagtt   17880
ataaatatcg ttaagaaaaa cactgtcgac ctgtcggcac cttgttctcc gactcccagc   17940
ctccagaact gtgacgagta agtgcttatt gtttaaacca cccagtctgt atgtggtatt   18000
ttgttataga aactcaagct gattaggaca ctagtaatca gtagactgaa actgaaacaa   18060
aaataagaac ctttttacc tgtcaaattg gcaaacatta agaatattca gattttgtc   18120 agaggtgata caaccttcta agaaggcaat ttgggaaaat ataaagcttt agattattat   18180
atgtctgacc tagcagtttt acctctaggg tgcttacccc taggaaagtg tgtaatgata   18240
ttggtgcagt gccccttcatc ccattagaaa attaaaaata accttaatgg cctaccacta   18300
aaaggggatt gaaaatttaa gatatattta tttatgtgtt tattgagatg gagtcttgca   18360
ctgtccgcct gggccagagt gcaatggtgc gatctcggct cactgcaacc tctgcttccc   18420
gggttcatgt gattctcctg cctcagcctc ctgagtagct gggattacag gctcacacca   18480
ccgcacccgg ctaatttttt gtattttag tagagatggg gtttcactgt gttggccaga   18540
ctggtctcga actcctgacc tcatgatccg cgcccctcgg cctcccagtg ttgggattac   18600
aggtgtgagc cactgcgcct ggccagatac atttatacaa gagaatgtta gttaacattc   18660
atagatattt atattttgtt tacttttat taaaaaaatt ttttttagag acaggatctt   18720
```

```
actctgtcac ccaggcagga tgcagttgca caatcatagc ccactgcagc ctgaactcct    18780
gggcttaagt gatccttctg cctcagcctt ttgagtacct gggggacttt aggcagtgct    18840
actatacctg gctaattttt aaatgtttta tagatgagat cttgctgtat tgcccaggct    18900
ggtctagaat tcctgggccc aagtgatcct cccaccttgg cctcccaaag cgctgagatt    18960
acaggcatga gccaccactt ctgaccaata gatatttata tttgtgactg gaaaatatat    19020
taacaatgtg ttaaaaaatt cagttaaaaa ataatgaaag atttttgctt ctggctaaga    19080
tagaataaca aggacagcat ttatcttctt gccttgaaat agttgaaaac ggaagaaata    19140
tatgtaacag tggttttcaa gttattgggc atcaggcaaa aagaatagt tatcccagga    19200
aaatgaatgt ggagagccct acaatttcct tacattactg cctggtcatg gcaagaggaa    19260
aaactgagag gagactgagg ctgagccagt ggtttgctgg gttgaggagg cagagctggg    19320
agtgcagaga tgcaaggtgg tgagagccca tatggaagaa taccagggaa gagagctgca    19380
gagggagctc cggagacctg caccctgccc tctcagtacc ctgtcatgtg tgtagctgag    19440
tactgacgag cacttgcttg tgcggaaatg acccagggct ggaggtagag ccacctgaaa    19500
ggattagaag gaacagttgc tgaaagtcac acagggccag gaagaatttc taatcacacc    19560
agttggagtg gaaaacctca gctctcatag agcaggtagg gtactcagaa gggtttgccc    19620
acctagcccc agactaagtt tcgttactct gaccctacct aatattaaaa agagattaat    19680
taaattgttc gcaacaaaaa taatatattt cagtgtttgt aacacgtaga agtgaattgt    19740
atgacaatag cataaaggct ggaagagcag aaattgacat gtatttgcgc tgggcagaat    19800
aatgctcccc tctttcccca aaagatatca agtcctaatc cctggagcct gtaaatatta    19860
ctttatatgg aaaattgttt tatgatgtga ttaaattcag gatcttgaga tgaggggct    19920
atcttggatg atctgggtag gcactaaatg caatcacata tatataaaaa ggaggcagag    19980
ggagatttta cacacagaga gaaggccctg tgaagatgga acagaaagat ttgaaggtgc    20040
tggccttgaa aattggagtg atgaagctat aagccaagga atgcagcagc caccaaagct    20100
ggaagaggca cggagcagtt ctcatttaga gcctactcca gagggaatgt ggtgctgcca    20160
attcctttt tttttttttt tttaagatat catttacccc tttaagttgg ttttttttt    20220
tttttttttt ttttagtatt tattgatcat tcttgggtgt ttcttggaga gggggatttg    20280
gcagggtcat aggacaatag tggagggaag gtcagcagat aaacatgtaa acaaggtct    20340
ctggttttcc taggcagagg gccctgccac gttctgcagt gtttgtgtcc ctgggtactt    20400
gagattaggg agtggtgatg actcttaacg agtatgctgc cttcaagcat ctgtttaaca    20460
aagcacatct tgcaccgccc ttaatccatt taaccttag tggacacagc acatgtttca    20520
gagagcacgg ggttgggggt aaggttatag attaacagca tcccaaggca gaagaatttt    20580
tcttagtaca gaacaaaatg gagtgtccta tgtctacttc tttctacgca gacacagtaa    20640
caatctgatc tctctttctt ttcccacatt tcctcctttt ctattcgaca aaactgccac    20700
cgtcatcatg gactgttctc aatgagctat tgggtacacc tcccagatgg ggtggcggcc    20760
gggcagaggg gctcctcact tcccagatgg ggcggccggg cagaggcgcc ccccaacctc    20820
ccagacgggg cggcggctgg gcgggggctg ccccccacct cccggacggg gcgggtggcc    20880
gggcggggc tgcccaccac ctccccggacg gggcggctgg ccgggcgggg gctgcccccc    20940
acctcccgga cggggcgggt ggccgggcgg ggctgcccc caccteccg gacgggcgg    21000
ctggccgggc gggggctgcc ccccacctcc cggacggagc ggctgccggg cggagggct    21060
```

```
cctcacttcc cggacggggc ggctgctggg cggagggggct cctcacttct cagacggggc   21120
ggctggtcag agacgctcct cacctcccag acggggtggc agtggggcag agacattctt   21180
aagttcccag acggagtcac ggccgggcag aggtgctctt cacatctcag acggggcggc   21240
ggggcagagg tgctcccacc ttcccagacg atgggcggcc gggcagagat gctcctcact   21300
tcctagatgg gatgacagcc gggaagaggc gctcctcact tcccagactg gcagccagg    21360
cagagggggct cctcacatcc cagacgatgg gcggccaggc agaaacgctc ctcacttcct   21420
agacggggtg gcggctgggc agaggccgca atcttggcac tttgggaggc caaggcaggc   21480
ggctgggagg tgaaggttgt agtgacccga gatcacgcca ctgcactcca gcctgggcaa   21540
cactgagcac tgagtgagcg agactccgtc tgcaatcccg gcacctcggg aggccgaggc   21600
tggcagatca cttgcagtca ggagctggag accagcccgg ccaacacggc gaaacccgt    21660
ctccaccaaa aaacacgaaa accagtcaga catggcggtg cgtgcctgca atcccaggca   21720
cttggcaggc tgaggcagga gaatcaggta gggaggttgc agtgagtaga gatggtggca   21780
gtacagtcca gccttggctc ggcatcagag ggagactgtg cgagggcgag ggcgagggcg   21840
agggaattcc ttaatttcag tttagtgata ctaattttgg actctggcct ctaaaactgt   21900
gaaagaaaaa attttttgtt tgtttgtttc ttttaagcca catagtttgt ggtaatttgt   21960
tacagcagct gcaggaaact aatttatgct gcatgtgaaa tggtgtaata aggtagattg   22020
tgatgaagat acatagtata aacaattaag caacaactaa aagcacaaca aggaattata   22080
gctaatgaac caaaaaagga gattagaata ataaaaatgg tgaatcccaa agaagccaga   22140
aatagggga gaggcaaata aaggaaagaa agagcttgat ggtagatttc aacctaacta   22200
tgtcaaaaag gacattacat gtaaaaggca gcgattttc agattgaatg gaaaagtaag   22260
actcggtata tgctgctgcc tgcaagaaac acattctaaa tataaaggca aaaataacct   22320
acaggtaaca gaacggaaag aagttcactg tgcttacaag aattagatgc aagctagact   22380
ggttctgtta atatcagaca aagtggattt caaagcaaag gctcttgccc aggatgagat   22440
ggtcatttca taatgatgaa ggggattcgt tcatcagcct ggcatagcaa gctgaaatgt   22500
ttatgcaccg gactacagag ctaaaataca tgaagcaaag cctgacagaa ctacaagtag   22560
aaacagacaa atccacagtg atagagattt cagtagccgc tctcaatgat tgtagaaca   22620
cgtagccata atatctggat ctagaacact tgaccaacac tgtcccctgt gcaacctcat   22680
tggcatttac aggacactcc acccagcacc agcagaagag acactctctc aagtgctcac   22740
agaatgtttg ccaagataga gcagatgctg ggccataaaa caagtctcta aattaaaagc   22800
attcaaatta ttcagagtat gttttctgac ctcagtatca ttaagttgga atatattata   22860
ggaagataac ctggaaaagc ctcagatatg tggaaaaacc catttccaca tggcccatgg   22920
gtcagaagtg aagtcaaaag ggaaatttga aagtcttttg gattgactga tataaaaaca   22980
atagatttct aaacttgtgg ggtgctgtta cagcatagta aatggaaatt tctagcatta   23040
aatgcctgtt ttaggaaaga aagatttcaa atcaatgacc tcagcttcta cctttggaaa   23100
cttgaaaatg acaagcaaat ggaatccaga gttaccagaa gggccaggta cggtggctta   23160
tgcctgcagt tctgccactt tgggaggccg aggcaggtgg attgtttgag actggcagtt   23220
gaagaccagc ctgggcagcc tagggagacc ccatatctac aaaaaacaaa aaattagcc    23280
aggtgtggtg gcatgtgcct gtagtcccag ctaaccagga gtctaaggtg ggaggattgc   23340
ttgagtctgg gaggttgagg ctgcagtgaa ctgtgattgt gccactgtgt tccatcctgg   23400
gcaacagaat gagaccctgt ctcaaaaaca aaaacagtta ctagaagaat ggacatcata   23460
```

```
aagataggag cagaagtcag taaaatagaa aacaaaaata cataggaaat caataaaacc   23520
aaaagctggt tcatcaagaa catcaataaa ttggtaaagc tgataggaaa aacagtgaag   23580
tcacaaatta gcaatatcag gaatgaggga gatgacagta gtatagatta tatagatatt   23640
aaaaggactg tatgaggcag gtgtggtggt tcacgcctgt aatcccagca ccttgggagg   23700
ccgaggtgga cagatcacct gaggtcagga gtttgggacc agcctggcca acatggtgaa   23760
actctgtctc tactaaaaat acaaaaatta gttggtcgtg gtgctgtgtg cctgtaatcc   23820
cagctacttg ggaggctgag gcaggagaat tgcttgaacc tgggaggcgg aggttgcagt   23880
gagctgagat tgtgccgttg cactccagcc tgggtgacag agcaagactc catctcaaaa   23940
caaataaata aataaaaagg actatatggt aatattatga acaactttat gccaataaat   24000
ttgacaactt atagatgaaa tgatgagtt ccttgaaaga cacagaaact attaaagctc    24060
tctcaagaag atatagataa gctgattagc cctatatcta ttttattgaa tttaaatgta   24120
aaaatcaata tttagttact ggaaaacttt taagtgtggt tggaaatggt atacgaactt   24180
tttcaactga atttatgaa gtctaatcac aggtaaaggt tttctgatga aaatttagtg    24240
tctgaattga gatatactgt aaaaaatgtt atatatctta attatttctt cacattaatt   24300
acatgttgaa ataatacttt gggtgtattg ggttaaatta aatattatga aaatcttgcc   24360
tgttttcttt ttacttttga tgcgtcagct aggaaaatata aaagtgtagc tcacattctg   24420
tttctgttga cagtactgct ttggagcaca gtgtttgaat gatctatcat ttcaaagacc   24480 ttttcctcagt tcgttattca tggctgtctg tattccacat agataaggtc tgaaatactg   24540
ctaagtggca tgttttgttt tatgctttta taagtttgtt gatcattact gatgtggact   24600
tttggtgcct cttaggctca ttgctatctt ccaaccattg tttgcaattt ttacctagag   24660
ataaagagaa agagacattt ggtttcagag tagttagatt gggatcatga aagagcaacc   24720
tcattttgat gcttcaaaaa tagcacatcc cccgtattac tgggatttgc tattcttggg   24780
attacttcaa gaacatcctt gtgttactgg tttggatgct tctgaatgct gtgaagtcag   24840
tttcatgtac atggctcatc agtttagctc tctcttggct ttgtttagac agttggagca   24900
tgatggccta aacagcttct ttcaattaaa cattttaaaa tagtttacaa atagtaaaca   24960
aactccagtt tttgtgactc tttgtctcgc acaacaaaaa cacaatctga ccatgatcat   25020
ctggcatctt agggtgaaat atggttatac tttggcccat accgaaagca agattaaaaa   25080
ggggcaggag agatagactg ctgaactgat tttcaaggtt ccaagaatat tgtaggttaa   25140
gagtaaaagt aaacttttgg tagaaagcag tgggttgtct aggattgaag tatctgaagt   25200
ttttaaacga aaatttaaaa agaaaaatga gaattgcctt acaagtacaa tctcttcttt   25260
tttaaaaaat aaactttatt ttgaaatagt tttagattta tagaaaaaaa ttagataggg   25320
taggaagttt tcatataccc tacatccagt taccccagtt attatcatcc taatttagtg   25380
tgagacattt tcatgtttaa tgaatcaata ttgatatgct attaacttaa gtccagactt   25440
tattcagatt ttcttaattt ctatgtaatg tccttttttct gttccagaat tccatgcagg   25500
acaccggata cctcattaca tttcattgtc atgtcacctt aggctcctct tgacagtttc   25560
tcttcttttt ttgcttagaa attctccaga atttcagaaa cttctgggca tcgctatgga   25620 acttttctg ctgtgcagtg atgacgcaga gtcagatgtc aggatggtgg ctgacgaatg     25680
cctcaacaaa gttatcaaag taagaaccgt gtggatgatg ttctcctcag agctatcatt   25740
gttgtaggct gagagaagaa gcgatcattg agtgttcttc tgttttgagt ccctgaggat   25800
```

```
gtctgcactt ttttcctttc tgatgtatgg tttggaggtg ctctgttgta tggtttggag     25860
gtgctctgtt gtatggtttg gaggtgctct attgtatggt ttggaggtgc tctgttgtat     25920
ggtttggagg tgctcttgta tggtttggag gtgctcttgt atggtttgga ggtgctctgt     25980
tgtatggttt ggaggtggtc ttgtatggtt tgcaggtgct ctattgcatg gtttgcaggt     26040
gctctattgt atggtttgga agtgctcttg tatggtttgg aggtgctctt gtatggtttg     26100
gagatgctct attgtatggt ttgcaggtgc tctattgtat ggtttggaag tgctcttgta     26160
tggtttggag gtgctcttgt atggtttgga ggtgctctgt tgtatggttt ggaggtgctc     26220
tgttgtatgg tttggaggtg ctcttgtatg gtttggaggt gctctattgt atggtttgga     26280
gatgctctgg tatctgcctg cattgcttgc cacacctgcc cggtcagaag gcgctatgtt     26340
gacaattgtg cctgcacggt gcctaggtca atgaagggaa ccgatggtag ccactggatg     26400
ctcctgggaa aatgtcacta caggcaccag agaagccaga gctatgccca aatttctatg     26460
agtctcagtt ttcttaacca taaaatggga tcaatgtttt tgtggcatgt gtatgagtgt     26520
gtgtctgtgt atgtgtgagg attaaattgt gtatgtgtga ggactaattg ccactactgg     26580
atcctcaaag tggtaagaag tgttcttatt aataatgaca tccttacact cttacccagc     26640
aagattgatg ggtgtggcac tgcttctctt tttccatcac atggtttcca tggtatcctt     26700
ttgcccaggg aatctttgct ttgtggctag cactttgttg tttggctaat cacgctttct     26760
gtggtcagga cgctggcttc tctggagcca tgggattcta gctccctgtc ttgtccctag     26820
agtggtcact gtcttctctc tccgcttgca attcctgctt tgctcgcatc tcacttatgc     26880
agtgacgtat atcagtttca ccttgttctc cgtgcctgct gatcattggc accacttgca     26940
tggtgccatt tagggcctgc ttccagttaa gcttgcttct ccacaggcct aaatatcctt     27000
gcttgcttct tttattctca ctggcaggac cagggcggtc tgtctttgca tgagacaggg     27060
tctcgctcag tcacccaggc tggagtgcag tggctgatca cggctcattg cagccttgag     27120
ctaccgggct caagctatcc tcctggcttg gccccttgag tagctgggac tacaggcgtg     27180
caccaccatg cccagctaat ttttaaaatt atttgtagag atgggatctc gccaggttgc     27240
ccaggctggt cttgaacgcc tgggctcaag tgatcctccc tccttggttt cccaaagtgc     27300
tgggatcaca ggtgtgagcc actgtgcctg gcccttgatg tttcagttct tgatatttga     27360
tcctcagagt cagaaaatct aaaaagaggg ctatcccagg ttgccttggt tcatggcaaa     27420
tgggacgtta agagggcaga gagaatatga acagaaactg ttctaatatt ggtcatttaa     27480
tgtgtaagta ttgttctttt ttaaacctcc ttcatttttt ttccaggaat tgctggacac     27540
agtggcttgg tgtgtgtctg aggactgtag gccatggccc taggttgtgg ttttaggtct     27600
caggtgctct tcctggctgt ctccttgctt ctttcccatg tcctcttctt tgtttccagc     27660
catttctccc ttatgcttaa gtttggtgca gcagggtttg gctgctctca gattcctgct     27720
tcctcagatg ctgtagttgt caggcccagc gggctggcag cgggatcagg atctggctag     27780
gtttgctctc actgtggcag agtagggga ggcgtgggag agcacgtgtg accccaggcc     27840
agctgtaggg agcataggca tggtcacgta gccttcaggt cctagacttt gtcttctcat     27900
gagtatggct gtgtgtgtat ggtgaaaact aggttctact tagcccaaga aaatgggcac     27960
attttgcatg tggtttctgt agagaaatgc actgggtatc tgacatagcc tggcagcatg     28020
cctccctcag gtaggttagt ctcaggcggt gaagcacgtg tgtccagcaa gaacttcata     28080
tgtggcataa agtctccgtt ctgtgagtg ctggcaaatc accaccaccg tcaagaggct     28140
gaagtgattt ttgtctaggg aggcaggaaa ggcttcctgg agtcagcagc cagtaggtga     28200
```

```
aagagtagat tggagacctt cttaatcatc accgcctctt gtctcaaggg gtgccaggaa    28260
gctgtggagg ctgaacccat cttatgctgc cagagagtgg gacaccatga gggtcaggtc    28320
aaggggttgt accttgtttg gtagagaatt aggggctctt gaagactttg gatgtggtca    28380
ggggagtgta tcatttagga agagtgaccc ggtgaggacg tggggtagag gaggacaggt    28440
gggagggagt ccaggtggga gtgagtagac ccagcaggag tgcagggcct cgagccagga    28500
tggtggcagg gctgtgagga gaggcagcca cctgtgtgtc tgcggaagca ggggcaagag    28560
ggaagaggcc agcagcgtgc tgccatcacc cagcgactgg cgtagattgt gagagaccat    28620
tccctgctct taggagggc tgagttttag ttttctcttg ttatacaata agcttggtat    28680
ttgtttacaa aacatttgta aagctaaatc aaggtttgat aaggcttcta gttttattta    28740
agaagtaatg ttgaaataaa tgtttgtcca attcgctttg ctcatttaag gactttcagt    28800
acaaactgca acaacaggat taggatttaa acgtttctga gatgttttta ctcctcagaa    28860
tttcccagaa tgtgatctgg ttttgatttt caagcttgct gacccaatag gttaacccac    28920
aagttttacg aagaccatct cagtccactt acatcaactg cccatgccac ggttaaagag    28980
atcatcgact gatgtttggc acagcttcct ccctcttggg tggcaagca tttggaagag    29040 aaggctccta tgggtgagag tggggcacca aagtcttccc tgtcccatcc cctagcttga    29100
gaagcccttc tctaatgtgg actttgtgcc gttagcatcg ttactagctt gaagttgacc    29160
atctggacgt actttctggt ttagcctcac aagtgagcaa ggagggttga gagatgtgct    29220
gtgaggaatg tggggcccca gctggcagca ggctctgggt caggggggca gggaccacgg    29280
gcatacctga cagtgaggag gggccacacc tgcagaaaag gatgcaggac tccgccttgg    29340
gaagtgttct aggccagagc gagggtctgt ggtttataag tacacccaca gtgctcggga    29400
ccctgcagat gtccagggtg ccgtctgagc ccgtatcatc caacagaatg ttctgctagt    29460
gaagattaaa gatttactcc agggctttta ggatttatta tatatatata aatcctatat    29520
atataatttt tttttttttt tttttgaga tggagtttcg ctcttgttgc ccaggctgga    29580
gtgcaatggc gtgatcttgg ctcactgcaa cctccgcctc ccgggttcaa actattctcc    29640
tgcctcagcc tctcgagtag ctgggattac aggcgcccac caccacccc ggctaatttt    29700 tgtattttt agtagagacg gagtttctcc atgttggtca ggctggtctt gaactcctga    29760
cctcaggtga tctgcccgcc ttggcctccc aaagtgctgg gattacaggc atgagccacc    29820
ccacctggcc aggatttatt gtatttgaac catctaccat tttaattttg atgttatgta    29880
gtatttgatg ataatgaaag ttaaattgtt tttctttcca tttttctgtt taagtgaatg    29940
acctgtatct agtttattca gtaacttcct gcatatattt gtttctttca ttcttaatga    30000
atatattctt aatttagttg ctattatgtt ttgctttgcc ccaaaattga aatcttagtt    30060
tccttttagc tcgttttaga actagtgatg ggatgtgtct tccataaatc tcttgtgatt    30120
tgttgtaggc tttgatggat tctaatcttc caaggttaca gctcgagctc tataaggaaa    30180
ttaaaaaggt gggccttgct tttctttttt aaaaatgttt taaatttaa attttatag    30240 gtacacgtat tttgtaggta catgtaaatg tatatattta tggggtacat gagatatttt    30300
gatacaggta tacaatacat aataatcaca ccatggaaag ttggatatcc atgccctcaa    30360
gcatttatcc tttgtgttac aaacaatcca gttacatgct ttacttattt tattttattt    30420
ttgagacaga gtcttgcttt cacccatgct agagtacagt ggcatgacct tggctcactg    30480
caacctccgc ctcccgggtt caaccgaact ttgggctggt ctcgaactcc tgacctcagg    30540
```

```
tgatccgccc gcctcggcct cccaaagtgt tgggattaca ggcgtgagcc actgtgccgg    30600
gcctgattgt acatttttaaa ataactaaaa cagtcagggc acagtggctc atgcctgtaa   30660
tcccagcatt ttgggaggct gaggcaggtg atcacctgag atcaggagtt cgagaccagc   30720
ctggccaaca tggagaaacc ctgtctctac taaaaataca aaaattagcc aagtgtggtg   30780
gcgggcgcct gtaatcctgg ctactcggga ggctgaggta ggggaatcgc ttgaacctgg   30840
gggtggaggt tgcagtgagc cgagatcacg ccactgcatt ccagcctgag cgacagagtg   30900
agactttgtc tcaaaaaata aaaatgaaat aaaattgggc cgggtgtggt ggctcacacc   30960
ttagtcccag cactttggga acctgaggca ggtggatgct tgagaccagg agtttgagac   31020
cagcatgggc aacatggcaa aacgctgtct gtacagaaat tagctgggtg tggtggtgca   31080
caactatagt ctcagctact tgggagattg aggtgggagg attaattgag cctggaaggt   31140
tgaatctata ggtagctgag attgtgccac tgcccttcag cctgggcgac caagtgagac   31200
cctgtctcaa aagaaaaaca aaaaaacaaa aacaaaccaa ctattatcga ctatatatta   31260
ttgtctatga tccctctgct gtgctgtcga ataccaggtc ttgggccctt atttccatca   31320
ctgagcaaac ttcactctgt taagcagcag gtgtgggatt tcatcgttat tcagtaattc   31380
acaatgttaa aaggaaatgc tgtttggtag acgattgctt tacttttctt caaaaggtta   31440
ctctttatta gatgagatga gaattaaaaa tggtaactta ctttatatct ttataattga   31500
agcccactag accttaaagt agttaccaga tgttttatgc atttaaatgg ccttttctct   31560
aaaattagaa agtaacaagg aaagaaaatg cttcgtttct atgcaaccct cttggtgact   31620
agtatgtgac tcttaatgca accctcattg cacccctca gaatggtgcc cctcggagtt   31680
tgcgtgctgc cctgtggagg tttgctgagc tggctcacct ggttcggcct cagaaatgca   31740
ggtaagttgt acactctgga tgttggtttt tgtcgggggc cagctgctac tgatcctta   31800 tgtctcagct cagatgtcat ttcaaaagtc tgctctgccc tctccaaatt gcagtcgacc   31860 ttgcccgtt tatgtttccc tcatagcact aatccatgtc agaaattgtc acgtacagtc   31920
tatctgtgtg cttgtttatt ttctatccca cccttccgca agagacttat gggatgtgtg   31980
ccccaggaca gcagggggtct tactgtctta tgctctgttg cagcccagca gcgataacag   32040
tgtctgcaca tagtacttgc ttaaaagata cttgccaaat tgttgaaggt tgaggtacca   32100 attcattat tgctgactat aggagttata gcaaaatatc catttgtctg ttacatgagt   32160
taaaaatatg gttgttgcac tgtgaatagt ttggtttagt caaaacagtt gtatcttaac   32220
ggattgagaa acaaaagcag gaccactttt catcagctcc ctccttctcc ttaaccagca   32280
atacatgctg atgctgatat cccatagacc ctcagctcca tcctgagtca ctgggaatgt   32340
ggtctaaacc ctcactatta atatgaactg agtttcaata agaatcttat atgggtcggg   32400
catagtggct cataccttg atcccagcac ttcaggaggc caaggcaggt ggattgcttg   32460
acccagacta ggcaacatgg tgaaacgccg cctctacaaa aaatacaaaa cttagccagg   32520
catggtggtg cgtgcctgtg gtcacagcca ctcgagaggc tgaggtggga ggatcacttg   32580
agcctgggag gtggaggtcg tgttgagcca agatcgcacc actgcactcc agcctgggca   32640
acagagtgag acctgtctca aaaaaaccaa atccagaaa agaacttata tggctgcaga   32700
ggtataatca ctaaggaaat ttccttttgt ataatctttt ttcttttact atcatttaaa   32760
aaaatgtgtt atatttctga agcaacacat ccaggttctg cacatagcag ccaaagtgac   32820
cttaaagaat ataactgggt cttgtcattc ccttatttaa actcttgtac ccatttccca   32880
gtgccgttta gatagagatt ccagactcgt caatggctct gtcacctcag acaccctgca   32940
```

```
ttgactcatt agtctgatta gagtcaggtt tttcttcctc ctgatggttt tttttttcccc   33000 cttagttctc agcggaacag tcacttcctt agggaggttt ccccagccac cctctgaggc   33060
cgtgcttgtt gccagactct gccactagag ggcagggctg caccactcct ggcacctcgc   33120
acccggcctg ccctgtcact ctgtgtgttg ggtgaattcc tgtgatctgt gactcactgc   33180
tctgtgtcct acacattcgg cttttcttct ctccccacaa ccccatttta taattctcct   33240
ttttcaggaa agctttattc ccatttaaaa attttttgttt ttaaaatggt attttcttac   33300
acttattttc taattaaaaa tgagtgtttt aagaagtatt atgatttact gcaaataatt   33360
tttaaaccca gccttttaga tcctctgtga tcataagaga aatgaaggat gtctcccaac   33420
acttgagctt catccacatt tcatcctcct gttctttcag ctgagttttc cccatcccat   33480
tagggactgt tggaatataa aactggcttt tccctaacag ggaatgaatt gcttctgttt   33540
ctcctgaagg agagctggaa gaatgacttg cgttcttttg catacacagg ccttacctgg   33600
tgaaccttct gccgtgcctg actcgaacaa gcaagagacc cgaagaatca gtccaggaga   33660
ccttggctgc agctgttccc aaaattatgg cttcttttgg caattttgca aatgacaatg   33720
aaattaaggt atgattgttg cctcaggtca caaacatgcg agtgatgctg tgagtgagtc   33780
tgtggagggt gagggcttct gaacagggag tcctgtggga gtgcttcttg gggtatgttg   33840
tatgtcgtaa tttagactac catcatttgt gttattttg aggcacctaa ggacttcttt   33900
ccacttctca tttcttactg tggggtgaag agttgaattg ggagatggtt tctagatgca   33960
aattgaaaag gcattttttcc agagcagatt tgttttcggc gtactagagt gactctttaa   34020
cctagctgcg ggaagatgac tgtgccaaga ctgcaggtag gagaaagctc actgacgagg   34080
ccttgtgggg ctgaacgtcc tgcagctatc agagcctgtt ggcttcctgt tgtgcattcc   34140
aacaaatcat cttcaaaccc actttagtgt tttgtttata atgtccagaa atagtgaccc   34200
tgtcacatgc tctacagatt acaggattct tagcctcttc cttttggta ggtcagtcct   34260 gggtttgagc ccaagtgacc ctcctgggag gtgatgatac acactgggta gagtggaatc   34320
agatggactt ggattagaat tctgtcctct ttactagtta ttttcctcta ggcaaactgc   34380
ccaacagctc taagctattt ccttcgtatt ctgaaaaata agccttaatg ggacccatat   34440
agggcaactc tgagagtaaa ataaaggaat atgtgttaga gtgtagcata gtcacccacg   34500
ggaagggctt agatgttagc tgctactgct cttattagct gaatgatttg gaataaactg   34560
ttagcctctc tcatgttttt tctcttgagc ttcgaagttt tcttgttaat actaaggaga   34620
tattcaaact agtcatgggg ttttggaatg acgaagggag atgatgaatc taaagaattt   34680
agtgtaatat ttcttcatgc tcagtaaatg gtagtttctg ctgctgttat tttattacc    34740 atctctttgg aatgggagta ggtgctcctt tgtggtcaga ggctgtgaga gctccacagc   34800
gccagtttgc ccatctgtac actggggtct gttgaaggca gtcccctctg tgatatctct   34860
ggctgtcaga gctcagatga tagatggtat ttttgtactc ttagttctca tcattttcat   34920
gatttcgatc accatttgag tatgatgatg ctaacacttt gttgaacgta gaatccgtta   34980
attacttcct tcctgaacct ttggcattaa aaaaaatcta ttctgctacc tctctgctca   35040
tttatggtta ttcaaattta ttatcaagag cctggtacag tggcttgtgc ctataattgt   35100
agctacttgg gaggctgagg taggaggatt gcttgaggcc aggagtttga gaccagcctg   35160
ggcaagatag tgagacccta tctctaaaaa aactgaaaaa aaattagctg gacatgatgg   35220
catgtgcctg tggtcctagc tactcaggag gctgagacag gaggctcggt tgagcccagg   35280
```

```
agttggagtt cgaggctaca ctgagctgtg attgtgccac cacactccag catgggtggt   35340
aaaacaagat gccatttctt aaaaaaaaaa aatatatata tatatattat caatgaaatt   35400
cagtagtacc aacaggatta taaacaaaga tagtagttcc cttcctactt tttctcttaa   35460
tccttgtgtc tcacaggcaa acataactct tagtatttct tccaatattt actttcatgt   35520
ttctttcttt ctttcttttt ttttctttga gatggagttt tgctcttgtt gccaaggctg   35580
gagtgcaatg acgcaatctt ggctcaccac aacctctgtc tcccgggttc aagcgattct   35640
cctgcctcag cctcctagta gctgggatta caggcatgca tcaccacgct cggctaattt   35700
tgtacttttt a gtagagatgg ggtttctccg ggttggtcag gctggtctcg aactcctgac   35760
ctcaggtgat cctcccacct cagcctccca aagtgctggg attacaggcg tgagccactg   35820
cgcccagcaa cttccacatt tctaaataac atgcttctac tgctattttt tttttcaatt   35880
ttagacattt ttttactttc actatagttc tatcagaatt cagtgtgtac gttattatgc   35940
ctaagtaaat agtcatggtt gcttacgtat tatatttctt tgattgtgtt tcttatttga   36000
tgagaaagct gtgttttttg ctctgggttg aaactggaga gaggacctgg ggaggaggag   36060
gaggacagat gaagttggtg actgtacctt catggccata gctgggttct cagcacccgg   36120
ggatctgctg atcacctact cataggccag gcccctatcg aagttctagg tgacccagtg   36180
ctggggacgg gggggccacc tgcaaggtct aatcatggag gtgggggcta cagtgttggc   36240
ttgtgctggg gccagcatcc ttaggaaggc atcttggagg tggaggagac agccgccac   36300 ttcttgattg gggccttcag cagcaccagc ttcttgggca ggctggtgct ggctttcatc   36360
accatgtcgt gttcaatctt cttccagatc ctgacttcta ggttcagctt tcctcagacc   36420
ctggttcctt tcagaggcca ttgctgctgc cttgctcttt gctggcttgt gccttgatta   36480
tatgtctttg tacaactttt tgttttcctg gagttaatct tcacatctgt tttcttggag   36540
ttaatcgtta cctctatatc gcttgcttat tattctttgg cctttttgtc ttctcacacc   36600
ttccaacttc tttgtaatat gtgtttagta caattttttca tgacaggtag tttactgaat   36660 cagttttttcc ccagtgtggt catccaactt gagttatcca gctctctgcc ccagtctggg   36720
caggttgatc ttcaggtctg tagtacactt gtatcctagg acttctcttt gccattagcc   36780
tggaatttcc tttgcagttc tcccgttgga tgcccagttc ctagatgcca tatgtttttc   36840
tatcgtctag tagcttcctg agagaagatg aatgggaggg aaattgtatg aggttttgca   36900
ttcataaaaa tgccattttt tttcctgtac acttggctgg gtatggtgtt ctggggtaga   36960
aatcattttc cctcagaaat gcaaagtctt tgccctgttg tcttaaaatc tccaacgtga   37020
cccgattcct taacctatga atgtactttt ctttggaagc tttccatttt tggggaggtg   37080
aagtgctagg tacttagtag gccttttaat ttggaaactt acatcccttc agttctggga   37140
aaattttctt aacatttctc tgagaagttc ttgcctttta ttttctgtgt tctctcctga   37200
aattggttag ttggatgttg gtcctcctag attgactcac atcttacctt tttcttttct   37260
ttttctggta ctttttagat atccatctca aactcttcta ttcattgtta tgttttttaac   37320 ttctttcttt tctttgtctc ttgatggggt cttgccctgt tgcccaggtt gtggtgcagt   37380
ggtgcgatca tagctcactg cagcctcaaa ttcctgggct caagcagctg ttctgcctca   37440
ccctcccaag tagttgggac tacaggtatg caccaccacg tccagctatt ttctttactt   37500
tttttttttt tttttttgaga tggagtccta ctctgtcgcc caggctagag tgcggtggtg   37560
ggattttggc tcacttaagc ctctgcctcc caggttcaag cagttctcct gcctcagcct   37620
ctcaagtagc tgggattaca ggtgtgcacc accatgcccg gctaattttt gtattttag   37680
```

```
tagagccaga gtttcaccat gttggccagg ctggtctcga acgcctgacc tcaggtgatc   37740
cgcctgcctt ggcctccgaa agtgccggga ttacaggcgt gagcccatca ttagatcttt   37800
aaataccagt atctataagt cttttcctct tgagtcagct agtatccctg gaaggaaatt   37860
actcattttc ctgcttggag gctataagct tggctatgtt tatcctgcaa ccggggactg   37920
gaagggaggg gactgacagt gttgctggtc agggtgccct cttactttt gttttctgtg   37980 tgcatctcac gtctgtcctc agcctatgta aacacctctt gagattatcc ctctcaatct   38040
ttgccggagg tgggggaggg gctgcttcct gggctgcctt ggattggagg gaagacctca   38100
ggtgagtggg tgggaatttg cccaaggagc catgagacca gccactattt caccctctcc   38160
atccctccac tttcagatgt atgtggcgcc tccaaagccc gagctcttct tggcgtctgt   38220
ggcttcaata agcttgcttt tgctggtat ccctcctacc ctcccctgtc cccagcaaag   38280
cttgcatttg aacttcttcc tacgggctaa caaatcagtc agttatgtag ctcttgttac   38340
tttttagctt ccgaagtttt gttgacaccc gtagtctgct aatgtccctg ttctgttctt   38400
tctgttcgtg taaatatatg ctttatacaa cttctttaca tgattttgt ggggtttctg   38460 ggtagcagag cttcacaagt tcaatccagc gtgttggatt agaaatctcc caccctctgg   38520
tttattctta ttctcaaaat tacctgccaa acactgatac tccctgtttt ttccttttcc   38580
tgacaggaaa tgtacatacc atacaggaca gaaatcatta gtgtatccct tggtgaataa   38640
ccacaaagtg aacttaaccc ttgtaaccgc cacccaggtc aagacagaat attaccaagc   38700
actcagaagc ctctccccta ttcccccgtc actgctcctg ccttcctccc caaggtcatg   38760
actgctggct tctaattcca gagtctgttt ttaaattctg tgtacataga ccatggatta   38820
agtgttcttt ttgtctggtt tattttggtc gacattaagt tcatgagagt cttctatatt   38880
atcgtgtgta ttagtattcc tgtagttta ggagcttcat agcattccat tgtagggata   38940
taccacagtt tattcattgt attatcactg ggttgtttct agttcttggc tattgcgagc   39000
agtgctactg tgaccactct taggtgtgtc ttttggagta catgtgcagg tttccatctt   39060
gcacagctag aggtggagtt gttgggtgat agggtgtgtg catctcagct gcagtagaaa   39120
ctgccaaata gctttccttg agtgcttgta ccagctcacc cttttgccac tgtgtatggg   39180
gattccagga gctctggtcc tcgctagcac ttggaattgc tgatgctttt actcttagcc   39240
ttcctgatgg gtgttttctg gaatcacatt atgatttaa tttccattcc ttaaagtacc   39300
cttggctctg aagtttaatg attcatgcat ctcttccctt ttgaagtact cttacaggta   39360
tgttgtgcat gtgttgaaaa gtggcactat ctattctaaa atacagtatg cctcctctgt   39420
gtttgaacag ttgtagcgtg gccttggggc ctcctgttag ctggcttgga aagggattc   39480 ttgggattgt agagattaga cctgaggagg ccccttggag ctctctgact aaatttttatt   39540 ctttattatt ccaaactatt taagctcacc gtgtgctgac tcatcataat aatgagtagc   39600
tctcattgtg cttgtctatt tggactcata caatgattt ttttttttct ttgagacaga   39660
gtcttgctct gttgcctagg ctggagtgca gtggcacaat ctcggctcac tgcagcctcc   39720
acctcccagg ttcaagtgat tcttgtgcct cagcttctca gtagctgag actgcaggtg   39780 cgtaccacca tgcctggcta atgtttgtat ttttagtaga cggggttt caccatgttg   39840 gccaggttgg tctcaaactc ctgacctcaa gtgatctgcc ttcttcagcc tcccaaagtg   39900
ctgggattac aggtgtgagc cactgagctt ggccaaagta gttttttaag atgttagtat   39960
cttttcttgc agctaaaaaa gtttgtcaga gatgattcta ctttgttctc caggtgtttt   40020
```

```
ctcagggaga aattggaggc agtaagccac tgggggagtc ctgtggctgg ggggtgggt      40080
agtcctgtgg ctccttgtca gggagtcctg tggctggcaa ggagagaagt cctgtggctg    40140
ggttgggagg gagtcctgtg gctggggtct catcctgtgc ctaacagtgt ccagaggtgc    40200
cgagaccagc tcagtcgggg agaccctaac ccagcagcgc tagaggaatt aaagacacac    40260
acacagaaat atagaggtgt gaagtgggaa atcagggtc tcacagcctt tagagctgag     40320
agccctgaac agagatttac ccacatattt attaatagca aaccagtcat tagcattgtt    40380
tctatagatg ttaaattaac taaaagtatc ccttatggga aacgagggga tgggccgaat    40440
taaaagaaga ggttgggcta gttaaccgca gcaggagcat gtccttaagg cacagatcgc    40500
tcatgctatt gtttgtggct taagaatgcc tttaagcggt tttccaccct gggtgggcca    40560
ggtgttcctt gccctcattc ctgtcaaccc acaaccttcc agtgtgggca ttagggccat    40620
tatgaacatg ttacagtgct tcagagattt tgtttatggc cagttttggg gccagtttat    40680
ggccagattt tgggggggcct gctcccaata cagaggtctc gtgtaaattc cctgggaggc   40740
gataagcctc tgagaaacag actatgctaa ccacgccatg aaagagaaac ttatttataa    40800
atcagatgcc agttactagt ttactgctta tttgcccagg cgtagctctg acagagtccc    40860
cgactcatag tgcttgctca gtgcatgctg aacaatgatt ggaatcaagt catggctcag    40920
agcatagttt tgaataatgg gaaatggatg ttcttaagta acatagtcac caagataatg    40980
cgactagctg ggtcacccct tttcaatttt aggatatttt tatcaagatt taaatggcca    41040
tcattagagt tatagcactt tctcctttgg attgtcctag aggcccatga gaaagtattc    41100
cctaatttct taggagaaca gtttgtgggt agtatgcggt catgtccagt taaattgcag    41160
atatttccga tcgaagatgt tccagtcctg agaacttcgt gacattagca ggacttctac    41220
aagccatctc ttagggtggg gcatttactg cagttggcta gtactctttt ctccttaact    41280
ttgtcatttg ttgatttttt tttaactgtc cccaaatact gtgggcagag tgtatctaga    41340
attgaggcct ccaccattgc ggagaggaca tggatgctga gcagtcccct gagtgaaggt    41400
tataaagaag caaatagact acacatgtct gtaaactgct cttgagtgtc ccaaatttgg    41460
ggtacttcag ttcagctgta ggaaaagcct caaactgttt atactttgca agaattggaa    41520
acttctaatt cacgttaagt tttatgtaat acatgataag cttcatagga gcttcatctt    41580
ttatctactt ggacttttgc ttccgtaggt tttgttaaag gccttcatag cgaacctgaa    41640
gtcaagctcc cccaccattc ggcggacagc ggctggatca gcagtgagca tctgccagca    41700
ctcaagaagg acacaatatt tctatagttg gctactaaat gtgctcttag gtaaggtgga    41760
ggcatatgag tggaagagtc tccagcatgt actcaagata gacctttgaa ataaataaaa    41820
ccagatgatc cctcagcttc tagaccaggc tatttggcac tggttgattg aatgtgaact    41880
gcactggggc tgctgtgagc ccgcatgggt ctctgtgacc ctgcagatgc agccgtgccc    41940
agggactggg cagtgggtgt gggctggtgt gagccctgtc tgccacccag ggcctggccc    42000
tctgtctgtg tcggccatga ctatggtgag tcttgtaggc ttgagactgt gcctcgggtt    42060
cctgcgggtt ctctgtaggt cagttgacag tttctcctgt tgtttgggta actgtggaaa    42120
cgaacactgg caagtgctga agcgagcatg tggacgtgcg atatgaaata cgacctggc    42180
tttcaaaggc agtgaggctc tctggaaagg accttgctga gctagggatg tgggtgtgta    42240
gccattccca gtgggcctca tggcgtactc gttcatgatc atgtttgtgc catcttgatc    42300
tctcaggatc tcttcttttt taacagatta agccgggaat ctccaaacag tgagtcagat    42360
gttaagatgt cttgcttcca cccccacagg cttactcgtt cctgtcgagg atgaacactc    42420
```

```
cactctgctg attcttggcg tgctgctcac cctgaggtat ttggtgccct tgctgcagca    42480
gcaggtcaag gacacaagcc tgaaaggcag cttcggagtg acaaggaaag aaatggaagt    42540
ctctccttct gcagagcagc ttgtccaggt aggagcacag ggtttactct aggccctgca    42600
tgtgaatgac tgacattcaa agaaccgatt aatttggaag agaagcggca gaaccgagag    42660
ttagaggtgt ggactctgga gctgcgctgc tcgtttccaa ccctaggtgc tgacctctag    42720
ctgtcttccc tctgtatgtc cctgtcaccg tgagtcaaat gcgggtgatg cctcctcagg    42780
tgccgtgtta cctaagcctc tcagagacca ctgctaccct gtttctaaaa ccagaggtca    42840
cgatatgtgt tcatccaccc agtaaatact gattgagcac ccactgtgtg ctaggctctg    42900
ggataggggc tgggtataca atggtgagta tttcagctgc agcttctgcc ccgtggaggc    42960
tgtggcctag cacactggtc taggcacggt ggtatatgct cactcaagga gatagggacg    43020
tggtcgtttg gggtgtcgga acaaaatgtc ggaacttctc tttccaatgc agagaaacct    43080
tgcagtaatt ctaatgtact gtgattggca gttgacttca gttctttgta gcacgcttac    43140
tcaggttatt tcactaacta tgtaaccatg cagcctcatt ttaagcaatt ggattttttg    43200
aactttactt aaaatgttat gtcagggttt ttattgtgct taatgtgtgc catttagcta    43260
agttttgtag gatacgaaat tgtaagtggc ttaaaatgat tcttaataga atcatgaatt    43320
gaagataatg ctaataattt aagcactgag ttaggtagtg tttgtaaaat gcttagaatg    43380
cttcctggca catgttaagg ccatgtaagt gctgcgtgtt gataaacagc tgagcaaaag    43440
tggactctta agaaagtatt ggggctgaga gttctgttcc aaccagctgc cctttggtta    43500
tttttcagaa taaaagcaga gtctcatggg atatgacatt tatatttcct tcacaaaaaa    43560
cactgctgag tgttttgttg agtaaaaagg gtgtagccat ggtaataata catttaaaat    43620
atagtttatt tcatctttac cttgccttgt ttttttttta agctagcttt ttattgagaa    43680
ttccacacat acaaaagtat caactcatga ccagttatat ttcatttata atcctacttc    43740 tcccttttt tattatttga aagcaaaccc caattatcct cttatttcat ctataagtat    43800
ttcagtatct ctatagatga ggactcttct ttatttttaa aactttattt ttaaaatgat    43860
ggtcagatgc agtgttcatg cctgtaatcc cagaactttg ggaggccaag ctgggcggat    43920
cacttgaacc tgggagtttg agaccagccc gggaaacatg gcgaaacccc atgtcttaaa    43980
gaaaaaaatc agccaagtgt ggtgatgcat gcctgtagtc ccagctactt gggaggctga    44040
gatgggaggg tcacatgagc ctggaagatc aaggctgcag tgatccatga ttgtaccact    44100
gcactccatc ctgggtgatg gagcaagatt ctgtctcaaa aaaacaaaac tgcaaaacaa    44160
cgtcacaaaa cagtgccatt gttagacctg aaaatattaa acatttccta catcaaatac    44220
ccaccaactc attatcaatt tttctctcta ctcttttgga atcagcatct aaataaaatt    44280
ggtcgataag gattgtaaat ctctttgatg aactggttcc cctccatccc agttttttc    44340 ccttagagtt catttattga gaaaccagat tgtttgtctt ctaagttttc ctgtggtctg    44400
atatactgct tccatctcca ctgtgtaaat taacaccttt ttctcttctc tgtatttcct    44460
gtaaatcaat aattggagga aaagccttgt cagatttagt gtatatttta tatctgagtc    44520
cagtatttct tatataatat tttaagataa gtgtactctt ttaaaagta ttgaaactat    44580 atgctcaatt ttttttaact gatgctttta agaaggctgc ttgatcataa aagtttagag    44640
atcattggtc tgatgggaaa agcaaataat tactaaaccg tttagcaagg ttgaggtgca    44700
catggtgggg cctggagaag ttcagtcatg agccgtcact tatgggcacg tggaatctga    44760
```

```
cccggcacag agttgggaga agacaggagc tttatagaca gaaaatgtgg tctttgctaa    44820
gtcccaggag tgaaagggtg agacagtgct cacagcacac gagtgtgggt gcgtagacag    44880
agcaagggtg ggtcctgaaa aggcctgcag gctttctcat agattagcaa gagtgctggt    44940
tacggaggtt tctaacattt gtgaacagat cgaaactgtg ttaaattggg attgcagtaa    45000
tcctggaagg acagggatag agggtgaagg ggaaaaaagg gtatggatgt gagacttaat    45060
tgctgatttt cttaagacct ttctccaaag taaataaatg atgtggcaca ttttgaact     45120 ggcaaattct aaactctaga tatgattatc tctataacat atcttactcc atcttctttt    45180
gactaaaaac tgttcttaat taaattacca tgagacgttc aattcagcaa atgtagtttg    45240
gctaaccata tttaattaga atttaatata atcctaggcc tggccaaact attaagcaag    45300
tgtgggcaaa atattgataa ttttagatat gcaggaactt agtttgcttt ccatgtgtgc    45360
ttttcgaaaa aggaataaat tgaaaaatag aggaagccct gaaatccaag aagcaaactc    45420
tctcacctag gcatgcagta aaagcaattc taggatgatt gctgtttggc gcgtagttcg    45480
tattagaaac cattcttctt gaataaatag tatgtttaag aagctgggca gagggaaggc    45540
atatgcatat attatcaaca aggagggaga aaaaggcaat tagtaaccat ccataggagg    45600
gtcagcaaga tttataaagg aaatttgtga tccaagtatg aagcaaaata aggtgcagaa    45660
taaattttaa gcaagtaata gattagagta agagaaccca tttgaccatt aaccttggga    45720
cattctcttt caaatgacat ggagtagtac tgaaatcttt ctttctttct gagtctaggt    45780
tattgtgact ggactcagaa agaaatattt cattattgca gtgaataaca tttgtgaaca    45840
ttattgttca taaattatgc agtgaataac atttatgaac acgtgatgtg taagatacat    45900
actgtttatt tttagttaag ttttttggct caacttctag gcagagaaca ttaaatgtaa    45960
atagtgttac ctaggagcat gtaaatggaa atctccatag tatgaaagca gtgctgttgc    46020
taacagaatt taggaggggg cagatgaggt gaaggaaatg tgggtgctga tttccttatt    46080
acattgagag gagccaggag attctttgtt caaaatggat ggcttaagaa gtcaaagtat    46140
aagctgatta cgtagagcag gtacccaaaa atgttttgtg taaggggcca gatagtaaat    46200
attttcagtc ttgcaggcca tcccaagtct gtggcagcta ctcaacacta cctttgtagc    46260
atgaaagcag ccacaggcag cccataaatg tggctctgtt ccggtgaaac tttaggtaca    46320
aaagcaggtg caggccagac ctgacctgtg cactgtggtt tgctgacctg ggattcaggg    46380
gtatagaagt taccatcaga agagctaaaa gtgagacttt ttactttata ctcttctaca    46440
ctgtctgatt ttgaaaaaaa gaaacatgta ttttataata ttaaagatag ggttggcaaa    46500
tagcaaataa aaatacagaa taccagtgaa atttgaactt cagatacatt atgagtaatt    46560
ttatggtgta agtatattcc aaatcatgtg ggacatactt acactacaaa attatttgtt    46620
gtttgtttac agtttaaatt tgagtgcctt gtattttatc tggcaactgt aattaaaggg    46680
aaaaagaata aattcattat gttcatataa tgtgatatag caggggtccc caaccccag     46740 gctgcagagt ggtactggtc catgggtccc caaccccag gctgcagagc ggtattggtc     46800
catggcctgt taggaaccag gctgcccagc aggaagtgag cagcaggtga gctggcattc    46860
ccacctgagc accgcctcct gtcagatcag tggcagcatt agattcccat aggagtgcaa    46920
accctattgt gaactgcaca tgtgaggggt ctaggttgtg cgctccttat gagaatctaa    46980
tgcctgatga tctgaggtgg aacagtctcg tcttgaaacc atcccctggc cctgtggaaa    47040
aattgtctcc catgaaacca gtctctggtg ccagaaaggt tgggtagcac tgtgatatag    47100
tattaaaagt gctaataaat atggcatact gcctttaaaa tgtctggtag ctctttctca    47160
```

```
gtggcactca taatagtgtt ttttgatttt taaatgtgtg tcaagctgac tctcccctcc   47220
gtgtatgctg ggctttattt tcccttcct agtcaccagt tttgggaaat agagatcttc    47280
attctcatgc tgctcctcta gtgcaagtgc tccatttatt tttaaggaat taatataaca   47340
aaaaatcatg ggaatttaga aaacaacatg gaagctaatg atcacattgg tggaagtgat   47400
agggaaatat ttaggggag aagttaaggt ataaactttg tcaatgaagt cctattaaaa    47460
acaacaaaaa agtgaagctt aggatgcatt ttataaactc tgaccagaac acctgtgttt   47520
ctctgtttct aggtttatga actgacgtta catcatacac agcaccaaga ccacaatgtt   47580
gtgaccggag ccctggagct gttgcagcag ctcttcagaa cgcctccacc cgagcttctg   47640
caaaccctga ccgcagtcgg gggcattggg cagctcaccg ctgctaagga ggagtctggt   47700
ggccgaagcc gtagtgggag tattgtggaa cttataggca agttattagc aaggtctact   47760
cttacaatta actttgcagt aatactagtt acactctatt gattatgggc ctgccctgtg   47820
ctaagcagtc tgcattccat cttccttgcc aaaacttata atacaaattt catctttatt   47880
ttataaatag gggagttggg ctgggtgtgg tggctcacgc ctgtaatttc agcactttgg   47940
aaggatcgct tcagcccagg agtttgagac aacctggcca agtgagaccc tgtctctaca   48000
aaaaaaaaaa aaaaaaaaa attagctggg catggtggca catgcctgta gtcccagctg    48060
ctttggaggc tgaggtggta ggattgctta agcccaagag gttgaggctg cagtgaatct   48120
tgatggcagc tgcactgagc ctggtgacag agcaagatgc tgtctcaaaa taaatttaaa   48180
aataaaataa gagaattaaa gtttagcagg ttgggtggca aaatgaggcc acacatttaa   48240 agccctcct cctgattctt ttctctgcct tggctgcctc ctgtggcatt ttaggtgctg    48300
agaaatgaaa acagtaggga aaatagttcc aggatcctca tgttaatttg ccagaaatgg   48360
catcttcaag tcgtcagagg gatctgagag ttccttcctg gcctgacttg agaaaatccg   48420
tctgtcccca gctctgcgtc tgcctccact gcccagtcac ctcctctcca tgctcttggg   48480
gctgggccct accccaccat gcagtgctgc cctggagcag tgagcttggt gggtcctgtc   48540
tggcatgaga gctgccttg ggagctggat cccagcctct accactgggt ctggtgccta    48600
gcaggctatg gataaacttc tgctgactcc ggcctctcct aagccactgc aacgtggtcg   48660
gtgtagtgca cagtgtgtgt gcagcgtggc cttactcaca gcctccacat tagagagaat   48720
ctgactgaag tcttactgct gcctcgtgtg aacataaatg tttgccagaa ccatgagcag   48780
gaaatgttaa tctgccttgt ttcctgtcct ttacacggaa gaattttttt ctgtatggaa   48840
tgcgtgcctt acaataatg agtggaaata cccatcgcta atgaaaagtt atacttgact    48900
gttagtcagc taaataatct gagatttcta atacttttaa tttggctttt acaatgcaat   48960
ttatcttagc ttttttgatt tcttaggtca tatctttaga actatatatt tgaatgttaa   49020
tgtaattttc atattgaaat taaaatgttg aactgcgatg ttaagtgttt cctgtggaaa   49080
aacgttcaca ttttctctag ttttaaagtt gaatcaagct gtttgaagat tttcacattt   49140
cttctagatt ttatcagctt gttactttat ctgtcacttt ctgtgatttg cagctggagg   49200
gggttcctca tgcagccctg tccttttcaag aaaacaaaaa ggtgattatt tcagaaatca   49260
gagtcttgtg ttgaatctta ctgattttct tgtatttctg taatgtaatg tatcttgtat   49320
ttcttgtaat actgtattgg actctgtgta tatctcttct cagatgagtg attatatgtg   49380
tgaatgttgc tggaatctga taaccaggcc tgaatagttt tgtagggtgg cttttaaaaa   49440
ttactttcat atcagaattg ctttgtcata aattttgaac gcatcataaa tttctaatgt   49500
```

```
tcggggtcag cagacttttt ttgtaaaggg acagagtgta aacatcttag ctttatgggc    49560
catatggtct cttttgcaac attcagctct gccctgtgac aggaatgcag ttgtaaagac    49620
atgagctact ggccagctat gttccagtag aactttactt acagaaacag acaggctgta    49680
gtttgccaat acctgcctta gggaatgtgt tgttatattt tgtgagttac cttctcagta    49740
aattttattt agtattagtc aggaatatta ttaagtagct tcttttccag cctggtcaac    49800
atagtgagac ccggtctcta ccaaaacaaa acaaaacaaa aaaacagcca cgcatgtggc    49860
atgtgcctgt agcctcagct gctgctcagg gggctgaggc aagaggattg tttgagccca    49920
ggagtttgag gtcacagtga gctgtagtca tgccactgca ctccagccta ggcaacagaa    49980
tgagaccttg tgtcttaaaa aaaaaaagtt tcctttgttg ggttatttta atttggacct    50040
ggttatcatt tttcagccat atttaacttt gtacatatca gaatgttctg ataaaactta    50100
acttttatta aagtgtttgt gatataatct gctagttttg gtacacatta tcttttgcaa    50160
tgccagttat tttcttttcc agtgtgggtt tgcataggaa aagaattgct gtcactttct    50220
attttgaaat cttaaaagac tgatcctttt ttgtgtcatg atttgagtat ttaattgaga    50280
gcctaatgcc taatattatt tgcagtatta aatgggatct aacaggaat agcattctag    50340 ccttcattga attaagtaaa catttcttaa gagaacttgg aatctataat atttgcgtca    50400
tcatagtatg agatacttaa tcaagtttga gattttagtg aaacattgtt tagaagccaa    50460
aaggattcta ggaaaaatta atgtctatat tcttgaatta ggagagattt tgggacgtgt    50520
gactaagtta cgctgacact tgtttgtttc ttagtcgctt tttccagtgg cggtgagaac    50580
gaagatgact gattcacatt gctcagatga gtttatcctc ttctggctgg acatgggat    50640 atatcctgtc tcttttaagc ctttttggta ttttttcccc attgagagct gtgtcttcaa    50700
actcttctgt tatagctgga aaatcctttt taagtgaaat ctgcccaaat tataagacag    50760
atgaaggtag agttgtgttg gatataggat tagggtgaaa gtagtggggg tgtcctggag    50820
cctctcttct ggtggcagcc tagctcttgt gcctttgagg aaattaccct ggggacggct    50880
ctgtggaaca tatttgcaaa ccactgattt ggaagataga gatggctttt gttaagatct    50940
gaattcacct ttttggcatt ttatttgatt tctcaaggta aagaacttat tttgtaataa    51000
agtttcctat tatttagtag ataggccaag ttgctgtgtt aattccatgt agattttggg    51060 tttccttttgc tcattttttc actcttaatc tcacatcatt gtaagtttat ggaagttatc    51120
atacttctga cttttctttt gaagagcaga aattagaaat tcccaataat tattttgata    51180
gtgtcattta atgacactca catgtgatgt agccacaaag atttaatgag ttcagtttta    51240
aatcatatta agactgttgg tttcatttgt tctcattaat gtaattctga agatgaacaa    51300
taaaatgtat ttttagaact ttcaaatgaa atattatttc atccttccag atcatataat    51360
gcttaagttc tgattgttaa tcataaagtc tagaaaatta aaagataata aaatgaaagt    51420
gacttttagg tattagagtt ttattataaa ttctggtgtg tcattggagc tatgacatga    51480
atatttcaaa ggccaatagc attggatctt tacagttata acttaccatt tttaagttta    51540
agtagtaata tagattattt aataatcaaa atcaataaat attaattatt aaaatgtttt    51600
gtggtatagt ttgagaatca ttgcttttaa cttttttccat ataggtttat tgactttaat    51660
agcattctaa acataacatc tctacattct ttgtgtttaa tactgtggag gtataaaaat    51720
acttatatat gatgataaac tatattagag taaattaaat attcttatga gtttcatttt    51780
agagtgcatt tacttaattt tgaagtcctt attttttagca aactaaaagg aatgttggta    51840
cattatttac taggcaaagt gctcttagga gaagaagaag ccttggagga tgactctgaa    51900
```

```
tcgagatcgg atgtcagcag ctctgcctta acaggtagtt ctcactagtt agccgctggt    51960
gtggaccttc actgtctgcc ttccacccct tgcccttcct gctcgtcccc ctgcacctgg    52020
tggacagcac gactgggggc agcagtggag ccaggttgct taaatggggc atattcgggc    52080 ttctttata  atacttactc tgaagcttgt gtgtctgtgg tgtttgcatc atatatttgt    52140
tgttttccat ggtttaggct gttttaaaat taggtttatg cttgagcat  agggctttgt    52200 gagtagggga tggcaggtcg aaacatctca tgagttggat gggttatgct gggggttggg    52260
aaatgggatg aaaaattatg ggatgaaaaa ttgcctatgg atagtttaac ttgaaagaat    52320
ctgcctttgt ttacagatag ttatcttttt tcttttttga gatagagtct cacactgtca    52380
cccagtgcag atacccagtg tcactggagt gcagtggtgt gctcttggtg cactgcagcc    52440
tccgccttct gggttccagc gattctcctg cctcagcctc caagtagct  gggactacag    52500 gtgcccgcca ccacgcttgg ctaatttttg tattttttg  tggagacggg ttttgccat    52560 gttggtcagg ctggtcttga actcctgacc tcaagtgatc tgcctgcctc agcctcccac    52620
agtgccggga ttacaggagt gagccactgt gcccggccag ttacagatac ttatctaatg    52680
aaattctctg tgtactttat aaaagatgag gattaactga aggtactaat aactggatta    52740
tatgagggtg gttttggttg tataatccta tctaaaagaa tattttagct ataactgaaa    52800
gtaagactta aatatttaga gaggaaaatc tgaataattc tagtagtaat tatttattta    52860
caaaataaaa atagatttt  ttttgattac acaaattaaa caacaataaa acatcacagc    52920
aatccggata ctataaagct cacatgctta ccgacccaac tgcccaggga gtgaccactg    52980
ccaacagctt catgtcgacc tttttgccat aattttata  tagcctttt  tgttttaaa    53040 tggtaattta gaaagtcaac taggaaaatg tgttacaggt ttatcttcca ggagaatagg    53100
actggagtcg agatcttgaa tgtggcttgg aagaaggcaa gcccacccca gagagatgag    53160
ttgacagttg tttctgacca ctgcttgctt agagggcctg cgtgtctgtg accgcctagc    53220
tttgcgcccc tgactaggct gccccttaat tacaaatgtc tttatatatt gctccagcta    53280
aggcttggag tagtcggtta agaacttgaa cttcggtttt tgcagtgaaa cagcatttga    53340
gaatatcacc ttctgataag ccttatttta taaggtgggt actgtagtgg gaggcagtgt    53400
gagagatgct tgaaggatgc actgctgtcc tgcatttcag catcttcagg atgctgtgca    53460
gctgaaacat ttgataacgg tggaactgtt cgttattttg caagcctgtg attccctatt    53520
gaatgttttc tctcgccatt tgacaaatga gtgtttctct gtcttcagcc tcagtgaagg    53580
atgagatcag tggagagctg gctgcttctt caggggtttc cactccaggg tcagcaggtc    53640
atgacatcat cacagaacag ccacggtcac agcacacact gcaggcggac tcagtggatc    53700
tggccagctg tgacttgaca agctctgcca ctgatgggga tgaggaggat atcttgagcc    53760
acagctccag ccaggtcagc gccgtcccat ctgaccctgc catggacctg aatgatggga    53820
cccaggcctc gtcgcccatc agcgacagct cccagaccac caccgaaggg cctgattcag    53880
ctgttacccc ttcagacagt tctgaaattg taagtgggca gaggggcctg acatcttttt    53940 tttatttt   tatttgagac agagtctcac tccatagtgc agtggaggcc gggcacaggg    54000
gctcatgcct gtaatcccag cactttggga gactgaggca ggcggatcac ttgaggtcag    54060
gagttcgaga ccagcctggc caacatggtg aaaccctgtc tctactaaaa atacaaaaat    54120
tagttgggcg tggtggcaca tgtctgtagt cccagctgtt agggaggctg aggcaggaga    54180
attgcttgag cctgggaggc agaggttgca atgagccgag atcgtgacac tgcactccag    54240
```

| | | | | | |
|---|---|---|---|---|---|
| cccgggcaac | agagcaagac | tccatttcaa | aaaaaataaa | aaaataaagt | gcagtggctc | 54300 |
| gttctcagcc | cactgcaact | tctgcctccc | aggctcgagc | gattctcccg | cctcagcctc | 54360 |
| ctgagtaggt | gggattacag | gtgggcacca | ccacactcag | ctaatgtttg | tattttcagt | 54420 |
| agagacaggg | tttcaccatg | ttggccaggc | tggtctcaaa | ctcctgacct | tagatgatcc | 54480 |
| acccaccttg | gcctcctaaa | gtattgggat | tatagttgtg | agccaccatg | cccggccctg | 54540 |
| ccacctgcca | tcttttgagt | tcttccctgg | agacctagac | ctgaaccctc | ctgcttgttc | 54600 |
| tcttgttatc | taataccccct | attgacagcg | cagcttagat | cattaatgga | gagcttgacc | 54660 |
| tcatctgata | ccttcactga | aggaaacaac | ttagtgtctt | ttgtgttgaa | cactgaggta | 54720 |
| aaaaattgga | atagttgatt | atatgaactc | tgctaaaatt | gagtgcattt | tacatttttt | 54780 |
| aaggccttgt | tgggccctgg | ttaaataatt | attttttaaaa | atccttaagg | agcctattat | 54840 |
| aaacagatct | gtggtcttaa | tgaaatgtga | ttaatactgt | gcattatttt | aagaactttt | 54900 |
| gacttttcaa | aaaacttttta | caacattttcc | catttgatag | cggcataggt | ttaagcactt | 54960 |
| ctcatctcta | agttagtgga | caaaaaccc | tcatggatag | tctaataatg | tttgctacaa | 55020 |
| gtccatgttg | agttttatac | tccattttat | tttcagtttt | aaaaactgtg | gttaaatatg | 55080 |
| tgtaacataa | aatttatgtt | cttaaccatt | ttttgcgtat | acagttcgct | ggtattaaat | 55140 |
| acatttaaat | aatgtcatgg | aatcattgct | accacccatc | tctgtaacct | tttgatcatg | 55200 |
| taacactgaa | gctctgttcc | cattgaactc | tattcctcct | ttcccgccaa | gtccctggca | 55260 |
| accacgattc | ttctttctgt | cttctgaatt | tgactacttt | gggttctcat | atactttagg | 55320 |
| agtcacacag | tatttgtttt | acttagcata | atgtccccaa | agctcatgca | tgttgtagcc | 55380 |
| tatgttagaa | cttcctaatg | tttcaggcca | aatactattc | cattgtatgg | ataggccaca | 55440 |
| ttttgctttt | ccattcctct | gtccatggac | acttgtattg | cttcatgttt | tagccattgt | 55500 |
| gaatcatgct | gttatgaacg | tgggtgtaca | gatagctcct | ggagactctg | ctttccattt | 55560 |
| ttttggctaa | atacccagaa | atggagttgc | ttttacattc | caattttaat | ttaaaacatt | 55620 |
| catatcattg | agtgttttac | ttaatagtat | agtagttaac | aaacttaata | aaatagtatt | 55680 |
| ttggtaataa | tttgctggta | gtccattgtt | cagttttttt | aggtaaatta | cacaggacat | 55740 |
| ttcaagtgga | catgaaacat | cttgtgatgt | ggaatcatgc | cccaagctga | tggctaaaca | 55800 |
| tatgaaatac | catacccctaa | atttagtaga | tttagtcttt | gcaatttagg | agataacctg | 55860 |
| ttatattgtt | aggttttttgt | cgaaaagctt | tgtcctcata | tttccaactt | gctgtaaaat | 55920 |
| ttgtttgtga | agacaaatat | ttttgtatgg | gttttttctt | tttcatatta | aaagaaatg | 55980 |
| tccacattgg | aattttttttg | gagttttttag | agctaataga | gcttttcata | atgtagtggg | 56040 |
| aatgagtgat | cagtaagctc | ttagcagttt | ccatgcgtgc | atttctgtgc | cttgaaataa | 56100 |
| atgacagatg | agtacatttg | tgttctgtgt | gtaaaatgtg | ctctttcctc | attgcacttc | 56160 |
| catgttggag | ggcttgtctc | ttggtgatca | cacttcaaaa | ttctcacagc | ccccccttgaa | 56220 |
| ccgtttaggt | gttagacggt | accgacaacc | agtatttggg | cctgcagatt | ggacagcccc | 56280 |
| aggatgaaga | tgaggaagcc | acaggtattc | ttcctgatga | agcctcggag | gccttcagga | 56340 |
| actcttccat | gggtatgtgg | actacaggtg | atgcgctaca | aagtggtttg | tattcagacc | 56400 |
| tggacatctt | aattatatct | ttgcttccaa | gaagaagtcc | tttgatactg | ttttctgagt | 56460 |
| tctgaatagc | tgatgaaaat | gaccaattga | ggaataatca | tacttttttct | tgatctaaat | 56520 |
| cttatacttt | tgagttatct | tagcataaat | gtataattgt | attttaagtg | gaaatttgtc | 56580 |
| acttaatctt | gatttctctg | tttttaaagc | ccttcaacag | gcacatttat | tgaaaaacat | 56640 |

```
gagtcactgc aggcagcctt ctgacagcag tgttgataaa tttgtgttga gagatgaagc   56700
tactgaaccg ggtgatcaag aaaacaaggt gagggacata ggcttgagac gacttggtgt   56760
ttctgagctt gtgtgaggat ttaaaatcgc cctggctact gtctacttta ttgctttccc   56820
atccctgggc ctttaaattt cccctttaaa taccagctct tcccaggcct gttgttttct   56880
gcctttccag gtactaccca cagccttgag aattgcctga gttctgcctc ctttgagagt   56940
gtgccccaga caaatctatt ctgtactgaa tgtttccttg tctgatttct tggatcattc   57000
atttgatggt tgcgtatggc ctgcaacgtt tcttgttttg gttctactga actgttctaa   57060
aagtctctct tcatattatc tttttacatg taaatgtaac tgtcttcact tttaattcct   57120
caaggacaag gaatagcgtt tcacagttcg tcccatcaat cagaattata gcctttggca   57180
tctccctatc taccaggccc acttcctctt agatttgggc ttccccaggc tgttgccttt   57240
ccccaagtag cttctgcttg tcctgtagaa gacctttcat gctttgcttc tgcagcagcc   57300
gttcctgaat gccagtgtc aactgccttc ttaccacgcc caccctccct gcatgctgca   57360
tttatcccct gccacagccc tgtgaccctg tgtcctgctg cctctgactt gtctgtttct   57420
gcttggccat ggtctctgtg aggtcaggtg tgcatatggg cacaaaccag ggcatctctt   57480
tatccccagc acctggctta agtgctgctc tggaactatc tgttgaatga actaatgcat   57540
gaatgtattg ttgagtatga gacaaacaag tgtcattgtc tcctttctag ccttgccgca   57600
tcaaaggtga cattggacag tccactgatg atgactctgc acctcttgtc cattgtgtcc   57660 gcctttatc tgcttcgttt ttgctaacag ggggaaaaaa tggtgagtac aaaaggggat    57720
gtgcacagtt gaaggaaata actaggtttc agaggtcagc ttggtggcct gttttttgcct  57780 tgcgtgcagc agaggaagta gaatctgagg atgagtttgg ttttcactag ccgaggggag   57840
ggaggaaatg atgggagcag gtaggttatt gggtctggtt ttgttcattt gaaaacaatc   57900
tgttgtttga ggctgaaggt ggcttgggtg atttcttggc agtgctggtt ccggacaggg   57960
atgtgagggt cagcgtgaag gccctggccc tcagctgtgt gggagcagct gtggccctcc   58020
acccggaatc tttcttcagc aaactctata aagttcctct tgacaccacg gaatacctg    58080 gtatgttaaa agttcacatc ttattttctc agatttaatc attattgtaa aaactatttc   58140
agtattgact attttagttt tagagcagta agtgttttga gttcatttgg gatatttgac   58200
ctgcgttgta gctcttcaga aaacacatga atagtgaagt tctttgtttc atgggttccc   58260
tttagatgaa acccatagag gagaaaagta gaaacctcag cacgtaagag ccaacatata   58320
tacacatcgg atttaaacct aaagcacaaa ttgtgcctgg tcgcagtggc gctgagtcgc   58380
actcagccag gccaggcatt cacactcagg gtgagtggga accaggactg gctgaggcag   58440
cagtggaccc aagtctccat cgcgcccatg cttactatgg agccttctcg ttctctcttt   58500
ttctttgggt gagagggtac acttgtgttt ttgaatttat atgaggtaag tgtgtaatag   58560
ggttttttct aatctttttt aagtggaatc tggaattta atcagattta ttatctgaca    58620
acctagaatt ataatccaga aagtctgtgg tattgaggac atattggcaa tatgatgaat   58680
ctctaattct taaatcctga aactttttt tttttaatca cttagggtta ttatagtgaa    58740
gtcatttctg aatttggatc ttctcttcac acctctttt ctctttcctg agaattaagc    58800
ttttgtttcg agttagaaag ttgatagtag ggaattgttc catggctgag caatttatct   58860
ccacagagga acagtatgtc tcagacatct tgaactacat cgatcatgga gacccacagg   58920
ttcgaggagc cactgccatt ctctgtggga ccctcatctg ctccatcctc agcaggtccc   58980
```

```
gcttccacgt gggagattgg atgggcacca ttagaaccct cacaggtaac ggccagtttt    59040
tcagctgtgt tttttctagt tatgcttact aaggtttaag tttagatgat gatgtttgtt    59100
gcttgttctt ctggttagga aatacatttt ctttggcgga ttgcattcct ttgctgcgga    59160
aaacactgaa ggatgagtct tctgttactt gcaagttagc ttgtacagct gtgagggtga    59220
gcataatctt ctgtggaacc atttcttcac ttagtggaca ttttatcatt gctacaatta    59280
aaattggagc ttaataggaa atatttccat gcactctaaa gctgtaacca gtaataccca    59340
ccatgtatcc atctctcagc tttagaaaga aaacgttgcc agtaaagtta atgcttcata    59400
aacttcagtt taagttctaa ttctcagaat atttgtttga aatagacctc ttcctaaagg    59460
atatatttag aaataaccta tcattaagtg taaagtctgt tgaatatgct gggcacggtg    59520
actcacacct gtaatctgac cactttggga ggccaaggtg gaaggattgc ttgagcccag    59580
gagttcaaga ctatgggcaa catagttgac cctgtcccta cagaaaatta aaaaaaaaaa    59640 aaaaaaagt agctgggtat ggtggtgcat acctgtagtc tcagctactc gggaagctga    59700
ggtggagggg ggattgcttg agccccagag atcaaggctg cagtaaggcg tggttacacc    59760
actgccctct agcctgggca acagagtgag actgtctcaa aaataatagt aataataatc    59820
agttgaatta aaaaaaaaaa aaaaaaacc actgtgctag gcccatagta tggtaagagt    59880
taaagtgagc cttagggatt atttactcaa cctctgtttc tgtataaagt ggaataggct    59940
caattcttta agtgatagca tgttgaacct ttccatacca actggctcat aagtcacaac    60000
tggccagtca acaagagtaa aaattaactg gtaaaaatca aagcaaaaaa cctacaattg    60060
tcaaatttgt gggataactc cccctttttaa aatgtcatgc ctgacagtaa tttctctcta    60120
gtttccaggt tttcagtcag ttgtgtcttt tttgagcaga aggaagcatg ctaagagctc    60180
aatcttgtgg ctagctgggg gtctttgtgt cagccatgca tgtgatggtg cccctggggt    60240
cttggggctg caggggaggg gtacagcagt aggggcctgt tctgttctct cgtgctgtgg    60300
agtacatagt gacatagtgg ggtggtcctt ggtgtaggtc ccttgttcct accccctgggt    60360 ctgagattta tttagaagtg gtgttggggc tgtgcggcag gcccctctgt aactgatcaa    60420
tgtttgtgaa gttgctgttt gagagttgaa accatgacat aagcagaaat ggaaggaaga    60480
aagaaccagt tatgtgaaag ggacacattt acttttaagc ttgtatttac tgagataaag    60540
tattcttaat caatgttctt gagaggtgtg ggaaaaatgc aacatcctgg ttgcagttaa    60600
acccagaaca ttgtgtgttg aagagtgacg ttctcaaac cgtcaagacg cgggtactga    60660
gtgggactaa cctgctgtcc tcttgccttg gaccttgtgt tccagaactg tgtcatgagt    60720
ctctgcagca gcagctacag tgagttagga ctgcagctga tcatcgatgt gctgactctg    60780
aggaacagtt cctattggct ggtgaggaca gagcttctgg aaacccttgc agagattgac    60840
ttcaggtaag tgagtcacat ccattagatt tcatgaacta agctcaattg aaagttctgg    60900
gatcacttga tgcaaggaat gatgttatca agtaccctgt ccatcagaaa tccgagtggt    60960
ttaggtagat gacagtgatt ttctcctccc agtggctttt tgctgaactt tgccctatgc    61020
ttggaatttt attttatttt attatttatt tagagacaag atcttgctct gtcgcccagg    61080
cttgaatgca gtagcacaat catagctcac tgaagctttg aactctagga ctcaagtggt    61140
cctcctgcct cagcctcccg attagctagg agaataggtg tgtgccgtca cactggctaa    61200
tattttttgt agaaatgggg tcttgctatg ttgcccaggc tggtctcaaa ctcctgggct    61260
tgattgatcc tccatcttgg cctcccaaag tgctgggatt acaggcatga gccactgtgc    61320
ctggcctaga attttaaaat ataagtagaa gagtagattt ttttttttgg tagtcctcgt    61380
```

```
catttaagta ttctggatag tgggaataaa agagcttaga attttcatc tttgtcttaa    61440 acttttaaaa aaatgtagct tatattaatt ctgcttgttt aaaaagaata tactcttcat    61500
tatactgaac ctaggtaaga cagctggttt atattttgtt gcaattaaaa aacgtgagct    61560
gtggttgcag tgagccaaga ttgtggccat tgcacttcag cctggcaaca gagtgagact    61620
tggcctcaaa aaaaaaaaaa taacatgagc tgtgttggca ctttcatttt ctaagagtag    61680
ttttggctgg agaagttttc tttcagtact ttcttttaga agggaaattt cctttataa    61740 tttagggttt gttttttttt tttccaagcc accttttata gagcccttgt gggttatttc    61800
atttaatcct tagaatgttt ataaatctgg gcttgttctc ggctccaccc acagataggg    61860
acgctgagcg tgcatgagtg ggcagcaaga tagcaggtta tggagggccc agctcacccc    61920
ttctgtggct tgagccaatt ttatagggca cttacagagt cttttgaaat agtatttatt    61980
ttgaagaaaa agaaaaacag tttactgagt actgtcttat tgagtctgga attgtgagag    62040
gaatgccacc tctatttatt taaagccatt ggccttttt gttgttttga gtaagtgctg    62100
cccaaggtcc ttccagggca cctggatgag cctgctctgg agcaagctgg cggtaagtgt    62160
ttactgagta actaaatgat ttcattgtta aatgtgctct tttgttaggc tggtgagctt    62220
tttggaggca aaagcagaaa acttacacag aggggctcat cattatacag gggtaagcgg    62280
tttatttttg tgagatgctg ttttaccttc aagaaggtga aagtgaggct ttccttgtgg    62340
aatttctcta aatgcattcg tcatgtttta gatgtttatt tcacagttta tatcatgaaa    62400
gttataatct tgtcatatgg atttaagtct agtaatgttg agttcttct cactagcttt    62460 ccaaaatatc ttacctaaaa tttagtcaaa tacaagatta tgtttatttt tattatcctt    62520
ctctctaaag cttttaaaac tgcaagaacg agtgctcaat aatgttgtca tccatttgct    62580
tggagatgaa gaccccaggg tgcgacatgt tgccgcagca tcactaatta ggtatttacc    62640
aatattttat ctcttttcct tttttggttg aagtactaaa agatacgaga atggaaagag    62700
agggaagaat tcaaaggatg tagagcagta ttcctgaatc tgagctcatt tcagccattc    62760
tattcttaaa ctataatgaa aaaaaaatcc aaaaaagtct aaaattataa ttaaaaaaac    62820
aacaaaatac taactgtcca ttgtaaaaag taatgcactt tcattgtaaa aattttggac    62880
tatagagaat agtactaaga agaaaaaaaa aatcaccttc aattctgctg ccacctggag    62940
gtaatcactg ttaatatttt gctatatact ctatgagttt cttgttcaaa atcaggtcaa    63000
aattacatgc aattttgtaa tctgacaatt tccacttaat attttattag cattttcctg    63060
ttatgaaaca gtaattttag ttatgggtcg ttgttttgct atgcggttgg gataaaattt    63120
tatatacttt ttttggcaat tacttattat acataaatgt ttgtgtatag ttttcttttt    63180
ctgagaattc ctggaagttg agttaccagg cccggctttg aatttttttt tttattttt    63240 ttttgagaca gagtcctgct ctattgtcca ggtgctatct cggctcactg caacctctgt    63300
ctccctggtt caagcgattc tcctgcctca gcctcccgag tagctgggat tacagggca    63360 caccaccacg cccaattaat ttttgtattt ttagtagaga cagggtttca cgatattggc    63420
caggctggtc tcgaacttct gacccgtga tccacctgca ttggcctccc aaagtgctgg    63480
gattacaggc gtgagccatg cgcctggcc aggcttaaaa tttaaaacaa atcttctaat    63540
agctttatgg aggttataat ttacattct tgaaatgtac tcactttgag tgtatagtaa    63600
actccaattt tatcacattt ctgtcacccc aaatgtatcc ttgtgcccat tgctgtaac    63660 ctccggttcc tgccccaact cctaggcagc cactcatcta ttttctgtcc cttaagattt    63720
```

```
gtgttttcgc caggcgctca tgcctgtaat cccagcactt tgggaggccg aggttggtgg   63780
atcacttgag gtcaggagtt cgagaccagc ctggccaaca tggtgaaacc ttgtctctac   63840
taaaaataca aaaattagtc ggatgtggtg gcacacgcct gtaatcccag ctactcggga   63900
ggctgaggca ggagaatcac ttgaacctgg gaggcggagg ttgcagtgag cagagatcgc   63960
gccactgcct tccaacctgg gcaacagaga gagactgtct caaaacaaac aaagatttgt   64020
attttctgga catttatag tactgggtc atagtataga tggacttttg catttggctt    64080
cttttactta attgtgagat tggttcttgt tgtagcatgt atcagtagtt tgttcatttt   64140
tattggcgaa agtattctat tatatgaata ataccatatt ttatctatcc atcagatgga   64200
tattatagag ttcatgtttt ggctaattta tgaattatgg tactgtgaac atttgcctgc   64260 aagatttgt gtagacatgt cttcatttct cttgagtaga tcacctagaa gtggattttt    64320
aaataatttt ggtacttact gtgaaactgc tcttcaaaaa cataccattg ttccttcctt   64380
ccttccttcc ttccttcctt ccttctttcc ttcctcctt cctccctccc ttccctactt    64440
ccctctccct ttccctttcc cttccctttt tcccttcccc ttcccgcctg cctgcctgcc   64500
tgccttcctt ccttccttcc ttcgtttctt tctacatata cacatttttt taaatttcaa   64560 tggttttgg ggtacaagtg gttttggtt acatggctga attttggtta catggtgaag    64620
tctgagattt tagtacacct gtcacccgag tagtgtacct tgtacccaat atgtagtttt   64680
ttgtccctca ccttccagcc ttccgccttg tgagtctcca atgtccatta taccacactg   64740
tatgcccttg cgtacccaca gctcagctcc cacttctgag aacatatagc agaaacatgc   64800
caaagtatac tcccactacc agaatgtgat tgtgcctgat tcttctcacc agtacaaata   64860
tttcaaaaaa agttaaatat gtatcagttt tttgggcaga agttgatact tctctttatt   64920
tatttatttt ttttgagata gggtctcatt ctatgatgcc caggctggag tgtggtggtg   64980
cgatctcggc tcactgcagt ctctgcctcc caggttcaag tgattcccac gtcagcctcc   65040
caggaagctg gaattacagg cgagggccac cactgccagc taattttgt atttttggt     65100 agagatgggg tttcaccatg ttggccagac tggtctcaag ctcctgacct caagtgatcc   65160
acctgccttg gccttccaaa gtgctgggat tacaggcgtg agctaccaca cccggctgat   65220 atttctttt aaaataactt accttctttt gaaagtaata catgtttaat gaacagaatt    65280
taaggaaaat ataaaaaaac gaaataatct ttgtaatcaa actactgaaa agaaaaccaa   65340
agttacattt tggtgcatat tctttttcat tttcatcatt gtaatttgca tttctttgat   65400
tacttgtgag acactccttt catttactta ataggtttat atgacttgcc tattcagaga   65460
ttttgcagct ttaccatttt ctgcaaatga tagcaacttc tttttgtttg tttgtttgtg   65520
gagacagagt ctcgctctgt cactcaggca ggaatgcagt ggtggaatct tggctcattg   65580
caactattgc ctcctggggtt caagcgattt tcctgcctca gcctcccaag tagctgggat   65640
tacaggagtg tgccaccatg cccggctaat ttttgtatct ttagtagaga tggggttttg   65700
ccatgttggc cgggctgatc ttgaactcct ggcctcaagc ggtcccctg tctcggcctc    65760 ccaaagtgct gggattacag gcgtgagcac cgtacccagc cagtagttac ttcttatatt   65820
ctagaaaaaa ttctactcat gatcaagtct ccatgaggaa agagacttta attgaagatc   65880
atggggcttg cagaccaata tgataaaata gttcattgtt tctaaaagta ttactgagtg   65940
ttgatggcag atatgaaccc ttttgttttt gtaggaaaat gttacccgta ttctccattt   66000
gaattcagtt tagatttgtt aggaatcgca gcttaagctt tgccatctgg gagtgtttgg   66060
gacagttttg cagacaaaat tgcaaaagtg cctaaggaat gcagctggca ttcagacctg   66120
```

```
ctctgtgctc agtactctgt ggacagacac tgttcagcac ttgttgatca gaaggtttag   66180
aaagagaact ttcaaagttg gttttaatt aaagcattta atagtgtaaa tagaaaggga   66240
ttaaatttta tgacagacaa aagaaagtac agcacccagc tgggcgtggg ggctcacgcc   66300
tgtaatccag cactatgggg ggctgaggtg ggtggatcac gaggtcagga gttcaagagt   66360
tcaagaacag cctggccaag gtgatgaaac cctgtctcta ctaaaactac aaaaattagc   66420
cgggcgcggt ggcaggcgcc tgtaatccca gctactcagg aggctgaggc aggagaatca   66480
cttgaacctg gacggcagag gttgcagtga gccaagattg caccattgta ctccggcctg   66540
ggccacagag tgacattctg tctcaaaaaa aaaaaaaaaa gaaaaaaaga aagtacagca   66600
cccagttatg tccgagtggg tgcatgagag tgaccctgag attggagaca acgctgtcac   66660
gtgcttgaag aacgccacct gagaaagggg gcgagaagtg gtgtccgctg gtaaccagag   66720
gtgttggctt agccatctgc agggaggagg gtggtctatc acaggtgagt ttcatctact   66780
ttcttaagca aattaacctt acttttgtgt taggcttgtc ccaaagctgt tttataaatg   66840
tgaccaagga caagctgatc cagtagtggc cgtggcaaga gatcaaagca gtgtttacct   66900
gaaacttctc atgcatgaga cgcagcctcc atctcatttc tccgtcagca caataaccag   66960
gtatgctgac ccagtggcat cttcacattg tcgggaaaat gcccttcct gatgcctttc    67020 tttaggcttt aattgaaaac attttatttt ctagaaaaaa gcttcagctc aggatgtttg   67080
agtgtaggtc agtcctttga taggatatta tcattttgag gattgaccac accacctctg   67140
tatttaagct ctgccacaat cactcagctg tgacactgta aatctcttaa tagtttatta   67200
cattccatgt gctgacagtt gtattttgt ttgtgacact tacgtattat ctgttaaaac    67260 atttcactt tagttgtgtt acctttaaag aggattgtat tctatcatgc ctgttgattt    67320
tttggtgagc gggctattaa agtcagtgtt atttagggtt atccactagt tcagtgattt   67380
gcgagattat cattcacatt tattgtggag cttttgaata tcgtgtcaaa tggccacata   67440
tatcccattc ttatctgctt cttaggtgag tgggacacag tgctttaatg aagctataat   67500
cttcagaatt ctagcttgca gagaagattg cagaagtgat aagacttgtg cttttaatt   67560 ttgtcttta aatgttattt taaaaattgg ctttatatga tactctttt ttctgctgag    67620 taacagtgtt ttacaaaact tggactaaat gacttctaag cttaaatgat cacttgatgc   67680 ttttttctg aattaggaac tcagcttatc aaatatcaaa gtcataattc ctgaataaat    67740
aacgtctttt ttcatgtaaa gactgcttta aaaacacat ggaaggctgg gtgcggtggc    67800
tcacgcctgt aatcctaaca ctttgggagg cccaggtggg caggtcgctt gagctcaggg   67860
gttcaagacc acccagggca acatggcaaa acccacctct actcaaatac aaaaaattag   67920
ccaggcgtgg tggcgggccc ctgtaatccc agctactcgg gaggctgagg gatgagaatc   67980
acttgagccc cggaggcaga ggttgcagtg agccaagatt gtgccattgc actcccagct   68040
tgggctacag agtgagactc tgtctcaaaa aagacacac acacaaacaa aaaaacatg    68100 gagacatttt tttggccacc ttaatatttc ccctcagata atttcctttg tttaaactca   68160
gaactggcat tttctctctt ggagaagatt caggacaaat actcctttaa gataagtaga   68220
agcagtgaaa gaggatttga ttatcaggaa tttgataagc ttagaataaa ttgttgcttc   68280
ttaatgtcat ttcagaagat gaatattat taatagatgc caactgagat atcattaaaa    68340
ttgattacta actactactt ggaaaagtct cccagttcca aacttcagca ggcctcttga   68400
caattcagct gtggtcaatt gggtcttgcg tgatagatac aatgaccaat tgtgcagcag   68460
```

| | |
|---|---|
| agtgtgctgc ttagctgcct attctgttag cattcatgtg ttaacttaaa atcataatct | 68520 |
| ccttagtttt gttgagtgtc tccgtggaca agacactgtg agggatacaa aatcagattg | 68580 |
| gctttattca aaccactggg gtattataat tcatttataa tttattttat tttttgcctt | 68640 |
| ttttccatgt gttctaaagg aattagagtt tgtatataac tataatgggg gatagaaatt | 68700 |
| gacatgtgcc atgaagggaa tgcaaaaaag tgccgtggga gatgagaagt ggagaaagga | 68760 |
| atttcttttt tcttggaagc aggaataact tcatgaagca tgtatttcaa cttaaacaga | 68820 |
| tagtaggcaa cgctgtaagg ggagtatggc tgcagcaaaa gtgttcgggg cagactggga | 68880 |
| ggaagggagg gaataaaattc agccattgtt atggaataat gatcaaaatt tattttcagc | 68940 |
| ccgtttcact taaaagttga gactgcttaa cttttttttaa tctttaatct taaactttta | 69000 |
| aatgccattt gatctttaaa aatatatgtt ttaatagtgt atttaagtc tctatatttt | 69060 |
| tgttattaga atatatagag gctataacct actaccaagc ataacagacg tcactatgga | 69120 |
| aaataacctt tcaagagtta ttgcagcagt ttctcatgaa ctaatcacat caaccaccag | 69180 |
| agcactcaca gtaagtctct ttcttgatcg gtccttactga cattgtaata gttttttggta | 69240 |
| gcttgtatgg ccagttagtt gtatggtcat cttacggtga ggtgcttgtc ttacagctct | 69300 |
| tacttatcca tgaggcttgc taagaaaattg tgcttctgtg aaaagaatct cagcttactc | 69360 |
| caggaatgta aatgactatg ttttttctga ttattaaagt aatacacgcc caaaataaaa | 69420 |
| aaattcagcc aatttaggaa gacacaacaa ttaaaataag ccaggcatgg tggctcatgc | 69480 |
| ctgtaatccc agcactttgg gaggccaagg ttggggggctc acttgaggtc aggagtcgga | 69540 |
| taccagcctg gccaacgtgg tgaaaccccca tctctactaa aaatacaaaa attagctggg | 69600 |
| cgtggtggcg ggcgcctgta atcccagcta ctcaggaggc tgaggcagga gaatcgcttg | 69660 |
| aacctgggag gtagaggttg cagtgagctg aggtcaagcc actgcactcc agcctgtgca | 69720 |
| atagagcgag actctgtctc aaaaaaaaaa aaaaaaaaag aaaagaaaaa agtaaactac | 69780 |
| tgtcacctgc attggtaatg tatcagaagt ttaaaatgtc tagattataa ttaactcagt | 69840 |
| gacctggtaa tatatactaa gggaaaaata tttataattt acatttttac attttatttt | 69900 |
| ttttaatttt attattttttt ttttgagaca gagttttgct cttgttgccc aggctggagt | 69960 |
| gcaatggcat gatctcagct caccacaacc tccacctccc gggttcaagc aattctcctg | 70020 |
| cctcagcctc ctgagtagct gggattacag gcatgcacca ccatgcccgg ctaattttgt | 70080 |
| atttttagta gagacagggt ttctccatgt tggtcaggct ggtctcaaac tcccaacctc | 70140 |
| aggtgatccg ccctcctcga cccccccaaag tgctgggatt acaggtgtga gccaccatgc | 70200 |
| ctggccttac atttttataa taagaattta tgttgctgac attagaaaag aaccataata | 70260 |
| tccaagaatc caagaataat taaattatgt acatatgcta gtatatagtg tgatgctttg | 70320 |
| gagaattttt aacaatatgg agatgtataa tctggattgt aatattgagt gaaaaaaggc | 70380 |
| agaatacaaa cctggtgggg gtatagtcgg atttcagtta agaaaaataa tatttacata | 70440 |
| tatacatttc tcacactggc agataatcac caagataaat tttgggattg tggatgattt | 70500 |
| ttttcttctt tatattttttc agatattctc aaattttcta aaatgagcaa gtataacttt | 70560 |
| tgttatcaga aaaaaataat atacaaaagt aatgttaatt tgctggtgac caggttaaac | 70620 |
| cttttattt ttattttttg agatggaatc tcactctgtt gcccaggcta gagcacagtg | 70680 |
| gcatgatctt ggctcactgc agcctccgct tcctgggttc aaatgattct ctggccccag | 70740 |
| cctcctgagt ggctggaatt acaggcgtgt ggcaccacac ctggctaatt tttgtatttt | 70800 |
| tagtagaggt agggtttcac caggttggtc aggctggtct cgaactcctg acctcgtgat | 70860 |

```
ccacccacct cggcctccca aagtgctggg attacaggcg tgagctactg cgcccagcca    70920 gacctttta ttttatttga caaaagaaat acttccatgt tatagaagac taaatattgt    70980
ttgggctgtc tgcagtatgg tcttcccttg atttgttcaa aatatcgtaa actttgctta    71040 tttatttta ttgtggccga ctgtgtcggg cactgttgta ggcttgggat ggaaaaacag    71100
gattcctgcc cttagggttt ctgcaggctg gtcagggaga cgatgtggta agctggagct    71160
cagctcctaa ggatgtgcag gggcagttga gaggcggaag ggtgggagat cattccaggg    71220
tgtgggcagc acaggaacct ctcttcattg ggatataatt gccattctga taacacgtgt    71280
ttgaggtgtc taaagtagga agttgtacca tggtgggaca gatatcctgt ggttatcata    71340
cacagatctc agttttcttc tcattgtttg tacttttat aaagggtaac aggagatata    71400
attcaataaa cctttgtggt gtttgggtgt gattttattg tttctttctt ctcagtttgg    71460
atgctgtgaa gctttgtgtc ttctttccac tgccttccca gtttgcattt ggagtttagg    71520
ttggcactgt gggtatgtat tttcctcagt atatattaat agttgctac aacagtatga    71580 cataaacata gttattagga tgcccttttt cttctttttt aagtctttta tcaatttggc    71640
tttttggaaa aatatctgat ggaatacttg tttctgctat attagctgtg tgagactagt    71700
gacaggagct gtgggaaatg aatgccaaat gttcttaggc attgatggga atttcagggt    71760
gtggtcttca agttcattta agggaatttt catatgctgg caaaaggctt ttctcattag    71820
cttgactctt tccaaaatta tttgctgtga attagaagtt taggaacctt ttttcactta    71880
attgtgacct agcatacgaa atggtgatga tttaggaact actgttcttg tattaacagc    71940
ttttatttaa aaatgatttt cctccagtag atggccctac tagcatctgg gaaataattt    72000
caagtcttct ccagcattca ggaataggct ttcattttgt gtatcaatta ctgagaatga    72060
ttttggtgac tcacatcaca tttgagaagt aaacctgcag atttcttgtg tgtgtcagca    72120
aatgaccaac tgatatttgc ttgaagtgga ttacattatc tgctctagaa tgattgcttt    72180
cccaccttcc tcacatacag actgagcagc tacggtttct aatcataggt ctggcactag    72240
acttcacttc tgggcaactt tggcattgga gtaaaatgta ttaatttaaa gaaagttaaa    72300
aatccgttca agtaaacata cagttctaat acttttaca atttaaaata tagatttaaa    72360
tgataaaata aaaagaaaa tatgggtaga caccataatc ctcgtttctg catctgttca    72420
caaggggttg atatttatga gttctattct ccatatccat tctatgttct cttaatgctc    72480
agtcagcacc tcaggtggtt ggagttcaat gcttggtagt ttgacttaca ctgtctttc    72540 taggggattg agccctgggt agtcctgctt atttgaggtt gcaatttgtc tttcaataac    72600 tttactaca agatatggcg tgttaaagga taccattggg gaaccaacat aataatatca    72660
ggaaaactaa ccacgtcaga cctgccccat tgtgtatcaa gtacactatt tttccatagt    72720
aataaagagt tcaccccagc caattctctt ttattttgtg cctgtttact caatggcatt    72780
aacatgccca aatgtctggg tagctgtctc atctccagtt cagcagaacc attgtcatat    72840
gccctagtaa aagcattcct tcattggaca cttaggcccc aatactttca ttcagatcta    72900
ctacctgatt tcatttctca aatgattttt atggagctct gatttatagg aaagatgtta    72960
gttgattaaa aataaaacaa tttctgagct ggtataaaat gtattgtgac atgccttcct    73020
cttggaattg caagagaaag gaagactgtt gtttgcttaa aaattgtcta taatttgact    73080
ttgcaaatgt ctgcttccag agtgcctcca ctgagtgcct cagatgagtc taggaagagc    73140
tgtaccgttg ggatggccac aatgattctg accctgctct cgtcagcttg gttcccattg    73200
```

```
gatctctcag cccatcaaga tgctttgatt ttggccggaa acttgcttgc aggtactggt    73260
actgagttga aacagggact ccaggacttg gattttgatt tccttagggg gaatgggggt    73320
ggtgagcata tgaggggaaa atactataag gtcattgcca gtgatggctt gtcccttag    73380 tcaaatttca gatgttacct atatgcataa acacatgcag ttggcagctg ttctgtgctg    73440
agtattttaa agtagcctct tcccaatata gcccctcagt taactacaag taaactcatt    73500
ttgaatttca ttttaatggg caccatatgc cagtactccc tcgggcactg ggatgttaag    73560
aaagtataat gtatggactt cattctcaag ttagttttag attagagggg gatacacgta    73620
aacaaaagtg cagtggtcac acagagtggc cctaatcact ctccttgggc agatttatgg    73680
gctggtagga aagagcacaa cacggagagg gtgtagcacc ttggcgatga taatggagga    73740
tgtggccagc aaggaagacg gagtccattg aaattgattt tgggagaagt tgccaatctc    73800
catgaaagaa ttggggcctg tgctatttgc ttcaggggc tataggagag tttcgtgaaa    73860
gggactaaaa gatgagtatt ttaataagat cattcatcca acttgaacat gggctggagg    73920
agaaggtagg gagactcagg agattaatgt tgatgctaag gcaagataat ggctttggga    73980
ctgtagggaa gacactgatt gtaagagaat gaaggaggca gaattgccag gcctggttca    74040
ccaactgaac ttcggttgtg aagacaaaga aacctgggat gacttcacat cctgggcagg    74100
tgtgtggtgg tgacagtcat ggaaattggg aacacagatt tgtgcgggaa acatcagttt    74160
cagtttgagt ttggcttatc agttgaatat caggcacaga tgtctggcca actctcaaca    74220
tagggtctta aatgacttca gttccccaag caatttgtcc ttcccatgct attggggtgg    74280
agaggtaatg tctgtgccca tatcacagcc agtgctccca aatctctgag aagttcatgg    74340
gcctctgaag aagaagccaa cccagcagcc accaagcaag aggaggtctg gccagccctg    74400
ggggaccggg ccctggtgcc catggtggag cagctcttct ctcacctgct gaaggtgatt    74460
aacatttgtg cccacgtcct ggatgacgtg gctcctggac ccgcaataaa ggtaatgtcc    74520
cacttgggtg ctggattcat acagccttaa tgactatggg tttccagact acctttgttt    74580
agtaatctgt cccttcttta ttctctttt gctttaaatg aacaaaattg ctcagattgt    74640
gacactaaat ttaacatcaa aatgtgacca tgtggatggg tgcagtggct cgtgcctgtt    74700
attccagcac tttgggagac tgaggcaagt ggatcacttg aggccaagag ttcgagacca    74760
gcctgggcaa catcacgaaa ccccctctct actaaaaata caaaaaatta gatgggttgg    74820
gccgggcgtg gtggctcaag cctgtaatcc cagcactttg ggaggccgag gtgggcggat    74880
cacgaggtca agagatcaag accatcctgg ctaacacagt gaaacccgt ctctactaaa    74940 aatacaaaaa aattatctga gcatggtggc gggcgcctgt agtcccagct gctcgggagg    75000
ctgaggcagg agaatggcgt gaatccggga ggcggagctt gcagtgagcc gagatcgtgc    75060
cactgcactc cagcctgggt gacagagcga gactccgtct caaaaaaaa attagatggg    75120 catggtggtg cgtgcctgta atcccagcta cttgggaggc tgaggcaaga gagttgcttg    75180
aacctgggag gcggagtttg cagtaagcct tgattgtgcc gctgcactcc agcctgggtg    75240
acagagtcag actctttcca aagaagaaa aaaatgtgac catgtgtttt atagctcttt    75300
tagtatcatc agtcactgtt atccctaaga gggaaatacc tagctttagt tttaggtttc    75360
cagcattagc caagaaagct cagaattgat gttcctggcc aagtacctca ttgctgtctc    75420
cttaaatctt ggttaatggc tactgtcctg gctagcatag ttatggagca tttccatggt    75480
tgtagaatgt tctgccaatc tcagggacag ttttgctttt ctgtgaagca ataaaatcaa    75540
cttcaaaaca aatgttaact atttgtacaa tggatttaag atagaccagt tcacatactt    75600
```

```
tttttttttt ttttttttga gatggagttt cattcttgtt gcctgggctg gagtgcaatg    75660
gtgtgatctc agctcactgc aacttctgcc tcctgggttc aaacgattct tctgcctcag    75720
cctctcgagg cagattacag ctgggattac aggcatgcac caccacaccc agctaatttt    75780
tttgtagttt tagtagagac gggggtttca catgttggtc aggttggtct caaactcctg    75840
acctgaagtg atctatccgc ttcggcctcc caaagtgttg ggattacggg catgagccac    75900
cacgcccagc ctaagataga ccagttcact tactgtttat atctgattac tctctctttg    75960
ccttgtcttc tacctttaaa aatctcccta ctaacttccc attctccttt agctgccatc    76020
agtcttctcc cttctctgca aacatctctg gagagtccca gcctcagccc acagagcttc    76080
ccactgctct gaggtggacc ttgtttgcaa ggcttctttg gctctcttgg cctggaccct    76140
gtctactact tcagccatcc ttccttaacc cctgctggtg gtttctgttg ccacactcca    76200
tagcagcgtt tcccgcccag atcatgtctt tacatctctg ggcactgctc tggtcctgcc    76260
tgcctttccc tctttgtatc ctgcaggctg ctaccccat cttgagtgtc ctcttcagtt     76320
ggctttcaga gggcctcctg ggtgttccct tacccacttg ccactcccca gtcactgggt    76380
tcagtccttc ctgcccacca gcacatgctt tctaggctct gtcctaggcc gtcttctctc    76440
tttgtagtct ctgggccagt gctgttctag agagtggcag aattttctat aaccatggca    76500
gtgctccata gctatgccag gcaagacagt agccactaaa cacatatagc tgttgagccc    76560
ttgaaatgca gctagtgtga ctgaagaact gaaccccgat tcggtttaat tttcattaaa    76620
tttaaattta aataaccttta tgtgggtagt ggctccagta ttgggcaggg cagcctgaga   76680 gtcgggctg ttctcctgtc ttcagtgtct agatgaggga cctcagagga cctgtctctg    76740
gagctgcagt tcaatgtagc cagctgcccc gtgacactta catatagctg atttgtggat    76800
atgtcagaca cggtgtgatg agctcagctt tctgtcctcc tccccacatc tgccctgcc    76860 ccatttaccc cactttgtgt cttatcaagc tagaaacagg tcaccacaag tcttcatttc    76920
cactcaccaa gtcttttgtt tccctacta aatattttgc gagaagaaag tgtgtacctt    76980
tgtattcaca tacatgtaca tgcacatata catgcacata tgcagggtc cccaaacctct  77040 gttaaaaacc ggactgcagg ccgtgcgtgg tggctcacgc ctgtaattcc agaactttgg   77100
gaggccgaga ccagtgcatc acaaggtcag gagatcgaga ccattccggc tcacacggtg   77160 aaacccgtc tctactaaaa atacaaaaaa aaattagccg ggtgtggtgg cgggcgccca    77220
tagtcccagc tacctgggag gctgatgcag gagaacggcg tgaacctggg aggcggagct   77280
tgcagtgagc cgagattgtg ccattgcact ccagcctggg cgacagagcg agactctgtc   77340
tcaaaaacaa aacaaaacaa aaaaaaaaa aaccaggctg cacaggaaga agtgagcaag    77400
cattaccatc tgagctctat ctcctctcag gccagtggtg gcattagatt ctcataggag   77460
cgtgtatgag ttcgttctca cacttctgta aagacatacc tgagacatat aaagaaaaga   77520
ggtttaattg gctcacagtt ctgcaggctg tacaggcttc tgtttctggg aaggcctcag   77580
gaaacttgca gtcatggcag aaggtgaagg ggaagtaggc acatcttcac atggcccaca   77640
ggaaaaagag agaaggagag agagagagag acagagagag agagagaaaa agaaagattg   77700
agagggagag aggagggaga aaggagagtg cctgtagggg gagttgctac acaaggagc    77760 accaggggga tggtgctcaa ccattagaaa ctaccccccat gatccaatca cctcccacca   77820 ggcccccacct ccgacactgg agattacaat tcagcatgag atttgggtgg ggacacagag  77880
ccaaaccata tcagagcatg aaccctattg tgaactgcac atttgaggga tctaggttgc   77940
```

```
atgctcctta tgagaatcta atgcctgatg atgatttgag gtggaacagt tcatcccga    78000 aaccatcccc cgccaaccct ggtttgtgga aaaattgtct tccacagaac cggtccctgg   78060
tgccaaaaag tttggggacc tctgcacata tgcatgcacc tgtacatgga cacataatac   78120
atgtacatat gcatacttta tattctctgc cacttctggt ccagactgat atactatctc   78180
atttggatta ctgcactagc cttttgtttt ggaaacagca ttttttaaaa aatttaattt   78240
aatttttttg atagggtg tcattctgtt gcccagcttg gagtgcagtg tcatgatcat     78300
agctcactgc ggcctcgatc tcccaggctc aagtgatcct tctgcctcag ccttctcagt   78360
agttgggact acaggcatac ccaccatgcc cagctaattt tttgattttt ttttttttt    78420 gagacagagt ctcagcctgt cgcccaggct ggagtgggtt ggcgcgatct cagctcactg   78480
caacttctgc ctcccaggtt caagtgattc tcctgcctca gcctcccgag tagttgggat   78540
tacaggcgcc tgccaccaca cccagctaac tttttgtatt tttagtagag acggggtttc   78600
accatgttgg ccaggctggt ctcgaacttg tgacctcgtg attagcccgc ctcggcctcc   78660
caaagtgctg ggattacagg cgtgagctac cgctcccagc caggaaacag cattcttgag   78720
ataattcata taattcaccc atttaaagta tataattcat tctctttagt atgcccacag   78780
agttgtacag ccatcaccag aatcagtttt agaacccata aaggaactct gtactcttta   78840
cccaaaacct ccatgcctcc agctgcaggc agccactaac ctgccttctg tctctgtgac   78900
tctacgtctt ctggacatta ctgtggatgg gctcatacag tcagtgagct tgtgactggt   78960
gccttctacc aagcagggtt ttcagtgtag cagcctctct gttttctttt ttttttttaaa 79020 ttgtgacgga acttctgcct cccggggttca agcgattctc ctgcctcagc ctcccgagtg  79080
gctgggacta caggcccatg tcaccatgcc tggctaattt tttttttttt tttttttagt   79140
agagatgggt ttcaacatgt tagccagggt ggtctcgatc tcctgacttc atgatccgcc   79200
tgcctcggcc tcccaaagtg ctgggattac aggcgtgagc caccatgccc ggctaacctt   79260
tcatttactg tctgcatttc ttccctgatg ccttccagtc catgcacccg attgtagcca   79320
ttcatcctat tatggtttaa ggtgactgtc ttagtcagca tgggttgcca taacaaaata   79380
ccatagcctg ggtggcttca acaacagaat ttacttctca cacttctgga ggttgggaag   79440
tccaagatcc aggactttcg ccttgccctc atgtggtgag ggggtgagga agctctgtgg   79500
ggcctcttat atatggatgc taatctcatt catgaggggt ctgccctcat gacccagtca   79560
cctcccaaag gccccacctc ctaataccat caccctggta attaagtttc agtgtataaa   79620
tttgggggac tatagacatt gaaaccataa caagcacttt tctaagatca gggagtgagt   79680
aagtagcaga gctaggacct caattccaca tgtcagtcat cttgccttca ctctgctcca   79740
tgatggctgc ctcctagagc attgggagtc tcgatgttct atatgctctc atgtgttgtg   79800
tattggagat agttgaggct ttatgaatac atctggattt gttgacttct agctttgctg   79860
gtaaccagct gtgaccttga ataagttact tcatctctga gcctgtttcc tcttttagaa   79920
acaggagttt aaaatgctgc tttgggttgg gcacggtggc tcatgcctgt aattccagca   79980
ctttgggagg ctgagatggg aggatcactg gagcttggag ttcgagacca gcctgggcat   80040
catagtgtga atcctgtctc cctcaagaaa ttaaaaaatt agctgggtga tgtggcgtgt   80100
gcctgtggtc ccatctactc tggaggctga ggtgggagga ttgcttgagc ccaggaggtt   80160
gaggctacaa tgaaatatga ttgcaccca tcctgggtga cgagtgagac cctgtctcaa   80220 aaagaaaaa aaaatgctg ctttgtaccc ctttcatgtc atggcgtcat ggccaacata    80280
gaatgccctg gttgtttgct gttggagggc atgggcctgg gggctccctg agggctcctt   80340
```

```
ccatcttcaa ctcattctct gtgcacctgt taggaagttg tgggccagtc cctaccatgt   80400
atcattgtgt gggtaaaagt aaataaaatg tgtacagtgt ctgaactgta catatcaggg   80460
tccaagaaca aaatgagtga catgggttag ctcttttaa taaatggtaa aaccaaatat    80520 tctaatttc agttttgtta tacttccatc acatgttttt gttttttgt ttttgtttt      80580 tgttttcta ttttaggcag ccttgccttc tctaacaaac ccccttctc taagtcccat     80640 ccgacgaaag gggaaggaga aagaaccagg agaacaagca tctgtaccgt tgagtcccaa   80700
gaaaggcagt gaggccagtg caggtaggaa acagcgtggg gaagggaggg acatgagtgc   80760
agcatctgtc atgtagaaac ataggattta agtaacttgg tgttttagag aaataaatat   80820
aatacacatc agtaaagtga gagaaagttt ctccaggtgc ggttcaagat attagaaact   80880
aatgactgat gtacacagac cacctttgg tctgaagcat ttctaagtgc cactggctga    80940
catgcagccc ctacagcctc caggcttcca gccctagcat ggagcatcac tctcctatgc   81000
ttccctggtt gcaggtgatg gctggagagg cctcctgatt ttcagtaagg gaagtggtgt    81060
agatgcttag gaatagatgt agtgagtgaa aaaactgatt ctgatatgtc aaaaattctg   81120
attggaaatg gaatatttac atttggaaga gctaaaggcg agagaaagtg gggataaagt   81180
catctgagtt ggaggagctt aaaccattca caagtttgga ggaccttttt ttacccatga   81240
aaaggtcaga acagaagggg ctaggattta ggtgtgactg cagtttattg aattcccatc   81300
catactgctc tcggtgggca gtggcagggg caggagagga gcctggcaaa gcatgaagtg   81360
actgctgctg cctctgctat ctgggacgcc tggccacctg tctgtacagt ctccctccag   81420
acccattctc acgctgtctc ttggcaccca ggggccagtg atggttctcc catttgtttt   81480
gtgtatatag catttatatc aaggctattt atttatttat ttattttatt tatttatttt   81540
tttgagacag agtctcactc tgtcacccag gctggagtgc agtggtgcaa tctcggctca   81600
gtgcaagctc tgcctcctgg gttcaagcaa ttctcctgcc tcagcctcct gagtagctgg   81660
gactacaggt gtgcaccacc acacctggct aattttttgt attttttatt agtggagacg   81720
gggtttcacc ttgttggcca ggatggtctt gatctcctga cctcgtgatc cgtccacctc   81780
agcctctcaa agtgctggga ttacaggcat gagtcactg acccggccta tttatttatt    81840
tttaattgac aaaattgtat atatctgtaa tatacaacat gatgtttgaa atatgtgtac   81900
attggccagg cgtggtggct cacccttt atcccagcac tttgggaggc tgaggtgggc     81960
ggattacgag gtcggggtt taaggccaaa ctggccagca tggtgaagag gtgccctac     82020 taaaatacc ccaaaaaaa aaaaaaaaa aaaagccgg gcatggtggc tcgcgccagt       82080
cgtcccagct acttgggagg ctgaggcagg agaattgctt gaatctggca ggtggaggtt   82140
gcagtgagct gagttcatgc cactgcactc tagcctgggc gatagagcga gactccgtct   82200 caaaaaaaa aaaaaagaa gaaatacata tgcattgtgg aatggctaat taacctgtgc     82260
atcacctcac gtatcattgt tttgtggtga gaacacttaa aatctactct ttcagtgatt   82320
ttcttgcata tggtacattg ctattaactg cagtcaccat gctatacagt agatctcttg   82380
aactcattcc tcctgtctat aaatgaaatt ttgtatcctt gaccaacaca ttcaaggttt   82440
tttttgagat ggagtcttct tcacccaggc tggagtacca tggcacgatc tcatctcact   82500
gcaacctccg cctcccaggt tcaagcaatt ctcctgcctc agcctcctga gtagctggga   82560
ttacaggcac atgctactgc acctggctaa ttttgtatt tttagtagaa gtggagtttc     82620
accatgttgg ccaggctggt ctcgaactcc tgacctcaag tgatccgcct gccttggcct   82680
```

```
gccaaagtgc tgggattaca ggtgtgagcc actgcacccg gcctcaagcg tttttaaaaga   82740 tgctctttc taaggattga ctgtagtaca ggaggaagat tgacctgttg aaaagcctca    82800
gcctttacaa gtgtaaaatt atcagtatat tactatcatc tttctgatga attaaataaa   82860
ctaaggactc caagtcaaaa gtcttcaaac tgaagtagaa tagttgtata tagtgcttgg   82920
cactttaata tttagtatcg gtttaatgat aatgtttgtg cctttgccgt ctttaaaaca   82980
tttttacatc atccctgttt gattacttgg tgtgctcatg aagttgttgg ccactaagga   83040
atcttaggct cagagaggtt ctggaattgg ccagtggtcc ttgaatcagc tgctcctatg   83100
attctctaac tgatttctca caaagcaaac aagcaatcat aacaaaacaa ctgtgcacac   83160
tgctcttctt atttttgttat ttaaaaagta cttaggctct acttatgttt gttagtcaat   83220
ttctcattac ttctagttaa tcaaaaggtc agaggaaata cttgaatatt ttcatactag   83280
aatactttaa aaaatcatga tttccagtaa tctctttaaa acttggcaag ttattttgat   83340
ctaaaagttt atcttttgtg tgcatatttt taaagcttct agacaatctg atacctcagg   83400
tcctgttaca acaagtaaat cctcatcact ggggagtttc tatcatcttc cttcatacct   83460
caaactgcat gatgtcctga aagctacaca cgctaactac aaggtatggg cctctgcatc   83520
ttttaaaaat atatatgcac acatacttac gtctaatgga tagttgatgt ttttcttatg   83580
atttgtagga tgtataagcc ctttgagata tgagttacat ttagtttttt caagtttgtt   83640
tgtctttcag ctttgtttat gatagcttct atcatacagg tgttttggat tttcatattg   83700
tttgtactca cagctaagat tgattacagt gacagagcta ggatgtgcag ccaggttata   83760
gggggaagtg gccctggtgg agtctggagg gatccgtgta caggcttcct tccctcccgt   83820
gaggctcaca caaaaataca gcaacatgct ggtcctgcag gtaccctctg cctaacatga   83880
gccacaattc cagactcaca gaagaaaagc aggtgttcgg cataaaccat gtgtttcaaa   83940
tagtctgggc atggtgagcc acttgttatc agctagggaa agtttatgtc agcgtaagaa   84000
actgttcacc agataccccc aagagccagc ctttctgtct agggatgttt tagttttta    84060 gttcattttt tttttaact ttaaaatttt ctgttcatct gcaatttgtt agatatgaag    84120
tatgtgtcta atttaattttt tgttttttggt tgtccccaat aatgtttaca gaagaatttt   84180
tctgcactaa ttggcttgag ttacttacat tctcatagtt ctctagtttc agtagtttca   84240
tttattattt tgttatatca atctatctgt ctgctcatct attagaagca tccttgttttt   84300 ttttttttct tttttagaca gagtcttgct ctgtcccag gttggagtgc agtggtgcaa    84360
ccatgcctcc ctgcagtctc agggctcaag tgatcctccc acctcagctc ctgagtacct   84420
gggactaccg gcatgtgcca ccacacccag ctaattttta cattttttgt agagacaggg   84480
tctccctaag ttgcctgggc tggtctcaag ctcctggctt aagtaatcct ccctccttgg   84540
cctcccaaag tgctgggatt acaggtgtga gcaactgcac ccggctacaa gtatacttct   84600
taattattgt agcttaatgg tatttatgag gggatcagtt cccctgttgt tctttagaat   84660
tttctggata ttccttcttta ttgattttgg gatgtgaaca atagaatcaa cttctacttg   84720
tagattgatt tagggagaac ttataccctca gatgttaagt caccctgtcc agaatgtggg   84780
atgctttcct atttgttcag aacttttaa attacctcag aagcacatga atttaaagg    84840 atttaaaaa aaacttaaag attatttcac atagctcttg cacatttctt gataaatgaa   84900
tcctcaggta ttcctctgtt tttgttacta atagttactt cttatgggtt ttttttcccc   84960
tgaaaatcat ttatcaaacg tatgtggctt attttctgaa ggatgtttga taattttgga  85020
agatatgaaa gtcttcatat tttacaaggt ttgaggtctc tttaagctgc atggttctca  85080
```

```
tgtcagctcc caaagcagaa gacggcatgt tgaaaaatgc cgtagagaag atacttcttt   85140
tccacctgtt ttcaactcat atcatcttga atttcagggc acctttccat gctcctagtg   85200
cttgctatct gtttattatt ttccttcctg aatacccctga actccagcat gttctgctgt   85260
aattctggcc tccctggcat cttggactcc tgtttccttt gctctgtcat ccccgcggtc   85320
agctcctgct gcgcagcttc tcagctgaag tgcgtttgga gtgcctggcg tgtcttgctg   85380
gatctttgag tattgcctct ggtttccttg gttccttctg ctgagttgct cagcgtctcc   85440
actccccatt tcttgtgtgg cccttcctgc actcctctga ttccttttgt cttccctggt   85500
ttcttgcttt ggtttcgagt ctccacagaa cttttgcagc tcttctgaag acctggaagc   85560
tttttcatct taattctcat ctcatgacct cttttccctt ctttgagagc tagaacttcc   85620
catggtgaac ttctctttcc agaattccat gccttctttt ccctcccact tacctgttgt   85680
ccaggagagg tcagattgct gtgcatattg gaggagaacc ctttcttccc tgggctcttc   85740
atctcacatg acatcaccac atcacctcgt tccttggacc ctcagtggtg tcactgctgg   85800
attttctttt cctttggctg gccttagggc acacccaggt tgactagcgt agtcatggta   85860
tttagatcca ctcacatttt cagtttctgt gtctgtctct tgcctgcttc tgacttcgcc   85920
cagagaaagc ttctctttca caagggttct tagatttatg ttcactgagc accttctttt   85980
ctgaggcagt gttttaccaa tatttatttt cctagtcagt ctcgccttac ctttcttgtt   86040
atgcatgtct ttggtcctga cccattctct gagtctgtaa aatagaattg ctgtataatt   86100
taattacatg aaatccttta gaatcttaac acatcttaca cctgatttaa tattttattg   86160
tatccaaatt gaaccaaccc tatgtgaatt tgacagtgat ttctcccagg atcctagtg   86220
tataaggaat aggacttagt attttctatt ttttgatata ccacatacca gatactgatt   86280
atgatggaca tttaaccctt ttttctcatt atgaaagaaa gttaggaatt atttcttcca   86340
gtagcgccag tgtaacctga aagcctttga aagagtagtt tttgtatagc tatctgaaag   86400
gaatttcttt ccaaaatatt tttccagtgc tgacaacaaa cacgcagaca caccctgcaa   86460
ggtgagtgta cggcgccgca cagtggaggc atctgctgca gccgtcgatg tttgtgtctt   86520
tggttgtaca ttatgagatc gtgacagggc cagtaaccgt gtgttctctc cttcaccttc   86580
ccaaggtcac gctggatctt cagaacagca cggaaaagtt tggagggttt ctccgctcag   86640
ccttggatgt tctttctcag atactagagc tggccacact gcaggacatt gggaaggttt   86700
gtgtcttgtt ttttctcctt gggttgtggc tggcacactt gatgtgcgtc ttctgggctg   86760
agttcatcta ggatggagcc tggttctcca gggtgcctcc gggagactcc tccctgcccc   86820
acgtgcttgc gtcacaggac ccaagtctga ctctgcctta gccatgaagt ttaggggga   86880
gtttctattt gtattctatt tttgtctgtt atcatgtatt agcttagacc cagtttagtt   86940
tggaaaatca gtgggtttca aaatgtgttt gtagagtcct ttatttctta acttgacctt   87000
ttcaagtgga aaggggcaaa acagacgggt aaggggcgg gcgggaggt gtgacttgct   87060
cttttgtgcc tgaggaagta acagagctgg ggttgacagt catattctct gacacagata   87120
gtctctgact tatctcacag aaagtcagcg gcagagcctg agttaaaagt ctcgtagatt   87180
ttcttttttct ttttttggt ggctaatttc agttttattt atatttgttt atttatttat   87240
tatactttaa gttctgggtt acatgtgcag aatgtgcagt tttgttacat aggtatacac   87300
gtgccatgat ggtttgctgc acccatcaac ccatcaccta cattaggtat ttctcctaat   87360
gttatccctc ccccagtccc ctcactcccc atgggccccg gtgtgtgatg ttctcctccc   87420
```

```
tgtgcccatg tgttctcatt gttcaatttc cacttgtgag tgagaacatg cggtgtttgg   87480
ttttctgatc ttgtgatagt ttgctgagaa tgatggtttc cagcatcatc catgtgcctg   87540
caaaggacat gaactcatcc ttttttatgg ctgtatagta ttccatggtg tatatgtgcc   87600
acattttctt aatccagtct atcattgatg acattcgggt tggttccaa gtctttgcta    87660 ttgtgactag tgccacaata aacatacatg tgcatgtgtc tttatcgtag aatgatttat   87720
aatcctttgg gtatatgccc agtaatggga ttgctgggtc aaatggtatt tctagttcta   87780 gaccttttgag gaatcgccag actgtcttcc acaatagttg aactaattta cactcccacc  87840
aacagtgtaa aagtgttcct atttttccac aacctctcca gcatctgttg tttcgtgact   87900
ttttaacgat cgccatccta actggcgtga gatggtatct cattgtgatt ttgatctgca   87960
tttctctaat gaccagtggt gatgagcatt ttttcgtatg tctgttggct gcataaatgt   88020
cttcttttgc gaagtgtctg ttcatatcct ttgtccattt tttgatgggg ttgtttgctt   88080
ttttttcgta aatttgttta agttctttgt agattctgga tgttaatctt ttgtcagatg   88140
ggtagattgc aaaaattta tcccattctg taggttgcct gttcactctg atgatagttt    88200
cttttgctat gcagaagctc tttagtttaa ttagatcccg tttgtcaatt ttggcttttg   88260
ttgccattgc ttttggtgtt ttagacatga agtcttgcc tatgcctatg tcctgaatgt    88320
tatggcccag gttttcttct aggattttta tggtcctagg tcttatgttt aagtctttga   88380
tccatcttga gttgattttt gtgtaaggta taaggaaggg gtccagtttc agttttctgc   88440
atgtggctag ccagttttcc caacaccatt tattaaatag ggaatctttt ccccattgct   88500
tatgtgtgtc aggtttgtca agatcagat gattgtagat gtgtggtggt atttctgagg   88560
cctctgttct gttccattgg tctatatatc tgttttggta ccagtaccat gcagttttgg   88620
ttactgtagt gttgtagtat agtttgaagt caggtagtgt gatgcctcca gctttgttct   88680
tctagcccag gattgtcttg gctatgcagg ctctttttg gttccatatg aagtttaaaa    88740
tagttttttc caattctgtg aagaaagtca gtgatagctt gatggggga tagcattgaa    88800 tctataaatt actttgggca gcaaggccat tttcacgata ttgattcgtc ctatccatga   88860
acatggaatg ttttttctatt tgtttgtgtc ctctcttatt tccttgagca gtggtttgta  88920
gttctccttg aagaggtcct tcacatccct tgtaagttgt cttcctaggt gtttcattcc   88980
cttagtagca tttgtgaatg ggagttcact catgatttgg ctctctgttt gtctgttatt   89040
ggtgtatagg aatgcttgtg atttttgcac attgatttg tatcctgaga ctttgctgaa    89100
gttgctaatc agcttaagga gattttgagc tgaaccaata gggttttcta aatatacaat   89160
catgtcatct gcaaacaggg acagttttac ttcctctctt cctatttgaa tacccttat    89220 tgctttctct tgcctgattg cgctggccag aacttccaat actatgttga ataggagtgg   89280
tgagagaggg catccttgtc ttgtgccggt tttcgaaggg aatgcttcca gttttgccc    89340 attcagtatg atattagctg tgggtttgtc ataaatagct cttactatgt tgagatacg    89400 tccatcgata cctagtttat tgagagtttt tagcatgaaa ggctgttgaa ttttgtcaaa   89460
ggccttttct gcatctgttg agataatcat atggttttg ttgttggttc tgtttatgtg    89520
atggattacg tttattgatt tgcgtatgtt gaaccagcct tgcattccag ggatgaagct   89580
gacttgattg tggtggataa gctttttgat gtgctgctgg attcagtttg ccagtatttt   89640
attgaggatt tcacatcga tgttcatcag ggatattggc ctaaaattct ctttttttgt    89700
tgtgtctctg ccaggctttg gtatcaggat gatgctggcc tcataaaatg agttagggag   89760
gattctctct ttttctattg attggaatag tttcagaagg aatggtacca tctcctcttt   89820
```

```
gtacctctgg tagaattcgg ctgtgaatcc atcctggact ttttttggtt agtaggctat   89880
taactattgc ctcaagttta gaacctgtta tcagtctatt cagagattca gcttttttct   89940
ggtttagtct tgggagggtg tatgtgtcca ggaatttatc catttcttct agattttcta   90000
gtttatttgg gtagagatgt ttatagtatt ctctgatggt agtttgtatt ctgtgggat    90060 cggtggtgat atcccctta tcgtttttat tgagtctatt tgattcttct ctcttttctt   90120
ctttattagt cttgctagcg gtctacctat tttattgatc ttttcaaaaa accagcacct   90180
ggattcattg attttttttg gagggttttt tttcgtgtct ctatctcctt cagttctgct   90240
ctgatcttag ttattttttg tcttctgcta gcttttgaat ttgttgctc ttgcttttct    90300 agttctttta attgtgatgt tagggtgtta attttagatc ttttctgctt tctcttgtgg   90360
gcatttagtg ctataaattt ccctctacac actgctttaa atgtgtccca gagattctgg   90420
tatgttgtgt cttcgttctc attggtttcc aagaaaattt ttatttctgc cttcatttcg   90480
ttatttaccc agtagtcatt caagagcagg ttgttcagtt tccatgtagt tgtgtggttt   90540
tgagtgagat tctcaatcct gagttctaat ttgattgcac tgtggtctga cagacagttt   90600
gttgtgattt ctgttctttt acatttgctg aggagtgttt tacttccaac tatgtggtca   90660
gttttagaat aagtgcaatg tggtgctgag aagaatgtat gttctgttga tttggggtgc   90720
agagttctgt agatgtctat taggtccgct tggtccagtg ctgagttcaa gtcctggata   90780
tccttgttaa ttttctggct cattgatctg cctaatattg acagtggggt gttaaagtct   90840
cccactatta ccgggtggga gtctctttgt aggtctctaa gaacttgctt catgaatctg   90900
ggtgctcctg tattgggggc gtgtatattt aggatagtta gctcttcttg ttgaattgat   90960
cccttaccca ttatgtaatg gccttctttg tctcctttga actttgttga tttaaagtct   91020
gttttatcag agactaggat tgcaatccct gctttttttt tgctttccat ttgcttgtta   91080
gatcttcctc catcccttta tttttgagcca atgagtgtct ttgcatgtga gatgggtctc   91140
ctgaatacag cacaccaatg ggtcttgact ctttatccaa tttgccagtc tgtgtctttt   91200
aattggggca tttagcccat ttacatttaa ggttaatatt gctatgtgtg aatttgatcc   91260
tgtcattatg atcctagttg gttatttttgc ccgttaactg atgcagtttc ttcatagcgt   91320
cagtagtctt tacaatttgg catgttttttg cagtggctgg tactggttgt tcctttccat   91380
gtttagtgct tccttcagga gctcttgtaa ggcaggcctg gtggtgacaa aatctctgca   91440
tttgcttgtc tgtaaaggat tttatttctc gttcacttat gaagcttagt ttggctggat   91500
atgaaattct gggttgaaaa tacttttttt aaagaatgtt gaatattggc tcccactctt   91560
ttctggcttg taggatttct gcagagagat ctgctgttag tctgatgggc ttccctttgt   91620
gggtaacccg acctttctct ctggctgccc tttccttcat ttcaatcttg gtggatctga   91680
tgattatgtg tcttggggtt gctcttctcg aggagtatct ttgtggtgtt ctctgtattt   91740
cctgaatttg aatgttggtc tgccttgcta ggttggggaa gttctcctgg ataatatcct   91800
gaagagtgtt ttctaacttg gttctattct ccccatcact ttcaggtaca ccaatcaaac   91860
gtagatttgg tcttttcaca tagtcccata tttcttggag gcttggttca tttctttttca   91920 ctcttttttc tctaatcttg tcttctcgct ttatttcatt aatttgatct tcaatcactg   91980
atatcctttc ttctgcttga ttgaatcggc tgtcgaagct tgtgtatact tcacaaaatt   92040
ctcgttctgt ggttttttagc tccatcaggt catttaagct cttctctaca ctggttattc   92100
tagccattag tctaacattt ttttcaaggt ttttagcttc cttgtgatgg gttagaacat   92160
```

-continued

```
gctcctttag ctcggagaag tttgttatta ccgaccttct gaagcctact tctgtcaatt      92220
catcaaactc attctccatc cagtttttgtt cccttgctgg tgaggagttg tgatcctttg     92280
gaggagaaga ggtgttctgg ttttttggaat tttcagcctt tctgctatgg tttctcccca    92340
tcattgtggt tttatctacc tttggtcttt gatgttggtg acctacggat ggggttttgg     92400
tgtgggtgtc cttttttgttg atgttgatgc tattcctttc tgtttgttag ttttccttct    92460
aacagacagg cccctcagct gcaggtctgt tggagtttgc tggaggtcca ctccaggccc     92520
tgtttgcctg ggcatcacca gcagaggctg cagaacagca aatattgctg cctgatcctt    92580
cctctggaaa catcgtccca gagcacgaag gtgtctgcct gtatgaggtg tttgttggcc    92640
cctactggga ggtgtctccc agtcaggcta catgggggtc agggaccccac ttgaggcagt   92700 ctgttcatta tcggagcttg aatgccgtac cgggagaacc actgctctct tcagagctgt    92760
caggcacgta tgtttaaatc tggagaagct gtctgctgcc ttttgttcag atgtgccctt    92820
cccccagagg tggaatctag agaggcagta ggccttgctg agctgcagtg ggctctgccc    92880
agttcgagct tccctgctgc tttgtttaca ctgtgagcat agaaccacct actctagcct    92940
cagcagtggt ggacacccct cccccagcca agctcctgca tcccaggtcg atttcagagt    93000
gctgcgctag cagtgagcaa ggccccatgg gcgtgggacc cgctgagcca ggcacaggag    93060
agaatctcct ggtctgctgg ttgtgaagac tgtgggaaaa gtgcagtatt tgggcaggag    93120
tgtactgctc cttcaggtac agtcactcat ggcttccttt ggcttggaaa gggaagtccc    93180
ccgacccctt gtgcttccca ggtgaggcaa caccccgccc tgcttcggct gccctccgt     93240 gggctgcacc cactgtccag caagtcccag tgagatgaac taggtacctc agttggaaat    93300
gcagaaatca cctgtcttct gtgtcgatct cactgggagc tgtagactgg agctgttcct    93360
attcggccat tttggaagca tcccttgttt tttgaggtgg agtcttgctc tgtcgcccag    93420
gctgacgtgc atcggcacaa tctcggccca ctgcaacctt gcctcctgg tttcaagcga    93480 ttctcctacc tcagcctccg gagtagctgg gattacaggc acctgccacc atgcctggct    93540 aatttttttgt atttttagtg gagatggggt ttcaccacat tggccaggct agtctcgaac    93600
tcctgacctt gtgatccacc cacctcagcc tcctagagtg ctgggatcac aggtgtcagc    93660
caccacgccc agccatattt tcagatctcc ctctctttgc cctaaaccac tgtgcttaat    93720
aagtagtttt tagtggccag cagtctccat gtataacaca ttttagcaaa atggaaaata    93780
ctatatgttt taaatttgaa cgtgagatta tactgaaata aaaatcatct aactgggatt     93840 cttttaaatag taagattttc ttttttgtat gtgggttttt ttttaacctt attattatga    93900
ctgtcatata tagaaatggc tgttttttcag ttacagtcag tgaatgtatc aaatgctgcc   93960
ttatccaaat aataaaagta aattattaat aagtcacaat ttaatgaaga ttgatgttag    94020 ttgatctttta tattcttgaa atcagccata tggttgtgtg tgtatgtata tatttttaaa   94080
ggtacataaa gataataagc tcatctctga aaattttttac atttggcata agaataactg    94140
gataattaag catcttattc tctggcctgt gtctttacag ttaaaggtag atttactcac    94200
ctctcctttt ttgttttttct aagttcatct ttttttgctgt tcaagacag aggcccattt    94260 tagctttctc gcatatcctt ttgtttgtac tttgaagcc tcacctgctt aattgttgag     94320
tttttatccg tggtctttta gagggggata tgtagggtag aagctttcac aggttcttgt    94380
ttgcacttgg cccctgactg ttttgaggaa tctccctcac tgactcacag catggcaagg    94440
tttcagatct ctttctgcca cacagcagtt ctgaggcagc tggaaagata tccagatgct    94500
tagattgtca ggccaggctt gagatataca aactattgag ccttatctgt gaccttgctt    94560
```

```
aggtgaaggc atcagagccc ctgcaccaac atgcataggc ctctgcatgt gtgcggggct    94620
gggtgttgag gtctgagcac aagtgtagct ggagaggtga gcttgatgtg gcgacgggta    94680
tgagcaggtt ttcttcagac ttctgtgagt ttacctagtt ccaggattta aaggcacaga    94740
gactttagaa ttaaaataga atcattttct ttttctaaat agcaacacta ggaataaaaa    94800
ataataattc cacattcttg acaggtaatg ttttttcttg tcttctaatc cttatttatt    94860
ccatactcat ttttatacat aattgaaatg tattatgcat tggattttc ttttgcatta    94920 tattatagac gattttcat gtaactcctt actgttccat tttatatgtt ttgtctggtt    94980
taagacttta tctgcaaacc gggaaactgt ctctacaaaa agaaaaacaa aaatagttgg    95040
ccgcagtggc atgcgtctgt ggtcccagct actcggggct gaggtgggag gattgcttga    95100
gccttgggag gttgaggctg caaagagcca tgatcatgcc attgcactcc agcatgggtg    95160
acagacttta tactgtctgt tttgggtgat ttgataatga tatgccctga tgtagttttt    95220
ttatatcttg tgtttcttgt gcctgggttt attgaggttg ggtctgtggc ttcatagtat    95280
ttttaaagtt tggaaaattt taggccattc tttctttctt tctttctttt ttttttttt    95340 gagacagtgt ctcgctctgt cgcctgcgtt ggagtgcagt gacactatct ggctcactg    95400 caagctctgc ctcctgggtt cacgccattc tcctgcctca gcctcctgag tagctgggac    95460
tacaggcgcc tgccaccacg cctggctaat tttttgtatt tttagtagag acgaggtttc    95520
actgtgttag ccaggatggt ctcaatctcc tgacctcgtg atctgcccgc ctgggcctcc    95580
caaagtgctg ggattacagg cgtgagccac tgcacccagc taggccatta tttcttcaaa    95640 gattttttt ctgccctgcc tccctccttt tttccctctc ttaaaggggc tgtgatttcc    95700
tgaatgattg cttagtgttg tcccatagct tactgatgct cttttcagtg tttgattgtt    95760
ttatgtgttt tctgttttgt atagtttcta ttattgtgtt ttcaagttct ctgatctttt    95820
cttctacagt gtctactctg ttgttaatct gttaatctgt tgttaatcct gtccagcgta    95880
tttttttttt tgttttgaa acagtctcac tctgttgccc aggctggagt ttagtggtgc    95940
gatatcagct cactgcaacc tccacctccc aggctcaagc aattcttctg cctcagcctc    96000
ccgagtagct gggactatag gcacgtgcca ccacacctgg ctaatttgtg tattttatt    96060 agagatgggg tttcaccatg ttggccaaac tggccttgaa ctcctgacct caggtgattc    96120
atccgcctcg gtcccaaa gtgttgggat tataggcatg agccaccgtg tctgcccct    96180 gttcagtgta tatcactaat tttgttttta tctctagaag tttgatttag gtcttttaaa    96240
aatgtctccc tgtgtttctg tttagctttg tgaacacaat tgtaataact gttttaatat    96300
ccttctctgc tagttctaag atcttctaat aacttcccag ttcttggtgt ttctcattgg    96360
ttgattgata ctcctcgttt tgggttgtat tttcctgcct ctttgtatgg ctgccaattt    96420
tttattggat gcccaacctt gtgaatttta ctttgttgga tgctatatat ttttgtgttc    96480
ccatagatct tcttgagctt tgttctgagg ttagttgagt tacatataga tggtttactc    96540
ttttgggtct tgctttataa tttgtcagat gggttggagc agtgcttagt ttaggactaa    96600
tttttttttt ggactaatta ttcctctta ggaataatta ggtaccatgc ttaggaggca    96660
agaccatcct gagtactcta cctaatgaac cagaaagttt gggttttcca gtccgcctgc    96720
tgagaacagt gacttttctag ccctgtgtga gcgctgagct ctgctccttc taatcctttc    96780
caatgcttct ttccctggcc tcagggagtt ttctcacaca catatctctg ctgagtactc    96840
gagagggacc ttccccagat ctccagagct ctctctgtct tgtttttctct tctctggtgc    96900
```

```
tctgtcttat gaactgtggc tgtcttggtc tccttagatt ctcagcacct cttcaattca   96960
gagggttgcc tgtccctcct ccttgtgcca cagcctagga actctctcaa agcagcgagt   97020
tggggcagcc atagggctga cttagtctct cgtctcccag ggatcactgt ccttcattgc   97080
tcatgtccag tgtcttgagg actctgggtt ttgtctgttt tgttttttgg tttgctttgg   97140
ttgtctcagg caggagggta aacccagtcc ctcaccctca ttgtgctcag tagtggaagt   97200
ctcactctat tacattagat attagtattt gtagcagagc cctggttccc tggtacttgg   97260
ggagctcttg aaaggccaga acagcatgc tttctcacct tttccagggc ttcagtttct    97320
ggtgcacatc aagcattcca tacacatttg ttaaagtcct tgttagaca agtagtgatt    97380
cacaggttct atttgtaatt ttttcagtta acatgtattg ggtatctgct gggagctagt   97440
aaaaacaaaa agtggtgtgt gacaaattca attctgacaa gaacaaccct aaacacttag   97500
aatatacttt gagcatatca gaattttaaa aatgtgtggc ccttgagtat ttgaaaccaa   97560
caagaatcta ttgcttatta gtagaggata ttttgttaaa caagtggaga gagaggcatt   97620
ttcagtctaa ttggtgttgg cttttagcag ctgatggaaa ccagttcgtg attagccagg   97680
cagtggtgaa acaggctgtg cattctgaat gcctaggtat ctaggcattc agaatggtgg   97740
cgctctttga gttagcatct tcttctttct tgattctttt tttttttttt ttgagatgga   97800
ctttcgctct tgttgcccag gtaacaactc cagtgcaatg gcgccatctc ggctcactgt   97860
aacctctgcc tccctggttc aagcgattct cctgcctcag cctctcaagt agctgggatt   97920
acaggtgtgc gccaccacgc ctggctaatt ttgtattttt ggtagagatg ggtttcact   97980
atattggtca ggctggtctt gaactcctga cctcaagtga tgcacctgcc tcgatctccc   98040
aaaatgctgg gattacaggc gtgagccacc actcccagcc ccttcttgat tcttgaaaag   98100
gacattgggt gctgtacatc tcgttataga tgttgataaa aatgcttgtg agaagagtaa   98160
cattaaggta gttatttggt catttttgca gattatttta agacaattct aggactgatt   98220
tgtggtaaat cacacattgc tgtatcatag ttgtgttcac tgaacatatt caggggctct   98280
acagatgcag ggctcttagc tgctttgcac acttctgaat tcctgccctg cgaacaggac   98340
tggataccta atagacaaca ggtacttgat aacagtttat tgaattaatg agtgaatgaa   98400
cagatacata aatgcatgaa agaatggttg taatgtatat aacttggatt tcaagacttt   98460
ttactgactg ttcaaaataa gaaattgaaa actttcctct gattttcctc tactatttac   98520
acaatttaaa tggaagttat cttgtacctt caatttctgt ctaggattcg tacaataacg   98580
ggtcatctct gagtcgctta atgtctcact tgtctttcta cagtgtgttg aagagatcct   98640
aggatacctg aaatcctgct ttagtcgaga accaatgatg gcaactgttt gtgttcaaca   98700
agtaagagct tcattctttt cctcttctgt taagacgttc gggtatgaca gcaaaacgct   98760
gctactcctt aagaggcagg cgctgttggc ataatcagct gggaggattg tggggtccag   98820
cgcagcactt tttggctcag tccatgattg agccaagagg ccatccttcc cttcactccc   98880
caggaggacg aggtctgtca ctgtggaggg cagaggacac cagaagctcc tctgcaacct   98940
cgctagttaa cttccagtcc ctcggagttt ctgtttagaa tgctcaatct catttagaat   99000
tgcaaggaaa cccaaaacgc ctatttaagg tacaaacagc acttcataca atatctcatg   99060
aggtattaat agtgattcac aggaagaatt tcacgctgtg agtctttgct aacatatcca   99120
gttatttaca gatggatttg atatttgtgt gggagattct taaaagtgtt gttcacgcca   99180
cattgttgat gcctcatttt tttcactgta gttgttgaag actctctttg gcacaaactt   99240
ggcctcccag tttgatggct tatcttccaa ccccagcaag tcacaaggcc gagcacagcg   99300
```

```
ccttggctcc tccagtgtga ggccaggctt gtaccactac tgcttcatgg ccccgtacac   99360
ccacttcacc caggccctcg ctgacgccag cctgaggaac atggtgcagg cggagcagga   99420
gaacgacacc tcggggtaac agttgtggca agaatgctgt cgttggtgga agcacgaaag   99480
agcaagcagg aaatactttg taaaagaata aaaacgaaaa atgttagcga acatcttcta   99540
atagtctgct gtattcagag aactctagga gatatatatg gttgatgcaa agatgattta   99600
aggcatagcc cggccttcca agaagtgtgt ggccagtgag tgagatgggc ttgggactta   99660
cacatctcag aggtgggggt agaggaggag gaacactgag tgggctgaga agcagccagc   99720
tctcattgcc aaagtgtgtc agcaaaccag aatgcagttc ataatgtccc cacccattca   99780
aagcacagga cctgtagagt ggtgtggcat gtgttggtgg cacttttcag gcctgtaaca   99840
aggatgaaag aacagcttca tagcagcaca gtagtgctgg tgttcagagg tgtgtgaagg   99900
ccatagaagc atcttggata tattaccttg tgttttgtca gctttatgac tagaagtctc   99960
ttttcactta aatttgtttt tttttttttt gagacggagt cttgctctgt cgcccaggct  100020
ggagtgcagt ggtgcaatct cagctcactg caagctctgc atcctgggtt catgccattc  100080
tcctgcctca gcctcccgag tagctgggac tacaggcgcc tgccatcacg cctggctaac  100140
ttttttttgt attttttagta gagacggggt ttcaccatgt tagccaggat ggtctcgatc  100200
tcctgacctc gtgatctgcc cgtcccggcc tcccaaagtg ctgggattac aggcgtgagc  100260
caccgcgccc ggcctctttt cacttaaatt tatgtttgtg tttttaatgc ctagtataca  100320
ggacttctta aattgcctta agtatgaaca ggtatttgag ttgctaatct gtatagtagc  100380
aataatagaa tcccttgttt ttccttttat aaatttagcg attaaatagc tacaattaaa  100440
acactagagt caggagtcaa ggaaaatacc catgttccag gctgtatgtt agtgatgtac  100500
ttactatata ttggagtttc aggagtaagt ctgtttcaat gctttctgta accatttggg  100560
gtattaataa gcatgtgagt gtgtgcatgt ttgggttaat ttcatatatg tttcttagaa  100620
gggatatcat tgatgtaaat attttaaagg cttgtcctcc aaaaaaatca tgtaatttct  100680
tctaaattac tgatctttta aatgaccttc acctttctct caaatctcac ttaagactgg  100740
gctgagtagt cagtttcctg tagcagaaaa aagctcagac ttgagtagcc ttctgcgagt  100800
gaggagactt gatggctgtc aggcagctgt aaactctaaa tagagtgtca ttatctgaag  100860
agggcgatgc tgccacactg agtggccttt caagttgttt ctcaatctga cacgttctga  100920
tcgtgtgaat gtgaaattgg tttgagcagg agtatatctg agtgcagagg agattattta  100980
aagatattct cattctctgc ttccctttta ttcccatttg gcagatggtt tgatgtcctc  101040
cagaaagtgt ctacccagtt gaagacaaac ctcacgagtg tcacaaagaa ccgtgcagat  101100
aaggtaaatg gtgccgtttg tggcatgtga actcaggcgt gtcagtgcta gagaggaaac  101160
tggagctgag actttccagg tattttgctt gaagctttta gttgaaggct tacttatgga  101220
ttctttcttt cttttttttct tttttataga atgctattca taatcacatt cgtttgtttg  101280
aacctcttgt tataaaagct ttaaaacagt acacgactac aacatgtgtg cagttacaga  101340
agcaggtttt agatttgctg gcgcagctgg ttcagttacg ggttaattac tgtcttctgg  101400
attcagatca ggtttgtcac ttttatcttt catccatcat acctgttcct aatttagtac  101460
aaattaccct aaaagacact gaaatctact ttaaagaaat gtggtctgca tgtttccctc  101520
atcagttgct gctgcttatc ttttttcatgc acctagctgg tgcagaaggc ctggggcata  101580
gccagcctca gcaagtcagc atccttgccc cagctcccctg gactcaaggc taacctgggg  101640
```

```
ttggctgtta gggatttcca aaggtttgtc ccatccactt gcctcccctc caaaataagt    101700
ttgaatttaa attgtgagat acaattaaga tttattgttt ggggaacatt tttgcaaaat    101760
ctagagttag tttaaacaga ttatcaatta ttaccataat tgatcatctg cagtttcaag    101820
ctatctaaca ggttcactta cctctttaaa aaggaatgga atttagcagg acagtaactg    101880
agacccgtgc tcctggagtc catgtgggag ctgtgtggct ctgcacaagc atttgcacgc    101940
ttcccctctt gactgcatta ccttcctcct atagttgctg tgggcaccag attctggcta    102000
gtcctgtccc ttcatgatgc acattttcct caagattcgt cccagttaaa tcactgcaga    102060
tgaaactgcc ttttcatcgt caaaatttaa ctgtcatttt tgagccgtga tcttgggcta    102120
ctttcttatg tggggtagga atatttgtga gttagaaata ttacacttct ctatttcctt    102180
ctagacgtaa atctgttaat cctgtcagca ctgttactca cctgaaaggg tctgtttccc    102240
taggagaact gagggcactc ggtcaacact gattttccac agtgggtatt ggggtggtat    102300
ctgcttgttt tttttgttgt tgttgtttgt ttttttttgt ttttttttg agatggagtc    102360
tcgctctgtc acccaggctg gagtgcaggg gtgcgatctc ggctcactgc cagctccgcc    102420
tcagaggttc acgccattct cctgcctcag cctcccgagt agctgggact acaggcaccc    102480
accactacgc caggctaatt ttttgtattt ttagtagaga cgaggtttca ctgtgttagc    102540
caggatggtc tccatctcct gacctcgtga tctgcccgcc tcggcctccc aaagtgctgg    102600
gatgacaggc gtgagccacc gcgcccggcc tgggtctgc ttttaatgaa ggaggcatca    102660
aggggtgggc tttgcgttgg cctgatgctt tcatctttct ttcacaaaac ctgtccgaag    102720
aaaatccgtc taaatgggcc attgctctcc tcaggaaata gtcattggga acttcttttc    102780
ctttcctttg acactaggag gctgactggg gagaagccct ggtctatggc tgtgggcagc    102840
aggggctgag aggagcaggc tctcaggggg gcacgggtac cccaagggaa gccagagccc    102900
tgatttgttc cattctagta agaacaaaga ctgctctggt ttcatgtttg ttctgattgc    102960
ctttcatcaa ccggtcccct ttctcccagt tcttaagatt cagtacagtg acagtttat    103020
gaacaagaat agaacactag aacagacaaa ccattgaact ctatgctgat aaagatttat    103080
tgagctcctg ctgtatgttt gcattctgcc cagaggctct gagaaaacca ggccatatgc    103140
tccatgcttt atccatggaa gctccccgtc aggttgggaa agctgacagc tgcagggaat    103200
acagtgtgac acaaaactgg ctcccatgca gcccttacgt gtcgcctctc agatggttgg    103260
gggacgaagg tcgactcctt tgggtatctt attactaaac cagtttcagg gaatctgtgc    103320
caccctatct gccattaacg tgaacagatg agtcccaag gtgtaatttt gggtattgtc    103380
tgatgtctct tggaatttat tatttgtttt tccaatgaga tttcacctca gggtatagta    103440
aagttgttga ggggattcct ggatgtgttc tgcaattatc taggctgatt tcagaataga    103500
gttatgctta tagtcaaatt tatcagctgt caagaatttt atttaaaatt tatgcagata    103560
agcaggagga aaagaagcct ggttttaca ttttaatcct attattgatg tgaaattta    103620
ttttccttcc tgtaggtgtt tattggcttt gtattgaaac agtttgaata cattgaagtg    103680
ggccagttca ggtaatagca ttttattatt ttagattttt ttcttcttct tgtgtactta    103740
catgtaattt aggttattaa gtgaatgttt aaactactgt taggcatttt tgctgttttc    103800
tttaaatgga aatctgacta acatactgtg cattttgct tctcttaaaa attaatgtat    103860
atctcaagac ttgtttggaa gtagttatgt atctgaaaat tccatatgtt gtcagtattc    103920
attgcacatt tcaaagcatt taattgtgtt gacagatggt ggaatgaaat cttgtggtgg    103980
agcactagtt tttaaatctt cttagagaaa gcagttttat ataatgttgt ctttagtaat    104040
```

-continued

```
tattatgcat ttgtattctc tgcagctttt tcttgctaga tgttgaggtt ttaatacttc   104100
ttgctagtcc attacaggtt tataattatt aaaagttaaa attcttttag tacctaaaat   104160
gcttaataaa cattgtaatt aggaaaattt agtgcagaag gaaagtgttc ccagattccc   104220
tggggtctgg aaacatagtg tttattctaa ttacatgaca cctccactgt gttttggggc   104280
aagttactgt ttctcttttg agtttcaatt tcttcaagag caaagaggca gaggagagct   104340
aggaagatcg tagctgctgt gccctgtgc cgtcgggtgc cttctacctg ctgcctccga    104400
acctttacac atgtccctgc tctgcgcgag ggcacagatg ggatgcactg tggcaggggt   104460
ggggttagag tagatcacgg acacctgtta gcttgatgtg tgcttgctgt caaggttgaa   104520
tcatgaatta ttttatgttg cttatattga tatgtatctt aattttaaaa gaaaggtcta   104580
aatggatgtt tttgttttta gggaatcaga ggcaatcatt ccaaacatct tttcttctt    104640 ggtattacta tcttatgaac gctatcattc aaaacagatc attggaattc ctaaaatcat   104700
tcagctctgt gatggcatca tggccagtgg aaggaaggct gtgacacatg gtaacgggac   104760
acacctttca ctgtcgtctt cggtgtcgtg atgtgcttgg cagtgttcgt tttcatatac   104820
ccactttgaa cgttgtcagt ggcagccatg tgcttctcag gctctgcatg tgtgtctgtg   104880
tatgtgaagg tactggttag agacgtttca aaagagaaga gagcatattc tttactctca   104940
gcaatttgta atcttctcag ggaaaaaaat tcaagaaaca gtaagataac ctaaggtaca   105000
gatagattct gaatataaag ttcctgttca ttcacatgaa acgctaaaag ttcttcactt   105060
gatcttagcc aaaaggccaa gaagcgatgc aacactaaaa attcttaaat cgaacttgcc   105120
gtgaattaaa ttttgatctc tcatccagtg gtattggaga tatagtttga cttgggttca   105180
gggctttctg ttttgcctga tgattttgct ggagcttaaa taaggaaccc aggagatggc   105240
cagctgtgca agcccccagc ctgtggaagg agctagtgtg gttttatgaa tgagttgcaa   105300
atctttcttt gagcttttg aactgatctt ccagcattgc cctattgacc cctccctgac    105360
tcctttgctg gaatctgtag gcttttgaac tttgacaggg acacatccta agaccccttgc  105420 aaactcccag atgtgagaat ggcactacta cttagagtct tttcgactca gcgtgtgtgc   105480
agaagagcat caaccgggct gtgttgcgag gcagggcctt ggctgacctc tcagtgttta   105540
catagctaag ccagttagtg tttgccacgg cctcacaagg gcttcagatt cacacagcca   105600
aagtatagat tattaaaggc ataggtgttt ggtttcctgg acttggaggg tctttggaca   105660
gaaaatcagt aggcaaccac acccagtact ttgtgctggg aagcttggtc atctgtgaga   105720
gggtcagaga gtatacccat gcgtgcatgc caccgaaggg tcagtgagta ttcctgtgtg   105780
tgcatgtctc agggccggag agagtatgtg tcactgagag gtcagagtgt ttgtgtgtgt   105840
gtcaaagagg gttgcattgt gcccttcact gaggggtcag agggtgcctc gcgtgtgtgt   105900
gtgtgtacgt gtgtgtgtgt cactgagggg tcagagtgtg cctgtgtgtg tgcttgtgtg   105960
tgcgtacatg tcactgaggg gtcagagtgt gcctctgtgt gtgtgctcat gtgtgtgcat   106020
acgtgtcact gaggggtcag agtgtgcctc tgtgtgtgct catttgtgag cgtatgtgtc   106080
actgaggggg tcagagtgtg cctctgtgtg tgtgctcatg tgtgagcgta tgtgtcactg   106140 aggggtcag agtgtgcctc tgtgtgtgtg ctcatgtgtg agcgtatgtg tcactgaggg   106200
gtcagtgttc ctatgtgctc atgacattga gggtcagagt gtgcctgtgt gccaatgaaa   106260
ggcatttctt atattttttt atatgtggtc atagtagacc agttaattta ttttgactcc   106320
tgtgttagac caaaataaga cttggggaa agtcccttat ctatctaatg acagagtgag    106380
```

```
tttacttaaa aaagcataat aatccagtgg ctttgactaa atgtattatg tggaagtctt    106440
tattgtcttt tcagatgaat caagtagatt attcttgaga ccaggaatgt tgctgttttg    106500
gttatttgga aagttttatc attttcaaat tgacttttga atttgagtca cctttttca     106560
gaagtggtgt taaattatag gagccctagg tttttttttct ttttttagaa gtcatcacaa   106620
aatgatcagt gttcagagga agagcttga ccttccacat ggtataatga ttgataacct     106680
taattcatct cttaccataa accaagtatg tgtaagggtt ttctttattt cttgaaagca    106740
ttttgtagat gttgagagca gttttccaaa tgtaatttcc atgaaatgcc tgataagggt    106800
acccttttgt ccccacagcc ataccggctc tgcagcccat agtccacgac ctctttgtat    106860
taagaggaac aaataaagct gatgcaggaa aagagcttga aacccaaaaa gaggtggtgg    106920
tgtcaatgtt actgagactc atccagtacc atcaggtaag aggaatgtat gttggaactg    106980
tcgtggatac tttattgacc cgtgcagatg aaggaagtg ccatgtggta acgctcactg      107040
ttaactgtgt tactttgaac caggtttggg ctttctgggg cctgggtaga tgccggtgca    107100
gggggatggg gagggaggcg gggggtgggg gggtgtggtg gagttgggga ggtgcagtgg    107160
caggaggtgt tgttggtgtg tatccttttt tttttttga gatggagtct ctctccgtcg     107220
cccaggctga gtgtggtgg cacgatcttg gctcattgca agctccacct cccgggttta      107280
agcaattctc ctgcctccac ctcccgagta gctgggatta caggcatgca ccaccatgcc    107340
cagcaaattt ttttttttgt attttagta gagatgggt ttcaccatga tggccaagct       107400
gtttcgaact cctgacctca agtgatcctc ctgccttggc ctcccaaagt gctaggatta    107460
caggcgtgag ccaccatgcc cagcctggtg tttatcttta aagtgggcac agccacagga    107520
gttcacctga ctcctggtct gagagtcacg agatcgttca agatagtgag gccctcttt     107580
ccaaaacgag gaccaaaaat caattgacag tgttggtcaa gatggtagaa accttaaaat    107640
gatagaaatc tcaactctga aataaaaact ttatttgtat atttatttac cactatttg     107700
acatagggct aaggtctttt tctttgagct gatttctggt tttgttttct taaagtggca    107760
taagaattca aagacatttt gaggaaggct gagtgcagaa atctctcttt ttaaatgact    107820
tctccttttct tttaacttgc actgttgtct agccctcact tattttgtca attcttttta   107880
gctgtttgtc tttgaatctt cataaagcca tagcttttct cataagaagc agcactttct    107940
ttgttcattc atatttttaat gaacccctgt agtatttaat taaatactta atgcctaatt   108000
aaatcacata attgcaatgc aaaagtacat gtatcataaa gaggtctgaa aatgagcaac    108060
tggcaagcag gtggtggcag gcagagctgc ttgggtgggt gggtgtcatg gagaggagtt    108120
catcagccac atgttcagtg agctctggat atgtctgttt agaaatgatc actaataaac    108180
ttgtgctcaa ccatgtatac ctctgggaag caggtgctct tcagtagatt gcctctgcag    108240
agaacacaga attgaagtga atgtccacaa aggcaatgag ccacctgcag aatagtttag    108300
tcaaggctgt gtttgaagtt tgccaaagat taatatacat ttgattttca tgttgtgcct    108360
tttctctgat tgtgaaatat tacaaattct atacaaataa caatgatggc aaatcctcct   108420
gagcaaagtg tgcaccttgt atgtgcccta gaggaacttg tgtttcgttc tgattcccct   108480
acatttctca tgtcatagag tgggggttgc attagtgtcc cctgtcctc gctgggatca    108540
catctgtttg gatcctagag tcttccagct gaactgggac aagtataaca gacggacacg   108600
taggggtgga aaggcgtctc ttggcagcag acttctctaat tgtgcacgct cttataggtg    108660
ttggagatgt tcattcttgt cctgcagcag tgccacaagg agaatgaaga caagtggaag    108720
cgactgtctc gacagatagc tgacatcatc ctcccaatgt tagccaaaca gcaggtttgt   108780
```

```
ccccgcagcc ttggcttgtt gttgcatagt gatggtagct taaggtcctt gtgaaaggtg  108840
ggtggctgga atcagctctt ccttcagtcc taatctgtgc cttgatagca gttctccgtg  108900
ctagtcatgg gacagctgac ttcatttctt ctcacaatgc catctcaggt tggtattgcc  108960
cacctacttt acagggggga tcccacagct ccgagaggtt atggaggtga tcaggcagca  109020
cacagcttta gagtgctggg gtgagggcgg gccaaggcta actctaaagc ccgaacccatt 109080 acctcctaca ctgcctcctg cattctggtc aacccagtgt tttatttggt ggttagattt  109140 ttgttttttgt taccttactg cttgtaattt agcagttttc cttccttc ccttcctttc    109200 cttccgaca gggtctcact ctgtcaccca ggctagagtg cagtcgtgta atctcactgc    109260
aacaacctct gcctcccagg ttcaaccaat tctcccacct cagcctcctg agtagcaagg   109320
accacaggtg tgcaccacta cgcctggcta gttttttgta tttttagtag atgtgaggtc   109380
tcgctgtgtt gcccaggctg gttttaaact cctgggcgca agtgatccac caaccttggc   109440
ctgccaaagt gctggcatta caggtgtgag ccacctcgcc tggcctattc atcactaatc   109500
agaatttcta tgatcaaatg acatgaatca ttgtttccac aactgcagtg gaaggaaatg   109560
gcctggcagt gccagtttca gaagcagcct gcccccagtc aggcacaggc cactgtgccc   109620
ccagtgtagc agcacctctg tagctcacag agaagggtgg tggggacctc cttgaggcag   109680
ctctgccaga aaatctcatg agctgcctgg cacagcttga ggttgccttt taagtggact   109740
cagcaaatac atgtttgttc atcttgatta tacacaataa acaactactc tgtatagtac   109800
gagtagtccg tggttttttgg catttgattt aaacttagag gcatgtgata ttgatgttac  109860
tgccttcatg actgcacccc cattctgatt tcataatgga atgttatctt gagaccagtt   109920
agacaacagg acagggatct tggcttctgg tgagattgac agcagtttta gtgtggtcag   109980
ggtctccctg cctacagatg gttttagaat ggtgccctgg aagctttatc ccattctttt   110040
ctgtgcgtaa tctgagtaga gtggagatcg aaggcctgaa tacatagtaa atacctgact   110100
taatatctgc cgcaatggaa attgtgtgat acaacatttta tgaaacgctt agtgcagcac  110160
ctgccaggta gctcaccaca ggtgcatgtt gcattcagaa gtagtgctag atactatcct   110220
gttactggca gtgcatacat cagtgatcaa agcagattaa agaaagaccc cctgccttct   110280
tggagtgaag attttgttgg gatgcgggta aggggacaga caatagaaaa gcaagtgagt   110340
gaagtctata ccatggcggc tgatcaggaa caccgtacag aagaatccag gagggaagag   110400
agttaggtgg tgtctgcggt gggagtggca ttgttcagct ggtgatgaga agaagctttg   110460
gtgatctggt gacatttgag tgaatttgca gaaaggaaag atacaagcct aggagatacc   110520
tggggaagga acattccagg cagagcaaat agcagtgcaa aggccctggc gggggcgga   110580 catgctgtta gggtacaagc aatgagggtg gaggagtggg gcagccatgg ggagggaagg   110640
gagtgaggcc tggtggggtg aggccagtgt ggaggagcct tgagagggtt tgcgctgatg   110700
tggtgtaggt tttagcagga tcattcttat tcctgagttg agaatagcct tgaggggag    110760 gtgagggcag agcagggcca cccatgtgag acccggcact ggagtggaat ggcccaagtc   110820
agcatccctt ggcagcatga aagcaaaacc agcaaggttt gctggtggct tagatgtggc   110880
atgtgagaga gagcagggct ttgggggtga tttcaggggtg aggacagggt ggctgtgac  110940 aaggtagggc agacattggg ggcagcagga ggtcagagcc tgtctggatg tagcagttga   111000
gaccccatag gtgcctaatg aggtgaggcc agcatcaggt gtatgagcct ggagttgtcg   111060
agagactgtg gggcagggg tcagcatctg agatgtccac tcacagtgga cccagactgg    111120
```

```
ctggagagga ggaggagctt gaataccgag cctgctgagt cccagctcca aggtcaggta    111180
ggtgagggga gccagtgctg gggcaggggg agtaggcagg tgtggggttc ctaaagccaa    111240
gatttttttt aaggcatttt gtgcaggagg gcgacatctg ctgtcagcac cttgggaact    111300
tggcccaggt ttggcagcac cgagggcact gatgagtgct tttggaggag caaagggagc    111360
caaaccctaa tgggaatgtg ttcctgaaag gacaggagag agacttggga aaaggtttta    111420
cttgaagagg gaacggagaa atagggcagt agccagagga ggagaggagt cggcaatggg    111480
ttaagttggc agaaatgaag gcctgtttac gcactgaggg cagaagcaac agggaggatc    111540
agttcatgac acaggagaca caaatcgccg ttgtggtgtt cacagacatg ggttaggatt    111600
ggctgcatgg atgacagagc actgtgggtt ctcccagagt tgctggggag gaggcagagt    111660
tggtgagcac aggcgagggt ccaggatgca ggaatcctgg agctcaagtc agttgttccc    111720
ttgttgtaag atgtggccag tgttgtgagc ttcacatctg tgccttgaaa aacaccacat    111780
ctgtttgcag agttgtttac tatgtataca cactcagtag aaacaaaaat tggaaacagt    111840
cagtgcccac catcaataag taatggttga acacactgtg gtataagctt agactatttt    111900
agcttgggct attttgcatg attaaaaatg ttctggccag gtgtggtggc tcatgcctgt    111960
aatcccagca ctttgggagg ccaaggcagg cagattgctt gagctcagga gtttgagacc    112020
agcctgggca acatggtgaa accctgtctc tactagaaat acaaaaagta gctgggtgtg    112080
gtggtgtgcg cctgtagtcc tggctaactc aggaggctga ggtgggagga tcacttgagc    112140
ccattcgtgc gccactgcac tcctggggca cagagtgaga ctctgttaga agagagaga    112200 gagaaagaag agagagggag ggaggaagga aggaagaaa taaatggaag aaatggaagg    112260
gaggaagggg agggaggaag gaagaaagga agttcagcca gttgccttgg gagttctcca    112320
ttgcactggg ttaagtgaga agagcagaga cgtttatgat ttttcaaaac aactaaaaca    112380
aaacctctgt gggtgagggg gcaaggatat ggctatagga acatgggca gattaagaaa    112440 gggatataca cacaccactt agcatttgtt acaactgttg tgggagggat ggagtgcaga    112500
aaaagaaaaa aaaagtgca caccatccca tgtatgtgta tacaaaggga cgcttggaag    112560
actggtcccc aaaatgttgg taatgattgt gtcagggtgc tgcagtgcta gttgattttt    112620
tttcacactt ttgtatattt gagtcttta cagaaagcat ttattattta tgtaataaaa    112680
atctaaatga caagatttct gttatgggaa aaatgtagct atacagtgtt gttgtaaaaa    112740
tgtttgcttg gttcaccact gaacttaaaa tgcttttaaa tgagggaagg tgacgatgag    112800
atgattatga tgatttgccc ttgagttaca tagctggtgt acaggaagct gtcgtttctt    112860
ttggcttacg tagaaatgtt tgtggtgtct aattccacag atgcacattg actctcatga    112920
agcccttgga gtgttaaata cattatttga gattttggcc ccttcctccc tccgtccggt    112980
agacatgctt ttacggagta tgttcgtcac tccaaacaca atggtgagtc tctcgcctgg    113040
ctcagcagat gaatctggac ggcttgttca ggctctgatt actgggacca cccccagaat    113100
gtctgagtca gtcagtttgg gtagggcttc ttgagagttt gctttttttt tttttttttt    113160
ttttggtgtg ggggtggtgc ggaacagagt ctcactctgt cgcccaggct ggagtacagt    113220
gtcatgatct cggctcactg caagctctgc cttccagctt cacaccattc tcctgcctca    113280
gcctcccgag ttgctgggac tacaagcgcc caccaccacg cccggctaat tttttttgtat    113340 ttttagtaga gatggggttt caccgtgtta gccaggatgg tcttgatctc ctgacctcgt    113400
gacccgccca tctcagcctc ccaaagtgct gggattacag gcgtgagcca ccgcacccgg    113460 ccttttatt ttttttggag atggagcctt gctctgtcac ccaggctgga gtacagtggc    113520
```

```
gctacctcga ctcactgcaa cctccgcctc ccgggttcaa gcaattttcc tgcctcagcc    113580
tcccgagtag ctgggactac aggtgcgtgc cactgtgccc ggctaatttt ttgtatttttt   113640 agtagagacg gggtttcact gtgttagcca ggatggtcgc gatctcctga ccttgtgatc    113700
cgcccgcctc ggcctcccaa agtgttggga ttacaggtgg ctctcgcacc aagccaagag    113760
tttgcatttt tagcaaattc ccaggtgaaa ctaatgcctg cttttctggg agcacacttt    113820
gggactcagt gatagagagg tttattggta ggatagtaaa ataggagtta ttttctttca    113880
caaaattggc aattggggga aatttaatct tcctttttt ttcagctgtg acttatgtat     113940
tatgtttatt ttaggcgtcc gtgagcactg ttcaactgtg gatatcggga attctggcca    114000
ttttgagggt tctgatttcc cagtcaactg aagatattgt tctttctcgt attcaggagc    114060
tctccttctc tccgtattta atctcctgta cagtaattaa taggttaaga gatggggaca    114120
gtacttcaac gctagaagaa cacagtgaag ggaaacaaat aaagaatttg ccagaagaaa    114180
cattttcaag gtatgctttc tatctgagcc tataactaac ccatgccttt tgggaagtca    114240
cgtgatgttt cacagtcagt aagtctggaa taatacctgg tcttgcttca cttctgagtt    114300
gggtaaagaa gtctgtatca gtgtaatttt ctaatccgtc ctgcattatc tatggctctt    114360
ggttcatacc tgtcttgaag ttctgtcatg ttctgtctct tgtcctcagt agagatgcta    114420
cagcagtggc tcgcctcagg cagggcaggg cagtggggtg gctgtcctgg gggcaggcag    114480
taggggcacg ctgacgtcag ggaagttgaa acccaagaga agccagtaaa agtgagtctc    114540
agattgtcac catgtgctgg cagttttaca cgctgtcagt aataaaagtc ttctccctgc    114600
agggcagcct gcctccaata aatacgtgta gtatcaaatc ctgtcttccc tcataaattg    114660
tttggaagct ccccaaggac agtgatgagg cactcgtaag tgcttgctgc ctagatgggt    114720
ccctctccac ctttgctaga ttctgagcat tcactgagtt agagctgctt ctgcaaatgt    114780
gctgcttctg ctaagtggct gtgacttcat gcagccttca cttggtttgt catcagtgga    114840
gatgccctgt gttgtcgaag gagataagcc cagtaagcct gctgggcacc ttttggtttg    114900
caggttcagc aggcagccca tggctttccc tgtgtcgcat tgaagcagct ggctaaaatt    114960
gatgatacat taaattcctg tgacagatga tcagcttgta tttgtgtaat ggtgtacagt    115020
tcacaaagct taaaaaaatg ctacctgcca tttcatcctc agtgaggaag gtgatacaca    115080
gagagaccaa gtgactgtgt ccacggcgac ggcgctctgc atttcacttt agcggttaat    115140
gtactctacc tatattttta ctttatattt accatatatc ttttcatgta tacttggcgt    115200
aagtgcttta tagtagtcac ctaattcact gtcatctttt ttgtttcttg gaaggtttct    115260
attacaactg gttggtattc ttttagaaga cattgttaca aaacagctga aggtggaaat    115320
gagtgagcag caacatactt tctattgcca ggaactaggc acactgctaa tgtgtctgat    115380
ccacatcttc aagtctggta ggtgaatcac attagtcttc ctggagtgtc tcgttcccca    115440
ttctgcacta tacactctca gagtgtagga gctgtgctgc ccggtagaaa ctctgccttg    115500
cccagtgtgc cagttgaaaa tatttgttgc tgtaagagta cacctgatac catgtgaccc    115560
agcagttcca ctcttgggta tatcccaaa  agaatggaaa gcagggtggt gaaaagatat    115620
ttgcatgcca gcattcatag cagcattatt cacgatagct aaaatgtgga accaactgaa    115680
gtgtccctcg atggatgaat ggataagcaa aatctggtgt atatttacag tggaatatta    115740
ttcagcctta aaaaaggac attctgacac atgctacaac atgggtgacc cttaaggaca    115800
ttatgctaaa tgaaataagc cagtcacaaa aggacaaata ctatgtgatt ccacttacat    115860
```

```
gagggacctg gagtagttaa ttcatagata tagaaagtag aatggtggtt gccaggggct   115920 gcagggagg  ggagttattt ttacaagatg aagagagtta ttctagaaat gaatggtggt   115980
gatggttgta taacattatg aatgtactta atgctactga actgtacagt taaaaatagt   116040
taagaggacc aggtgtcatg gctcatgcct gaaatccaag cactttgaga ggccaaggca   116100
ggaggattgc ttgagccaag gagtttgaga ccagcctcag caacatggta ggaccccatc   116160
tgtacaaaca aactagccgg ggatagtggt gtgcatgtgg tcccagctac tcaggagact   116220
gaggctggag gatcgcttga gcccaggagg ttaagtctct agtgagatgt gttcatgcca   116280
ctgcactcca gcctcggcta tagagtaaga ccctgcctca aaaaacaaa  acaaaacaag   116340 acaagagcca aaaatggtta agatgggcca atcacagtgg cttatgcctg taatcccaac   116400
actttgggag gtcaaggtaa aaggatcact tgaagccagg agcttgggac cagcctgagc   116460
aacatatcga gacccctatc tctacaaaga aaatcaaaaa ctagctagat atggtgggca   116520
catgcctgta gtcccagcta cttgggaggc tgaggtggga ggatctcttg agctcaggag   116580
ttcgaggctg cagggagcta ttattgcact ccagcctggg ctacagaatg ataccctgcc   116640
tcttattaaa aaaaaatcca aaaaaaaaaa aaagtaaacc tgagagcttc ctcctcctgt   116700
gttaaatttg gaggccaaga tgttttgtt  acttttacaa atgatcaagg acggtgaagg   116760
ttgggcatgg tagctcacac ctgaaatccc agcactttgg gaggctgagg cggggtgatc   116820
gcttgagctt gagaccagcc tggacaacat agcaagagac cccatctcca caaaaataaa   116880
aaaataaaaa aaaatagcca ggagtagtgg catgagcctg agcccaggag gtcaagctgt   116940
agtgagccat gatcatgcca ctgcactcca gcctgggcga gatcgagacc atgtctctag   117000
agaaagaaaa tgacaaggac agtgaaccca agaaagtcat aagatgccag ctgtgcagca   117060
agcatggaaa gcagccagtc caaattagga cagtgtgttt tccaagaaga acgatcgttt   117120
gtaatgagaa tgctttgctt taaataaatg actaaatagc tagaagccta gttctagggg   117180
ataggcacgt ctttcttctc tcaagaaaat agaaaggcaa ttctaatttc tagtaacagc   117240
aaacagcatt aagtcatggt ccaaatatga ggcaaaccaa aatgtggctt gattgttcag   117300
cagttgatct gttggaagcc cttgatatta aaaaggttct cctttaagcg gcttaggagt   117360
cacgatcaaa gacctataga aagagatgcc atccttctag gatccttggc tctcttggga   117420
actagattca gatagtcata atgtaaatac tgcttgagct ttctttcttt ctttctttct   117480
ttcttttttt ttttgagaca gagtttcact cttgttgccc atcctggagt gcaatggtgc   117540
catctcggct caccgcaacc tctgcctccc aggttcaagc aattctcctg cctcagcctc   117600
ccgagtagct gggattacgg gcatgcacca ccacgcctgg ctaattttt  gtattttag    117660 tagagacagg gtttctccat gttgaggctg gtctcgaact cctgacctca ggtgatccac   117720
ccgcctcggc ctcccaaagt gctgggatta caggtgtgag ccaccgcacc cggcccgagc   117780
tttcattttt gaaatcaatg tatgactgaa acactgaaga cttactgact taattatggt   117840
ttcagaacag aatgaaaatg tcttcggttc tgatgaatat aaaaggaaaa ctaaccaagt   117900
taatttggca agtagatggt agagatagag gtggggagtg gaagggggaac taaaatcttc   117960 acctagcatt gttgggatta tatggttaca tcatctgaag ttgacagacc aaaatataga   118020
ggcttcagag gtctccaaat agaactaaac atgtaattca gattgttagg aggtagtata   118080
aatgagctaa atctcatctt tattacggta gagttaatgg gtgatgtcta aagttgtctg   118140
aagtctataa atcatgacaa attatgatgt ggtgattgta ttcaacagtc tttcagttgc   118200
agggataaaa ccccagttta aactagagta agagaaagaa tgtgttggtt taagctcctg   118260
```

-continued

```
gaaagtgcag gcaagggtag ttggtaggac tgcatctagt gttgtaattc tgtggtctgc  118320
attgtatatt tatgcatctc agctctgctt tcttcttttc atttatataa ttttaaatt   118380 ttattttaaa gatagggtct cactttgtcg cctaggctga agtgcagtgg catgaagtgc  118440
agtgcgaggc tcactctagc ctcgaactcc tgggctctag agttcttcct gcctcagcct  118500
tctaagtagc tgagacaata ggcatgtacc aacatgcctg gataggtttt aaaattttt   118560 tgtagaaatg gaagtcttgc tgtgttgccc aggcgggtct ttaactctta gcttcaggcg  118620
atcctcctgc ctctgcctcc caaaatgctg aggttatagg tgtcacccac cacgcccagt  118680
ctcatctctg cttcctgtgt tagttttgtt ctctggtggg ctgttttcac atgaccgaag  118740
atgacctcta gcaggctgtg ttctcagccc ctcaagtagg cctatgtgat tggccttgca  118800 tgagtaaatat gggtgaccat aaaccctga atgctctggt ccacatgggc caaatggag    118860 actggacagc attccattga tgaggaggtg gggctggtct ccgggagtaa gggagaggag  118920
cacatgcagt aactgatggt ctgctgcaag ggatagcagc acagcagtta gaattttgga  118980
ggtaactacc agaactgaaa acagaaatga taacaagtag ttgccttaaa aagggatggg  119040
agcagggtgc ttttgtgatc aaagctcctt tctcttactg gattttgta cacattttgc   119100 atacatatct tagagtaaaa gatagcattt tcagccttgg tccatttgag gatactcttg  119160
gcgtggcccg cctccatgct agcaggctct ggttgtgcca agttcagttg agcatcctgg  119220
ctcttgcctg cacggaactt ccagtcagtg cgtcagtatc acaagtcttg atatttccta  119280
tgaagaagaa cagtagtgca gtgacagacg aaatgggtgg gcaggcagag gcaggatttc  119340
tgagggagag aagtagctag cttttttgcag agaagagttc cggcacccaa gagagcagct  119400
gagagtacag gcaggcaggc aggatgccgg tagggcccgg ccgcacggcg ccacagaatc  119460
ctggagaaag gggcctcttc atggcctctg cattcagctg ctgtcaccct ccgcacaggc  119520
catggccaaa atttaatttt catagtggac tctagttttt gagccttact tgctattatt   119580
gaaataattt tcttgtttct ttttaaagat cttcggatta tgcttcactg accactgtaa  119640
taagtttaaa gttgagaaaa tatggcttgt taatgaatga taggtcaatt ttagtatgtt  119700
ggtcatttta atattttgcc accagttggt ttggatttga tgccaggagg agacagcctc  119760
atttctaagg actagtcttg cctttgtggg ataagggtgg tgtgttctgt gtccttctac   119820
atgtccgagc gatctctgtg cagctcaaat gtggtcactg tcttattgcg ctgatttcct   119880
ctccttccat ctcacaattg aggcaaaata ttgttactgt tgaagtgttg tccaatagga  119940
cttccagcag agacaggatg tctgcactgt ctaatttagt tgcctttagc cacatgtggt  120000
gttctgtacc tgaaatgtgg ctggtctgat tggatagctt aatttataat tttatttaat   120060
tttaattaac ttaaatttaa acagctcgtg tggatagtg gctcctgtat gagacagtgc   120120
aggtctgttg agaagcagct ttactggtgg gagtggaggg cttggagagg gcacgtgggt  120180
ttcctgctgg tatcttttga ccttatttaa tctgcccaac atttgcaagt aagttgtgtg  120240
tgtgtgtata tataaatgtg tgtttctgtc ttcttgtttc ctttgactgc atttatttga   120300
aagacactag gtggcagaat tactgtatt gattggtttc aagataagag ttgaaataat    120360
tcatctcgtg tttttatata agtaaggtgt gtttagcatg taaaattggt aatatgtatt   120420
cacgtactgc ttaaacaaag gctatgaatt ccacccataa accgaaaatg aagacctta   120480 aatttgtcca tttcaggcgt gggtacttct taaataatac ctggttcagg aactagtcag  120540
aatggcaccc ttgactttt gtttcctgct tttcctcttg ttgggagagg agggtattca   120600
```

```
tcccaaagtg gtttgcctat ttcacattcc atctaggata agcagaatag ccaagaaaga  120660
tagctgtcct cctgtttaca acatttgggg taaccagcat ccctctcttt tggtccaaga  120720
tagactggtt tagaaacaga tgatggcacc agaggcccag gaggtggaaa catcagcttt  120780
gtttgttgtc catgtggctg aattagagct gtctggcctt gtagcctcaa cacggccttc  120840
cagctttgct caccgtgatt ttcaaggaca catcttgtgc tcttccctgc ctgccatcca  120900
gactataccc agtcagggtg gcaggagctg ctgcccctte ctccctgagt cctggtcgtg  120960
ggtggtggag atgtgccatg acgctcacgg aggcatgctc accccttcct ctgtggcaga  121020
ggggatggct gcacgacagc tcttccctgt cctttccaaa gcgtctgtgg ttccactttt  121080
tggggcaaag caggaatact ggaagagaga gaaagtggtc ctttctatag taataaagtt  121140
gacattgatt caagttcatg cttggggaaa ggacagggct actaacaatt ataatgctgg  121200
gagcaatgga attttctcat gggtatgtgg taggtttaat tttaattatc ccagttaatt  121260
cttagaactg ctctgtgaag tatttcccgc tttgtgctta agttctaaaa gatcctgtgc  121320
caaaaccaag aatgaaaacc caagcattct ttcttgccca tcgatctttc tctcatcagg  121380
ccacttcttg ggttgatagt ggtgagtgta gccgctgcca cttcagaat acccaccatg  121440 ggccccagtc actgtgtggc gtggagaaga gatggttctc tctgtgtcat agctgaacaa  121500
gcccagccca gagaggtttc tgccctagga gctctcgatg gtggaattgg gatgcgatcc  121560
cacatcctgc ctgttttgaa aacagcattc tttatttcca attcctgctt ccattgttcc  121620
ttttaatatt tctttgttta gctcacaaaa acacggcttg cggagctgct gcgtgcagct  121680
gtagctgttt ctctgggtgc agcctgcatc cgccttcctg cccgcctcct ttcctgcact  121740
gccatcgtgg tctccgggca cttggtccct ttctcttccc ctgagtccct ttggctcccc  121800
tgtgccaccc ttgtgatcca caggctctgc cttctttctg tctcagactg ctgctcatca  121860
ctactcggga ccctaggaag ggaggttcca ccgagaagca tcttctcatc tcagccacgt  121920
tctcagtgcc actgttgtct ttgttaggta atggtagcta ctgtaacaaa taaaccaaca  121980
tttccatggc ttcacaccag agaaggttgt ttcttggttt tatgacaatg tattgagggt  122040
gttcttggtt cacggatggt tttcctccat gtgggaattc ggggacccag gctcctttcc  122100
ttcttttggt tctgttctcc aggccttcac atcctctgtg tctggttggg gacaaggaga  122160
gggaaggtaa agaaggcttt gtggccttgg ataagtgaca ggcatgcctt tgctggtgtt  122220
ctctcgtggt gacaggtcac agccccaccc tgtaaaaggg gactgagaga cgtcgtcctg  122280
ctgcttccca gcagcagcac tgtggtctct gatgtgtttt ctgtgaggat aaaaacaggt  122340
gattccagga tgaggaaagt cagggaaacc cttgaaggga ggggaccagg cgggtgtcac  122400
catgggatta gtggtggctt cagaatgagc tgcagcgagt gccatgcctt ctaaagcttt  122460
tgctattctg atatgcccac accatgccca gcaggtgtct gccttgctct ccgcagagag  122520
agtgatgaat ccttctcatg agcctctgtc cagttgttcc tccctccacc tggaagggac  122580
cctgggttcc tcataacatc ccagcggaac aggggacctt ctatcctgtc cccaagttca  122640
tcctcatcct cctgccggct tcctggcccc tcttatgtct gcttcctgac gccacatcct  122700
tctggattct ctggaattga attttgcctt tgatgcttat ttaaaaatat ccattgcagg  122760
ccaggtgtgg tggctcacac ctgtaatcct gtgcactttg ggaagccaag gtgggcagat  122820
tgcttgagcc caggagtttg agattagcct gagcaacatg ttgaaatcct gtttctatag  122880
aaaatacaaa aattagctgg gcatggtggc gcacacctat actcccagct actcaggaac  122940
ctgagacagg aggatcaatt gagccccgga ggccaaagct acagtgggct gtgatcgtgc  123000
```

```
cactgtactc cagtctggtc aaacagagtg agaccctgtc tgaaaaaaaa aaaaaaatcc 123060
attgcatact tcaccgtagc gaaacatgta tgtcttacct ttcctttcct gcctgtagct 123120
gctcttttac acttaacagc cacactaagc cagccttaaa tgaaaaacaa accagcactt 123180
cctgtgccct cctgcttcct tcatgagggg tccctccctc tgtgtacact ccattctcat 123240
tgcccatggt ggtttgtttc cctcttgttt ctcaagccat ggcagcctgc ctcttgccct 123300
ctttactaaa aaggcctttg cagaggctgc ctgtgttctt tctttctagg tctctctcat 123360
cctaggccct ccagcttgat tctgtggagc tgccctcttg tcactcagta gcttgtgggg 123420
tcttctctgt ctagccactt aattgattgt gttcctcgag ttgctgtcca tggtctctcg 123480
ttactgtttt ctctgtgttt ctgcctctct ccttggcctt ggtaggtcca tcccctttgt 123540
gaccttggct gttgctctca tggacaactt tctcttgctg gtccttgtag tcctggcatc 123600
cagcttctcg acacgggact tgtcctgcca gtacctcaga cttgcactta aaattgaact 123660
agcaccactg tcactctcca gggcctcttc ttgttaatta gatcattagg gatgttcaga 123720
atcccagcat catagtatgt tcctcctccc gctaccccag gaaccctaac cttacctcct 123780
cctctctatc tactaggagg tggccctcag agtccgtctc atcttccacc tgaacttccc 123840
taataggctc cagcagctgc caccccgggg gctgagtact tcctccatgc cttgtgcagt 123900
gctgagccct ttacctgggt tctcctgttt gctccttatt acagccctgc gaacagatac 123960
tgctcttaat tccatcttac acctaaggaa gctgaggccc caggtaaggt gcatccaagg 124020
tcacccaggt agtagacagt agagccacga tctgaaccag gcagtctgat tcagagcctg 124080
tgttgacact cagccaccta gaacacagct tggattgtgg gtttctatta cctgttcaaa 124140 accctacat cccgggtctg tccctgcacg tgctctgtgg cctggctgca tcttccttga 124200
aggcagtgca tgcctcttca ctcaggggc ccatgcagga acagagggcc ccacagaagg 124260
atgaggccag tgcagaatgg gctggagggg acaatgctga ccaggaagca agtgtagaga 124320
aatcccagga aacctggagg agccagagac aaggcattag aactcctcgt cgtgacctgg 124380
tctgcattct ctgagtgtgc tgcttctgtt agctcgcttc cttggtctca ggttatagtt 124440
taaggcattg tggagcccta aaaagcctgt actctgtttt tacctgtttt aggacccttt 124500
cactttgggg atgtgttgat ttttttttt ttttttttt ttttttgag atagagtctc 124560 gctccattgc ccaggctaga gtgcagtggc acgatcttgg ccactgctgc ccctgcctcc 124620
tgggttcaag caattcttgt gctcccgcct cccaaatacc tgggattaca ggcacccgcc 124680
accacactcg gccaatttt gtatttttag tggagacagg ttttaccat gttggtcagg 124740 ctggtctcga actcctgacc tcaagtgatc tgcccacctt ggcctcccaa agtgctgtga 124800
ttataggcgt gagccaccac acccggcctg aaatttaaat cagaaataaa attttgatcc 124860
caacagtgat gccaggcagc ccagatctgg gggagagggt ggccttggcc agctgggcct 124920
ttctctgttt cccaagtctt gctgcctctc cctgctgggc tttgcagcct gtgcatgtct 124980
ctgtgccttt gaccttgttt atccaaagga gaggatagaa tgaagtcatg attcctggag 125040
ccctgagaag gatgctgtgg agaaatttgc cggtagaatc tagctgagtg tgttgctgag 125100
gtgccagcat tgtgtgtggg gaggctgacc gcttggcctg cctaggccca ggatgctcca 125160
tggccgggca cagaggccac ttggctgtca ggtgtcagga gcctgcagag ggcacacaga 125220
gcctggaccg caggggggtc ctgctttctc acctggcctc cttcagcatt tctgtccctc 125280
agtccttagc aagcccagga gctgttgagt ttggcaggtg ccgagtgctg ttcctgcctg 125340
```

```
tgtagctgtg gctcagtcct gtgggggccc cgctgtggcc cgagtgcagt gattcgaggc   125400
gctgagtgtt ccctgactcc ttctccagga gctgtgttca gactttcgca gctcttggct   125460
tggagctcct ggagggcttg gcattgccga ccaatgtgga ggtcgacagt gagagaggag   125520
gaatgctagc tttcttgacc agtccattaa ataagtggga tattggccag gcacggcggc   125580
tcacgcctta atcccagcac tttgggaggc tgaggcgggt ggatcacgag ctcaggagtt   125640
caagaccagc ctggccaaca tggtgaaacc ccctctatac taaaaataca aatattagct   125700
gggcgtggtg gcaggcgcct gtaatcctag ctacttggga ggctgaggca ggagaacagc   125760
ttgaaaccgg aaggtggagt ttgcagtgag ccaagattgc gccactgcac tccaacctgg   125820
gcaacaagag caaaactcta tctcaaaaaa aaaaaaaaaa gtaggatatc tgtttctgct   125880
tagaaaaatc agaattttct aaatgccagg tgttctgaat acgtaagtat gggagacgac   125940
tcagcctgtt tcatttttat gtaaaatctt cgcgtagcca tgtggcactg gaccgagatg   126000
aaagcaaaga catttctcct taactttgtt tctaggaatg ttccggagaa tcacagcagc   126060
tgccactagg ctgttccgca gtgatggctg tggcggcagt ttctacaccc tggacagctt   126120
gaacttgcgg gctcgttcca tgatcaccac ccacccggcc ctggtgctgc tctggtgtca   126180
gatactgctg cttgtcaacc acaccgacta ccgctggtgg gcagaagtgc agcagacccc   126240
gaagtaggtt cataatgccc cacagcccag ggcgccagcc cagcaccctg tcctgagact   126300
cccagtaacc tgagctttgg ccaccgttaa agcatttttca ttttccattt tttgtgaggg   126360
cttgtgaaat ttctgctgca tattaatatt cctttcatgg acagcatatt attgggacaa   126420
acatgcggtc cagctaaagg cattcaaaat agcagttgct ttctaaatgc gattttcttt   126480
ggcaggttct ttgacaccat tgcatcttgt gggatatgct tgtcatgctc tgtggctcct   126540
actaagttct agtccttaaa ttggttccat agccagacat gttgcaatgt cttaacctca   126600
ttataaagta aatgtggttc tggttatcct tagataatga agtaacagtg tagcaaattt   126660
caaaacctct tggaaatgtt attttaccat tcaaaaaggc ttactaaggt tctcgttatg   126720
ggtggccctc ttttttgcaaa aggttttcag gcttaagctc catttctagg tgctccaaca   126780
ctccattatt tgtatatgta tggaaataaa agctgtgacc acccccaacc ctggcccccg   126840
cccagctgaa tcctcagcac agtatttctg gaaggctcaa gatcccacgc tggggaaaag   126900
aagttctgga gacaaaagag ggcaggtgct gccgtgcctc tctgctcagt atggatactg   126960
gaccttgtgc tgccagggct cccagtaggg ccagttcatg gcactcagct ggaaagtcca   127020
ctgttgggag gcattcttaa ccatccactc tgtgccgtat gtagtggggt ctggtcattc   127080
tgttggagga gacagaccag tgacgacatt tgaaatgctt ggtggatgtc ttaggcctgt   127140
tacgatgact gagcactgtg ggggcaggag acagaaagtc agtgtctcct agttctgtgc   127200
tgctttaacg tgcatagaaa tcagctgcgg attcagcaga tcactccttt tctgacagat   127260
gggcctgctt actctgatgt tatatcagaa agctctgaat ctgggaattg tgtccctga   127320 attggagtaa cagaaatgct tagatgatga gtgtttaaaa gaaataaacc aaaggtaaat   127380
ttagtttgga attcagcaag cgtcttcatt cagccctctg agggcaaact acagcttttt   127440
gtaaatgtag gtaaattctg tgactgtttc gtgaccccct ctgatccagt tttcctttat   127500
aaccttctgt attgttcctt ctattatcct gaaataacat taatagatta ggctgggcgt   127560
ggtggctcat gcctataatc ccagcacctt gggaagccaa ggcgggcaga tcacctgagg   127620
ccaggacttc gagaccagcc tggccaacat gatgaaatgc tgtctctact gaaaataaca   127680
aaaattagcc gagcatggtg acaggtgcct gtagtccctg ctactcagaa ggctgaggcg   127740
```

```
ggagaatcgc ttgaacctag gaggaaaagg ttgcagtgag ctgagatcgc gccactgcac   127800
tctagcctgg gtgacagagt gagactccat ctcaaaaaaa aaaaaaaaaa aaaaaaatta   127860
atggatcaat ggattttaa cctaataatt aaatttcaaa aaatatcgtt ctttaatggt   127920
aatgtaaagg taaaattaag ataatatgta acaagcatgt gagtgtctaa ggtgtccccg   127980
tggtggaagg aaaaaataaa tccccataag tgtccaagat gcccatagag agcagagctg   128040
ttctggttta aacccctgct cttagcactg tgtttttcca gctgtgggtg gtggggatg    128100 agtatctttt tatttccatg agatgagaaa aatgaattac tagaagtgtg aaatacaaaa   128160
cacagctgct cttttttag ccatagactc agcagccata aaattgctgt atccagttgc    128220
agaaattcct gctgcttact cttgaccctc tctcggtttg tgtgcatctc ctctcaggct   128280
ggctcccaga tgggagctgg ctccaggcga cactgggtgc tctgctccag gaggtcctta   128340
tgtgggtcct gccctagcct agcccctctc ttatggactc tgtcactgtg ggtttatgat   128400
tcactctcaa tctgtcttac ctcttggtga actgttagag tcctgcctat actttggcgc   128460
ttgtgggtgt gttgtggtac acatgatgtg ttggtcactt cccagctcat cttgttctga   128520
gtcaccctag atttgggaca ttcattcgcc accagtaccg gcggtgtat ggcctgagat     128580 ttggggggc ttgtgctgct acaaattggg gctgaatttg agttgacagt ggaccttctt    128640
tatgtctact gctcatattt gaattgcaaa tactgcctct tctctttcag aggctcatta   128700
ccctatagct gtattattgc aaagtgcaca attacagctt gagtgtaagt cacactgcgc   128760
tggcaggacg gcccactgag aaagggcacg tttcctgttc gttagttttc acattgacac   128820
ataatttaca atacagtaaa atgtactttt ctatcaactg tagtcagtaa cagccccct    128880 cccccaacca catcaagata tagaggagtg ctgtcacttc aaacagttcc ctcttcctct   128940
gccacatcct gcccctcccc aggtctaacc accaatccgt gctctgtccc tctgttcagc   129000
ccattgcaga aggccataga aatagaatct ataggctagg tgtggtggct catgcctgta   129060
atcccagtat tttgagaggc tgaagtggga ggatgacttg aggctgggag ttcaagacta   129120
gcctgggctg cctagcaaga cccccatctcc agaaaaaaaa aatttaaaaa ttacaatcac   129180
gtccctgtag ttcagctgct tgggaggctg aggcaggagg atcacttgag ctcaggagtt   129240
agaggttaca gtgagctatg atcgtgccac tgtgctccag cctaggtgac acagcaagac   129300
gttgtctctg gggaaaaaag aaagaaacgg aaccacgcgg tgtgcagcct tctgagtctg   129360 gccccttcg gtgagcagtg tctaaagttc tgtcgcgtgt tgcccacgcg tcggtggctc    129420
gctccttgca actgctgagc attgtatggc taggctgtag tttgttttca cttcaccagt   129480
tgggaaacag agaaaaggca cttttaaaa agtttaaatc tgtagaattt tggttttac     129540 cagttctctt ctaaatcctg agggattaca ggaaagttg ttgtatttca gaatattctt    129600
agcttgatgt gacctctgtc cccgttaagg ccctttgccg caatgggaag gacgtcgctc   129660
ggtcagaccc tgaaggtcag agggggcagtt tgggagtgtg tcaacatttt aactgtatgg   129720
actagagcca agagtctcaa ggtttataat tcccacgtat tcaaaaagaa aaaacaata    129780 aagtgagaag tcagtgtaga gtgaaataac ctgtgttagt ggggaagaag tgttttaaa    129840 caggatttcc ataacgtata acatcaacat gtttagagtg gtgatgttc attgggaaac    129900 gaacagtaaa acatgaaagc agggaggttt tcattctggc agttggcaac tttcacggca   129960
gatggagaat ttcaaaagca attgctcaat tatcaaacat agccagtgtg agttctgaaa   130020
taaaggtgct gattgaatgt gcagctttat ggtggatttt gctattcagg caagcatttt   130080
```

```
aattttctgc ctgttaaatt ctgttttctt tagttttca tatgtggttt attgtagctt    130140
aggaatagat aactgagagt atatattaca catacaacat tctgatatgg caatatttaa    130200
aacaacttgt ctgttttaga actagaatta aacataatca tcttcagtat tttgcaaata    130260
agctcactgc catccagaaa cattgtcaat gcatctgttg ctccttctag aagacacagt    130320
ctgtccagca caaagttact tagtccccag atgtctggag aagaggagga ttctgacttg    130380
gcagccaaac ttggaatgtg caatagagaa atagtacgaa gaggggctct cattctcttc    130440
tgtgattatg tcgtaagttt gaaatgcctg taaacggggt tgagggaggt ggggaccagg    130500
agaacatcct gtgtagatga cacttgcatg gaccctctgg aacccagacc gcccggtgtc    130560
ctgccaagct ccatcgaaac taaatctaga atgaatgttt acttctgctg tgacatataa    130620
ttggagacca ggcctggcct tccagtcact ggattctaag ttggactgtg agagttttg     130680
cagctgactc atttatcaaa tgcccggcta ttggctcacg cctacatgat gctgggtatg    130740
tttgttaatt tgagggaagc aatggaataa taataactaa tgatttaaaa aacaaagtaa    130800
gtgcattgac tgtagtgggg ttctgatttt aaatttttt aaaaattaat accaggagca     130860
gtggcttatg cctaaattcc agcaactcga gaggctgagg taggaagatc acttgagccc    130920
aggagtttga gacaagcctg gctatggtg tgagacaccc atctctaaaa aataaaaaa      130980
taaaaaatta tccaagtgtg gtggctcgtg cctgtaatca cagctctttg agaagctgag    131040
ggcggaggat ggcttgagcc tgggagttcg agaccagcct ggcaacacag agaaaccctg    131100
cctctaccaa aaaagaaag agaggaagaa agaaaaatta gcctggcgtg gtggtgcatg      131160
cctgtggtcc cagccacctg agagactgag aagggaggat tgcttgagcc cagaagtttg    131220
aggctgcagt gagctgtgac tgtgtcactg cactccggcc tgggtgacaa ggcgagaccc    131280
ctgctctaaa ataattttt taagttaatt tgtagaaaag gtgttagatg ttctttgtca     131340
catttatga tggattcctg tttaaatgcc gttctcttta agaaaaaaa aataacttgt       131400
gggagtttt aaccataaaa ctagcatcac atatttacca tggagaattt acaaaaaaac     131460
aaataaacgg aggaaaataa aacctcctgt aatcatacta ctcagagata acttgctgtt    131520
agattttggt ctagatttaa tactttttct atatttatat taaaaatatt taaaacatat    131580
gcatttcttt gtcacaaaca tggtatctta tagatactac tgtcacatag caaaacagtg    131640
ttaaatattc tgaatcagaa aaggaagccg actctccaac tgaaagaggt gttatcctag    131700
agacttttc tggtgatgac aatttattaa tagtcacttt ttgctttact ttctctattg     131760
aagtagtttt tctattttgt tctactttta aggataataa aatttataat gctgttttc     131820
acagaaatat aagaaaaaag atactaattt tataagttaa taaagtttga tcatcccaaa    131880
tccaaaaatc tgaaatccaa aatgctccaa attctgaagc tttttgagtg ctgacattat    131940
gttcaaagga aatgttcatt ggaaggtttc agattttcgg atttagggag ctcaacaaat    132000
aagtataatg cacatatttc aaaacctgaa aaaaatccta aattcagaat acttctgatc    132060
ccaaacattt cagataaggg ttattcaacc tgtactgtca gatgatccca aatgaaaaat    132120
attaatcgtt aaccaaatat caaggaattg atcacatttt acagtttctg cctaggatta    132180
tgaatcaaga tgaaaaggct ctgcatgttt aaaaatatat atttttattt tcttataaat    132240
cttaaatatc tacacttaag atttatttga tatgtgggat ccattcatat tttggattca    132300
acagttctgt caaaactgtg gcagtgatag gggattcttt ttttcccact gaactatcac    132360
aaaattggaa aaagagtaat tggagaaccc cactggctta gccggcccga agcccgggag    132420
agggcaggca gtgctgtgga tggggtcatc ccagcgcaac gctgcccctg ctacctgcgg    132480
```

```
atctcgctga ggcctgcctt tgtcctttga cccttggcca tttgttagtg tctctgagag  132540
ctggactgct gtaccctact tccccagggg gcctaacttc acacagcctc tgccgcagtg  132600
cgtggttgga ggtgacggcc ttggtaaatc gagtttccta cctcctcaat tatttgtgct  132660
catacactgt atattttag tgaggttat atttgggatg tgttttctcc ttcttaccct  132720
ttctggcctt tctatggcat taatacctgg tctcttcttg tgtacttgaa aatgaatctc  132780
tcatcatatt tttccttagt gtcagaacct ccatgactcc gagcacttaa cgtggctcat  132840
tgtaaatcac attcaagatc tgatcagcct ttcccacgag cctccagtac aggacttcat  132900
cagtgccgtt catcggaact ctgctgccag cggcctgttc atccaggcaa ttcagtctcg  132960
ttgtgaaaac ctttcaactg tacgtcttca tcctgccgac tattgccagt tgcagttttc  133020
cctgccttaa aaatggagta ttgaaatttt taactttaat ttctgatttg caaaatagtc  133080
atcttttgtt cttttccttc ttgctgttag ccaaccatgc tgaagaaaac tcttcagtgc  133140
ttggagggga tccatctcag ccagtcggga gctgtgctca cgctgtatgt ggacaggctt  133200
ctgtgcaccc ctttccgtgt gctggctcgc atggtcgaca tccttgcttg tcgccgggta  133260
gaaatgcttc tggctgcaaa tttacaggta ttgggaagag aaaccctgat attgatttat  133320
attgaaaatt tagcaggcca agcaaaacag gtggctggct ttttcctccg taagtatggt  133380
cttgacatgg tcaccgatag aaacatggaa acatctgcaa acttgccgtt actcgtgtgt  133440
ccgatctgac tgtttcttgt attttttct agtctgccct tactaggatg aactgtacac  133500
atcagttcat cctttttaaa tgagcatgag gttattttgg gttgttaggt gttacaaaca  133560
cactaatgtg tttttgtcta ttagagcagc atggcccagt tgccaatgga agaactcaac  133620
agaatccagg ataccttca gagcagcggg ctcgctcaga ggtaatgctg gaaacacagg  133680
tcgtccttgt gttaggacaa cccaggatat aaaggatata gatttgtacg ggaataaatt  133740
cacaggacaa gaaatcgatg tgccttatag gtgggtttac tgcagaagtg ccataataga  133800
accttcctac ttttaaaaca accagatctc actttctaaa gagtaaagga tgaccggcag  133860
gatcacgtct gtgacgtgag tggaggcagt ttgcactcct ggtggctgtt tgagaggtag  133920
catttagaat gcctgtattc actgtcctgt gatgagtggg aaaataggtt atcaggttta  133980
tcttagcaaa atcaaagcat gtcatctaat tgctaaacaa gagttggcaa atctgagaga  134040
cattactcaa tccttggcat gcaggactta catctgcatc ctgttgccat tttatgtctt  134100
caaagcattt aatcatttag ttgtgtttgc aaagtctttg agaagccttt gtcagaaatc  134160
cctacatctc ctatgtgagt gtatttccat gactgcagaa taagttaaac tttacccttt  134220
ttccttccct tgcggggcgg ggtgggggc agggattgtg tgtgtgagag ggagagagag  134280
acagcagaga aggagaatat aattatcatg ctgtgtactt tgagctgaaa ctgcaaaaaa  134340
ggaaaaacac acaaaaatta ttatgctttt cagtctttag agtaccttgt ctattatgct  134400
tttcagtctt tagagtacct tgttgatggt gttttaaat gggattgggc acaattaggt  134460
ggacagtttg ggatgatttt tcagtctgta gggccaagct cttttgtaat ttgcattatg  134520
aagttgtcac tctcatagca gatggcggga gataaactat tattactttt tgaccctaga  134580
cttagtcttc agtccagatg agggagatta aaagattata aatatcttgt gccagatgag  134640
gtgattttat tttgaaatga ccatgaattc ctatcagttg tcttactggg atatttgata  134700
gtggaatttg tgcatttgag tcttagatga tctgttttac atttattaag aaagccttta  134760
ttagctttta tactgtgtat tgcctgttgc agtgtttgag tataaatgaa atttctggaa  134820
```

```
aatattaatg gagtacaaac tgtgatactt aaaagtaaac tagggcctgc atttgtatca    134880
tgacctgttt gagtattgat gagaagatag ctgtgaagaa aaaggtttaa acaagtgtat    134940
tttcctttaa gaagccacta atagtgcatc tccttagagt gtatatttct agaatcctag    135000
tgtgcagagt ttagactaag actaaaaaaa aaaaaaaaca aattatactg taatttcatt    135060
tttatttgta ttttagacac caaaggctct attccctgct ggacaggttt cgtctctcca    135120
ccatgcaaga ctcacttagt ccctctcctc cagtctcttc ccacccgctg gacggggatg    135180
ggcacgtgtc actggaaaca gtgagtccgg acaaagtaag tgtccagcgt gtctgcatgg    135240
gaggcacagg gcgctgagtg cctctgtcac ctgtggcaga tacagagagt gcagaggagg    135300
tgccgtggac ccaaggagtt ctggcgctcg gctcggctca gtgaagctgt ggttagagac    135360 gtgggggggcc atcaaggtct gagggagcca agcagtgctg atgtgggacc cttttggtag    135420
gagtgtgggg tgagtagtta gtgggtgaat caaggaatag tcggccgtgg cctgcaggcc    135480
cctgactgca caggccttca agcacatgtc aatgccgtta gcctccctcc atctcctcat    135540
accttctggc cacctgtgag ttgcactgcc actgccagcc attctggtat gttgtcagca    135600
cctccactgc tcatacctca tggttaggga ccacctggag ccttggtaga gccttggtag    135660
agccttggta ctctactttc ctggacaaag ttcagcttat gaatatgaat ttagatttca    135720
aaaaccagca gcccaagtat aagaaagcga aggttcagtc ctgccttctt aggctctatt    135780
cgctaagcac ctgccctgcc ctggttgctg ggagagatg agtaaagcag acaacccagg    135840
agaggatggc aaaggggccg ctaaccctta gtggtttagc tatatttgga aggcctattg    135900
gaagttcacc aggtgaaggg ggaggctgtg agggtgccca ggcaggtaac agaagtccaa    135960
aggggaaaac ctgtggtgtg gtgagccgta tagccacagc ctgccggccg gcagccctct    136020
cagcctagtg cggtgttccc aagcactggc ctaggcctgt agctccaggg atgtgaagtc    136080
cccttgaacg ccgcccatca tgttcccctt atccattttt ttcttcccag gactggtacg    136140
ttcatcttgt caaatcccag tgttggacca ggtcagattc tgcactgctg gaaggtgcag    136200
agctggtgaa tcggattcct gctgaagata tgaatgcctt catgatgaac tcggtacggg    136260
gggagcagtg gaggcaagga atcctcagct tttcttgtga cttccaagtg ggatttgtct    136320
catcatcatg tgacccactt gttgacaaca catgttgggg actccagtct gggcagggac    136380
gggatgtcgg agagactcca ctctgaatgg ggccgggaag tggggaggac tccatttcag    136440
atggggtcgg gacatggggg ttatgctgat cgagacagaa aagcacattg tttcagccac    136500
attagaatcc acggaggtgt tgttttgaaa tccagctggc cccaaggctg ggtgtatggt    136560
ttgggatgag aactatctgg cctccactgg aggaacaaac acaggatgtt atcatctaag    136620
ctccatggcc aagacagaat ggaagtcaag gttgcgtatt tgccgtagac ttcaacacag    136680
tgtcgtaatg cgtgacgtca ataacttgtt tctagtgtct tggaagttga tctttagtcg    136740
taaaagagac ccttggatgc agcgagattt cctctactca cacctctgtt agatgtagtg    136800
aggttcttca ccccccaacc ccagatgtca gagggcaccc tgcgcagagc taggaggcca    136860
tgcaaagcct tggtgtccct gtccctcacc cgtgggcagg tcctgtgagc agtgggggg    136920 ccacctcttg ggtatggtgc agccatggcc caagcagggc ttcttctcag acctactagg    136980
acgggagaaa cctcctggtg ctttagccct gcgttgatat gcagcaaatg ggagggaagt    137040 ggcacctgg gaggacaaat gcctgtagag gccgggagtg acggcaggtg ttcatgaaaa    137100
gagaccttgt ggggagggca acacaacagt gtgttctgat gtactgaaga gctcaactga    137160
aaacaacagg agaattagcc caaaatccat ttactaaaat tgtttatctt ttttttttt    137220
```

```
tttgagacaa agtctcgctg ttgtccccca ggctggagtg caatggcgct atcttggctc   137280
actgcaacct ccgcctcctg ggttcatacg attctcctgc ctcagcctcc caaatagctg   137340
gtattaacag gcatgcacca ccacgcccgg ctaattttg tatttttagt agagacggga    137400
tttcaccatg ttggccaggc tggtctcaaa ctcctgacct caggtgatcc gcccacctcg   137460
gcctcccaaa gtgctgggat tataggcctg agccaccacg cccggcctaa aattgtttat   137520
cttaagattc atgcagtgaa agctaactta ctgagtgata aatttgctta gtgatctgtt   137580
tattaggttt tccaaatttg ctaattgggc tttgaacagc tgtaaaagtt ctgactgtaa   137640
aagaaagctt caacttttgg cattcatgat gcttttctga gtattaaact aagatagatg   137700
ttttacctga aggatcggcc accaatcttt aaatggctaa acaaagggt tgctaaaaca    137760 taatccaaat tgacataaga aataccattt ttccaaccaa aattttggca ttcatatggc   137820
tacttttacg tatttcagct gcatttgaac atctttttca aactttaggg tggttggtgt   137880
atcactgagg tcttggatga cactttagct ttgattttgt ttttatgaat taaaattgtc    137940
ataccaaaat ttttatttca agcaaatcca agagcataaa aaattaaaat attacttaaa   138000
atactaagag agaacagata tatattttac taagcatatg ttgaatgaaa ttgttcaaat   138060
atttataaca ggcatagagt agaattttct taaaaatatt tttgatggta taccaatttg   138120
tattttctca gaaacatttg ccttattctt ttttctgttg tgttttcttt acctgattga    138180
aagctcataa tctgttgtta ttgttttgtta acctttaatg ctctgatttc aggagttcaa   138240
cctaagcctg ctagctccat gcttaagcct agggatgagt gaaatttctg gtggccagaa   138300
gagtgccctt tttgaagcag cccgtgaggt gactctggcc cgtgtgagcg gcaccgtgca   138360
gcagctccct gctgtccatc atgtcttcca gcccgagctg cctgcagagc cggcggccta   138420
ctggagcaag ttgaatgatc tgtttggtaa ttaaaattaa aatttatctt atttttaaaa   138480
agcattccag ggccagtata gtactttgca ccaagtaaat gtacaataaa ggcagtggat   138540
ctaatacatt gaaagcgttt acagaggtag ctaaagagca gcacgggtgt cctcggctca   138600
gaatttcttc ctgtgtgttt gccactttgc cattcattga catggtcatg gacatagggc   138660
tctaagccct tgaggaaggc tgggccagac ctcaggggag atgcagcccc aaaccacgtg   138720
cagtcctgtg gacggatgtg tagatgtgcc actgaggaac aatgtcttga gctttcatca   138780
gattctcaga gaattgcttg actgcctttc gaagttgatg catctgtgct cacgtttgca   138840
cccacccacg aggtccttct gtttcagggg atgctgcact gtatcagtcc ctgcccactc   138900
tggcccgggc cctggcacag tacctggtgg tggtctccaa actgcccagt catttgcacc   138960
ttcctcctga gaaagagaag gacattgtga aattcgtggt ggcaacccctt gaggtaagag   139020 gcagctcggg agctcagtgt tgctgtgggg aggggcatg gggctgacac tgaagagggt    139080
aaagcagttt tatttgaaaa gcaagatctc tgaccagtcc agtcactttt ccatctcagc   139140
ctggcagtaa gtcttgtcac cgtcaagtta ttgtagccat ccttcaccct cacctcgcca   139200
ctcctcatgg tggcctgtga ggtcagccag gtccccttct catctgcacc taccatgtta   139260
ggtggatcct aattttagag acatgaaaaa taatcatctg gaagtacttt atgtcttaag   139320
ttggcctgga catgtcagcc aaggaatact tacttggttt gtgttagtgc ttgtaattcg   139380
cccccagaat gtgtacacgt tctggatgca ttaaagtctg gcctgtatcc ttaaagggcc   139440
atcgctgtgc tgcctgccct cagcaaggac acactttgca gacccacaga ggctccgcct   139500
ccacctcaca ccaaagaaag ggaggagtcc aaagggcatc agtgccatta ctcacaaaat   139560
```

```
gataaataca cccttattct gaaccacgtg gagtcatatg gtttgtgatc cctgtccttc   139620
aggtttcagc ttagtgggga agtgggaaag tcagcgtgtg atcacagcac agggtgattg   139680
ctgctgatta tattatgtgc ctgctgtatg caggatgaaa tactttatat gcgtcatctt   139740
atttgactct cacaaccccc tgtgagatag gctctgttac tcccatttga caggtgagga   139800
aagcaaggct tagagaattt cagtgacttg cccaggtcct ctgagctagg aagtagccat   139860
tctggcattt gaacccaagg cctgctatcc ctagaaccca cgctctcaaa ttcaacctat   139920
gacagaggca agccctggtg ctgtgggagc cccaaggaag agcctctggc ctggtggcca   139980
cgtagcccag gagagatttc tacaggagcc cacagcgctg aaggagagag aggcagcaga   140040
gtaaggggc tttgtggcag agaggggact ggcactttgg ggaataggtg ggtcaggact   140100
gaatgtaatg gagccatgtc agagctgtcc ttctggaagg gcaagggcac ctggacgcgc   140160
tgcccctcag tgctttggac ggttccacaa ctgtgattca cacggcttcc ccaaacgaag   140220
gtacacgagt gggcattctg tgactcggta cttccctta ggccctgtcc tggcatttga   140280
tccatgagca gatcccgctg agtctggatc tccaggcagg gctggactgc tgctgcctgg   140340
ccctgcagct gcctggcctc tggagcgtgg tctcctccac agagtttgtg acccacgcct   140400
gctccctcat ctactgtgtg cacttcatcc tggaggccgg tgagtccccg tccatgaacg   140460
gtgggttcct atcatagttc ctgtctgctt caccatgttt ttattttgtg ctgcctgttt   140520
gccaggtact aagctaggaa ttggggatgg agaggtagat aaaatatgca tcaggaaggg   140580
ctgggcccca tctcttactc tccaatatat tggagtctac actggaattt aactggaatt   140640
tgctttttta gtcatttat ttagattttg aagtttcagc tttcatcaaa atacctcta   140700
aactttatgt ctctgtgatc tttggtctta gctgttttat gtatttagtc ttatatgatc   140760
ataagattaa taacattaca ttcagaagat tatttgtttt ctgtcagagt taaaatgttt   140820
gttttatac tgcattgtaa tattaacgta ctgtaaaata aaagtggctt gttcttttca   140880
aggaacagta tcctcaacaa gggtcattag ccacaatttt taaaaaattg gacgtcatag   140940
tttacatgtt agagggcgtt ttgaagcttt gtatttttaa attaaatgtt atagagtgat   141000
gttttcatgt ttcataattg ttttcatctg tgcatttgta gccaacttga aaacaaagat   141060
ccagggatta ctacttaaaa gccagacttc ttggaggtta tagtgatgat tttgatagta   141120
tcttgagccg tctcataata acctcagggt gagagatggc caacaggaga cagtcgaggg   141180
acttagaaat ctgaatgaaa tctgaagttc aaatcttcag acatatacca ctaaccaaga   141240
gattggtacc tcagtctagt attgtctgtt tgtctaaaat tggttctaag gaatctaggc   141300
tagtctgtct atcccttca acttttgtga ggctgcacaa atgtaaaatg ttgaataaaa   141360
agcactgatg gaagtgtgta gaaattcttc tctttgttct gttgtaattt tagttgcagt   141420
gcagcctgga gagcagcttc ttagtccaga aagaaggaca aatacccaa aagccatcag   141480
cgaggaggag gaggaagtag atccaaacac acagagtaag tctcaggacc catttttttc   141540
ttacatgttg ttcctccagg acttaaaaat cattcacaga gacgtgcacc gcggtgagtg   141600
tggactcctg gaagcgcacc gtagctccgc tgtgtcctgc tgctcctccc tagctgtcag   141660
ggaggctgta gtccattgct ttgccagctc ttttgtttcc gagtgaacac cttatccgta   141720
cacatgcggc tgtctctgac cctacagacc agctgggatg ccactggggg agcgctccct   141780
tcccccgca cttcccacac tctgcagtta ttctgagatc cttgagggca gggaacaggt   141840
ttgtcttctt tgtgttctca gaaattaatg ctcggcctct ggtcagcaag caacaacctt   141900
ttgttgagtg ataatgaata aataaatgtt tcccacatga gtattcagta acctcagtgt   141960
```

```
caggttcagc catctgtttt ggtggatatt taaaagaaaa ttccgctttt cctacagaaa   142020
aaaaaaaaaa tccaaatccc agtgatttaa gccagttata gacttagaca tatactacgg   142080
cttttcatgc actttcctcc caattctaga gtaggtattt tactaggaaa atggtggcag   142140
tgcctgttgg gaggaagatt ctttggccaa gtgtcttttg ttcttgccag ggcccctagg   142200
ctgctggggt gcttcagctt ctttagccca gtgtctggtg gggaatggcc cctgttgcct   142260
gtcccacaga ggtgggggtg cctcacctgg agcctgtcca cacattttac acagcacgct   142320
tacctggagc atcaggcatc ttttccatgc tctgtggctc aggaaacacg ccttttcaat   142380
catgagtgca ccagtgcttt tgggcttttt ctccccgctt ttgtgcaatc ctggttgtgg   142440
atggagtttt cctgtcttta gtcttctgca tagtactttt ctcttctggt tcccggttca   142500
aggttttgta attagagaat gacccagaag caatggcatt taatgcaca gccaaggact   142560 tctctgaatt tgtatctcaa acctctgtgg gtccttcagg cttcagtttg tgatttcatg   142620
atttcttgtt gctacctaag gaatatgaaa acacccacct ccctactctg catcttccag   142680
ccgagtggca cctcaggctg tggatcctgt gcttctgtgg tgaggataag aatagtgcca   142740
accgtgtgga ttgaaatcaa tcagttaatc cctccatgta aagcacctgg aacggatgac   142800
agtcttgtta tgaatactca acaaatgcta tcatgatttt tagttagatt tccattgctt   142860
taaaacagtt gagacatctt ggcggtttga gttagagcaa cgggccctga agtgggttct   142920
gtttgggtga agatgattat gcttattccc catggccctc tttaggcaag agtgggaagc   142980
tttctttgtt tttttaatca cctcgatagg acgttacttc ttaaaggtca tccaataaat   143040
attaataggc cgggcgcggt ggctcacgcc tgtaatccca gcactttggg aggccgaggc   143100
gggcggatca cgaggtcagg agatcgagac catcccagct aaaacggtga accccgtctc   143160 tactaaaaa tacaaaaaat tagccgggcg tagtggcggg cgcctgtagt cccagctact   143220
tgggaggctg aggcaggaga atggcgtgaa cccgggaggc ggagcttgca gtgagccgag   143280
atcccgccac tgcactccag cctgggcgac agagcaagac tccgtctcaa aaaaaaaaa   143340 aaatattaat aaagccaact cgttagcgtg gggcttaatt gcttaagtcc aatgagaagt   143400
ccttctctat cctaggaagt tgcccaaact gtagaatctc gtggcctgtg ggtaatagcc   143460
acgtaataca cactcactgc ctcaacaaat catattttag taggtatgat attctagact   143520
caagacacca ttctgtggat cttcccaagg gtgtgaagtg tccacagcgt ctgccttggg   143580
agtttccatg cccaccagaa ccatgcccca gcccctcaa gcactctgac ctaggaaagc   143640
cagtgaagca aggatgacaa catggccctt tgatactagc tgagggacag acacaggtcc   143700
tgggagacca gagaaagacg aggggcagag gaggtgtcct aaaggaagtc tgaggctgag   143760
gagccacagg atggcttcca gctgtcacag gctgctgctg gccttatcac agagagtggg   143820
ccagagggct gggaaccaag gccagagctc aggttcagga ccattccagc aatcccagca   143880
gaaaatgggg agaattgtat ggtataggcg gatatgaagg tagaatctgc aggccttcag   143940
tggccaactc agagtctaag tggattccac agttacagct tgagcagctg gttgtaggtc   144000
atgctttcta cactgggcat ataggatgtg ttttttaaaa agtcctctct taaccgttgc   144060
ttgtttagat cctaagtata tcactgcagc ctgtgagatg gtggcagaaa tggtggagtc   144120
tctgcagtcg gtgttggcct tgggtcataa aaggaatagc ggcgtgccgg cgtttctcac   144180
gccattgcta aggaacatca tcatcagcct ggccgcctg ccccttgtca acagctacac   144240
acgtgtgccc ccactggtga gtctgctcgt tccttgcaga agaccaagta cggtgaaagg   144300
```

-continued

```
caccggtagg ccctgggctg ggcacacgtg agagggcggg acagaatccc cgcagcccag 144360
aggctgcctg ctgtggttct ggtgcccact gtggttctgg tgccaggctg ctttcctcag 144420
gcaccacgtg tggaggtcgc tagtagaaat actgggtttt ctaaaatgaa ctgaggccct 144480
acatccctaa gagattagtg ttagacctga ttctagagca actagaccac tttgcttaat 144540
agcagaccag aaaccacacc ccctcgagtg agtgagattt cctttggag ataattcatg 144600 tttttctaca cagttttgca gttgtcttca gaattggttt aaagtaggtg ttattgccag 144660
gcgcagtagc tcatgcctgt aatcccagca ctttgggaag ccaaggtggg cggatcactt 144720
gaggtcagga tttcgagacc agcctggcca acatggtgaa accccatctc tactaaaaat 144780
ataaaaatta gccaggtgtg gtggtgtacg cctgtaatcc cagctactca ggagactgag 144840
acaggagaat cgcttgaacc caggaggcga aggttgcagt aagccgagat cgcgccactg 144900
cactctagcc tgggcaacag agcaagactc cgtctcaaaa aaaaaaagg taggtgttat 144960 tgatcagaac ccttgtttca gataacatga ggagcttagc ttgaggagag tgagggttga 145020 tggagggga ctgacttctg cccagtgaaa tggcatcatc tcccaccagc ccgctgaaat 145080
aagatgatgg ggcctgttcc ttagggcctg cagcatcctc aggcaggaaa gaaaggccga 145140
cctggcaggg tgtgagccag caggtgtagg tcagggagaa tggagccagg tcccaggaa 145200 gaggcttgtg gctgcctgag aagggtgcgt gcctgcctgt gtgtgtgtgt gcacgtgtgt 145260
gtatgtatgc tggagagtct agggaggctt gctccaagga cgcagtattg tttgatcctg 145320
agagataagg attctgccgc agggaatgaa ggtattccag atggcgggct tattccgaag 145380
aagaggccag tgcctggcgg tgctggaagc agttgcagaa cagggagttg taggcttttcc 145440 tgggaagaga gcagcagggg tgctggagaa gcaggccaca cttgctgcat ggggttgctc 145500
tcggccccac tcttggtgca cagcgagtca ctgtgggttc attagcatct ggttatgaga 145560
cagtaactgc tccttttggag gggctcgtgg agaccatgca ggagggcacg gtcttgaggt 145620
catgccgtcc agagcacacc tgaggatagg ccaggacggg ctgcacgctg taggtaaaat 145680
tcctccagca agctcttcac tggcattgag gagttccctg agtgcggtca tctggaaggc 145740
agctgtaaca ggcactgcag tctctcccctg ggtgggtacc agagaggagc ataggggagc 145800
ataaccgatt taagagagg gctttcctgt ggtgaggtaa gagattagct ggtcattatc 145860
atagagcccc ctctgccttt gtgcagatgg gctgtgggaa tcctggggtt ccgtgggtc 145920 ctttgtcacc tcactgaagg catgtaagct gagctggcca gaccgtgagc tgatcctgcc 145980
acttgaacag catcaagcct gcctctggat tcttctgtgc atggcacttg tctgagcacc 146040
tcacgcacag agaactggac ttcagagttt acagaaataa gctgtatggt tcattttcat 146100
gcctgcttgc caataaacat atctgagctg aacctcattg aacgcctgcc tttattctag 146160
cacagcacct gctgtttgtg ggcgagggggt gctgtctcta actcctgcct gcttctccca 146220
gcactccctg agtggggtgt gccagcagcc tcaggatgag gacaggaagt gggagggcag 146280
agcagatttg ggagggccac ttgatgggga aggaagtccc aggaagcagt tggagctgtt 146340 ttctgggga gaaggtgcca gctctgggac agtgttgggg tagtgaggag ggagcccagt 146400
ggagagaagt cgggcttcct gcttcctcac agtatgtctg tcctgactca actcggatga 146460
tgtcacttcc tttttcatctt ctcaggtgtg gaagcttgga tggtcaccca aaccgggagg 146520
ggattttggc acagcattcc ctgagatccc cgtggagttc ctccaggaaa aggaagtctt 146580
taaggagttc atctaccgca tcaacacact aggtactctt ggggcctctc cttcaggtca 146640
ccattgtcgg acatctaccg ggaggaaatc cagagccccc agtactggga tcttctcatt 146700
```

```
tgactccaga aaagatttaa gcatgataat aatacaaacc tatgtgaata cattttgcag   146760
tgttggcaaa actccttta tactgagaaa atagatccca gttcctgtgt tttgtggctt    146820
gaatcccagc tttgtgtatt ccgggcttgt ttgaagtcag gaaaggttca tgtgtagtgg   146880
acaacgtgag accaaattct gccttagatt ttgcatttag gctaaacagt ggcagcactt   146940
gtctcagaat gttttcttgt gttcaccagt ctgatcctgt tgtgtctcag tggtccattt    147000
tctcatatgg gaacaagcag acgggagcag atggagtcag gtttcttggc actcgccttc    147060
cccagagcct agaggcagca tgggagaaa gcaggcttgg ggctcagaca gtcctggtct     147120
gcttccagcc ctcctacctg agcagcgcag ggcaagtccg tctaacctct agagaccctc    147180
agttttgtca tatgtaaaat gggggtcgtg tctatttcat agaattgttg cagatttaga    147240
aattacattt ctaaacaaat gttaccccctt atttctaaat aagtgtctaa atgaataagt   147300
caccactttt gcccctattt gatggcaaga ggtgtgatct tgtggtggga ctgtaatcag    147360
tcagttctca gtgactgtgc cctgctgtgg tgtttcctgg aatgttcctg tcttgtccta    147420
gaaagtctgg caggggcacc ctgactccac tgtccagtcc tctccccagt ccctcgggct    147480
tctgcagatt tgaggcttgt ttggatccca gaaggttgtg gcaggagaca ccttgcctct    147540
actttcccct ttataattca atgtccaaag agagccctga gcaggtacct cacgccagct    147600
gcctcacgga gctcctcctc ttcctggctg tgaggatcgg tatcagtggc ctcctgctct    147660 ctccccttg cctaacacga gcacctttgc ttacttgggt gcccttgctc ttgaactgcc     147720
catcggacgt gcgtgaccca agactgtgcc gcagtccttg ccttgtctgt gctcattttc    147780
tttgttcatt ttttccctg taacgtaaat tgttatattt gtctgtatct gtgtctgaat     147840
cagtcctgca cgctctcctt ctctctgtct cttgttcttt ctttaccccg tttatcacgg    147900
ggaccccgat gtccattgct ctagttctcc tgtcctaagc accccatccc gtctctctgg    147960
ccttaccaca agtggcgtgg ctgcctcaga catcatgatg gggacatgaa gcacagctgt    148020
cagaaacaac tgttcgttag atacactcga atgcagctca tcaataggga tggagggtct    148080
gtcggatgta ttttcactga atccccgttc ctaccttgat acactctttt taatctattc    148140
ttctagacag gtcagaggaa ccattacttt gacttttaaa ttttttagcag ctttattgag   148200 gtagaattca catactacag atttcaccca ctctaagcgg acagcttggt ggccattagt    148260
tttatccaca gagttgtgca gccagctgca cagtctcagg gctggactcc agggaagatt    148320
ttagcccatt tagtgagtgg ggcagaagtg gccctggccc tgcacgaggt tgcctgcatg    148380
ggcgtccctg ccctgtccct gtgtctgctc cactgggggt tgaccaggct gccagggccg    148440
acttgggcct gtgccacctg cctctcatgt gtctcggaca gtgcagccga tgtctatact    148500
tcggtttcct caatgatgaa atggagggga tagtgttccc cgcatcatag aactgtgtga    148560
ggtttaaggg actcactgcc cttggcgtgg agccttctcc aggggccgtg ctgtgtcggc    148620
gtagctgtca gctctccgtt acaggcttga gaagggttga cactctctca tgtaacattt    148680
atatttctag gctggaccag tcgtactcag tttgaagaaa cttgggccac cctccttggt    148740
gtcctggtga cgcagcccct cgtgatggag caggaggaga gcccaccaga agtaaggcca    148800 cacccctgtgc tggttggcac atgggcagtt atggccgctt gcaggccttt ggtggggaat   148860
aaaataaggc agcaagctgg tgttctttt ttctcttacc ttatttttga aagagtagct     148920
gaatggtgtc ttgactgata ttccagagca gggacaaagc ctgctgaggt ctgggggctg    148980
cgattaccaa tggctggaat gcatttttatt acggtgcatt ccatgttaag gatcaatacg   149040
```

```
attgtgccct ttctggaaaa tatcttttag tttatcaata ttcagaggag tgtaggttga   149100
attaaaatga aaaggcactt tataaaggcc atgagtagta cctggtttca tttttctaat   149160
gtcttgcaga gattttatca ggcttcttga agtgttcacg tacattacgc taacacgata   149220
ttaataataa ctgtgctctg gtacagcgga gccagcagaa tgggaagttg tggaatgcag   149280
gcccttgatt ctgatagaag gtgtggtttg aactcacaga aatgacagtt tggagggtag   149340
acatatgtca caagtcatca agattgtctt taaattcatg catagaagct aacagggtgt   149400
cataagcaag gcctgtaaaa tgtatgaggg aattcaaaga taatttatta aaaagtaatt   149460
catgtttgga gttttgtgcc caaaggagtc cttgatttga aaaatgggct tttgcccatc   149520
agattgtttc agggcccgtg tgtgcggagg ccctgccttg tccccgtga gctcagcctg    149580 acagaaatcc tttggtagca cttaaggctc ctcttcctcc cattgaggca gggaagactc   149640
tgggttctgc aggcagaggt ggttgtgggt gtcttgctgc tcttgttgac atgtgggctc   149700
tccttccagg aagacacaga gaggacccag atcaacgtcc tggccgtgca ggccatcacc   149760
tcactggtgc tcagtgcaat gactgtgcct gtggccggca acccagctgt aagctgcttg   149820
gagcagcagc cccggaacaa gcctctgaaa gctctcgaca ccaggtttgc ttgagttccc   149880
acgtgtctct gggacatagc aggtgctggg acagtgggt tccccgctga agcgtccagc    149940
agcttcaacc aggccgtttt ccttcattgc tagaattgaa acaccgtcc gtgtggcctg     150000 tgcaggagat gcagacccaa aggtggcctc ctggtcagtg agaagctgga acgtgacag   150060 gaactgacgt ggggttattg agcattagg ggaagacgtt agcagagcag gaatgagcag    150120
gcaactagta gaacacccac ttaagggctc acggacaggt gctcacttag gaagtgagtt  150180
tcatttggta ttacaccagg ttcctttagg caaagcggag ggaaagttct ggtgtttttc   150240
acttgtaaga ttttgaagga aacaaaacac tcttttacctt ttttctaaaa tgtaggtttg  150300
ggaggaagct gagcattatc agagggattg tggagcaaga gattcaagca atggtttcaa  150360
agagagagaa tattgccacc catcatttat atcaggcatg ggatcctgtc ccttctctgt  150420
ctccggctac tacaggtacc tgagggaaag ggtgcggggg agcggttgta cttgggctag  150480
aatgagagaa gactggcatg ctcaccacac cagtgatgcg ggaagacctg agtgtggtct  150540
gagttggagg ctgtggtgct aaatacgctg ccccttttcat aagcaggagt cttagtcagg  150600
cccagggagg aagtaaaatc tggaaatgaa tgagaagcat tctctcctgc cagtcaagaa  150660
atgagaagcg aaagaattct cacgggctgt aagaccagca ggatttaaaa gttgaattag   150720
ttgcttatgt taagaactca accaagttca tctacacaag ctgaatctcc agcttttcct   150780
aagaaaccat gtgtggcagt ggctgcaggg cagggcacag ctgggcctga gcaccccgct   150840
ccctgcacct ctcccctccc tgggccctgc ctgtcactgc ccactctccc accaagcctt   150900
ccggttgtgt gcctgcccta tcacaggcat cggagcttgt cacctggttt aaaagaagag   150960
agttgtgtgg ggatttggga tgcacgtttt tcactcaaaa gtattttagc gtagagctct   151020
gtgattccgt agctatttag gagtttaagc accttgaagg ctttaattgc agaaagttct   151080
atgtggacgt gcaatgtgtt atacgcagtg tctatgagac tcaaatgttt attagggcgt   151140
tgaagtaaac tgagcacttg gagggccatg gatccagcct tcaaggagct cataagtcag   151200
gaggacccag gagcaatgac ctgtcataga aggcagaaaa gaggggcaca gaggtgggtg  151260
ggaggcatac acaggcagct cctggagctc caagggagc aagtgcttcc agggaagggg    151320
gcgtggaggc ccctttggag gaggcaagtt gatctgggt ctggcagagg gttagctggg    151380
gacatttagc gggaggctgg tgcccgggaa ttgggggat gcccagcaga aagacatgag   151440
```

```
gaggctggcc tggggcgtgg gggggtgtga aaggttaagt gggggcatta tcctgctccc   151500
gctcctgccg gctgtatctg gtcagcctgg gcaccgaggt ggggttctgg aaggcactgt   151560
tcaccaaaat gcttatctgg gtcccccaga gagcttgcct gcctggactg tcggctcgcc   151620
tgcaactgct gactcctaag cttttgcagc tcagcccaca accagttcct attcacagag   151680
gtgggagctg aggggtgaca agtgactgct gcagtcttat ttgtcataga gaaaagtga    151740 cagagtccag cttgcccact ggccctgcca gcttaactgg ttataaagtg acaaatcccc   151800
aagacccaca gggctctgca caacctgggc cctcctgcca gtggcggcga gggcaggtgg   151860
ctcacggctg ggtgcctgtc tgggcaggag ctgggctggt atggggtggg cctgcggccc   151920 tgccccctg tgcagatcaa gactcagggt gctggtgttc acaggtgccc tcatcagcca   151980
cgagaagctg ctgctacaga tcaacccga gcgggagctg gggagcatga gctacaaact   152040
cggccaggtc agtctcgcgc ccccgccgcc tggcctctgt ccgtttctgt cctcagactt   152100
tggcgcttga cacacccagg agaaaagctc agtgcacttt ttaaatgaaa ggaagttttc   152160 cttttttta aaaaaaatt taatgttcat tgtttttatc tgttttattc ctaggtcccg    152220
caagcagagg aagcattagt tttgttttta tttatgttct gtattccaga aagtagttaa   152280
gagacctcac atgtagcgat agagatgtgt gtaagagaca gtgagagggc gtgacttgga   152340
cttaagcaag gaccgtgaga cacaaaaagg ggggtgagga cagagtggag tcagctgaaa   152400
tgctcaggag gaagtagacg ccatgaaggg ccatggtatg gggggccgca ggcgtggccg   152460
tgagtgtccc tggggccagc tcttgggggg ctccctgagt gtccctgtcc ctgtggccag   152520
ttctgggtgg gagccccgtg tgcaggcaga cagctcggcc acttcctagc aggtcacatt   152580
ggtctgtgct tctgtttcct cctcagataa gtgaagggat tcaagggtct gggtgtggtg   152640
gctaacacct gtaatctata acattttagg aggctgaggc aggaggctta cctgagctca   152700
ggaggttgag gctgcagtga gccatgattg caccactgca ctccagcctg gcaacagac    152760 cagtactctg tcccttaaaa aaaaatgtaa acagaaacgt agggccattt gcatatgatg   152820
gcacatggcg tggagcccta caggtgtatg ctgggcgggg cccggctgtg ctggccgact   152880 tgcaccttc cctccacccc ggtgctgtgt ctttcgctca ccgggttcct gatttagtga    152940
aagcagttgt gcaggacagt tctctttgta gcttttgttt ctgtggaaat gggtcagaat   153000
atggtgttta gaaacactta tgagctctga gagtttcctc ttctgagttc ctggcctgca   153060
gccttcacag cagaaaccct gtgatgtcac aagcctgttt ctgttccctg ctctctgcct   153120
gtactgtcct gttttgtgcc tgccggtttc agtgacagga agcagggagc tactggacca   153180
gcctgtattt ttctagacat agttggaaaa agaagtccca ctcttctgtc ctttcaccct   153240
tgacagatgt ttccacccca agataagtga aaatgaccaa taggatgcac tgtatttttc   153300
atgaaagtgt ttctgaaggg caggctgaga gtgagaggcc tggggctcac tgggtgcctc   153360
tggccttgtc ctgggcccag ggacactggt ctgtgcccga ggtattccct atcccccaa    153420 ccccgctgca tttggccaca tccttcaatg tttgcgttgt gtccagcgtc cgcaaaccaa   153480
ctgtcatggg atcatactgg ggctgaagta cggtcccacc cctgccctgt ctggggctga   153540
agtacagtgc cacccctgcc ctgtctgggg ctgaaggaca gtgccacccc tgccctgtct   153600
ggggctgaag tacagtgcca ccccctgccct gtctggggct gaaggacagt gccacccctt   153660
ccctgtctgg ggctgaagga cagtgccacc cctgccctgt ctggggctga aggacagtgc   153720 caccccctgcc ctgtctgggg ctgaaggaca gtgccacccc tgccctgtct ggggctgaag   153780
```

```
gacagtgcca cccctgccct gtctggggct gaaggacagt gccacccctg ccctgtctgg   153840
ggctgaagga cagtgccacc cctgccctgt ctggggctga aggacagtgc caccccctgcc  153900 ctgtctgggg ctgaaggaca gtgccacccc tgccctgtct ggggctgaag acagtgcca   153960 cccctgccct gtctggggct gaaggacagt gccacccctg ccctgtctgg ggctgaagga   154020
cagtgccacc cctgccctgt ctggggctga aggacagtgc caccccctgcc ctgtctgggg   154080 ctgaaggaca gtgccacccc tgccctgtct gggatgttta gccctagat gccactggac    154140 tgagccgcta cttgcttttg ggaagaggg gtggggtta ggggtctggg cgaggggagt   154200 gcagggctc ctccttggcc tgagagctgt tcatacagac tcctcgccca ctccctgcag   154260
ggtgctgggt cccaggggg aaatggccct tggtgccaag aacgtgagtt ggggctagtg   154320
ccagtgatga tggagaacag ctttttatgg gcacacagcc cacagcactg tgccaagtgc   154380
tcgaggcttc ccgagaacca ggcagaaagg aggacagtcg aggtgtgctg actgcgtggt   154440
ggctgcgtga tctagagcgc gggtcacaaa ggcgcgaggg agctctggcc ttgggtttac   154500
cgcaatgact gccagtgcgg gagactggaa aaggaatctc acgtattggt tccgtgtttt   154560
ggggactcca ttcagatgtc acttaggagt gaaagcatcc cttcgtagag cctcttttctg   154620 tgtcaccctc ctcagctgct cctggggttg actggcccct gattcatgcc tttagcatgt   154680
gctggagctt cccagcagct gtccagcccc tgccccaccc tctctgtggg ctcccttgcc   154740
cgtaacctgg ggtgtctgaa cgacccttgc taaggggcag actgttagac ggtaggcatg   154800
tgctgagtcc cagtggccac acccacccac caggagcctg gcactgtggc cgcagcactg   154860
agcagtgccc cgtttctgtg gcaggtgtcc atacactccg tgtggctggg aacagcatc   154920 acacccctga gggaggagga atgggacgag gaagaggag aggaggccga cgcccctgca   154980
ccttcgtcac cacccacgtc tccagtcaac tccaggtttt ccaatggcct ttttcttttt    155040
aacagaaatt tgaaatttct tatcagtcat ttgatttgtt tgaggtgctt cttgaaatga   155100
gcctctcatc tcatgtactt ggaaaatacc catctcgcat attccacagg aaacaccggg   155160
ctggagttga catccactcc tgttcgcagt ttttgcttga gttgtacagc cgctggatcc   155220
tgccgtccag ctcagccagg aggacccggg ccatcctgat cagtgaggtg gtcagatccg   155280
taagtgagcc ttcccattcc cctcacacct gcacgtgcca cacgcaccac acacgccaca   155340
ccccccacac acacacaccg cccacacaca tgccacttgc acacacaccc ctcatgcatg   155400
caacacacac acaggccaca cgcaccatag acaccacaca cacatgccac atgcacacac   155460
atacacggca tgcaccatac acacaacaca cacagcacac atgccacaca cacacgccac   155520
accacatgca ccacacacat gccacatgca cacacactcc acatgcatgc accacacaca   155580
cacacacaca ccacacacac cacatgcacc acaccacaca ggttacatgc acacaacaca   155640
cacatgccac gtgcacacac cccacacacc acatgtatgt gccacacaca gcacacaacc   155700
acacacatgc accacacaca tgccacatgt gcatgcacca gacacatggc acacactaca   155760
cacacgccac gtgcacacac cccacacaca tgtacgcacc acacacatgc cacacacaca   155820
tgcaccacac acatgccaca tgtacacaca tgtatataca caccccacac cacacacaca   155880
ccacttgcac accacgcaca cacaccacat gcgcacacac accacata cgccacatgt   155940 acacaccata cacacaccat acatgcacca cgtgtaccac gcacccacac agacacagca   156000
cacgcataca ccacacacac acgcacacat gcgtcccgca cagtaatgtc tcttgggtgt   156060
aagaacacga cttgccagta gtagcgttct ggatgcgttg cctggattct aacagcgcga   156120
ttctcccctt gccctcctgg ttttccacat ctccagcttc tagtggtctc agacttgttc   156180
```

```
accgagcgca accagtttga gctgatgtat gtgacgctga cagaactgcg aagggtgcac    156240
ccttcagaag acgagatcct cgctcagtac ctggtgcctg ccacctgcaa ggcagctgcc    156300
gtccttggga tggtaagtga caggtggcac agaggtttct gtgctgaagc cacggggcc     156360 catctgcctt gggacctggt gttggccaga ggtgccgggt gcggctgcct ccttccaaga    156420
gttgacccga accggactcc acggcccacg tgagctgcag tgcttctcag atggaggggg    156480
ttcagcgacg gtcagtgcca ttcacaggtc actgtgatgt gggttgtggc ggccaagcca    156540
tggtttgggg tcccgtatcc ctgggcttat gacatcattg tagtagccca tccccacaga    156600
accacggtgt gtggtggcgc tgaggcatcg tagatggtgg aaatgctact ggcttcccca    156660
tgctctgccc tgaggcctga ctgcctcact ccccttctca gttatgttcc aggcccccg     156720 agcttcctgg ctggacagct tctctcctgg gggccgtttt gtcacagtga ccctgtgttt    156780
ctagtcccaa atctgggtgc tatagtctct ttttagcgtg gtggttgtct tagtcttttt    156840
tggctgctac cacaagttac cttagactgg gtaatttata aacagtggaa atttacttct    156900
caccgttctg ggggctggaa gttttcatgg tcaaggtgcc agcagatttg gtgtgtgatg    156960
agggctgctc tctgcttcat agatggcatc ttctggctgg gtcctcacgg tggaaggagt    157020
gaacaagctc cctcaggcct tttagaaggg ccccaatcca caagggctct cccatcatga    157080
cctcatcacc tcccaaggcc ccaccttctt gtactgtggc actgcaaatt aggtgtcagt    157140
gtaggagttt caggagggat agaaacattc agaccatccc agcggtcaag tgttcatcct    157200
cttgagttcc tccttattct gcttctggtt tatcaggatt cagccagtgc agcatggtac    157260
ctgtattctg tggcacatca ccacatggta tttgccaagt atccatcacc tgcacacgtg    157320
aaatcattgc ccgtgggtcc cgacatctgg cgaagcatat tcaaggatgg cagaactgtc    157380
agagctggca cctctggttc cttgtcatgt ggcattacct agtaatccat tttatgatag    157440
caatggaaac tcatttcttc aacaaacacc tgagtgctg ccgtgtgcca gccgtctggg     157500
gcccttggtg agaatggcat ggtggtgccc atcagggcct gcctagcccg tgctctggac    157560
gggctcctgt gtgtcaggaa cgacaatgct gtcatgacgg tgaatgattt tttttttgc     157620 catcactcca gccgctaaca tttgcggagc tcttcctccc gcaccccac ctgacaaggc     157680 caagggtgac cttggcccca ccctaggcgg ccaaggtcag aggttagctg gcttgtctgg    157740
gtcacacaaa atgcagcaga ggttgaggtg agcacatgtc cgtgacctgg agcctgactc    157800
cctctctgcg agtcttgact gctcttgcct agactctgtc ctccccgagc caaacgcca     157860 gtcatcttcc cttgtgggtg tccttcagcc tggtgccatg ctggtgactc agcagccgtc    157920
cagggagtgg aaacaattga gtgtgtgggt tccctgtgtg ggcatctctc ttcacggcga    157980
acaccctctg ggtgttgccc acacgatgtc aaagcggctc ttggaagggg tccttctcct    158040
ttgtgggaag tttcagctgc tgggctaact tgaattgtaa ctgtggtttt gtgctcaggc    158100
ccagatcccc ctaggcaagt gttgtgccat cagtaatcaa atgagaaata atcatttga    158160 aaagcagatc ctaaggcagg atggtcatgg acactcactc ccagctcttt gtgcactcat    158220
gctttctgga agatggccat cctctgtgaa ggttttcagc gcgtcatgct tggtacccac    158280
gtatccagag catgtcgttt tgaggtattt gcccaccgtt gtgaaatccg tgccaccga     158340 gagcaggtcc tgatgtgggg ctttcagaag tgggacctgg ggccgtacgc agtccttagg    158400
gaggggccgt gtggcgttgt gcgtgtgagg ggatagcaca gggtgaggtg ggggcccaag    158460
aaggaagtga cccacaaaga acagcctcct ctttttggtcc ttgttcctgg gatggctggg    158520
```

```
agtggcttct gtgtcgtccg gccatttccc ctgcggagag gctcctacca ctgccgagaa  158580
cctcatcatt ccacaaaaac aagaggccgc ctggccatcc agcgctccat gggaattctg  158640
tgtccccata gtcttgggct gaaggagggt gacattcctt gctgacttct gcagggggtct 158700 cctcactgtt aaagagcaga ttgaaagtga agaacgtggg ctaagtgttt aggtcgatat  158760
ttaaccctgc taggttttgg atactaagtg aaattgaggc cattttggtt gaagttgaca  158820
gaaaccacta tcagggatcc ccaagactac cccaggcttt tctagaaaga ctctcagcta  158880
agatgtgtta tggtaaaagc acacaaaaca aaatcagcaa agaaaattag caagggcaga  158940
ggcccatggg gcgatgtccc gaggacacca ggcttgagct tccagaatcc tctcccagcg  159000
gggtcgtgca ggacgcactt aactccccgc acagtgagcc gtgacagcgc gtgtgcagtg  159060
tcgtcgccag gaaagcacac tagagactcg gtgccagggt ttttactggg ggctgggcac  159120
atgggcaccc tctgcctgcc tcgtgcccag actctggact cccggaggga aggcaagttc  159180
tcagcaccaa ccctggtgcc cacacaagca gctgagcaca gggagcccct cctcagtgag  159240
gatggtgggc accgtcccaa caccagccag gggccagcct gcacacagg  cctctcagga  159300 tggtctccgg cctgctgtgt agtctcttct gcacacaagc gtgagggcag cgcccccgcc  159360
tcggctgtgg ggaggagcca ctgggacgtg agctctggtg gcatgcagca gcttttgtct  159420
gtgtgtgcct aggacaaggc cgtggcggag cctgtcagcc gcctgctgga gagcacgctc  159480
aggagcagcc acctgcccag cagggttgga gccctgcacg cgtcctcta  tgtgctggag  159540 tgcgacctgc tggacgacac tgccaagcag ctcatcccgg tcatcagcga ctatctcctc  159600
tccaacctga aagggatcgc ccagtgagtg ggagcctggc tggggctggg gcgggggtct  159660
cagaatgagc tgtgaaggaa gcagcatcac cctctccaag tgcccaggct cctggccaga  159720
tggcaggcca ggtatcagtg ggaacccagg tgggtgccat ggctgaggtc agtgagacgc  159780
aagagcacag gtgcgtccta gaggcttcct cgggcacctc cagcgagctg agctctcgc   159840 ctctgctgct gtctcatgtg gcgcttagca cactctccca cgtgcccatt cctgactctg  159900
ctctcgaggc catcggctct cattctctgc tcccagaacc ctgttattac ccaggctagc  159960
ctcctctctg caccttcccc gccctggccc agtacctccc tcttgtttcc actgtgattc  160020
cgacctcacc ttatcttaaa gctgctggac ggcaggttct gtacacacgt gtccttgaca  160080
aagcacggct ggtgccgcaa cccctcagcg agcaagtcaa gctcttcaca gcgatgtctt  160140
acaagcgcag agggctctgt gacaccctgg tctcaccgcc actcttccaa agtcgcagag  160200
gctttagcag agatgggccc agcctctctg agtcataggc ttctgcacac gggagctgtc  160260
tttagaggga gggtggaatt tcatcagcca cccacatggg ggagttgagg gcaagaatta  160320
ggagcaaaga tgggaagggg tctgggagga atggccagtg atccccttgg acaagtgggc  160380
aggaaacggg ggctaggtca aagttgagtg gaagacctgg agggagacgg gaaggtctct  160440
gtaggcacag ttcagacagg agggaggtgt gagccagggc acatgccggt ggccgtctgg  160500
caggatttgg gacatgctgg agcagggaca gcggctcatc aggggccatt gccctcatcc  160560
aggccagagt gtcacaagcc cgtggggagg cccttctcgc ctgtcatcct gctgggcag   160620 tgggtgctgt gctagcagga caggcggacg gctggcaact gtctctgcat ccctggagcc  160680
tggcataggg ccaagtcaca cggggcacag gcctgcaaat caggcacata tgttggtgca  160740
gtgacgtgat tttgggggc agccccagaa caggccccag acacaggcca aagccctgcc  160800
tgtgctggtg tgttggctg ttctatggct cttgctgtgg gcatgaggaa ctcagggaag  160860
gagagttgag gtggtccagg agttgcgttt gggatgcaga gagcttgtgg catccaggta  160920
```

-continued

```
gaaatggtgc gtggggctga cctcagcacc atgggcagag gggccgtgtc acgtgcctcc    160980
gaggtggagg tgggaccacg tggtgacaga tatacgcatc actgggcacg ttttttgtggg   161040
tgttgggggg catcgtattg gctcctctgt tcacagtggc cactcattca gtccctggct    161100
accaggtcct cactgtgcca tggggaaggc cggcgctgtc gggggatcac agaaggcagc    161160
acgtcatgat ggcatgtgcc atgaaggaaa agcacagggc actcaggaag tagaggggac    161220
tggcctgggg tgtgggaatc tagggcctcg ttgagggaca gagagaggaa gtgtgtggtg    161280
gccagcatgg aggtggccac aggggaggct gagttaggcc gagagggcag ggcgttgggg    161340
aggtagacgg gctcagccac tcagggagtg gtcaagcaga ggctgaaggg tcaggccagg    161400
ttgcaggggc ctggggagc cactcagggt aggcgctccc gggagcccgc ctggcccata     161460
gctctacact cccgcgtggg gccggacatg ctgtgaagcc ctctccacgt tggatggggg    161520
tggctgagcc tggatgctgt ctcccgtttt cagctgcgtg aacattcaca gccagcagca    161580
cgtactggtc atgtgtgcca ctgcgtttta cctcattgag aactatcctc tggacgtagg    161640
gccggaattt tcagcatcaa taatacaggt gagtgggccc tggctgtctt cctctgcaca    161700
cggggagtgg gcttcccttc tcttttcctt gcaggatcat accagtgggc cagttttgac    161760
ttggtcggga ggaggcatga acacctgaga ctgtgcagcg attctttgac acagaggcct    161820
ttctccctgt gcagatgtgt gggtgatgc tgtctggaag tgaggagtcc acccctcca     161880
tcatttacca ctgtgccctc agaggcctgg agcgcctcct gctctctgag cagctctccc    161940
gcctggatgc agaatcgctg gtcaagctga gtgtggacag agtgaacgtg cacagcccgc    162000
accgggccat ggcggctctg ggcctgatgc tcacctgcat gtacacaggt gagcatgtac    162060
acggtgccca taaggccagc ccaagtcctg ttcaagggag gcaggagcat gctcactcaa    162120
gggacctcga ctaggtgccc tctgatttca cacttctggt gttgccccaa gccggcccca    162180
tcaccttgca agaaaggctc tggagccccc agggctggag tacctggtca gggttgaccg    162240
tccctgtggt cactcatccc atgtggctga gctgggctgg gtcctgggca agcaagggc     162300
tgatatcacc tgcttttcaga tctccaggga ctcactggac ccctgtgtac aaagcactgt    162360
ctacagagcc tattggggttg tatagaggta accttcgtac tgaacacttt tgttacagga    162420
aaggagaaag tcagtccggg tagaacttca gaccctaatc ctgcagcccc cgacagcgag    162480
tcagtgattg ttgctatgga gcgggtatct gttcttttg ataggtaaga agcgaagccc     162540
catccctcag ccgttagctt ccctagaact ttggcctgaa gctgtgcttt tgtgtgtgtc    162600
tgctgatccc ctggcgctgt tgctggagtc ctgccagtga ttccccacca cagcctgacc    162660
atgggctgcc ttggctcagg gttccactgg cgagctggtg gtccttggac cccagcactc    162720
aggtgtagcg ttgaccagtt ccaaggttgt cccagtgcct gcccatctct cctgagggct    162780
cagggacagt acctggcagt tgggggtgtg gcaggggca ggaatgacca gcctctggga     162840
gggtggggca gaagcctgta cagtgaggag gagctggctc agcctggctg cctatcgtga    162900
gaggggagcc cacggggctg tgggaggggg gccgtggtgc ctgtgagcag ggtgaggagc    162960
agcggcagga ggatgaaggt ggaacccaca catgcatctt tgagacccgt gtggtcagtg    163020
gcttctgccc cccaccaccc cccactgctg tgcgtgcata gaattggctt ccctcacctg    163080
ctctggaagt gggttaggag cttggtaggg cttttttctca aggacaaggg cccctgattt    163140
gctctcaggc ctcagtcctg gcgacatggt ggatctggag ccttgttgca ctgccttgcc    163200
tgtgctctcc aatcagggtg gccagtgggg agccatttgg ctttttctcaa gagcatactc    163260
```

```
aggtggacct tgctccactg tttgaccaga tgaggcattc tgaacagcca agcctgtgct    163320
ggtctgtttt catgttgatt ttttttttc ttttcttttt gagatggagt ttttcccttg    163380
tcacccaggc tggagtgcaa tggtgtgatc tcggctcact gcaacctccg cctcccgggt    163440
tcaagtgatt ctcctgcctc agcctccta gtagctggga ttacaggcac acaccaccat    163500
gcccagctaa ttttgtgtt tttagtagag acggggtttc accgtgttgg ctgggctggt    163560
ctcgaactcc tgaactcaag tgatccaccc tccttggcct cccaaagtgc tgggattgca    163620
ggcgtgagcc actgcgcccg ccccccatgt cgatttttaa atgcacctct gcatcgttct    163680
tcagtcccca tatgctcact gagcaccact gcgactggca gacgggcaca gggaggcgcc    163740
acgaccagtc ctggccttca aggggcttgt ggtctagtgg gcccaatgct aggtggcgag    163800
tgctccaaag agtgtggtgc acgccttccg cttgaccgct ctccagacgc acagggagg    163860 cacctcgcag ctgaccacag atttctctct gtggagcagt gtcttcagag cggctgccat    163920
gccactgctg ggcgagggtc tgcgggcggg tagagccagg agcacctgtg aggaagtgca    163980
ctgccatttt cgtagctgct tcccgtgtgt ctcagttaca cacggctggc atgtgtgcac    164040
tgatgagacg ggaacgtgat ggttgctttt cagcactgaa agggatactg ctcaggggc    164100 gtgtttcagg atctggttag ggaagaagca gcgagagcac agatgggcc ctgtgtgta    164160 acaagaaaaa agtcctggtt gacaacagtg ccacgaagcg ttagaacaca tagggatgtt    164220
tgtggagcat ttgcatgtgg aaagcagcaa aaacataatg ggaacgggtt cttttgttat    164280 gattttaaa aatctctttt gtaacatcct tcccgctgcg ccgtttctgc atattccttt    164340
atgtagcttt caaactcctc ttaggagttc tggtccctac agggcgtggg agcccaggct    164400
ttacgtagct ttcaaactcc tcttaggagt tctggtccct acagggtgtg ggagcccagg    164460
gcctgtgccg agcagcctgc ctccacgagc tagacagagg aagggctggg gttttgcctt    164520
tttagtctca aaattcgtac tccagttgct taggctctga cttcccac ttggaaagtc    164580 cctcacggcc gagggtccct cccagccctg atttcacatc ggcatttcc ccagtattag    164640 agccaaggcc ctccgcgggc aggtggggca gctgtgggag ctggtgccag tctctgacct    164700
gcgtccctcc tcccaggatc aggaaaggct ttccttgtga agccagagtg gtggccagga    164760
tcctgcccca gtttctagac gacttcttcc cacccagga catcatgaac aaagtcatcg    164820
gagagtttct gtccaaccag cagccatacc cccagttcat ggccaccgtg gtgtataagg    164880
tgaggttgca tgtgggatgg ggatggagtg ggaaagcctg gaggtggagt tgcctccgac    164940
ttcccagcag attcgccagc agagcccagc tcctccgctt taaagcagca atgcctctgg    165000
cccccacccc acccccgcca cccaggcgca gcaggtgctt cccgtccccc cagccctgac    165060
actcaggcac ctgcttgctc cttgcaggtg tttcagactc tgcacagcac cgggcagtcg    165120
tccatggtcc gggactgggt catgctgtcc ctctccaact tcacgcagag gccccggtc    165180 gccatggcca cgtggagcct ctcctgcttc tttgtcagcg cgtccaccag cccgtgggtc    165240
gcggcgatgt atcctctctg ggtccctggt gctggccccg tttcccttgt caacaccgag    165300
gctcatgttt catgataagg ttttgaaacc taacctttgc aaaaacccca cagatgccag    165360
ggtgacaggc cctcagcccc aggaagtaa atgctgaca ggggtacaga aaggagcacg    165420
tccagacatt tgctgaccag ggcctctcag aggggccggt gtatggcagg agggtcgcag    165480
ctgaggggcc tttctgtgga gggcctgggt gaggggagcg agggtgggcg gtggtctctg    165540
cagacgtccc gcccactcgc gggctctgtg tggctgggct tctcctgaca ctgcttctca    165600
ttagctttgg tcattgtgcc tcgatcgccc tctcggggaa aggcttaagt aaagatccag    165660
```

```
ttcccacccc cagatgctgg ctgccaggag tttcccttc cacagcccttt ccccaagaca  165720 gaccacaaga gcctccaagc agcacagttg tcctggtgct gacagcacag ccttgcccgg  165780
cgtgcctggc acggctctgc cctcactgca ttggagcagg gctagtggag gccagcggaa  165840
gcaccggcca ccagcgctgc acaggagcca ggccaggtga gtgctgccga gtgggtgccc  165900
tgcctgcagg gcatccagcc agccaagggt gcaggaatg gaggtggagg cgctgatgca  165960
gctggaggca tccaggtggc ccttccgggg ctctgctcgc tctccaggct ccctggaccc  166020
ctttgtagac tgtttcagga gaggaactcc caggtgagga cagggaggca gcattcccct  166080
catttgccgg cctttttcct taactcctgc accagcctcc cacatgtcat cagcaggatg  166140
ggcaagctgg agcaggtgga cgtgaacctt ttctgcctgg tcgccacaga cttctacaga  166200
caccagatag aggaggagct cgaccgcagg gccttccagt ctgtgcttga ggtggttgca  166260
gccccaggaa gcccatatca ccggctgctg acttgtttac gaaatgtcca caaggtcacc  166320
acctgctgag cgccatggtg ggagagactg tgaggcggca gctggggccg gagcctttgg  166380
aagtctgcgc ccttgtgccc tgcctccacc gagccagctt ggtccctatg ggcttccgca  166440
catgccgcgg gcgccaggc aacgtgcgtg tctctgccat gtggcagaag tgctctttgt  166500
ggcagtggcc aggcagggag tgtctgcagt cctggtgggg ctgagcctga ggccttccag  166560
aaagcaggag cagctgtgct gcaccccatg tgggtgacca ggtcctttct cctgatagtc  166620
acctgctggt tgttgccagg ttgcagctgc tcttgcatct gggccagaag tcctccctcc  166680
tgcaggctgg ctgttggccc ctctgctgtc ctgcagtaga aggtgccgtg agcaggcttt  166740
gggaacactg gcctgggtct ccctggtggg gtgtgcatgc cacgcccgt gtctggatgc  166800 acagatgcca tggcctgtgc tgggccagtg gctgggggtg ctagacaccc ggcaccattc  166860
tcccttctct cttttcttct caggatttaa aatttaatta tatcagtaaa gagattaatt  166920
ttaacgtaac tctttctatg cccgtgtaaa gtatgtgaat cgcaaggcct gtgctgcatg  166980
cgacagcgtc cggggtggtg gacagggccc ccggccacgc tccctctcct gtagccactg  167040
gcatagccct cctgagcacc cgctgacatt tccgttgtac atgttcctgt ttatgcattc  167100
acaaggtgac tgggatgtag agaggcgtta gtgggcaggg ggccacagca ggactgagga  167160
caggccccca ttatcctagg ggtgcgctca cctgcagccc ctcctcctcg gcacagacg  167220 actgtcgttc tccaccccacc agtcagggac agcagcctcc ctgtcactca gctgagaagg  167280
ccagccctcc ctggctgtga gcagcctcca ctgtgtccag agacatgggc ctcccactcc  167340
tgttccttgc tagccctggg gtggcgtctg cctaggagct ggctggcagg tgttgggacc  167400
tgctgctcca tggatgcatg ccctaagagt gtcactgagc tgtgttttgt ctgagcctct  167460
ctcggtcaac agcaaagctt ggtgtcttgg cactgttagt gacagagccc agcatccctt  167520
ctgcccccgt tccagctgac atcttgcacg gtgaccccctt ttagtcagga gagtgcagat  167580
ctgtgctcat cggagactgc cccacggccc tgtcagagcc gccactccta tcccaggcc  167640 aggtccctgg accagcctcc tgtttgcagg cccagaggag ccaagtcatt aaaatggaag  167700
tggattctgg atggccgggc tgctgctgat gtaggagctg gatttgggag ctctgcttgc  167760
cgactggctg tgagacgagg caggggctct gcttcctcag ccctagaggc gagccaggca  167820
aggttggcga ctgtcatgtg gcttggtttg gtcatgcccg tcgatgtttt gggtattgaa  167880
tgtggtaagt ggaggaaatg ttggaactct gtgcaggtgc tgccttgaga cccccaagct  167940
tccacctgtc cctctcctat gtggcagctg gggagcagct gagatgtgga cttgtatgct  168000
```

```
gcccacatac gtgaggggga gctgaaaggg agccctcct ctgagcagcc tctgccaggc  168060
ctgtatgagg cttttcccac cagctcccaa cagaggcctc cccagccag gaccacctcg  168120
tcctcgtggc ggggcagcag gagcggtaga aaggggtccg atgtttgagg aggcccttaa  168180
gggaagctac tgaattataa cacgtaagaa aatcaccatt ccgtattggt tgggggctcc  168240
tgtttctcat cctagctttt tcctggaaag cccgctagaa ggtttgggaa cgaggggaaa  168300
gttctcagaa ctgttggctg ctccccaccc gcctcccgcc tccccgcag gttatgtcag   168360
cagctctgag acagcagtat cacaggccag atgttgttcc tggctagatg tttacatttg  168420
taagaaataa cactgtgaat gtaaaacaga gccattccct tggaatgcat atcgctgggc  168480
tcaacataga gtttgtcttc ctcttgttta cgacgtgatc taaaccagtc cttagcaagg  168540
ggctcagaac accccgctct ggcagtaggt gtccccacc cccaaagacc tgcctgtgtg  168600
ctccggagat gaatatgagc tcattagtaa aaatgacttc acccacgcat atacataaag  168660
tatccatgca tgtgcatata gacacatcta aattttaca cacacacctc tcaagacgga  168720
gatgcatggc ctctaagagt gcccgtgtcg gttcttcctg gaagttgact ttccttagac  168780
ccgccaggtc aagttagccg cgtgacggac atccaggcgt gggacgtggt cagggcaggg  168840
ctcattcatt gcccactagg atcccactgg cgaagatggt ctccatatca gctctctgca  168900
gaagggagga agactttatc atgttcctaa aaatctgtgg caagcaccca tcgtattatc  168960
caaattttgt tgcaaatgtg attaatttgg ttgtcaagtt ttggggggtgg gctgtgggga  169020
gattgctttt gttttcctgc tggtaatatc gggaaagatt ttaatgaaac cagggtagaa  169080
ttgtttggca atgcactgaa gcgtgtttct ttcccaaaat gtgcctccct tccgctgcgg  169140
gcccagctga gtctatgtag gtgatgtttc cagctgccaa gtgctctttg ttactgtcca  169200
ccctcatttc tgccagcgca tgtgtccttt caaggggaaa atgtgaagct gaaccccctc  169260
cagacaccca gaatgtagca tctgagaagg ccctgtgccc taaaggacac ccctcgcccc  169320
catcttcatg gaggggtca tttcagagcc ctcggagcca atgaacagct cctcctcttg  169380
gagctgagat gagccccacg tggagctcgg gacggatagt agacagcaat aactcggtgt  169440
gtggccgcct ggcaggtgga acttcctccc gttgcgggt ggagtgaggt tagttctgtg   169500
tgtctggtgg gtggagtcag gcttctcttg ctacctgtga gcatccttcc cagcagacat  169560
cctcatcggg ctttgtccct ccccgcttc ctccctctgc ggggaggacc cgggaccaca   169620
gctgctggcc agggtagact tggagctgtc ctccagaggg gtcacgtgta ggagtgagaa  169680
gaaggaagat cttgagagct gctgagggac cttggagagc tcaggatggc tcagacgagg  169740
acactcgctt gccgggcctg ggcctcctgg gaaggaggga gctgctcaga atgccgcatg  169800
acaactgaag gcaacctgga aggttcaggg gccgctcttc ccccatgtgc ctgtcacgct  169860
ctggtgcagt caaaggaacg ccttcccctc agttgtttct aagagcagag tctccgctg   169920
caatctgggg ggtaactgcc agccttggag gatcgtggcc aacgtggacc tgcctacgga  169980
gggtgggctc tgacccaagt ggggcctcct tgtccaggtc tcactgcttt gcaccgtggt  170040
cagagggact gtcagctgag cttgagctcc cctggagcca gcagggctgt gatgggcgag  170100
tcccggagcc ccacccagac ctgaatgctt ctgagagcaa agggaaggac tgacgagaga  170160
tgtatattta atttttaac tgctgcaaac attgtacatc caaattaaag gaaaaaaatg   170220
gaaaccatca gttgttgctg tgtgaggctt gctttgcttc atgagaacct agaccttgct  170280
gagctggagt cttaggaagc agtctcctaa gtgcttctcc agcaggggca gaaactgtcc  170340
caccagctaa catctggcat tatggagggt cccccaggca gctgccagca gggacaggcc  170400
```

-continued

```
ccgtgttttc tgtagccagg gatgaggaag tggccccagg gcatgggcct ggctgggtgc    170460
ttctgcaagg gccttcccaa accacagtac aggtggtctt cctgccctgc agatgggagc    170520
tgtgggagct gctggagctg ctggagcctt catggtcaag tgacatcata agcttatatg    170580
acatacacaa gcctcaggac ttggcccatg gcactgaagc aggtcatcag gcccagcaca    170640
gagactagag ctgtgttctc acagggccca ccacccttcc acctccttgg ccattgacac    170700
ctgcgtccct ggcccagctg ctcccaggta accccccaaag cagctggcac atcccacctc    170760
tggtgtggcc ggggctgctg tgtgtccgca gggcctgccc cgtctattct agcttgtttg    170820
tcctgtctga accagcgcct actccaagaa gcctctgctc agcccagcgg ggatgcttct    170880
aagctccgga cgagcctctc ggaagccttg gtgattggtg gtgtagtcat cttgggatgc    170940
agatgtctta ccaacctgca agaacaaaaa ccctgtggct tcctctggtg cagggtattt    171000
agtcaatgtt tgctgaggtc ccgtctggtt ctggctaatt ggcaggggtc gtccacccat    171060
tctttccctg ctctgctgtc tgtgccagga gagacggggg ccagtcggcc aaggggccag    171120
ctcctgctgc ctgctcctct tgggcacgtg cgggggcccc ctttctctga gcagggatag    171180
ggatcagtct gccggaggga tgtggtggac aggcctaaag catttggggc ggggcatgcc    171240
acttgagctc cctaaatctg tctcctcata ggtgacaccg ctccagggcc ccccagtggc    171300
ctctcctttc agagctacct aaattctggt cacttcagag aaatggagca ccccttctc    171360
cctggtccag gtgtggacag cctggcacac tgagcacacc tggcatggct ggtaatttca    171420
gaaagaagag gggccggggt ccagtgggaa gcagcggtga acccctcgtg agtgggcttt    171480
gcagtccctc cccatgccac ggcagagctg ccctcaacac agccttcctc ttcctcatcg    171540
gagagcacac cctgtcccct tgccgagctg tgccctgtgc cttcggtggt atttgatttt    171600
ggctgctact ggctttgttg ggatctggaa gtcgcttccc ctgcgtggtg cgtggagcac    171660
tgtaagtcag atgagggaag tagccagggt gaggtgagta ccgggtggag ccgccactga    171720
agggactggg tagggggggcc ttgcctctac atgatgtgac acagccaacc gaggacagag    171780
gaagccccgt tcctggggggt gtggggtgca cccctcaggg aagcctgcag tggggcctga    171840
ggaaaggcat cctccgcgag cccacgagtc tggtccatga gcaccgtgac agtgtctgtg    171900
ggtagaggtg gacccggcct tgtgtcatca ccaggacctc tttttgggaaa ccatgtggac    171960
atcgcttgcg ggtcccccag gctctgcagc cccagcagcc t                        172001
```

<210> SEQ ID NO 3
<211> LENGTH: 10081
<212> TYPE: DNA
<213> ORGANISM: Mus musculus

<400> SEQUENCE: 3

```
gcactcgccg cgagggttgc cgggacgggc ccaagatggc tgagcgcctt ggttccgctt     60
ctgcctgccg cgcagagccc cattcattgc cttgctgcta agtggcgccg cgtagtgcca    120
gtaggctcca agtcttcagg gtctgtccca tcgggcagga agccgtcatg gcaaccctgg    180
aaaagctgat gaaggctttc gagtcgctca agtcgtttca gcagcaacag cagcagcagc    240
caccgccgca ggcgccgccg ccaccgccgc cgccgcctcc gcctcaaccc ctcagccgc    300
cgcctcaggg gcagccgccg ccgccaccac cgccgctgcc aggtccggca gaggaaccgc    360
tgcaccgacc aaagaaggaa ctctcagcca ccaagaaaga ccgtgtgaat cattgtctaa    420
caatatgtga aaacattgtg gcacagtctc tcagaaattc tccagaattt cagaaactct    480
```

-continued

```
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaagaatgg tgctcctcga agtttgcgtg     660
ctgccctgtg gaggtttgct gagctggctc acctggttcg acctcagaag tgcaggcctt    720
acctggtgaa tcttcttcca tgcctgaccc gaacaagcaa agaccggag gaatcagttc     780
aggagacctt ggctgcagct gttcctaaaa ttatggcttc ttttggcaat ttcgcaaatg    840
acaatgaaat taaggttctg ttgaaagctt tcatagcaaa tctgaagtca agctctccca    900
ccgtgcggcg acagcagcc ggctcagccg tgagcatctg ccaacattct aggaggacac     960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagcacca agaccacaat gtggtgacag ggcactggga gctcctgcag cagctcttcc   1260
gtaccctcc acctgaactc ctgcaagcac tgaccacacc aggagggctt gggcagctca    1320
ctctggttca agaagaggcc cggggccgag ccgcagcgg gagcatcgtg gagcttttag    1380
ctggaggggg ttcctcgtgc agccctgtcc tctcaagaaa gcagaaaggc aaagtgctct   1440
taggagagga gaagccttg gaagatgact cggagtccag gtcagatgtc agcagctcag    1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtatttta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga acccacagg    2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattcctttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gacagctcc tactggctgg    2700
tgaggaccga actgctggac actctgcag agattgactt caggctcgtg agttttttgg    2760
aggcaaaagc agaaagttta caccgagggg ctcatcatta tacaggggttt ctaaaactac   2820
aagaacgagt actcaataat gtggtcattt atttgcttgg agatgaagac cccagggttc   2880
```

```
gacatgttgc tgcaacatca ttaacaaggc ttgtcccaaa gctgttttac aagtgtgacc    2940
aaggacaagc tgatccagtt gtggctgtag cgagggatca gagcagtgtc tacctgaagc    3000
tcctcatgca tgagacccag ccaccatcac acttttctgt cagcaccatc accagaatct    3060
atagaggcta tagcttactg ccaagtataa cagatgtcac catggaaaac aatctctcaa    3120
gagttgttgc cgcagtttct catgaactca ttacgtcaac aacacgggca ctcacatttg    3180
gatgctgtga agccttgtgt cttctctcag cagccttttcc agtttgcact ggagtttag    3240 gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ttcatggacc tctgaagaag aagccaactc agcagccacc agacaggagg    3480
aaatctggcc tgctctgggg gatcggactc tagtgccctt ggtggagcag cttttctccc    3540
acctgctgaa ggtgatcaat atctgtgctc atgtcttgga cgatgtgact cctggaccag    3600
caatcaaggc agccttgcct tctctaacaa accccccttc tctaagtcct attcgacgga    3660
aagggaagga gaaagaacct ggagaacaag cttctactcc aatgagtccc aagaaagttg    3720
gtgaggccag tgcagcctct cgacaatcag acacctcagg acctgtcaca gcaagtaaat    3780
catcctcact ggggagtttc taccatctcc cctcctacct caaactgcat gatgtcctga    3840
aagccactca cgccaactat aaggtcacct tagatcttca gaacagcact gaaaagtttg    3900
gggggttcct gcgctctgcc ttggacgtcc tttctcagat tctagagctg gcgacactgc    3960
aggacattgg aaagtgtgtt gaagaggtcc ttggatacct gaaatcctgc tttagtcgag    4020
aaccaatgat ggcaactgtc tgtgtgcagc agctattgaa gactctcttt gggacaaact    4080
tagcctcaca gtttgatggc ttatcttcca accccagcaa gtctcagtgc cgagctcagc    4140
gccttggctc ttcaagtgtg aggcccggct tatatcacta ctgcttcatg gcaccataca    4200
cgcacttcac acaggccttg gctgacgcaa gcctgaggaa catggtgcag gcggagcagg    4260
agcgtgatgc ctcggggtgg tttgatgtac tccagaaagt gtctgcccaa ttgaagacga    4320
acctaacaag cgtcacaaag aaccgtgcag ataagaatgc tattcataat cacattaggt    4380
tatttgagcc tcttgttata aaagcattga agcagtacac cacgacaaca tctgtacaat    4440
tgcagaagca ggttttggat ttgctggcac agctggttca gctacgggtc aattactgtc    4500
tactggattc agaccaggtg ttcatcgggt ttgtgctgaa gcagtttgag tacattgaag    4560
tgggccagtt cagggaatca gaggcaatta ttccaaatat attttctctc ctggtattac    4620
tgtcttatga gcgctaccat tcaaaacaga tcattggaat tcctaaaatc atccagctgt    4680
gtgatggcat catggccagt ggaaggaagg ccgttacaca tgctatacct gctctgcagc    4740
ccattgtcca tgacctcttt gtgttacgag gaacaaataa agctgatgca gggaaagagc    4800
ttgagacaca gaaggaggtg gtggtctcca tgctgttacg actcatccag taccatcagg    4860
tgctggagat gttcatcctt gtcctgcagc agtgccacaa ggagaatgag gacaagtgga    4920
aacggctctc tcggcaggtc gcagacatca tcctgcccat gttggccaag cagcagatgc    4980
atattgactc tcatgaagcc cttggagtgt taaataccct tgtttgagatt ttggctcctt    5040 cctccctacg tcctgtggac atgcttttgc ggagtatgtt catcactcca agcacaatgg    5100
catctgtaag cactgtgcag ctgtggatat ctggaatcct cgccattctg agggttctca    5160
tttcccagtc aaccgaggac attgttcttt gtcgtattca ggagctctcc ttctctccac    5220
```

| | |
|---|---|
| acttgctctc ctgtccagtg attaacaggt taaggggtgg aggcggtaat gtaacactag | 5280 |
| gagaatgcag cgaagggaaa caaaagagtt tgccagaaga tacattctca aggtttcttt | 5340 |
| tacagctggt tggtattctt ctagaagaca tcgttacaaa acagctcaaa gtggacatga | 5400 |
| gtgaacagca gcatacgttc tactgccaag agctaggcac actgctcatg tgtctgatcc | 5460 |
| acatattcaa atctggaatg ttccggagaa tcacagcagc tgccactaga ctcttcacca | 5520 |
| gtgatggctg tgaaggcagc ttctatactc tagagagcct gaatgcacgg gtccgatcca | 5580 |
| tggtgcccac gcacccagcc ctggtactgc tctggtgtca gatcctactt ctcatcaacc | 5640 |
| acactgacca ccggtggtgg gcagaggtgc agcagacacc caagagacac agtctgtcct | 5700 |
| gcacgaagtc acttaacccc cagaagtctg gcgaagagga ggattctggc tcggcagctc | 5760 |
| agctgggaat gtgcaataga gaaatagtgc gaagaggggc ccttattctc ttctgtgatt | 5820 |
| atgtctgtca gaatctccat gactcagaac acttaacatg gctcattgtg aatcacattc | 5880 |
| aagatctgat cagcttgtct catgagcctc cagtacaaga cttttattagt gccattcatc | 5940 |
| gtaattctgc agctagtggt cttttatcc aggcaattca gtctcgctgt gaaaatcttt | 6000 |
| caacgccaac cactctgaag aaaacacttc agtgcttgga aggcatccat ctcagccagt | 6060 |
| ctggtgctgt gctcacacta tatgtggaca ggctcctggg cacccccttc cgtgcgctgg | 6120 |
| ctcgcatggt cgacaccctg gcctgtcgcc gggtagaaat gcttttggct gcaaatttac | 6180 |
| agagcagcat ggcccagttg ccagaggagg aactaaacag aatccaagaa cacctccaga | 6240 |
| acagtgggct tgcacaaaga caccaaaggc tctattcact gctggacaga ttccgactct | 6300 |
| ctactgtgca ggactcactt agccccttgc ccccagtcac ttcccaccca ctggatgggg | 6360 |
| atgggcacac atctctggaa acagtgagtc cagacaaaga ctggtacctc cagcttgtca | 6420 |
| gatcccagtg ttggaccaga tcagattctg cactgctgga aggtgcagag ctggtcaacc | 6480 |
| gtatccctgc tgaagatatg aatgacttca tgatgagctc ggagttcaac ctaagccttt | 6540 |
| tggctccctg tttaagcctt ggcatgagcg agattgctaa tggccaaaag agtccctct | 6600 |
| ttgaagcagc ccgtggggtg attctgaacc gggtgaccag tgttgttcag cagcttcctg | 6660 |
| ctgtccatca agtcttccag cccttcctgc ctatagagcc cacggcctac tggaacaagt | 6720 |
| tgaatgatct gcttggtgat accacatcat accagtctct gaccatactt gcccgtgccc | 6780 |
| tggcacagta cctggtggtg ctctccaaag tgcctgctca tttgcacctt cctcctgaga | 6840 |
| aggaggggga cacggtgaag tttgtggtaa tgacagttga ggccctgtca tggcatttga | 6900 |
| tccatgagca gatcccactg agtctggacc tccaagccgg gctagactgc tgctgcctgg | 6960 |
| cactacaggt gcctggcctc tgggggtgc tgtcctcccc agagtacgtg actcatgcct | 7020 |
| gctccctcat ccattgtgtg cgattcatcc tggaagccat tgcagtacaa cctggagacc | 7080 |
| agcttctcgg tcctgaaagc aggtcacata ctccaagagc tgtcagaaag gaggaagtag | 7140 |
| actcagatat acaaaacctc agtcatgtca cttcggcctg cgagatggtg gcagacatgg | 7200 |
| tggaatccct gcagtcagtg ctggccttgg gccacaagag gaacagcacc ctgccttcat | 7260 |
| ttctcacagc tgtgctgaag aacattgtta tcagtctggc ccgactcccc ctagttaaca | 7320 |
| gctatactcg tgtgcctcct ctggtatgga aactcgggtg gtcacccaag cctggagggg | 7380 |
| attttggcac agtgtttcct gagatccctg tagagttcct ccaggagaag gagatcctca | 7440 |
| aggagttcat ctaccgcatc aacacccctag ggtggaccaa tcgtacccag ttcgaagaaa | 7500 |
| cttgggccac cctccttggt gtcctggtga ctcagcccct ggtgatggaa caggaagaga | 7560 |
| gcccaccaga ggaagacaca gaaagaaccc agatccatgt cctggctgtg caggccatca | 7620 |

```
cctctctagt gctcagtgca atgaccgtgc ctgtggctgg caatccagct gtaagctgct    7680
tggagcaaca gccccggaac aagccactga aggctctcga taccagattt ggaagaaagc    7740
tgagcatgat cagagggatt gtagaacaag aaatccaaga gatggtttcc cagagagaga    7800
atactgccac tcaccattct caccaggcgt gggatcctgt cccttctctg ttaccagcta    7860
ctacaggtgc tcttatcagc catgacaagc tgctgctgca gatcaaccca gagcgggagc    7920
caggcaacat gagctacaag ctgggccagg tgtccataca ctccgtgtgg ctgggaaata    7980
acatcacacc cctgagagag gaggaatggg atgaggaaga agaggaagaa agtgatgtcc    8040
ctgcaccaac gtcaccacct gtgtctccag tcaattccag aaaacaccgt gccggggttg    8100
atattcactc ctgttcgcag tttctgcttg aattgtacag ccgatggatc ctgccatcca    8160
gtgcagccag aaggacccccc gtcatcctga tcagtgaagt ggttcgatct cttcttgtag    8220
tgtcagactt attcaccgaa cgtacccagt ttgaaatgat gtatctgacg ctgacagaac    8280 tacgagagt gcacccttca gaagatgaga tcctcattca gtacctggtg cctgccacct    8340
gtaaggcagc tgctgtcctt ggaatggaca aaactgtggc agagccagtc agccgcctac    8400
tggagagcac actgaggagc agccacctgc ccagccagat cggagccctg cacggcatcc    8460
tctatgtgtt ggagtgtgac ctcttggatg acactgcaaa gcagctcatt ccagttgtta    8520
gtgactatct gctgtccaac ctcaaaggaa tagcccactg cgtgaacatt cacagccagc    8580
agcatgtgct ggtaatgtgt gccactgctt tctacctgat ggaaaactac cctctggatg    8640
tgggaccaga attttcagca tctgtgatac agatgtgtgg agtaatgctg tctggaagtg    8700
aggagtccac cccctccatc atttaccact gtgccctccg gggtctggag cggctcctgc    8760
tgtctgagca gctatctcgg ctagacacag agtccttggt caagctaagt gtggacagag    8820
tgaatgtaca aagcccacac agggccatgg cagccctagg cctgatgctc acctgcatgt    8880
acacaggaaa ggaaaaagcc agtccaggca gagcttctga ccccagccct gctacacctg    8940
acagcgagtc tgtgattgta gctatggagc gagtgtctgt tctctttgat aggatccgca    9000
agggatttcc ctgtgaagcc agggttgtgg caaggatcct gcctcagttc ctagatgact    9060
tctttccacc tcaagatgtc atgaacaaag tcattggaga gttcctgtcc aatcagcagc    9120
catacccaca gttcatggcc actgtagttt acaaggtttt tcagactctg cacagtgctg    9180
ggcagtcatc catggtccgg gactgggtca tgctgtccct gtccaacttc acacaaagaa    9240
ctccagttgc catggccatg tggagcctct cctgcttcct tgttagcgca tctaccagcc    9300
catgggtttc tgcgatcctt ccacatgtca tcagcaggat gggcaaactg aacaggtgg    9360 atgtgaacct tttctgcctg gttgccacag acttctacag acaccagata gaggaggaat    9420
tcgaccgcag ggctttccag tctgtgtttg aggtggtggc tgcaccagga agtccatacc    9480
acaggctgct tgcttgtttg caaaatgttc acaaggtcac cacctgctga gtagtgcctg    9540
tgggacaaaa ggctgaaaga aggcagctgc tgggcctga gcctccagga gcctgctcca    9600
agcttctgct ggggctgcct tggccgtgca ggcttccact tgtgtcaagt ggacagccag    9660
gcaatggcag gagtgctttg caatgagggc tatgcaggga acatgcacta tgttgggggtt    9720 gagcctgagt cctgggtcct ggcctcgctg cagctggtga cagtgctagg ttgaccaggt    9780
gtttgtcttt ttcctagtgt tccctggcc atagtcgcca ggttgcagct gccctggtat    9840
gtggatcaga agtcctagct cttgccagat ggtctgagc ccgcctgctc cactgggctg    9900
gagagctccc tcccacattt acccagtagg catacctgcc acaccagtgt ctggacacaa    9960
```
aatgaatggt gtgtggggct gggaactggg gctgccaggt gtccagcacc attttccttt    10020
ctgtgttttc ttctcaggag ttaaaattta attatatcag taaagagatt aattttaatg    10080
t                                                                    10081

<210> SEQ ID NO 4
<211> LENGTH: 168002
<212> TYPE: DNA
<213> ORGANISM: Macaca mulatta
<220> FEATURE:
<221> NAME/KEY: misc_feature
<222> LOCATION: (8794)..(8848)
<223> OTHER INFORMATION: n is a, c, g, or t
<220> FEATURE:
<221> NAME/KEY: misc_feature
<222> LOCATION: (11952)..(12155)
<223> OTHER INFORMATION: n is a, c, g, or t
<220> FEATURE:
<221> NAME/KEY: misc_feature
<222> LOCATION: (13733)..(14137)
<223> OTHER INFORMATION: n is a, c, g, or t
<220> FEATURE:
<221> NAME/KEY: misc_feature
<222> LOCATION: (17299)..(17497)
<223> OTHER INFORMATION: n is a, c, g, or t
<220> FEATURE:
<221> NAME/KEY: misc_feature
<222> LOCATION: (18993)..(19355)
<223> OTHER INFORMATION: n is a, c, g, or t
<220> FEATURE:
<221> NAME/KEY: misc_feature
<222> LOCATION: (30628)..(32144)
<223> OTHER INFORMATION: n is a, c, g, or t
<220> FEATURE:
<221> NAME/KEY: misc_feature
<222> LOCATION: (37234)..(37641)
<223> OTHER INFORMATION: n is a, c, g, or t
<220> FEATURE:
<221> NAME/KEY: misc_feature
<222> LOCATION: (56357)..(56602)
<223> OTHER INFORMATION: n is a, c, g, or t
<220> FEATURE:
<221> NAME/KEY: misc_feature
<222> LOCATION: (66208)..(66275)
<223> OTHER INFORMATION: n is a, c, g, or t
<220> FEATURE:
<221> NAME/KEY: misc_feature
<222> LOCATION: (72472)..(72756)
<223> OTHER INFORMATION: n is a, c, g, or t
<220> FEATURE:
<221> NAME/KEY: misc_feature
<222> LOCATION: (82608)..(83314)
<223> OTHER INFORMATION: n is a, c, g, or t
<220> FEATURE:
<221> NAME/KEY: misc_feature
<222> LOCATION: (108856)..(108875)
<223> OTHER INFORMATION: n is a, c, g, or t
<220> FEATURE:
<221> NAME/KEY: misc_feature
<222> LOCATION: (131686)..(132275)
<223> OTHER INFORMATION: n is a, c, g, or t
<220> FEATURE:
<221> NAME/KEY: misc_feature
<222> LOCATION: (143992)..(145163)
<223> OTHER INFORMATION: n is a, c, g, or t
<220> FEATURE:
<221> NAME/KEY: misc_feature
<222> LOCATION: (147895)..(148388)
<223> OTHER INFORMATION: n is a, c, g, or t

<400> SEQUENCE: 4
atacaggcgt gagccaccgc acccagctgg aacttaattt ttttaaagat cgtgttgctc       60
tatcgcccaa gctggagtgc agtggtgcaa ccatagctca cttgcagcca caaattcctg      120
gtttcaggtg atcctcctac atcagcctcc caagaactgg gaactaacgg ctgtttctct      180

| | |
|---|---|
| gctgtccttc tcaagagaag ggagggagac aatgctgggt ttcccttttgg gacaggctct | 240 |
| gagacaaggt ggaggtgctg cttgtggcca cagagcaggg gactctgggt tgcaggtgtg | 300 |
| gcctggcttg agtaggcttt agtgggcttc tctctgcctg caccacccc gggctgggtg | 360 |
| gttgtctctg aggccaaccc tactccctaa tgggcaggct ggacagctgc cctctctgtt | 420 |
| tgcccctcta ccacccaaaa ggcgggaggc tctggagacc aggaccctgc ctgcgccggc | 480 |
| ctgtgcccca ggcgtgaggg ggtgcccac agatctctgc tgagctgagg ctgaatggca | 540 |
| ccccttgggg gtcctgccag gtcagagcag ggtgctttcc catacagaaa cgcccccagg | 600 |
| tcgggactca ttcctgtggg aggcgtcttg tggccacaac tgcttctcgc tgcactaatc | 660 |
| acagtgcctc tgtgggcagc gggcgctgac catccgggcc tgcctcagac cctctcctcc | 720 |
| cttccggggc gctgcgctgg gaccgatggg gggcgcaggg cctgtgggca ccgcctgca | 780 |
| ggggccgctc cagctcactg gggggtgggg aggtcacac ttggggtctt cagatggcgc | 840 |
| cgaccacgcg caatctctgc gctctgcgca ggggctcgcc caccctctcc ccgtgcagcg | 900 |
| agtccccagc aggctccccg cagggctgtc caggtgagcc tggctctggc cgcgggccag | 960 |
| tgtggcgggc gggcaagccc cgaggccacc tcggctcaga gcccacggcc ggctctcgcc | 1020 |
| cagctccaga cgtctgcgag ggttccattc cgcttgggcc ggcgcccgc gcgccgcgcc | 1080 |
| ctggccccgc ccctccctca tcccgccccc tctgcacccc accctccct ggccccgccc | 1140 |
| tccgcgcccc acctctcatc ttcccgcccc gccccagcc acgcccctca cggtcagccc | 1200 |
| cctcccctat ccgcccccgcc tctcatcgtc tcgcctcgct ccgcccctca gccgtcccgc | 1260 |
| ccctcagccg ccctgcctaa tgtccccgcc cccagcctcg ccccgctccg ccccagcctc | 1320 |
| gccccgcccc gcccctcagg cgccctgcct gctgtgcccc gccccagcct cgccacgccc | 1380 |
| ctcgttacca tgtagtcccg ccccgtccct tccgcgtccc gcctcgcccc tacccccttca | 1440 |
| cagcttcgcc ccaccccatt acagtcttgc cacgccccgt ccctgtccg ttgagccctg | 1500 |
| ctccttcgcc caggtggggc gctgcgctgt cagaggcttt ggtggctctg tgaggcagaa | 1560 |
| catgcgggcg cagggactgg ctggctccct ggccagtcat tggcagagtc cgcaggctag | 1620 |
| ggctgtcaat catgctggcc ggcgtggccc cgcctccgcc ggcgcagcgt cttgagacgc | 1680 |
| aaggcgccgc gggggctgcc gggacgggtc caagatggac ggccgcttcg gttccgcttt | 1740 |
| tacccgcggc ccagagcccc attcattgcc ccggtgctga gcggcgctgc gagtcggccc | 1800 |
| gaggcctccg gggactgcct agccgggcgg gagaccgcca tggcgaccct ggaaaagctg | 1860 |
| atgaaggcct tcgagtctct caagtccttc agcagcagc agcagcagca gcagcaacag | 1920 |
| ccgccgccgc cgccgccgcc gcctcctcct cctcctcagc ttcctcagcc gccgcaggca | 1980 |
| cagccgatgc tgcctcagcc gcagccgccc cgccgccgc ccccgccacc acccggcccg | 2040 |
| gctgtggctg aggagccgct gcaccgaccg tgagtttggg cccgctgcag ctccctgtcc | 2100 |
| cggcgggtcc cagcctacgg cggggatggc ggaatcctgc agcctgcggg ccggcgacac | 2160 |
| gaaccccccc ggccccgcag cgacagagtg acccagcaac ccagagccaa tgagggacac | 2220 |
| ccgcccctc ctgcggcgag accttccccc acttcagccc cggtcccgca cttgggtctt | 2280 |
| gtcctcccgc gaggggaggc agaacctcgt tgggacctgt cctgaattca cggaggggag | 2340 |
| tcacggcctc agccctctcg ccctttccag ggtgcgaaga gttggggcga aaacttgttt | 2400 |
| cttttttattt gcgagaaact agggcggggg tttaactgtg ttctgaagag aacttggaag | 2460 |
| agccgagatt tgctcagggc cacttccctc atctagtcag agaggaaga gggctggggg | 2520 |

```
cgcgggacac ctcgagagga ggcggggttt ggagctagag agatgtgggg gcagtggatg   2580
acataatgct tttaggacgc ctcggcggga gtggctggag tgggggggcgg ggagtgaggg   2640 cgcgtccaat gggagattta ttttccaagt ggcatttaaa acagcctgag atttgaggct   2700
cttcctacat tctcagggca tttcatttag ttcatgatcg cggtggtagt aacacgattt   2760
taagcaccac ctaagagacc tgctcatcta agcgcaagtt agtgtgcagg catttgaatg   2820
agttgtggtc gccaaataag tggtgaactt acgtggtatt aataaaatta tcttaaatat   2880
taggaagagt tgattgaagt ttattgcctg tttgtgttgg gaataaaact aacacgttgc   2940 tgaggggggag gttaattgcc gagggatgaa tgaggtatac attttaccag tattgcagtc   3000
aggcttgcca gaatatggga ggtctgcaga ctccgtggac atctcatgtg ccagtgaaag   3060
ggtttctgtt cgcctcattg ctgacagctt gttactttt ggaagctaga ggtctctgtt   3120
gcttgttctt ggggagaatt tttgaaacag aaaaagagac cattaaaaca tctagcggaa   3180
ccccaggacg tgggagtgtg tgctgagtgt ttagcaggat ttaggaagta ctccgctgca   3240
gttcaggcct ttctcttacc tctcagtgtt ctatttccga tctggacgtg tatcagatgg   3300
catttgataa gaatatctct attaagactg attaattttt agtaatattt cttgttcttt   3360
gtttctgtta tgatccttgc cttgtcttga agtttaattt agaagaggag gatttgggaga   3420 gcagtgttag cttatttgtt agagtaaaat ttaggaataa attcttctaa aggatggaaa   3480 aacttttttgg atatttagag aaattttttaa acaatttggc ttatctcttc agtaagtaat   3540
ttctcatcct tccagaaatt taatgtagtg ccttttctagg aggtaggtgt catagaagtt   3600
cacacattgc atgtatcttg tgtaaacact aaactgggct cctgatggga aggaagacct   3660
ttctgctggg ctgcttcaga cacttgatca ttctgaaaat atgccgtctc tttcctgtgc   3720
tgatttgata gaacctgcgt ttgcttatct tcaaatatg ggtatcaaga aatttccttt   3780
gctgccttta caaggagat agattttgtt tcattacttt atttttaaggt aatatatgat   3840 taccttattt taaaaattta atcaggcctg gcaaggtggc tcatgccttt aatccgagca   3900
ctttgggagg cttaggcgga tgaatcacct gaggtcagga gttcgagacc agtctggcta   3960
acatggtgaa accccatctc tactaaaagt acaaaaatta gttggtcatg gtggcacgtg   4020
cctgtaatgc cagctacctg ggaggctgag gcaggaaaat cgctggaacc cgggaggcag   4080
aggctgcagt gagctgagac tgcgccactg cactccagcc tgggtgacag agcgagactc   4140
ttgtctcaaa aaaaaaaaa ttattatttt tgcataagta atacattaac atgacacaaa   4200
ttccgtaatt acaaaagagc aatacttaaa atatcttcct tccacccctt tcatctgagt   4260
acctaacttt gtccccaaga acaagcacta ttacagttcc tcctgtatcc tgccagatat   4320
aatctatgca tattgtaaga tagatttaaa atgctgtaaa aataaaagta gtttacagta   4380 ataattttt ttctttattt tttttgagat gtagtctcac attgtcaccc aggctggagt   4440
gcggtggtat gatcttggct cactgcaacc tccacctccc aggttcaaac gattctcctg   4500
cctcagcctc cagagtagct gggattacag gtgctcacca ccatgtccag ctgattttg   4560 tattttagt agagatgggg tttcaccatg ttggccaggc tggtcttgaa ctcctgacct   4620
cggaatccat ccacctcggc ctcccaaagt gctgggtta caggtgtgag ccactgcccc   4680
tggctagaat aataactttt aaaggttctt agcattctct gaaatcaact gcattaggtt   4740
tatttatagt tattttaaat aaaatgcata tttgtcatat ttgtatgtat tttgctgttg   4800
agaaaggagg tattcgctaa ttttgagtaa caaacactgc tcacaaagtt tggatttttgg   4860 catttctgtt catgtgcttc agccaaaaaa tcctcttctc aaagtaagat tgactaaagc   4920
```

```
aatttagaaa gtatctgttt ttatggctct tgctcttttg tgtggaactg tggtgtcatg    4980
ccatgcatgg gcctcagtct aagtatgagc gtatgtgctc tgctcagcat acaggatgtg    5040
ggagttccgt gtggggctgg ccacagtctc agcaaatcta gcatgcttgg gagggtcctc    5100
acagtaatta ggaggcaact gatacttgct tctggcaatt ccttattctc cttcagattc    5160
ctatccggtg tttccctgac tttattcatt catcagtaaa tatttactaa acatgtacta    5220
tgtacctagc actgttctag atgcagggct cagcagtgag cagacaaagc tgtgccctca    5280
tgaagctttc attctaatga aggacataga caataagcaa gatagataag taaaatatac    5340
agtatgttaa taagtggagg aatgtcaaag cagggaaggg gatagggaaa tgtcagggtt    5400
aatcaattgt taacttattt ttattaaaaa aaaattttttt taagggcttt ccagcaaaac    5460
ccagaaagcc tgctggacaa cttccaaaaa aactgtagca ctaagtgttg acatttttat    5520
tttatttat tttattttgt tttgttttgt ttttgaggc agtcttgctt tgtcagccag    5580
gctgcagtgc actggtgtga tcttagctca ctgcaacctc tgcctgttgg gttcaagcga    5640
ttcttatgcc tcagcctcct gattagctgg gattatagac atgcaccgtc ccgcctgggt    5700
aattttttt ttttccccct gagacagagt cttgctctgt cgcccaggct ggagtgcagt    5760
ggcacaatct ggctcactg caagctccgc ctcccaggtt catgccattc tcctgcctca    5820
gcctcccagg tagctgggac tacaggcgcc tgccaccacg cccagctaat ttttgtatt    5880
tttagtagag atggggtttc actgtgtcag ccaggatggt cttgatctcc tcacctcgta    5940
gtccgccccc cttggcctcc caaagtgctg ggattacagg cgtgagccac cgcgcccggc    6000
ctgtaatttt ttttttttt ttttgagaca gagtcttgct tgttgctag gctggactgc    6060
agtggtgtga tcttggcaca ctgcaacctc tgcctcccgg gttcaagcga ttctcctgcc    6120
tcagcttccc gagtagctgg gactacaggc acgtgccatc acgcttggct acttttgta    6180
tatttagtag aaacggggtt tcaccatgtt agctgagatg atctcgatct cttgacctcg    6240
tgatccgccc gcctcggcct cccagagtgc tgggattaca ggtgtgagcc actgtgcctg    6300
accacgcctg ggtaattttt gtattttag tagagacggg atttcaccac gatggccaga    6360
ctggtctcga actcccagcc tcatgtgatc tgcctgccta ggcctcccaa agtgctagga    6420
ttacaggcat gagccaccat gactggccag tgttgatatt ttaaataggg tgttcaggga    6480
aggtccactg aggtgacagc tgttttttg ggggagtgg tgggacaggg ccttgctctt    6540
taacccaggc tggaatacag catcacaatc gtagcttact gcagccttga actcctaggc    6600
tcaagtgatc ttcccacctt gacctcacaa cgtgttggga ctgtaggtgt gagtcaccat    6660
gcctggccag atgatggctt tgagtaaaga cctcaggcga gttaagagtc tagcgtaaag    6720
gtgtatggag tagggtatt ccagataggg ggaacaggtc caaagtcttc ctgtttgagg    6780
aatagcaagg gtgccatttt agttgggtga attgagtgag ggcgacattt gtagtaagag    6840
gtaaagtcca agaggtcaag ggagtgccat atcagaccaa tactacttgc cttgtagatg    6900
gaataaagat attggcattt atgtgagtga gatgggatgt cactggagga ttagaggaga    6960
ggagtagcat gatctgaatt tcattcttaa gtgaactctg gctgacaaca gagtgaaggg    7020
gaacatggac aaaagcagaa accagttagg aagccactgc agtgctcaga taagcgtggt    7080
gggttctgtc agggtaccgg ctgtgggcag tgtgaggaat gactggattt tgaatgcaga    7140
agcaactgta cttgttgaac tctgctaagt ataactattt agcagtagct ggcattatca    7200
gttaggtttg tattcagctg caagtaacag aaaattctgc tgcaatagct taaactggta    7260
```

```
acaagaaaga gcttatcaga agacaaaaat aagtctgttt ggggaaattc aacaataagt    7320
taaggaaccc aggctctttc ttttttttt tgaaatggag ttttgctctt gtcacccagg    7380
ccggagtgca atgatgcgat cttggctcac tataacctcc gcctcctagg ttccagtgat    7440
tcttctgcct cagccttcca ggtatctggg attagaggcg cacgcacacc accatgccca    7500
gctaattttt gtatttttag taggcacggg gtttcatcat gttggccagg ctggtctcga    7560
actcctgacc ttaggtgatc aacccgcctc agcctgccaa agtgctgaga ttacaggtgt    7620
gagccactgc actcggtcag aacccaggct cttttttaca cttagcttgc aaaccccttgt   7680 tctcattctt ttcccctttgt attttattg tcgaattgta acagttcttt gtgtattctg    7740
gatactggat tcttatcaga tagatgattt gtgaaaacat tctctcttcc tttggattgt    7800 cttttttactt tcttgatcat gtcttttgaa gtgtgaaagt ttttaatttt gatgaagtct   7860
agtttatcta gtttgtcctt ggttgctatg ctttgagtgt catatctaag aaatcattgt    7920
ctaatccaaa gtcaaaaagg tttacccgta tgttttcttc taagaatttt agagttttac    7980
atttaggtct gatccatttt gagttaattt ttatatgtgg ttcaggtaga agtccaactt    8040
cattcttttg catgtggtta ttcagttgtc ccagcacagt ttgttgaaga gactgtactt    8100
tccccatgga attgtcttag catccttgtt gaaaattcat tgtccttgat tgtatagatt    8160
tatttcttga ctctcagttc tacctattgg tctttatgtt gatcctgtgc cagtaccata    8220
cagtcttgat tactgaagtt tgtgtcacaa tttaaattca tgaaatgtga gttctccaac    8280
tttgttcttt ctcaagattg atttggccat gctgggtccc ttgcatttcc atatggattg    8340
taggatcaac ttgtcagttt ctacaaagaa gccaaggagg attctgagag ggattgtgtt    8400
gaatctgtag atcaacttgg ggagtattac catcttaaca gtattgtctt ccatctctga    8460
actgggcaaa ctttgtgtaa atggtcagat ttaggtattt caggctgtgt gggcacaatg    8520
tctctgtcac agctactcag ctctgccatt gtagcgtgaa atagccataa gcaatatgta    8580
tgagtgtctg tgttccagta taattttatt aatgacaagg aaatttgaat tcgtgtaat    8640 tttcacctgt catgaaatat tatttggttt ttttggtcaa tcatttaaaa atgtaaaaac    8700
ttttcttagc tttgaactg gccaaacata tgcaggttat aattttccca ctcctagatt    8760
aaaatatgat aggaccacct ttgaaaagca tgtnnnnnnnn nnnnnnnnnn nnnnnnnnnn    8820
nnnnnnnnnn nnnnnnnnnn nnnnnnnnaa cactttggga ggccgagcca ggtggatcac    8880
ttgaggccag gagttcgaga ccagcctaac caacatggtg aaaccccatc tctactaaaa    8940
ataaaaaaat tagctggggg tggtggtggg tgtagggtcc agcccatgg ggcttagcgg    9000 gtgttctccc cgtgcgggga gacgagagat cttaagaaat aaagacacgg ccgggcgcgg    9060
tggctcacgc ctgtaatccc agcactttgg gaggccgagg cgggcggatc acaaggtcag    9120
gagatcgaga ccacggtgaa accccgtctt tactaaaaat acaaaaaatt agccggggcgc    9180 ggttgtgggc gcctgtagtc ccagctactc gggaggctga ggcaggagaa tggcgtgaac    9240
ccgggaggag gagcttgcag tgagccgaga tcgcgccact gcactccaga cggggcgaca    9300
gagcgagact cctgtctcaa aaaaaaaaa aaaaaaaaaa agaaaagcat gttttttttt    9360
ttttgagatg gagtttcgct tttgttgccc aggctggagt gcagtggcgc gatctcgggt    9420
caccacaacc tctgcctccc aggttcaagc gattctcctg cctcagcctc ccttgtagct    9480
gggattacag gcatgtgcca ccatgcccgg ctaattttgt atttttagta gagacggggt    9540
ttctccaggt tggtcaggct ggtctcgaac tcctgacctc aggtgatctg cctgcctcgg    9600
cctcccgaag tgctgggatt acaggcgtga gccactctgc ccagccagaa agcatttctt    9660
```

```
ttttggctgt tttttttgttg ttttttttaa ttaactagtt ttgaaaatta tagaagttac    9720
acatatatgt tataaaaaca tctccaagca gcacagaaga tgaaaaacaa agcccttctt    9780
gcaagtctgt catctttgtc taacttccta agaacaaaag tatttcttgt gtcttcttcc    9840
cagattttaa tatgcatata caagcattta aatatgtcat tttttgttgg cttgactgag    9900
atcacattac atacgtattt ttttacttaa caatttgagt acaatgtgtc atggaaattg    9960
ttccatagca gtatctgtaa ttcttattaa ttgctgtgta atattgtaga atttcttttt   10020
aaaagaggac ttttggagat gtaaaggcaa aggtctccca ttattctggc tgtacaacgt   10080
tctggtgaca tattctctct accctgagag gtccccatac ccatcacctc catttcctgt   10140
aaataagtca accacttggt aaactacctt tgaatggatc cacactcaaa acatttagtc   10200
ttattcagac aacaaggagg aaaaataaaa taccttataa agcactgttt catatgtatt   10260
aaattggatc aatttgcgtg ctagaatgta tgttagagac atgatatgcc cataggtcct   10320
tgctatcacg gtgaggtctc agggacagca gtttggtatc atttggtatc tcataagcag   10380
actctgtctg cctgacttaa caaatcagag tctgcgtttt aacaggttca gtgagtgact   10440
tacatgcaca ttggagtttg ggaagctcca ctataggtgc ttagacctta cctttgttgt   10500
tgctaataac aatgcaagca tttgggagga agacctgtgt tgctcgtatg tgtccaggtg   10560
tagctgaggt ggccttgctt gtctgctgta gggccattga gcatttgcgt agctgtgatg   10620
aatgagctga ggtgagcctg cggagagctc ccagccattg gtagtgggac ttgcttagat   10680
gaactagaag gacctgagca tccactttgg ggaaaaacaa ccgaatgaag ggagaggcaa   10740
catgcagttt tatttagggt acgaaggaga gctgtggtta aaggtgaca tttgagtgga    10800
aaggggggcaa cccatgtgtg gagcgggaga agagcggtcc aggcagagtt aacagaaggc   10860
agaaatgctt tccatctttg aaaactagga aggatgccag tggctgaagt aagatgaagg   10920
acagaaatag gggatgaggc ttcgagagat gagaggttag agacgagggt cttgtgcacc   10980
aagataagct tgtgtggtca aaacaagtag tttcgttttt gtttttaaaa gatcactttg   11040
gctgggtgca atggttcatg cctgtaatac cagtactttg agaggctgtg gtgggaggat   11100
tgcctgaagc caggggacca gcgtagccaa catagcagca cctataaggt ctctacaaaa   11160
aactttaaa aagtagctgg gtgtagtggt gtgtgcctgt agtcccagcc acccaggagg   11220
ctgaggaggc tggaggggttg cttgagtcca gcagtttgag gctgcagcga gcaatgattg   11280
tgccactgca ctacagcctg ggcatgagag tgagaccctg tctctaaata tatgtgtata   11340
tataaagaa aagatcactt tgacaacacc acatgctggt gaggatttag aaaaactagg   11400
tcacttattg ctggtgggaa tataatatag tacggccact ctggaaaaca gtttggcagt   11460
ttctcataaa actgaatgta caattagtat acaacccagc aactcctgca atcctgcgca   11520
ttaatcctag agaaatgaag ccttcatgtt cacataaaaa cctatactca agcgtgcata   11580
gcagctttac ccataatatc taagaactgg aatcagctca gatgtccttc tgcaggtgaa   11640
tggttaaaact actcagtaat aaaaaggaat gatctactga tagcatgcaa cagtgtaggt   11700
gaagttatgc taatgaaaaa agccaatccc aaaaggttac atattatatg attctatgta   11760
tataacgttt tggcagtgac acagttttag ggatggagaa tagattagtg gttgcctggg   11820
gttagagatg gggttgtaga gtaggttagg ggtggcagag gagagaaaag agagggaggc   11880
gagtgtggtt ataaaaggac aacacagggg gatacttgta acagaaatgc tttgtctttt   11940
tttttttttt tnnnnnnnnn nnnnnnnnnn nnnnnnnnnn nnnnnnnnnn nnnnnnnnnn   12000
```

```
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnngctca ctgcagcctc tgcctctggg    12180
gttcaagcga ttcttctgcc tcagcctcct gagtagctgg gactacaggt gcacgccacc    12240
atgcccggct aattttttgta tttttagtag agacagggtt tcatcatgtt ggccaggctg    12300
gtcttgatct cctcacctca tgatccgccc acctcgccca cctcggcctc ccagagtgct    12360
gggattacag gcttgagcca ccgcgtccgg cctattttat ttttttttgag acagagtctc    12420 actctgtatc ccagactgga gtacagtggc gcgatcttgg ctcactgcag cctctgcctc    12480
tggggttcaa gcgattctcc tgcctcagcc tcctgagtag ctgggactac aggtgcacgc    12540
caccatgccc ggctaatttt tgtatttta gtagagacgg ggtttcacca tgttggccag    12600
ggtggtcttg atctcctcac ctcatgatcc gcccacctcg gcctcccaaa gtgctgggat    12660
tacaggcatt tttgtgtttt tcgtagagac agggtttcat tatgatgcc aggttggttt    12720 tgaactcctg acctcctgtg atctgctggc ctcgcctccc aaagtgttgg gattatagac    12780
gttgagccac tgcactcggc caaggaaaga gatgctttgt cttgagtgtg gtggtgtata    12840
gaaattgtat agaactaagg ctgggcacgg tggctcactc ctgtaatccc agcattttgg    12900
gagaacgagg tgggcagatc gtgagttcag gagattgaga ccatcctggc taacatggtg    12960
aaaccctgtc cctgctaaaa ataccaaaaa ttggccgggc gtggtggctc acgcctataa    13020
tcccagcact ttgggaggct gaggcgggtg gatcacgagg tcaggagatc gagaccatcc    13080
tggctaacac agtgaaaccc tgtctctact aaaaatacaa aagcaaaatt agccgggcgt    13140
ggtggcgggc gcctgtagtc ccagctactt gggaggctga gcaggagaa tggcgtgaac    13200 ctgggaggtg gaggttgcag tgagctgaga tcgcgccact gcactccagc ctgggcaaca    13260
gagtgagact ctgtctcaaa aaaaaaaaa aaaagaaat tgtatagaac taaatacaca    13320
aatgaacaac aataaaactt gaaactctaa gtaagatcac tggattgtat cagtgtcaat    13380
attctggttg tgataatgta gtatattaaa tagttttgca aagtgttacc attggggaaa    13440
actggataaa gggcacactg gatctctgtt atttcttaca actgcacgtg aaccaataat    13500
tatcttaaaa aaacttcaat tcaaaaaagt ctgccctgat ccagttggga ggctactgaa    13560
gtaatcaaag ctagacatgc tggtgtcttg tgactggtag cagtggtgat ggtaagtggt    13620
cagattctgg atctcttgga gaaagatctg acaagatttg cagattcttt aaaaaaaatg    13680
agattaggct gggcacggtg gctcacgctt gggaggctga ggagggcgga tcnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnttg ataatttata aaatgtgatt    14160
atagaatgct gtagtgtcct tgagtttaca tgcccttcct tacacttgtg tgcctgtgca    14220
gatgccttga tttcacaatt agaggaggct gactgagatt tgtttaattt ttttttttt    14280 tgaggcagag tcttgttatg tccccaggc tagagtacag tagcgcaatc ttggtgcact    14340
gcaacatccg cctcctgggt tcaagcaatt cttctgcctc agcctcccga gtgcctggga    14400
```

```
taacaggtgc cagccccac gcccagctat tttttgtatt tttagtagag acgggatttc   14460
accatgttga ctgggctggt ctcaaactcc tgacctcaga tatctgccgc cccagcctcc   14520
caaagtgctg ggattacagg cgtagccaca cctggccgtt tgttttaatt tttaaggtga   14580
cgttaaagtg actgcattta ccaaaagtgg ttgagaagcc aggactgttc ttatcctgtt   14640
tttccagttc ttgctcagag caaggtggtt tattttcac ttaattacca tacttacttt    14700
tcatgtagaa caagtcagtt tgagttatca gttcatcatc taactaaatt ccatggggga   14760
aggaatagtt ttagtttctt aaacttccaa ggttgcttat tggacaaaat gagatagcaa   14820
ggcggtgttt ttaagttaga tttttttattt ctttggtaat ataattttct caaaaactta  14880
gtagtctttt agtttagttg ttttttagttg gtcctatgtt ttgcatcccc cctctctact  14940
tttattttga tagtgccaat tgcgaagaca tctgaagcca taggtttggg tgggaaggcg   15000
gcacctttag cctgattatc tttgccaggc tgtttatctc cttttgcttg gctgagaagt   15060
cttaatagga ggcttattcc cagctacttg gggacataga agcggttagc tattgttcat   15120
gttttactga ggtctgtgtg gtatgttgac tgcagtcagt tactggtttt gagaattgaa   15180
ggcagcctgg tatatagagt aggtattata ttgtgtttct ttgaattgaa tttcctatct   15240
cttgtaatct ttgccatcat cttctgtgaa agaaaaaaag tttctatcaa actataccat   15300
tggttgtaag atgcagttcg gctttagtga tgctaacaca tgatccaaac gtgaaactga   15360
gtattggtga aatacagagg agatttaaag ccagaagacc tgggtttaaa tgctggctct   15420
atgacttcaa atctgtgtgt tcttgggcac gtcatggttg gcacttcaat ttcttctctc   15480
tgtaatgggg gaaatgaggc cagtcatggt ggctcatacc tatgatccca gcactttggg   15540
ggccaagatg ggaagatcgc ttgaggccag gaggttgagc aattgggcaa catagtgagg   15600
ccccgtctct acaaaacatt taaaaaaaat tagccaggcc cagtggtgca tgcctgtggt   15660
ccccaccact caggaggctg agatgggagg atcctttcag cccaggagtt taaggctaaa   15720
gtgagccatg attgtgctac tgtactctag cctgggcagt agagcaagat cctgactcta   15780
aaaaaaagta aaatgaaata aaatggggga aatgaactgc tttagtaaca tcatctgttt   15840
tttctgtgag cagtgtagct tgaaagccat tggtgaactc atgcactgtg cttccctgtc   15900
cagatcccca ttctgcccc agcatggagt ataacagttt attagtagta gtcgagaaac    15960
cctcattgaa tgaatgaatg agatgtagaa gtaagtggag tgggtaattg aacacatatt   16020
catttccttt tctttttttct tattttaga aagaaagaac tttcagctac caagaaagac   16080
cgtgtgaatc attgtctgac aatatgtgaa acatagtgg cacagtctgt caggtaattg     16140
cactttgaac tgtctagaga aaataagaac tttgtatatt ttcagtctta atgggctaga   16200
atattctgtg tccagttat tttaaatgga ttcaaaaatc cttgaagaag gaccctttc     16260
ccatatttct ggctatatac aaggatatcc agacactaaa atgaataatg ttcccttttc   16320
gtaatctttt atgcaaaaat taaaaccatt atggtaattg aacaacatgt ttatgtttag   16380
ttaacaccct tagcaactat agttatttta aaatcctgtg tggtttgata ttttttgcgtt  16440
tattgtaaca gtgggaacag cacaaggcgg tccactttgt ctctctcatt ttgcagtttg   16500
ctgtcctgtt gtgctggtgc tcctagcagt ggctggagcc cacttctctg tgctttggga   16560
ttagtgggt catggggcat tgactggagg tcagctttcc ttgcttgatc tttctcactg    16620
gggtgaacta gcagcacctt cttttgtagc tgctttgctt ttggctatct ttctgaccgt   16680
tgttcctagc agctgtagat ggtaaatatg tttaggcctg tttccaatgg ctgagtagga   16740
```

```
gacatatgca cctatgatat ctgaattctg ttacccagat gggcgtgtgt gaaatagtta    16800
ccttgcttta ctttcccttg gaataaataa ttcatgttat tctcctggta gaagctagaa    16860
aaagctcttt atagtcagtc agaaaaaaat ttttagacaa ataatcttga ttttagtact    16920
gacaaaaatg tgtggtgatt ctttttttta gtttttttg agatggagtt tcactcttgt     16980
tgcccaggct ggagtgcaat ggtgcgatct cggctcactg caacctccgc ctcctgggtt    17040
caagcgattc tcctgcctta gtctcctgag tagctgggt tacaggcatg tgccaccacg     17100
cccagctaat tttgtatttt tagtagagac agggtttctc catgttggtc aggctgatct    17160
caaactccca acctcaggtg atccgcccgc ctcagcctct caaagtgctg ggattacagg    17220
cgtgagccat ggcacctggt gattcatttg ttttttaaa aatttcctct tggccattgc     17280
ttttcactgt tttcttttnn nnnnnnnnnn nnnnnnnnnn nnnnnnnnnn nnnnnnnnnn    17340
nnnnnnnnnn nnnnnnnnnn nnnnnnnnnn nnnnnnnnnn nnnnnnnnnn nnnnnnnnnn    17400
nnnnnnnnnn nnnnnnnnnn nnnnnnnnnn nnnnnnnnnn nnnnnnnnnn nnnnnnnnnn    17460
nnnnnnnnnn nnnnnnnnnn nnnnnnnnnn nnnnnntgt agaaatattg tgggaagaaa     17520
atgaaataac aaatgagcat gtgtcctgaa aataaaaata taaaaattct aagttagcat    17580
gctattgtag aatacaacac tatgataaaa gtagggaaaa aaaagtttga attccacgtc    17640
tgctgcctgt gtaagctggg tgactttaga taagctttaa cgtgtttgag ccttactggc    17700
tcatgtttga agtgtaatcc ctcgttacac agttcttgtg ggatcagacg atgcatgtga    17760
aacactgtga agaagtaact gcgatagatg tgttcattag ccgcctgaac gggaagcaca    17820
tcccattgcg atgcccatca tccaaagcta tatgttatct ttactttttt tgttttttg     17880
agacagagtc tcactctgtc gcccagactg gagtgcagtg gcgccatctc ggctcactgc    17940
agtttctgcc tcctgggttc acgccattct cctgcctcag cctcccaagt agctgggact    18000
acaggtgccc gccaccacac ctggccaaat ttttgtattt ttagtagaga cagggtttca    18060
ctgtgttagc caggatggtc tcgatctcct gacctcgtga tccgcccacc tcagcctctc    18120
aaagtgctgg gattacaggc gtgagacact gtgcccagcc atcttcactt tcttgtgaa     18180
atgatgactc taaatgtttg gcaaacattt ggtgattgtt catctgattt ccactatcca    18240
ggtctcagag aatataattt atctctgaaa gcttattgac ccaggaaaca agatctcttc    18300
caatctgagt acatcaggct ttattcttgt cattttgtct tttgagaatt ttcaaatgga    18360
attcatggaa tgttggctca tattcacata ttagtaaagt acgctgagac atcttaagat    18420
tgatttgtgg ttctatttgc catattaaat caaaataata actgttaatg gttttctttt    18480
tttttttttt ttttttgag acggagtctt gctctgtcgc ccaggccgga gtgcagtggc    18540
ccgatctcag ctcactgcaa gctccgcctc ccgggtttat gccattctcc tcctcagcc     18600
tcccgagtag ctgggactac aggcgcccgc tacctcgccc agctagtttt tttgtatttt    18660
ttttagtaga cgggggtttt cgcccgtgtt agccaggatg gtctcgatct cctgagctcg    18720
tgatccgccc gtctcggcct cccaaagtgc tgggattgag ccaccgcgcc cggcctgtta    18780
atggttttca cattagtctg tctcttgttt ttatggagta atgctgagag ttcattatgc    18840
ttcttgttct acagaagagc atgttaaaag gattttttgg gatcagagag gttatccatg    18900
gtttcatagg atactctgta ctttgcaggg atttcagggt atatagccaa aggtgatatt    18960
ttatataaat atgttttatg gaaacttact gannnnnnnn nnnnnnnnnn nnnnnnnnnn    19020
nnnnnnnnnn nnnnnnnnnn nnnnnnnnnn nnnnnnnnnn nnnnnnnnnn nnnnnnnnnn    19080
nnnnnnnnnn nnnnnnnnnn nnnnnnnnnn nnnnnnnnnn nnnnnnnnnn nnnnnnnnnn    19140
```

```
nnnnnnnnnn nnnnnnnnnn nnnnnnnnnn nnnnnnnnnn nnnnnnnnnn nnnnnnnnnn    19200
nnnnnnnnnn nnnnnnnnnn nnnnnnnnnn nnnnnnnnnn nnnnnnnnnn nnnnnnnnnn    19260
nnnnnnnnnn nnnnnnnnnn nnnnnnnnnn nnnnnnnnnn nnnnnnnnnn nnnnnnnnnn    19320
nnnnnnnnnn nnnnnnnnnn nnnnnnnnnn nnnnncctgt agtcccagct actcagaagg    19380
ctgaggcagg agaatagcgt gaacccggga ggcagagctt gcagtgagcc gagatcgccc    19440
cactgcactc cagcctaggt gacagagtga gactctgtct caaaaaaaaa aaaaaacaaa    19500
aaaacaaaaa aaccaaaacc ttatgtatat tgtgaaaatg tagtctgctt taagctctct    19560
aaagaggtct aagttactgg ttcctaagta tggatgagca tcaaaatcat ctggaaaatt    19620
tgttaaaaat acaataatga aggtacctca ctgtccttt  tcccaaacac acttctgcat    19680
tctgtttgag taggtagggc ctacacattt ttcacaagta ttctcttggg aatcccagg    19740 aatgctcact tgagcaacct cttactaata ccatatactt tgataaagtg gctaggtaaa    19800
aataaatata taaaaatcca tcaatctccc atatattagc ataaatcagc tagaaaacag    19860
taatgtttaa agatctagtt cacagtagca ctgaagtatt gaattccaag aaattgataa    19920
gaaatatgca gaaactttat aaaaacttct gttaatgttt ctgaaagata taggtgacca    19980
ctttctagac aggaagattt tatatcatta agttgacttt tctctaaatt aacacagaaa    20040
tttaaaataa tcttgattaa aattctagta gaggtatttt tgaacttgtt cactgtaaga    20100
ataaatacat aactgcaaag aatatcttaa aatcatcact aggcccggtg tggtggccca    20160
cgcctgtaat cccagcactt ttggaggcca aggcaagcgg atcacctgag gtcaggagtt    20220
tgagcccagc ctgaccaatg tggtgaaacc ctgtctctac taaaaataca aaaattagct    20280
gggtgtggtg gtgcatgcct gtagtcccag ctacttggga ggctgaggca ggagaatcgc    20340
ttgaatccag gaggtggagg ttgtggtaag cctagatggc accactgcac cactgcctgg    20400
gtgacgagca aaattgtgtc tcaaaaaaaa aaaaaaaaa gaaaaaaga aaagaaatc     20460 aacgctaata tggtgagact tgatatatgt gacattaaaa tagtgattgg acattagaac    20520
aggtatagaa cagaaagaag agtgtgtgta tctgtgtgga tttatgatgg gtgtagcata    20580
ttgtattagt agggaaatga gggaaatgat atatttctt  gactttggga caacattata    20640
tctctacctc atattgcaaa caagcataaa attctgatta attacctaaa tgtgaaaaaa    20700
tgaaatactt tcttcaaaaa atgtaatctt agtttgagga agactaacat tatgaaggaa    20760
aaacctgttt tgactggaat atagttcaat atgtcaaaat ccaccttcaa caaaattgaa    20820
agtaaattga acttggggaa agtattgata gcatgtagat caaaggttac tagcctgtgt    20880
aaagagcaat tataaatcat taagaaaaga ctgtcaaccc gtcggcacct tgttctccga    20940
ctcccagcct ccagaactgt gacgagtaag tgcctgttgt ttaaaacacc tagtctatat    21000
gtactatttt gttatagcaa ctcaagctga ttaggaccct agtaatcagt agactgagac    21060
taaaacaaaa ataagaacct tttttacctg tcaagttggc aaacattaag aatatgcaga    21120 ttttttgtcag aggtgataca acctttaaga aggcaatttg ggaaaacata aagctttaga    21180
ttattaatgt gtctgatcta gggcacttac cctaggaaag tgtgtaatga tattggtgca    21240
ctgctgttca tcccattaga aaataaaaat aaccttaata gcttaccact aaaagggga    21300 ttgaaaaatt aagatacatt tatttattta tttattgaga cagagtcttg cactgttgcc    21360
tgggccggaa tgcaatggtg cgatctcagc tcactgctac ctccgcctcc tgggttcaca    21420
tgattctcct gcctcagcct cccgagtagc tgggaataca ggctcacacc tccacaccca    21480
```

```
gctaatttttt tgtatttttta gtagagatgg ggtttcactg tgttgaccag actggtctcg    21540
aactcctgac cttgtgatcc atcccctcg gcctcccaaa gtgtcaggat tagaggcgtg      21600
agccattgta cctggccaga tacatttata caagagagtg ttagttaaca ttcatagatt    21660
ttttttttct tgtttacttt ttattaaaaa aatttttttt tagagacagg gtcttactct    21720
gtcacccagg ctgaatgcag ttgcacaatc gtagcccact gcagcctgaa ctcctgggcg    21780
gaagtgatcc ttctgcctca gcctttttgag tacctggggg actttaggca gtgctgctat   21840
atatacctgg ctaagtttta aatgttttat agatgggatc ttgctatgtt gcccaggctg    21900
gtctagaatt cctgggccca agcaatcctc ccaccttggc ctcccaaagc actgagatta    21960
caggcattga gccaccactt ctgatcaata gatatttata tttgtgactg gaaaatatat    22020
taacaatgtg ttaaaaaatt cagttaaaaa ataatgaaag attttttgctt ctagctaaga   22080 tagaataaca aggacagcat ttatcttctt gccttgaaat agttgaaaat ggataaaata    22140
tatgtaacag tggttttcaa gttattgggc attaggcaaa aagagtagt tatcacagga    22200 aaattaatgt ggagagccct acaatttcct tacattgctg cctggccatg gcaagaggaa    22260
aaactgaaag gaaactgagg ctgagccagt ggtttgctgg gttgaggagg cagagctggg   22320
agtccagaga tgcaaggtgg ctagagcccg tatggaaaaa taccagggaa gagagctgca   22380
gagggagctc cggagaactg cacagtaccc tctcatgtgt gtagctgagt attgatgagc    22440
acatgctggt gaggaaatga cccagggctg caggtagaac cacttaaaag gattagaagg   22500
aacaattgct gcaactcaca cagggccagg aagaatttct tttttttttt tttttttttt    22560
gtatttttag tagagatggg gtttcaccat gttagccagg atggtctcga tctcctgacc    22620
tcgtgatccg cccgtctcgg cctcccaaag tgctgggatt acaggcttga gccaccgcgc    22680
ccggccaaag ggccaggaag aatttctaat cacacaagtc ggagtggaaa acctcggctc    22740
tcatagagca gcaggtagag tactcagaag ggtttgcctg cctagcccca gactaagttt    22800
cgttactctg acccgccta atattaaaaa aagattaatt aaattaattg tttgcaacaa     22860
aagtaatata tttcagtgtt tataacgtgt agaagtgaat tgtatgacaa tagcataaag   22920
gctggaagag cagaaattga catgtatttg tgctggacag aataatgttc ccctcttttc    22980
ccaaaagata tcgagtccta atccctggaa cctgtaaatg ttactttata aggaaaatgg   23040
tttcatggtg tgattaaatt caggatcttg agatgagggg gctgtcttgg atgatttggg   23100
taggcactaa atgcaatcac atgtgtatgc aaaggaggca gagggagatt ttacatacac    23160
agagaaggcc atgtgaagat agaacagaaa gatttgaagg tgctggcctt gaaaattgga   23220
gtgatgaagc tataagccaa ggaatgcagt agccaccaaa gctggaagag gtaggagcaa   23280
ttctccttca gagcctactc cagagggaac gtggtgctgc cagttcctta atttcagctc    23340
agtgatacta attttggact ctggtctctg aaactgtgaa agaataaatt ttttttgttt   23400
gtttgtttaa gccacacagt ttgtggtaat ttgttacagc agctgcagga aactaattta   23460
tgctgcatgt gaaatggcat aatatcatta agatagattg tgataaaggt acatagtata   23520
aacaattaag caacaactaa agcacaaca aggagttata gctaatgaac caaaaaagga    23580
gattagaatc ataaaaatag tgaatcccaa agaagccaga aatagggaa gaggcaaata     23640 aaggaaagaa agagcttgat ggtagattta aacctagtta tgtcaaaaag gacattaaat   23700
gtaaaagata tttttcggat tgaatggaaa agtaagaccc agtatatgct gctgcctgca   23760
agaaacatat tctaaatgta aaggcaaaaa tagcctacaa gtaacagaac agaaagaagt   23820
tcaccgtgct tacaagaatt agatgcaagc tagactggtt ctgttaatat cagacaaagt   23880
```

```
ggatttcaga gcaaaggcta ttgcctagga tgagatggtc gtttcataat aacgaagggg   23940
attcgttcat cagccgcaca taacaaactg aaatatttat gcacctgact acggagctaa   24000
aatacacgaa gcaaagccta acaactacga gtagacacag gcaaatccac agtgagagag   24060
atttcagtgg cttctctcag tgatttgtag aacacgtagc cataatatct ggatctagaa   24120
cagttgaaca acactgtccc tatgcaacct gattggcttt tacaggacac tccacccggc   24180
accagcagaa gagacactct ctcaagtgct cacagaatgt ctgccaagat agagcagatg   24240
ctgggccata aacaagtct ctaaattaaa cgcattcaaa ttattcagag tacgttttcc    24300
gacctcagta tcattaagtt ggaatatatt ataggaagat aacctggaaa agcctcagat   24360
atgtggaaaa actcatttct aagtggccca tgggtcagaa gtgaagtcaa aagggaaaac   24420
tgaaaatctt ttggattgac tgatatgaaa acaatagatg tctatacttg tggggtgctg   24480
ttacagtata gtaaagggaa atttctagca ttaaatgcct gttttagtaa agaaagattt   24540
caaatcaatg acctcagctt ctaccttggg aaacttgaaa atgacaagca aatggaatcc   24600
agagttacca gaaaggccag gtacagtggc tcatgcctgc aattctgcca ctttgggagg   24660
ccaaggcagg cggattgttt gagactggca gttcaagacc agcctgggca gcataggag    24720 actccatatc tacaaaaaac acagaaaatt agccaggtgt ggtggcatgt gcctgtagtc   24780
ccagctaacc aggagtctaa ggtgggagga ttgcttgagc ctgggaggtt gaggctgcag   24840
tgaactgtga ttgtgccact gcgctccacc ctgggcaaca gaatgagacc ctgtctcaaa   24900
aacaaaaaca gttactagaa gaatggacat catagagata agagcagaag tcagtaaaat   24960
agaaaacaaa aatacataga aaatcaataa aaccaaaagc tagttcatca agaacatcaa   25020
taaattggtg agactaatag gaaaaaaagt gaagtcacat attatcaata tcaggaatga   25080
gggagatgac agtagtatag attatataga tattaaaagg gctatatgag gcaggtgcgg   25140
tggctcacgc ctgtaatccc agcactttgg aaggccgagg tggacagatc acctgaggtc   25200
aggagtttga gaccagcctg cccaacatgg tgaaactccg tctctactaa aaatacaaaa   25260
attagctggt catggtgcca tgcgcctgta gtcccagcta ctcgggaggc tgaggcagga   25320
gaattgcttg aacctgagag gcagaggttg cagtgagctg agatggcgcc attgtgctcc   25380
agcctgggtg acagagtgag actccgtctc aaaaaataat aataataaaa aggactatat   25440
gggaatatta tgaacaactt tatgccaata aatttgataa cttatagatt aaatggataa   25500
gttccttgaa agacacacaa actattaaag ctctctcaag aagaaataga taaactgatt   25560
agccctatat ctattttatt aaatttaaat gtaaaaatca atatttagtt actgaaaaac   25620
ttttaagtgt ggttggaaat ggtatatgaa cttttcaac tgaattttat gaaggctaat    25680
cacaggtaaa ggttttctga tgaaaattta gtgtctgaat tgagatgtgc tgtaaaaaat   25740
gttgttatgt atcttaatca tttcttcaca ttaattacat gttgaaataa tactttgggt   25800
gtattgggtt aaatgaaata ttatgaaaat cttgcctgtt ttcttttac ttttgatgtg    25860 tcacctggga aataaaaaag tgtgacttac attctgtttc tgttgacagt actgctttgg   25920
agtgcagtgt tggaatgatc tagcatttcg aagacctttc ctcccttcgt tattcagggc   25980
tgtattccac atagataagt ctgaaatact gctaagtggc acgttttgtt ttgtgctttt   26040
gtaagtttgt tgatcgttac tgatgtggac ctttggtgcc tcttaggctc atggctatct   26100
tccaaccatt gtttgcaatt tttacctaga gataaagaga aaagagatt tggtttcaga    26160 gtaagttaga ttgagatcat gaaagagcaa tctcatttg atgcttcaaa aatagcacat    26220
```

```
cccccgtatt actgggattt gctattcttg ggcttacttc aagaacatcc ttgtgttgct   26280
ggtttggatg cttccgaatg ctgtgaagtc agtttcatgg acgtggctca tcagtttagc   26340
tctcttggct ttgttaggc agttggagca tgatagcctg aacagcttct ctcaattaaa   26400
catttacaaa tcgtttacga atagtaaaca aactccaggt tttgtgactc tttgatagtt   26460
catctagcac aacaaaaaca caatgtgacc atgatcacct ggcatcttag ggtgaaatac   26520
tttggcccag actgaaagca aaattaaaaa ggggcaagag agatatactg ctgaactgat   26580
tttcaaggtt ccaagaatat cataggttaa gagtaaaagt aaactttga cagagagcag    26640 cgggttttct gggattgaag tatctgaagt tttcaaacga aaatttaaaa agaaaaaatg   26700
agaattgcct tataagtaca atctcttctt ttttaaaaaa taaactttat tttggaatag   26760
ttttaggttt atcgaaaaaa attagggtag agagttttca tacccctac atccggttac     26820 cccagttatt atcttaatta agtgtgagac attttcatgt ttaatgaatc agtatcgata   26880
tgctgttaac taaagtgcag actttattaa gattttctta atttctatgt aatgtccttt   26940
ttctgttcca gaattccgtg caggacaccg gatacctcat tacatttcat tgtcatgtca   27000
ccttaggctc ctcttgacag tttctcttct tttttgctta gaaattctcc agaatttcag   27060
aaacttctgg gcatcgctat ggaactttt ctgctgtgca gtgatgacgc agagtcggat    27120
gtcagaatgg tggctgatga atgcctcaac aaagttatca agtaagagc cgtgtggatg    27180 gtgttctcag aaatgtcatt ggtgtaggct aagagaagca gccatcgttg agtgttcttc   27240
tgtttggagc ccctgaggat gtctgcactt ttttcctttc tggtgtgtgg tttggaggtg   27300
ctctggtatc tgcccgcatt gcttgccaca cctgcctggt cagaaggaac tgtgttgacc   27360
cttgtgcctg catggtgcct aggtcaatga agggaaccaa tggtgaccac tggatgctcc   27420
tgggaaaatg tcactacagg taccagagaa gccagagcta tgcccacatt ttttttttt    27480 tttttttgag acggagtctc actctgtcgc ccaggctgga gtgcagtggc gcgatctcag   27540
ctcactgcaa gctccgcctc ctgggttcac gccattctcc tgcctcagcc tcccgagcag   27600
gtgggactac aggcacctgc caccgcgccc ggttaatttt ttgtattttt agtagagaca   27660
gggtttcact atggtctcga tctcctgacc tcgtgatccg cccgcctcag cctcccaaag   27720
tgctgggatt acaggcgtga gccaccgcgc ccggcgctat gcccacattt ctatgagtct   27780
cagttttctt aactataaaa tgggatcaaa gttttgtgg catgcgtatg agtgtgtgtc     27840
tgtgtgagga ttaaatgcac taattgccac taccggatcc tcaaagtggt aagaagtatt   27900
cttattaatc atgacatcct cacactctta tgcagcaaga ttgatgggtg tggcactgct   27960
tctctttttc catcacatgg attccatgct atccttttgc ccagggaatc tttcctttgt   28020
ggccagcact ttgttgtttg gctcatcacg ctttctgtgg gcaggacgct ggcttctctg   28080
gagtcttggg attctagctc cctctcttgt ccctagagtg gtcactgtct tctctctctg   28140
cttgcaattc ttgcttgct cgcatctcac tcatgcggtg acctgtatca gtttcacctt    28200
gttctccgtg cctgctggtc gttggcacca cttgcctgtg gatggcatcc catagcgtat   28260
ttagggcctg cttccccagt taagcttgct tttccacagg cctgaatatc cttgcttgct   28320
tctgttattc ccactggcag gaccacggcg gtctttttg gatgagacag ggtcttgctc    28380
agtcacccag gctggagtgc agtggctgat cacggctcac tgcagccttg agctactggg   28440
ctcaagctat catcctggcc tggcttcttg agtagctggg actacaggcg tgcaccacca   28500
tgcccagcta attttaaaaa ttatttgtag atatgggatc tcgccaggtt gcccaggctg   28560
gtcttgaaca cctgggctca agtaatcctc cctccttggt ttcacaaagt gccgggatca   28620
```

```
caggtgtgag ccactgtgcc tggcccttga tgtttcagtt cttgatattt gatcctcaga    28680
gtcagaaagt ctaaaagag gactatccca ggttgccttg gttcacggca aatgggacgt    28740
taagagggca gagaaaacaa tatgaccaga aacgcttcta atattggtca tttaacgtgt    28800
aagtattgtt cttttttaaa cctccttcat ctttttctag ggattgctgg acacagtggc    28860
ttggtgtgtc tgagggctgt aggccatggc cctgggttgt ggttttaggt ctcaggtgct    28920
cttcctggtt gtctccttgc ttcttttccca tttcctcttc tttgtttcca gccatttctc    28980
cctttttgctt aagtttggtg cagcagggtt tggctgctct cagattgctg cttcctcaga    29040
tgatgcagtt gccaggccca gtgggctggc agtgggatca ggatctgact aggttttgctc    29100
tcactgtggc agaggagggg caggcgtggg agagcacgtg tgaccccagg ccaggtgtag    29160
ggagcccagg catggtcact tagccttcag gtcctagact ttgtcttctc atgagtgtgg    29220
ctgtgtgtgt atggtgagaa ccaggttcta cgtagcccaa gaaaatgtag agaaatgcac    29280
tgggtatctg acatagcctg gcagcacgcc tccctcaagt aggttagtct caggcggtga    29340
agcatgtatg tccagcaaga acttcatatg tggcataaag tctccgttct gtgcggcact    29400
gacaaatcac caccgtcagg aggctgaagt aatttctgtc tagggaggca gggaaggctt    29460
cctggagaca gtagccaata ggtgaaaggg tagattggag accttcttaa tcatcaccgc    29520
ctcttggttc gagggtgcc aggaagctgt ggaggctgag aggaggggga acccatctta    29580
tgctgccaga gagtgggaca ccctgagggt caggtcaagg ggttgtacct tgttgggtgg    29640
agaattaggg gctcttgaag acttttgatg tggtcagggg agtgtatcat ttaggaagag    29700
tgacctggta aggacgtggg atagaggagg acagaggtgg gagggagtct aggtgggagt    29760
gagtgggccc agcaggagtg cagggcctcg agccaggatg gtggcagggc tgtgaggaga    29820
ggcagccacc tgtgtgtctg cggaagcagg ggcaagagag aagaggccag cggcgcgccg    29880
ccatcaccca gcaactggcg tagattgtga gagcccattc cctgctttta ggaggggccg    29940
agttttagtt ttctcttata aaataaactt ggtatttgtt tacaaaacat ttgtaaagct    30000
aaatcaaggt ttgataaggc ttctagtttt atttaagaag taatgtttaa ataaatgtcc    30060
aattcgcttt gcttatttaa ggactttcag tacaaacttc aacaacagga tcaggattta    30120
aacatttctg agatgttatt acccctcaga atttcccaga acgtgatctg gttttgattt    30180
tcaagcttgc tgacccagta ggttaaccca caaattttac taagatacac ctcagtccat    30240
ttatatcgac tgcccatgtc acggtcaaag agatcatcga ctgatgtttg gcacagcttc    30300
ctccctcttg ggtgggcaag catttggaag agaaggctcc catgggtgag agtggggcac    30360
cagagtcttc cccgtcctgt cccctggctt gagaaaccct tctctaatgt ggactttgtg    30420
ccgttagcat cgttactggc ttgaagttga ccatgtggac ataatttctg gtttagcctc    30480
acaagtgagc aaggagggtt gagagatgtg ctgtgaggaa catggggccc ccgctggccg    30540
tgggctctgg gtcaggggg cagggaccca tgggcatacc tgacagtgag gagggccac    30600
acctgcagaa agcatgcggg actcggcnnn nnnnnnnnn nnnnnnnnn nnnnnnnnn    30660
nnnnnnnnn nnnnnnnnn nnnnnnnnn nnnnnnnnn nnnnnnnnn nnnnnnnnn    30720
nnnnnnnnn nnnnnnnnn nnnnnnnnn nnnnnnnnn nnnnnnnnn nnnnnnnnn    30780
nnnnnnnnn nnnnnnnnn nnnnnnnnn nnnnnnnnn nnnnnnnnn nnnnnnnnn    30840
nnnnnnnnn nnnnnnnnn nnnnnnnnn nnnnnnnnn nnnnnnnnn nnnnnnnnn    30900
nnnnnnnnn nnnnnnnnn nnnnnnnnn nnnnnnnnn nnnnnnnnn nnnnnnnnn    30960
```

```
nnnnnnnnnn nnnnnnnnnn nnnnnnnnnn nnnnnnnnnn nnnnnnnnnn nnnnnnnnnn    31020
nnnnnnnnnn nnnnnnnnnn nnnnnnnnnn nnnnnnnnnn nnnnnnnnnn nnnnnnnnnn    31080
nnnnnnnnnn nnnnnnnnnn nnnnnnnnnn nnnnnnnnnn nnnnnnnnnn nnnnnnnnnn    31140
nnnnnnnnnn nnnnnnnnnn nnnnnnnnnn nnnnnnnnnn nnnnnnnnnn nnnnnnnnnn    31200
nnnnnnnnnn nnnnnnnnnn nnnnnnnnnn nnnnnnnnnn nnnnnnnnnn nnnnnnnnnn    31260
nnnnnnnnnn nnnnnnnnnn nnnnnnnnnn nnnnnnnnnn nnnnnnnnnn nnnnnnnnnn    31320
nnnnnnnnnn nnnnnnnnnn nnnnnnnnnn nnnnnnnnnn nnnnnnnnnn nnnnnnnnnn    31380
nnnnnnnnnn nnnnnnnnnn nnnnnnnnnn nnnnnnnnnn nnnnnnnnnn nnnnnnnnnn    31440
nnnnnnnnnn nnnnnnnnnn nnnnnnnnnn nnnnnnnnnn nnnnnnnnnn nnnnnnnnnn    31500
nnnnnnnnnn nnnnnnnnnn nnnnnnnnnn nnnnnnnnnn nnnnnnnnnn nnnnnnnnnn    31560
nnnnnnnnnn nnnnnnnnnn nnnnnnnnnn nnnnnnnnnn nnnnnnnnnn nnnnnnnnnn    31620
nnnnnnnnnn nnnnnnnnnn nnnnnnnnnn nnnnnnnnnn nnnnnnnnnn nnnnnnnnnn    31680
nnnnnnnnnn nnnnnnnnnn nnnnnnnnnn nnnnnnnnnn nnnnnnnnnn nnnnnnnnnn    31740
nnnnnnnnnn nnnnnnnnnn nnnnnnnnnn nnnnnnnnnn nnnnnnnnnn nnnnnnnnnn    31800
nnnnnnnnnn nnnnnnnnnn nnnnnnnnnn nnnnnnnnnn nnnnnnnnnn nnnnnnnnnn    31860
nnnnnnnnnn nnnnnnnnnn nnnnnnnnnn nnnnnnnnnn nnnnnnnnnn nnnnnnnnnn    31920
nnnnnnnnnn nnnnnnnnnn nnnnnnnnnn nnnnnnnnnn nnnnnnnnnn nnnnnnnnnn    31980
nnnnnnnnnn nnnnnnnnnn nnnnnnnnnn nnnnnnnnnn nnnnnnnnnn nnnnnnnnnn    32040
nnnnnnnnnn nnnnnnnnnn nnnnnnnnnn nnnnnnnnnn nnnnnnnnnn nnnnnnnnnn    32100
nnnnnnnnnn nnnnnnnnnn nnnnnnnnnn nnnnnnnnnn nnnnggtggg agaatcactt    32160
gaacctgggc ggtggaggtt gccttgagcc gtgatcacgc cactgcactc cagcctgggc    32220
aacaaagtga gacttcgtct caaaaaataa aaataaaaat gaaataaaat cagtccgggt    32280
gtggtggctc gtacctgtag ccccagcact tcaggaagct gaggcaggtg gattgcttga    32340
gaccaggagt ttgagaccag cataggcacc atggcaaaac gctgtctgta cagaaatgag    32400
ctaggtgcgg tggtgcacaa ctatagtccc agttacttgc gaggtggagg tgggaggata    32460
aatggagcct ggaaggttga atctacagtg agctgagatt gtaccactgc ccttcagcct    32520
gggcgagcaa gtaagaccct gtctcaaaaa aaaaaattat tgactatatc ttattgtcta    32580
taatccctcc tctgtgctat tgaataccag gttttgggcc cttatttcca tcactgaaca    32640
aacttcactc tattgagcag catgtgtgga atttcatctt tattcaataa ttaacagcta    32700
ggaggaaatg ctgtttgcta gactattgct ttacttttct tcaaaaggtt actctttatt    32760
agatgagatg ggaattaaaa atggtaactt actttatgtc tttataattg aagcccgcta    32820
gatcttaaag tagttaccag atgttttatg catttaaatg gccttttctc taaaaataga    32880
aagtaacaat gaaagaaaat gcttcgtttc tatgcaaccc tcttggtgac tagtgtgtgt    32940
gactcttaat gtgacactca ttgcaccccc tcagaatggt gccctcgga gtttgcgtgc     33000 tgccctgtgg aggtttgccg agctggctca cctggttcgg cctcagaaat gcaggtaagt    33060
tgtacattct ggatgttgat ttttgttggg ggccagctgc tactgatcct ttatgtctca    33120
gctcagatgt catttcagaa atctgctctg ccccttccaa attgcagtcg accttgccct    33180
gtttatgttt ccgtcatagc actaatccgt gtcagaaagt gtcacgtaca gtctgtgtgc    33240
ttgttcattt tctatcccac cctcccccaa gagacttatg ggatgtgtgc cccaggacag    33300
caggggtctt actgtcttat gctctgttgc agcctaaaca gcagtaacag tgtctgcaca    33360
```

```
tagtacttgc ttaaatgatt cttgccaaat tgttgaaggt tgaggtacca gtttcattat    33420
tgctgactat aggagttaca gcaaaatatc catttgtcta ttacatgagt taaaaatatg    33480
gttgtttcac tatgaatagt tttgtctagt caaaacagtt gtgtcttaac ggattgagaa    33540
acaaaagcag gaccactttt catcagctcc ctcctcctta acctgcagta tacgctgatg    33600
ctgatgtcct gtagaccctc agctccatcc tgagtcactg gaacgtggt ctaaaccctc     33660 attattagta tgaactgagt ttcaataaga atctcacatg ggtcgggtgt agtggctgat    33720
acctgtaacc ccagcacttc aggaggccaa ggcaggtgaa tggcttgatc cagactaggc    33780
aatatggtga aacccgcct ctacaaaaaa tacaaaaatt agctgggcat ggtggtgcgt     33840
gcctgtaatc acagctactg gagaggctga ggtgggagga tcagttgagc ctgggaggtg    33900
gaggtcgtgt tgagccaaga tcacatcact gcactccagc ctgggcaaca gagtgagacc    33960
tgtctcaaaa aaacaaaaaa caaagaaaca aaaaaaagct tatatgggtg cagaggtata    34020
atcactaagg aaatttcttt ttgtgtagtc ttttttcttt tactgtcatt tcaaaaaatg    34080
tgttatattt ctgaagtaac acatccaggt tctccacata gcagccaaag tgaccttaaa    34140
gaacataatt gggtcttgtc attcccttat ttaaactctt gtgcccgttt cccagtgccg    34200
tttagattga ttccagactg gtaactggct ccgtcacctc agacactctg cattgactca    34260
ttagcctgat cagttcttca gatgagtcag gttttcttc ctcctgatgg tttgtttgtt     34320
ttgtttattc ccctcagttc tcagcaaaac agtcatttcc ttagggaggt ttccctagcc    34380
tccctgtctt tccctgtccc aggagcctgg tggtgtggtc actgccctct gaggccctgc    34440
ttgttgccag gctctgccac tagagggcag ggctgcacca ctcctggcac ctcacacctg    34500
gcctgccctg tcagtgtttg ttgggtgaat tcctgtgatc tgtgactcac tgctctgtgt    34560
cctacacatt ctgcttttct tctcccctca caataccatt tataattctc cttttcagg    34620 aaagctttat ttccattaaa acattttgt ttttaaaatg gtattttctt acactattat     34680
tttctaatta aaaatgagtg ttttggcagg gcgtggtggc tcacccctgt aatcctagca    34740
ctttgggagg cccagatggg cggatcacaa ggtcaggaga tagagaccat cctggctaac    34800
atggtgaaac cccgtctcta ctaaaaatac aaaaaaaaat taggcgagtg tggtggtggg    34860
cgcctgtagt cccagctacg tgggaggctg aagcaggaga atggtgtgaa cccgggaggt    34920
ggagcttgca gtgagccgag atcacgccac tgcactccag cctgggcgac agagcgagac    34980
tccgtctcaa aaaaaataa aaataaaaaa aaaaaataa ataaaagta aaaaaaaaa       35040 agagtatttt aagaagtatt acgatttact gcaaataatt tttaaaccca gcctttaga    35100 tcctctgtga tcataagaga aatgaaggat gtctcccgac acttgagctt catccacatt    35160
tcattctctc gttctttcag ctgagctttg cccatcccca ttagggaccg tttggcatat    35220
gaaactggct tttccctaac agggaatgaa ttgcttctat ttctcctgaa ggagagctgg    35280
aggaatgact tgcgttcttt tgcatacaca ggccttacct ggtgaacctt ctgccgtgcc    35340
taagtcgaac aagcaagaga cccgaggaat cagtccagga gaccttggct gcagctgttc    35400
ccaaaattat ggcttctttc ggcaatttg caaatgacaa tgaaattaag gtacgattat     35460
tgcctcagat cacaaacatg tgagtgacgc tgtgagtgag tctgtggagg ttacggctt     35520 ctgagcaggg agtcatgtgg gagcgcttct tagagtatgt tgtatgtcgt aatttagact    35580
accgtcattt gtgttatttt tgaggcacct aaagacttct ttccacttct gatttcttac    35640
tgtggggtga agagttgaat tgggagatgg tttatagatg cacattcaaa aggcatattt    35700
```

```
ccagagcaga ttggttttca gtgtattaga gtgactgttt aacctagctg tggaaagatg    35760
gctgtgccag gactgcaggt aggagaaagc tcactgacga ggccttgtgg gtctgaacat    35820
cctgcagcta tcagggcctg ttggctccct gttgtgcatt ccaacaaacc accttcaaac    35880
ccactttagt gtttgtttat aatgtccaga aatagtgacc ctgtcacatg ctctacagat    35940
tacaggattc ctagcctctt ccttttggt gggtcagtcc tgggtttgag cccaagtggc     36000
cctcttggaa ggtgatgata cacagtggg agagtggaat cagatggact tggattagaa     36060
ttctgtccgc tttactggtt cttttcctct aggcaaacta tccaacagct ctaagctatt    36120
tccttcgtat tctgaaaact aagccttaat gggacccata tcgggcaatt ctgagagtga    36180
aataaatgaa tatgtgttag cgtgtagcat agtcgcccac aggaagggct tagatgttag    36240
ctgctactgc tcttattagc tgaatgactt ggaataaagt gttagcctct ctcatgtttt    36300
tttctctgag ctttgaagtt ttcttgttaa tactaaggag atattcaaac tagtcatggg    36360
gttttggaat gacgaaggga gatcatgaat ctaaagaatt tagtgtggta attcatcatg    36420
ctcagtaaat ggtagctgct gcttgctgtt atttttatta ccatctcttt ggagtgggag    36480
taggtctcct ttgtggtcag aggctgtgag agctccgcag cgccagtctg cccgtcagta    36540
cacccgggctc tgatgaaggc agttccctct gtggtatctc tggctgtcag agctcagatg    36600
atagatggtg ttttttgtact ctcagttctc atcattttca tgatttcgat cactatttga    36660
gtatgatgat gctaacactt tgttgaacat agagtccatt aattacttcc ttcctgaacc    36720
ttaggtatttt aaaaaaatct attctgctac ctctctgctc atttatgatt attcagattt    36780
attatcaaga gcctggtaca gtggcttgtg cctataattg tagctacatg ggaagctgag    36840
gtaggaggat tgctggaggc caggagtttg agaccagcct gggtaacatg gtgagaccct    36900
atcgctaaaa aatgaaaaaa gttagctggg catgatggca cgtgcctgtg gtcctagcta    36960
ctcaggagac tgaggcagga ggattgcttg agcccaggag ttggagttcg aggctatact    37020
gagctgtgat tgtgccacca cactctggga tgggtggcaa aagaagatgc catttcttca    37080
aaacaaaaca aaacaaaaaa aggtattatc ggtgaaattc aatagtacca acaggattat    37140
aaacaaagat agttctcttc ctactttttc tcttaatcct tgtgtctcag aggcaaacat    37200
aactcttagt gtttcttcca atatttactt cgannnnnnn nnnnnnnnnn nnnnnnnnnn    37260
nnnnnnnnnn nnnnnnnnnn nnnnnnnnnn nnnnnnnnnn nnnnnnnnnn nnnnnnnnnn    37320
nnnnnnnnnn nnnnnnnnnn nnnnnnnnnn nnnnnnnnnn nnnnnnnnnn nnnnnnnnnn    37380
nnnnnnnnnn nnnnnnnnnn nnnnnnnnnn nnnnnnnnnn nnnnnnnnnn nnnnnnnnnn    37440
nnnnnnnnnn nnnnnnnnnn nnnnnnnnnn nnnnnnnnnn nnnnnnnnnn nnnnnnnnnn    37500
nnnnnnnnnn nnnnnnnnnn nnnnnnnnnn nnnnnnnnnn nnnnnnnnnn nnnnnnnnnn    37560
nnnnnnnnnn nnnnnnnnnn nnnnnnnnnn nnnnnnnnnn nnnnnnnnnn nnnnnnnnnn    37620
nnnnnnnnnn nnnnnnnnnn nggagtacaa tgacatgatc ttggctcacc acaacctccg    37680
cctcccgggt tcaagcgatt ctcctgcctc aatctcctga gtagctggga ttacaggcac    37740
gcaccaccat gctcggctaa ttttgtattt ttagtagaga cggggtttct ccagattggt    37800
caggctggtc tcaaactcct gacctcaggt tatccaccca cttcagcctc ccaaagtgct    37860
gggattacag gcatgagcca ctgcacccgg caacttccac atttctcagt aacatgcttc    37920
tactgctttt tttttttttt ttttttcaat tttagacatt ttttactttc acactataat    37980
tctatcagaa ttcagtatgt acattattat acctaagtaa atagtcatgg ttggttgtgt    38040
attatatttc tttgtatttc ttatttgatg agagagctgt gttttttgct gtgggttgaa    38100
```

```
actgtggaga gaggacatgg ggaggggaag gaagacagat gaagttggtg actgtacctt   38160
cctggccata gctgggttct cagcaccctg ggatctgctg atcacctgct cgtaggccaa   38220
gcccctagcg aagttctagg tgacccagtg ctggggatgg ggggtcacc tgcaaggtct    38280 agtcatggag gtgggggcta cagtgttggc ttgtgctggg gccagcatcc ttaggaatgc   38340
atcttggagg aggaggagac agccacccac ttcttgactg gggccttcag cagtgccagc   38400
ttcttgggca gactggtgct ggctttcatc accacatcgt gttcaatctt cttccagatc   38460
ctgacttcta ggttcacctt tccttagacc ccggttcctt tcagaggctg tcgctctgcc   38520
ttgctctttg ctggcttgtg ccttgattat atgtctttgt acaactttt gttttcctgg   38580 agttaatcct cacatctgtt ttcctagagt gaattgttac ctttatatca cttgcttatt   38640
attctttgac ctttttttct tctcacacct tccaacttct ttgtaaaatg tgtttagtac   38700
aatttttcat gacaggtaat ttaccaaatc agttttcc cagtgcagtc atccatcttg      38760
agttacccag ctcgctgccc cagtctgggc ggattgctct tcaggtctgt tgtacacttg   38820
tatcctagga cttctctttg ccatcagcct ggaatttcct ttgcagttct cctgttggat   38880
gcccagttcc tacatgccat atgtttatct ttctatcctc tagtagcttt gtgagagaag   38940
atgaatggga ggtaaattgt ttggagtttt gcattcataa aaatgccatt ttttctcgcg   39000
tacacttggc tgagtatagt gttctggggt agaaatcatt tttcctcaga aatgtgaagt   39060
cttttcccgt tgtcttaaag tctccaacat aacccaattc cttaacccat gaatgtgctt   39120
ttctctggaa gctttccatt tttggggagg tgaagtgcta ggtacttagt aggcctttta   39180
ttttttattt ttatttgttt tttgaggcgg agtctcactt tgtcgccgag gctggagtgc   39240
agtggcatga tctcggctca ctacaagctc tgcctcccag gttcacgcca ttctcctgcc   39300
tcagcctcca agtagctggg actacaggcg cacaccacca cgcccggcta gttttttttt   39360 tgtatttta gtggagacgg ggtttcaccg tgttagccag gatggtctcg atctcctgac    39420
ctcgtaatcc gcctgcctcg gcctcccaaa gtgctgggat tacaggcgtg agccaccgcg   39480
cccagccagt aggccttta atttggaaac ttatatactt cagttctggg aaaattttct    39540
tacatttctc tgataaattc ttgccttta ttttctgtgt tctctccttc tgaaattagt     39600
tagttggatg ttggtcctcc tgggttgact cacatcttac ctttttcttt ttctggtact   39660
ttttagatat ccatctcaaa ctcttctatt cagtgttatg tttttaactt ctttcttttc   39720
tttgtctctt gatggggtct tgctttgttg cccaggttga ggtgcagtgg tgcaatcata   39780
gctcactgca gcctccaact cctgggctca agcaaccgtt ctgccttagc ctcccaagta   39840
gttgggacta caggtatgca ccaccatgtc cagctatttt ctttactttc tttcttttt    39900 ttttttttt tgagatgga gtgctgctct gttacccagg ctgagtgca gtgatgcgat      39960 tttggctcac ttaagcctct gcctcccagg ttcaagcaat tctcctgcct cagcctccta   40020
agtagctggg attataggtg tgcaccacca cgcccggcta attttgtat ttttagtaga    40080 gacggggttt cgccatgttg gccaggctgg tctcaaacac ctgacctcag gtgatccacc   40140
tgcctcagcc tcccacagtt ctgggattac aggcgtgagc ccatcattaa atcttaat     40200 actagtatct gtaagtcttt tcctcttgag tcagccagta tccctggaag gaaattcctc   40260
attttcctgc ttggagacta taagcttggc tgtgtttatc ctgcaaccgg ggactggaag   40320
gggatggaag gggactgaca ctgttgctgg tcagggcgcc ctcttttgt tttctgtatg    40380 catctcacat ctgtcctcag ttatgtaaac acctcttgag attatccctc tcagtctttg   40440
```

```
ctggaggtgg ggaaggggct gcttcctggg ctgccttgga ttggagggga gacctcaggc   40500
gagtgggtgg gaatttgccc aaggagccat gagacaagcc actgttccac cctctccgtc   40560
cctccacttt cagatgtatg tggtgcctcc aaagcccgag tgcttcttgg agttctgtgg   40620
cttgaataag cttgcttttc actggtatcc ctcatacctt ctcccccatc cccagcaaag   40680
cttgcatttg aacttcttcc catgggctaa caaatcagtc agttatgtag cccttgttac   40740
tttttagctt ccgaagtttt gttgacacac gtagtctgct agtgtccctg ttctgttctt   40800
tctgtccgtg tacatttatg ctttatacaa cttctttaca tgattttcgt ggggtttctg   40860
ggtagcagag cttcacatgt tcaatccagc atgttggatt agaagtctcc caccctctgg   40920
tgtattctca ttctcagaat tacctgccaa acaccgatac tcccttgttt ttccttttcc   40980
tgacaggaaa tgtacatacc agacaggaca gaaatcatta gtgtatccct tggtgaataa   41040
ccacaaagtg atcttaccct cgtaaccacc acccaggtca agacagagta ttaccagcac   41100
tcagaagcct caccccatc ctcccatcac tgcttcttcc ttcctcccca aggtcatgac   41160
tgtcctggct tctaatgcca gagtctgttt ttaaattctg tgtacataga ccatatagta   41220
tgtattcttt ttgtctggtt tcttttgctc gacagtaatt tcttaagagt cttctatatt   41280
atcgtgtgta ttagtagttc ctgtagtttt aggagcttca tagcattcca ttgtaggtat   41340
ataccacagt ttattcattg tgttatcact gggttgtttc tagttcttgg ctattgtgag   41400
caatgctact gtgaccactc tcaggtgttt ttttggagc acatgtgcag gtttccatca   41460
tgcgcagcta gaggtggagt tgttgggtga tagggtgtat gcatgtcagc tgcagcagaa   41520
actgccaaat agctttcctg agtgcttgta ccagctcacc ctttggttgc tgcgtatggg   41580
gactccggga gctctggtcc tcgctagcac ttggaattgc tgatgctttt acttttagcc   41640
ttcctgatgg gtattttctg gaatcacatt atgattttaa tttccgttcc ttaaagtacc   41700
cttgactctg aagtttaatg attaatgcat ctcttccttt ttgaagtact ctgaaaggta   41760
tgttgtgcat gtgttgaaaa ctggagctat ctagtctaaa atacagtgta cctcctccct   41820
gtttgaagag ttgtagcatg gcctcgggc tcctgttag gtgccttgga aagggattc    41880
ttgggattgt agagattaga cctgaggagg ccccttggag ctctcagact aaattttgtt   41940
ctttattatt ccaaactatt taagctcacc gtgtgctgac tcatcataat aatgagtagc   42000
tctcattgtg cttgtatatt tggaccaata gaatgatttt tttttttga gacatagtct   42060
tgctctgtca cctaggctgg agtgcaatgg cacaatcttg gctcactgca gcctctgcct   42120
cccaggttca gcgattctt gtgcctcagc ttctcgagta gctgggactg caggtgtgta   42180
ccaccatgcc tggctaatgt ttgtatttt agtagaaacg gggtttcacc atgttggcca   42240
agttggtctc aaactcctga cctcaagtga tctacccgct taagcctccc aaagtgctgg   42300
gattacaggc gtgagccgct gcgcttggcc aaagtagttt tttaagatgt gaatatcttt   42360
tcttgcagct aaaaaagttt gtcagagata attctacttt attctccagg tggttttca   42420
gggagaaatt ggaggcagta aaccacgggg ggagtcctgt ggcttggtgg gtgggtgggg   42480
gaggtgtggc tggggtgggg agaagtcctg tggctcgctg ggtttggggg gagctgtggc   42540
tggggtgggg agaagtctag tggctgggt ggggagaagt cctatggctc ggtggtggt   42600
ggggagctg tggctgggt ggggagaagt cctgtggctc ggtgggtggt ggggagctg   42660
tggctgggt ggggagaagt cctgtggctc ggtgggtggt ggggagctg tggctgggt   42720
ggggagaagt cctgtggctc ggtgggtggt ggggagctg tggctgggt ggggagaagt   42780
cttgtggctg gggtggggg cagtcctgtg gctggtgtct catcatgtgc ctaacagtgt   42840
```

```
ccagaggtct cgtgtaaatt ccctgggagt cgataagcct ctgagaaaca gatgatgcta    42900
accacgctgt ggaagagaaa cttgtttata aatcagatgt ccgttactgg tttactgctt    42960
gtttgcccag gcatagctcc gacagagtcc ccgactcata gtgattgctc agtgcgtgct    43020
gaacaatgat tggaatcaag tcatggctca gagcatagtt ttgaataatg ggaaattgat    43080
gttcttaagt aacatagtca ccaagataat gcaactagat gagtcacccc tttttcaattt   43140 taggatattt ttatcaagat ttaagtggtc atcattagaa ttatagcagt ttctcctttg    43200
gattgttcta gaggcccagt gagaaagtat tccctaattt ctcaggagaa cagttgtggg    43260
tagtgtgctg tcatgtccag ttaaattgca gacgtttccg gttgaagata ttccagtcct    43320
gagaactttg tgacattagc aggactttta caagccatct cttagggtgg ggcattactg    43380
tagttggctg gtactctttt ctccttaact ttgtcatttg ttgattttt ttttttaact     43440 gtccccaaac actgtgggca gacagtatct agaattgagg cctccacccc tgcagagagg    43500
acgtggatgc tgagcagtcc ccgagtgaag attataaaga agcaaataga gtacacgtgt    43560
ctgtgaactg ttcttgagtc tcccaaattc ggggtacttc tgttcagcta taggaaaagc    43620
ctcaaactgt ttatactttg caagaattgg aaacttctaa ttcaagttaa gttttacgga    43680
atgcatggta agcttcatag gagcttcatc ttttatctgc ttggactttt gcttctatag    43740
gttttgttaa aggccttcat agcgaacctg aagtcaagct cccccactat tcggcggaca    43800
gctgctggat cagcagtgag catctgccag cactcaagaa ggacacagta tttctatagc    43860
tggctactaa atgtgctctt aggtaaggtg gaggcataca ggtggaaggg tctccagcat    43920
gtattcatga tagacctttg aaataattaa aatcagatga tccctcagct tctagaccag    43980
gctatttggc actggttgac tgaatgtgaa ctgcattggg actgctgtga gcacgcatgg    44040
gtctctgtga ccctgcagat gcagccatgc ccagggacac ctagctgggc agtgggtgtg    44100
ggctggtgtg agccctgcct gccacccagg gcctggtcct ccgtctgtgc cggccctgac    44160
tacggtgagt ctgtgaggct tgagactgtg ccttgggtcc ctgtgggttc tctgtaggtc    44220
agttgacagt ttctcctgtt gtttgggtaa ctgtggaaat gaacactggc aagtgctgaa    44280
gtgagcactg gacgcgtgat atggaccctg ccaagccagg gatatgggtg tgtagccact    44340
cccagtgggc ctcatggtgt actcgttcac ggtcatgttt tgtgccatatt gatctcttgg   44400 gatctcttct ttttaacaa attaagcggg gaatctccaa acagtgagtt ggatgttaag     44460
atatcttgct gctgccccca caggcttact ggttcctgtc gaggaggagc actccaccct    44520
gctgattctt ggcgtgctgc tcaccctgag gtatttggtg cccttgctgc agcagcaggt    44580
caaggataca agcctgaaag gcagcttcgg agtgacacgg aaagaaatgg aggtctctcc    44640
ttctgcagag cagcttgtcc aggtaggagc acagggttta ctctaggcct ggcatgtgaa    44700
caactgacat ttgaagaact gattactttg gaagagaagc ggcagaaccg agggttagag    44760
gtgtggactc tggagctgtg ctgctcggtt ccgaccctag gtgctgacct ctagctgcct    44820
tccttctgta tgccattgtc accgtgagtc agatgcaggt gatgcctctt caggtgccac    44880 tctgttttcta aaaccagagg tcacgatatg tgttcataca cccagtaaat actgattgag    44940
cacccactgt gtgctcgggt ctggggtagg tgctgggggt cctgtggtga atatttccgc    45000
tgcagcctct gccctgtgga gcctgtggcc tggtgcactg gtcgaggcag ggtggtatgc    45060
cccctcaggg aggtggggac gtggtccttc ggggtgtcag aacaaaatgt tggaacttct    45120 cttttccaatg cagagaaacc ctgcagtaat tctaatgtac tgtgattggc agttgacttc    45180
```

```
agttctttgt agcgtgctta ctcaggttat tttcactaac tgtgtaacag tgcagcctca   45240
ttttaagcaa ttgaattttt tgaactttac ttaaaatatt aggtcagggt ttttattgtg   45300
cttaacatgt gccatttagc taaattttgt aggatataaa attgtaagtg acttaaaatg   45360
attcttgcat agaatcatga attgaagata atgctaataa tttaagcact gagttaggta   45420
gtgtttgtga agtgcttaga atgcttcctg gcacatgtga aggccatgta agtgctgctt   45480
attgataaac agctgagcaa gagtgaactc taagaaatga atggggctga gagttctatt   45540
ccacccagct gcccttttggt tattttacag aataaaagca gagtctcatg ggatatgaca   45600
tttaattata tttccttcac aaaaaacact gctgaatatt ttgtggagta aaaagggtgt   45660
agccatggca ataatacatt taaaatatag tttatttcat ctttaccttta cctgtttttt   45720 tttttaagc tagctttata ttgagaattg catacatgca aaagtatcaa gtcatgacca   45780
gttacatttc atttataatc ctacttctcc ctttttttt ttattatttg gaagcaaacc   45840
acaatcatcc tcttacttca tctataggta tttcagtatc tctatagatg aggactcttt   45900
tttattttta aaacttaatg atggtcaggc gcagtggctc atgcctgtag tcccagaact   45960
ttgggaggcc aaggcgggca gatcacttga gcctaggagt ttgagaccaa cctgggaaac   46020
atggtgaaac cccatgtctt taaaaaaaaa aaacaaagtc agccaagtgt ggtgatgcat   46080
gcctgtagtc ccagctactt gggaggctga gatgggagga tcacatgagc ctggaaggtc   46140
gaggctgcag taagccatga ttgtaccact gcactccagc ctggttgatg gagcaagatt   46200
ctgtctcaag aaaacaaaac gaaactccaa acaatgtcta caaaacagtg ccattgttag   46260
acctgaaaat attaaacatt tcctacatca aatacccact aactcattgt caattttct    46320 ctctactctt ttggaatcag catataaata aaattggttg ataaggattg taaatctctt   46380
tgatcaactg gttctcctcc atccgaattt ttttttccct ttagagttca tttattgaga   46440
aaccagatta tttgtcttct aagttttcct gtggtctgat atactgctta catctccatt   46500
gtgtaaatta cacctttttt ctgttctctg tatttcctgt acatcaataa ttggaggaaa   46560
aacctggtca gatttagtgt atattttata tctgagttca gtatttcgta tataatattt   46620
taaggtaaga gtatactctt ttaaaaagtg ttgagactat atgctcaatt ttttttaaca   46680
gatgcttttg aaaaggctgc ttgatcataa aagtttagag accattggtc tgttgggaga   46740
agcaaataat tacgaaacag tttagcaagg ttaaggtgca catggtaggg cctggagagg   46800
ttcagtcgtg agccgtcact gatgggcacg tggaatctga cccggcacag agagctggga   46860
gaagacagga gctttataga cagaaaacgt ggtctttgcc aagtcccggg agtgaaagag   46920
tgagagaatg ctcacagcac atgagtgtgg gtgcgtagac agagcaacgg tgggtcctga   46980
aaaggcctcc aggctttctc atagattagc aagagtgttg gttatggagg tcagaaggag   47040
gtcgaaactg tgttaaattg ggattgcagt aatcctggaa ggacagagat agagggtgaa   47100
ggggaaaaaa gggtatggat gtgagactta attgctgatt tcttaatac ctttctccaa    47160 agtaaataaa tgatatggca cattttttgaa ctagcaaact ctagatatga ttatctgtat   47220
aacatatctt actccatctt cttttgacta ataactgttc ttaattaaat tactgtgaga   47280
tgttcaattc agcaaatgta gtttggctaa ctatatttaa ttgaatttta atataatcct   47340
aggcctggcc aaactattaa gcaagtgtgg gcaaaatatt gataattta gatatgcagg    47400 agctcagttt ctttctatgt gtgcttttttg aaaagaaag aaattgaaaa atagaggaag   47460
ccctgaaatc caagaaacaa agtctctcat ctaggcatgc aataaaagca attctaggat   47520
gattgttgtt cggcatgtag tttgttagaa aacattcttc ttgaataaat agtatgccta   47580
```

```
agaaagtggg cagagggaag gcatatgcat atattattaa caaggaggga gaaaaaggca  47640
attagtaacc atccatagga gagccagcaa gatttataaa ggaaatttgt gatccaagta  47700
tgaagcaaaa taagatgcat aataaatttt aagcaagtaa tagattacag taagagaacc  47760
catttgacca ttaattttgg ggcattttct ttcaaatgac atggagtagt aatgaaatat  47820
ttctttcttt ctgagtctag gttattgtga ctggactcag aaagaaagat ttcattattg  47880
cagtgaataa cattttgaa cattattcat aaattatgca gtgaataaca tttatgaaca  47940
catgatacat aagatacata ctgtttattt ttaattaagt ttttcagctc aacttctcgg  48000
cagggaacat taaatgtaaa tagtgttacc tagtagcatg taaatggaaa tctccatagt  48060
atgaaagcag tgctgttgct aacagaattt aggaggcgac agatgaggtg aaggaaatgt  48120
gggtgccgat ttccttatta cattgagagg agccaggaga ttctttgttc aaaatagatg  48180
gcttaagaag tcaaggtata agctgattac ctagagcagg tacccacaaa tgttttgtgt  48240
aaggggccag atagtaaata ttttcagtct tgcaggccat tccaagtctg tggcaactag  48300
gccccactac cttcgtagca cgaaagcagc cacaggcagc ccataaacgt ggctgtgttc  48360
cagtgaaact ttatgtacaa aagcaggtgc gggccagacc tgacctgtgt actgtggttt  48420
gatgacctgg gattcagggg tataggagtt accatcagag gagctgaaag tgagacttt  48480 tactttatac tcttctacac tgtctgattt ttaaaaaag aaacatatgt attttataat  48540
attgaagatg gggttggcaa atagcaaata aaaatacagg atgccagtga aatttgaact  48600
tcagataaat tatgagtaat tttatgatgt aagtatattc caaatcctgt gggacataca  48660
ctacaaaatt atttgttgtt tctttacaat ttaaatttaa ctgggtgccc ttgtctttta  48720
tctggcaact ctaattaaag ggaaaaagaa taaattcatt atgttcatat aatgtgatac  48780 agcagggtc cccagccccc acgctgcgga gcggtattgg tccatggcct gttaggaact  48840
aggctgccca gcaggaggtg agcagcaggt gagctggcat tcccacctga gctccgcctc  48900
ctgtcagatc agtggcagca tttgattctc atagtgcaaa ccctattgtg aacagcacat  48960
gtaagggatc tagattgtgt gctccttatg agagtctact gcctgatgat ctgaggtaga  49020
acagtctcat cttgaaacca tccctggcc ctgtggaaaa attgtctccc atgaaaccag  49080
tctctggtgc cagaaaggtt ggggagcact gtgatatagt attgaaagtg ctgataaatg  49140
tggctactgc ctttaaaatg tctggtagct cttttctcagt ggcactcata atagtgtttt  49200 ttgatttta aatgtgtgtc aagctaactc tcccctcagt gtatgctgga ctttatttc  49260 cctttcctag tcaccagttt tgggaaatag agatcttcat tctcatgctg cttctctagt  49320
ggaagtgctc catttattt taaggaatga atataacaat gaaaaaatca tgggaattca  49380
gaaaacaaca tggaaggtaa cgatcacatt ggtagaagtg atagggaaat atttagggg  49440 agaaattaag gtgtaaactt tgccaacgaa gtcctgttaa aaaaaaaaa gtgaagctta  49500 ggatgcattt tataaactct gaccagaaca cctgtgtttc tctgtttcta ggtttatgaa  49560
ctgacgttac atcatacaca gcaccaagac cacaatgttg tgaccggagc cctggagctg  49620
ttgcagcagc tcttcagaac gcctccccc gagcttctgc aagccctgac cacagtgggg  49680
ggcattgggc agctcaccgc cgctaaggag gagtctggtg gccgaagccg tagtgggagt  49740
attgtggaac ttataggcaa gttattagta aggtctactc ttacagttaa cttttcagtg  49800
atactagtta ccctctattg atgatgggcc tgccctgtgc taagcagtct gcattgcatc  49860
ttccttgcca aaacttataa tacagatttc atctttattt tataaatagg ggagtttggc  49920
```

```
tgggtgtggt ggctcaggcc tgaaatttca gcactttgga aggatcactt cagcccagga    49980
gtttgagaca gcctggccaa gtgagaccct gtctctccaa aaaaaaaaaa aaaaacaaaa    50040
actgggcatg gcggcacgtg cctgtagtcc cagctgcttt ggaggctgag gtggtaggat    50100
tgcttaagcc caaaaggttg aggctgcagt gagttgtgat ggcagctgca ctgcagcctg    50160
gtgaccgagc aagatgctgt ctcaacaaaa tttaaaaatc aaagaagaga attaaagttt    50220
agaaggttag gtggcaaaat gaggccacac atttaaagcc cctcctcctg attctttctc    50280
taccttgact gcctcctgtg gtggttcagt tgctgagaaa tgaaaacagt agggaaggcc    50340
gggtgcggtg gctcaagcct gtaatcccag cactttggga ggccgagacg ggcggatcac    50400
gaggtcagga gatcgagacc atcctggcta acaccgtgaa accccgtctc tactaaaaaa    50460
tacaaaaaac tagccgggcg ccgtggcggg cgcctgtagt cccagctact cgggaggctg    50520
aggcaggaga atggcgtaaa cctgggaggc ggagcttgca gtgagctgag atccggccac    50580
tgcactccag ccggggcaac agagcgagac tccgtctcaa aaaataaaa acaaaacaaa    50640
acaaaaaaaa aaaaaaaaag aaaatccatc tgtcccagc tctgcatctg cctccactgc    50700
ccagtctgct cctctccatg cgcttggggc tgggccctgt cccaccatgc agtgctgccc    50760
tggagcagtg agcttagtgg gtcctttctg gcatgagagc tgcctttggg agctggagtg    50820
ggtgggaatc tctgaatccc agcctctacc gctgggtctg gtgcctagca ggctatggat    50880
aagcttttgc tgactctagc ctcccctagg ccactgcagc gtggtcggtg tagtgcactg    50940
cgtgtgcagc atggccttta ctcacagcct ccacattaga gagaatctga ctgaagtctc    51000
gttgctgcct cgtgtgagca taaatgtttg ccggaaccat gagcaggaaa tattaatctg    51060
ccttgttcc tgtcctttac actgaagaat ctttttctgt atgggatgca tgccttacaa    51120
ataatgagtg gaaatactca tcgctaatga aaagttatac ctgattgtta gtctaccaaa    51180
taatctgaga tttctaatac ttttaatttg gcttttaaaa tgcaatttat cttagctttt    51240
ttgacttctt aggtcatatc tttagaacta tgtatttgaa tgttaatgta attttcatat    51300
tgaaattaaa atgttgaact gtgatgttaa gtgcttcctg tggaaataca ttcacatttg    51360
attcaacttt gaatcaagct gttttgaagat tttcacattt cttctagatt ttatcagctt    51420
gttactttat ctgtcacttt ctgtgattta cagctggagg gggttcctca tgcagccctg    51480
tccttttcaag aaaacaaaaa ggtgattatt tcagaaatca gagtcttgtg ttgaatctta    51540
ctgatttcct tgtatttctg taatgtaatg tatcttgtat ttcttgtaat actgtattgg    51600
actctgtgta tgtatatatc ttctcagtgg agtgattgta tgtgtgaatg ttgctggaat    51660
ctgataacaa ggcctgaata gttttatagg gtggcttta acagttactt tcatatcaga    51720
attgctttgt catacatttt gaatgcatca taaatttcta atgttcgggg tcagcagact    51780
ttttctgtaa agggacagag tgcaaacatc ttagctttat gagccatatg gtctcttttg    51840
caaccattca gctctgccct gtggcaggaa tgcagttgca gacaatacac gagctactgg    51900
ccagccatgt tccagtagaa ctttacttac aggaacaggc aggctgtagt ttgcccatac    51960
ctgccttagg gaatgtgttg ttatatttta tgaagttaac ttaccttccc agtgaatttt    52020
gtttagcatt agtcaggaat attattaagt agcttctttt ccagcctggg caatgtcatg    52080
agacccggtc tctaccaaaa caagaccaaa caaaaaaaca gccaggcatg gtggcatgtg    52140
cctgtagcct cagctgctgt tctggaggct gaggcaagag gattgtttga gcccaggagt    52200
ttgaggtcac agtgagctgt gatcatgcca ctgcactcca gcctgggcaa cagaatgaga    52260
cctcgtgtcg ttaaaaaaaa caacaaaaaa agtttccttt gttggactgt tttaatttgg    52320
```

```
acctggttat cattttttcag ccatatctaa ctttgtacat atcagaatgt tctgataaag    52380
cttaactttt attaaagtgt ttctgatagt tttggtacac attatcattt gcaatgccag    52440
ttattttctt ttccagtggg gatttgcata ggaaaaaaat tgctgtcact ttctattttg    52500
aaatcttaaa agactgatcc tttttttgtgt catgatttga gtgtttaatt gagagcctaa   52560
tgcctaatat tatttgcagt attgaatggg atcttaacag gaataacatt ctagccttca    52620
ttgaattaag taaacatttc ttgaaagaac ttggaatcta taatatttgg gtcatcacag    52680
tatgagatac ttaatcaaat ttgagatttt agtgaaacat tgttgaaaag ccaaaaagat    52740
tctaggaaaa attcatctct atattcttga attaggagag attttcggac ctgtgactaa    52800
gttactctga cacttgtttg tttcttagtc actcttccca gtggcagtga aaagaagat     52860
gactggttca cattgttgag attagtttat cctcttctgg ctaggacatg ggatatatcc    52920
tgtctctttt aagccctttt ggtattttt ccccatta gagctgtgtc ttcaaactgt       52980
tttgttatag ctggaaaatc ctttttttaa gtgaaatctg cccaaattat aagacagatg    53040
aaagtagagt tgtgttggat ataggattag ggtgcaagtg gcgggggtgt cctggagcct    53100
ctcttctgag ggcagcctag cgcttgtgcc tttgaggaaa ttaccctggg gatggtctat    53160
ggaacatatt tgcaaaccac tgatttgaaa gatagagatg gcttttgtta agatctgaat   53220
tcaccttttt ggcattttat ttgatttctc aagggaaaga acttatttg taataaagtt    53280
tcctttatt tagtagatag gccaagttgc tgtgttaatt taacctagag tttgggtttc    53340
ctttgctaat ttttttcacc tttaatgtca catcattgta aatttgtgga agttatactt   53400
ctgacttatt ctttgaagag cagaaattag aaatttccaa taattatttt gatagtgtca   53460
tttaatgaca ttaatatgta atgtagccac aaagatttaa tgagttcagt taagtcatat   53520
taagactgtt ggttttcattt gttttcatta atgtaattct gaagatgaac aataaaatgt   53580
attttttagaa ctttcaagtg aaatattatt tcatccttcc agatcatata atgcttgagt  53640
tctgattgtt aatcataaag tcaagaaaat taaagataa taaaatgaaa gtgacttta   53700
ggtgttagag tttatgtac aaattctggt gtgtcattgg agctatcaca tgaatatttc   53760
aaaggccaat agcattgggt ctttacagtt aaaacttact attttttaagt ttaagtagta 53820
ctatagatta tttaataatc gaaatcaata aatattaatt attaaaatgt tttgtggtat   53880
actttgagaa tcattgcttt taacttttttc catataggtt tattaactttt aatagcattc 53940
taaacataac atctctacat tctttgtgtt taatactgta gaggtataaa aatacttata   54000
tatgatgata aaccatatta gagtaaatta aatattctta tgagtttcat tttagagtgc   54060
atttacttaa ttttgaaatc cttattttta gcaaactaaa ggaatgttgg tacattattt   54120
actaggcaaa gtgctcttag gagaagaaga agccttggag gatgactctg aatcgagatc   54180
ggatgtcagc agctctgcct ttgcaggtag ttctcactag ttagccactg atgtggacct    54240
tcactctctg ccgtccaccc catgcccttc ctgcctgtcc ccctgcacct ggtggacagc    54300
acaactgggg gcagcagtgg acccaggttg cttaaatggg ggatatttgg gcttctttca   54360
taatacttac tctgaagctt gtgtgtctgt ggtgtttgca tcatatattt gctgttttct    54420
gtggtttaga ctgtttaaa attaggttta tgctccttga gcatagggct ttgtgagtag    54480
ggatggcacg ttgaaacgtc tcatgagttg gatgggttat gctgggggtt ggaaatggga   54540
tgaaaaattg tgggatgaaa aattgcctat ggatagttta acttgaaaga atctgccttt    54600
gtttacagat agttatcttt tttttttttt tttgagataa agagtctcac tctgtcaccc   54660
```

```
agtgccgata cccaatgtca ctggcatgga gtggtgtgct cttggcgcac tgcagcctcc    54720
gccttctggg ttccagccgt tctcctacct cagcctccca agtagctggg actacaggtg    54780
cccgtcacca cggctggcta agttttgtat tttttgtaga gacgaggttt taccatgttg    54840
accaggctgg tcttgaagtc ctgacttcaa gtgatccgcc tgtctcagcc tcccacagtg    54900
ctgggattac aggcgtgagc cactgtgcct ggccagttac agacagttat ctaatgaaat    54960
tctctgtgta ctttataaaa gataaggatt aacttaaggt actaataact ggattatatg    55020
agggtggttt tggttgtata atcctatcta aaagaatatt ttagctgtaa ctgaaagtaa    55080
gacttaaata tttagggagg aaaatctgaa taattctagt agtaattatt tacaaaataa    55140
aaatagattt tattttttgat tacacaaatt aaacaacaat aaaacatcac agcgatctag    55200
actagtataa aggtcacacg cttaccaacc caaccgcccc aggagtgacc actgccaaca    55260
gcttcgtgtt gacctttttg ccatgatttc tatatagtct tttttgtttt taaatggtaa    55320 ttaaaaagt caactaggaa aatgtgttag aagtttatct tccaggagaa taataggact    55380
ggagtcgaga tcttgaacgt ggcttggaag aaggcaagcc cacccagag agattacagt    55440 tgttcgggac cactgcttgc ttagaggacc tgcgtgtctg ggaccgccta gttttgtgcc    55500
cctgactagg ctgcccctta attacgaacg tctttataaa ttgccctagc cagggcttgg    55560
agtagttggt taagaacttg aacttcagtt tttgcagtga aacaccgttt gagaatatta    55620
ccttctgata agccttattt tattaagatg ggtactgtag cgagaggcag tgtgagtggt    55680
acatgaggga tgcactgctg tcctgcattt cactgtcttc aggatgctat gcagtgatga    55740
catttggaaa catttcatca aacattccat caaatgaaa cattggatga cagtggaact    55800
ttgtgttatt ttgcaagcct ttgattccat attgaatgtt ttctctcgcc atttgacaaa    55860
tgagtgtttc tctgtcttca gcctcagtga aggatgatat cagtggagag ctggctactt    55920
cttcaggggt ttccactcca gggtcagcag gtcacgacat catcacggag cagccacggt    55980
cacagcacac gctgcaggcg gactcagtgg atctggccag ctgtgacttg acaagctctg    56040
ccacggatgg ggatgaggag gatatcttga gccacagctc cagccaggtc agcgccgtcc    56100
catctgaccc tgccatggac ctgaatgatg ggacccaggc ctcctcgccc atcagcgaca    56160
gctcccagac caccaccgaa gggcctgatt cagctgtcac cccttcagac agttctgaaa    56220
ttgtaagtgt gcggaggggc ctgccatctt ttattttta tttgagacag agtctcactc    56280
tatagtgcag tggaggccgg gcacagtggc tcacgcctgt aatcctagca ctttgggagg    56340
ccgaggtggg cagatcnnnn nnnnnnnnn nnnnnnnnn nnnnnnnnn nnnnnnnnn    56400 nnnnnnnnnn nnnnnnnnnn nnnnnnnnnn nnnnnnnnnn nnnnnnnnnn nnnnnnnnnn    56460
nnnnnnnnnn nnnnnnnnnn nnnnnnnnnn nnnnnnnnnn nnnnnnnnnn nnnnnnnnnn    56520
nnnnnnnnnn nnnnnnnnnn nnnnnnnnnn nnnnnnnnnn nnnnnnnnnn nnnnnnnnnn    56580
nnnnnnnnnn nnnnnnnnnn nnccacccat cttggcctcc taaagtattg ggattatatt    56640
tgtgagctac catgcccaac cctactgtct gccatctttt gagctcttcc ctggagaccc    56700
agacctgaac cctcctgctt gttctcttct tgtctaatac ccctaatgac agcgcagctt    56760
agatcactag tggagagctt gacctcatct gataccttca ctgaagggaa cagcttagtg    56820
tcttttccac tgaacactga ggtaaaaaat tggaatagtt gattatgtga actctgctaa    56880
aattgagtgc attttacatt ttttaaggcc ttttaggcc ctggttaaat aattattttt    56940
aaaaatcctg aaggagccta ttataaacag atctgtggtc ttaatgaaat gtgattaata    57000
ctgtgcatta ttttaagaac ttttgacttt tcaaaaaact tttacaacat ttcccatttt    57060
```

```
atagcagcat aggtgtaagt acctctcatc cctgagttag tggacaagaa accctcatgg    57120
atagtctaat aacgtttggt acaagtctat gttgttttat actccatttt attttcagtt    57180
ttaaaaactg gttaaatatg tgtaacataa aatctaccett cttaaccatt ttttacgtat    57240
gcagcttgct ggaataaata attaaataat gtcatggaat catcgctcca cccatctgtg    57300
taaccttttg atcatgtgac actgaagctc tgttcccatt gaactctcta ttcctccttc    57360
cccgccaagt ccctggcaac caccattctt ctttctgtct tctgaatttg actactttag    57420
gttctcatat actttagggt cacaccgtat ttgttttagt tagcataacg tccgcaaagc    57480
tcatgcatat tgtagcctgt gttgaacttc ctaatgtttc aggccaaatg ctattccatt    57540
gtatggatag gccacatttt gcttttccat ttctctgtcc atggacactt gtattgcttt    57600
catgctttag ctattgtgaa tcgtgctgtt atgaacatgc gtgtacaaat gtctcctgga    57660
gactctgctt tccattttt tggctaaata cccagaattg gagttgcttt tacattctga    57720
ttttaattta aaacatttat atcattgagt gttttactta atagtataat agttagcaaa    57780
ctaatatttt ggtaataatt tgctggtagt tttagagtcc attgctcagt tttttttaggt    57840
aaattacaca ggacatttca gtggacgtg gaacaacttg tgatatggaa tcatgcccca    57900
agctgatggc taaacatacg aaataccatg ccctaaattt agtagattta gtctttgcaa    57960
tttaggagat aacctgttat attgttaggt ttttgtctaa aagctttgtc ctcatatttc    58020
caacttgctg taaaatttgt tcgtgaagac aaatattttt gtatgggttt tttctttttt    58080
atattaaaaa gaaatgtcca cattggaatt ttttttggagt ttttagagct aatagagctt    58140
ttcataatgt agtgggaatg agtgatcagt aagctcttag cagtttccat gcacacattt    58200
ctgtgcattg aaataaatga cagatgagta catttgtgtt ctgtgtgtaa aacgtgctct    58260
ttcttcgttg catttccatg ttggagggct tgtctcttgg tgatcacact tcaaaattct    58320
cacagccccc cttgaaccgt ttaggtgtta gacggtaccg acaaccagta tttgggcctg    58380
cagattggac agccccagga tgaagatgag gaagccacag gtgttcttcc tgacaaagcc    58440
tcggaggcct tcaggaactc ttccatgggt atgtggacca caggtgacgc gctacaaagt    58500
ggtcttgtat tcaggcctgg acatcttaat tatatctttg ctctcaagaa gaaatccttt    58560
gatattgttt tctgagttct gaatagctga tgaaaatgac caattgagga ataatcatac    58620
tttttcttca tctaaatctt acgcttttga gttatcttag cataaatgta taattgtatt    58680
ttaagtggaa atttgtcact taatcttgat ttctctgttt ttaaagccct tcaacaagca    58740
catttattga aaaacatgag tcacagcagg cagccttctg acagcagtgt tgataaattt    58800
gtgttgagag atgaagctac tgaaccgggt gatcaagaaa acaaggtgag ggacataggc    58860
ttgagacaac ttggtgtttc tgagcttgtg tgaggattta aaatcgccct ggctactatc    58920
tactttattg ctttcccatc cctgggcctt taaatttccc cttaaatac cagctcttcc    58980
caggcctgtt gttttccgcc tttcaggtgc tactgacagc gttaagaatt gcctgagttc    59040
tgcctccttt gagagtgtgc cccagagaaa tctattctgt actgagtgtt tccttgtctg    59100
atttcttggg ccattcattt gatggctgcg tatggccttg caccatgttt tggttctatt    59160
gaactgtttt aaaagtctct gtttatatta ccttttttaca tgtaaatgta actgtcttca    59220
cttttaattg ctcaagggca aggaatagcg tttcacagtt tctcccagca atcagaatta    59280
cagcctttgg catctccctg tctaccaggc ccagttcgtc ttagctttgg gcttcccag    59340
gctgttacct ttccctgagt agcttctgct tgtcctgtag aagaccactc atgctttgct    59400
```

```
tccagagcag cctttctga atgcctggtg tcaggtgcct tcttactgtg cccaccctcc   59460
ctgcatgctg catttatccc ctgccacagc cctgggaccc tgtgtccagc tgcctctgac   59520
ttgtctgttt ctgcttggtc atggtctctg tgaggtcagg tgtgcatatg agcacagacc   59580
agggcatctc tttatcccca gcacccagtg taagtgctac tctaggacta tttgttgaat   59640
gaactaatgc atgaatgtat tggttgagta tgagacaaac aagtgtcact gtctcctttc   59700
tagccttgcc gcatcaaagg tgacatcgga cagtccactg atgatgattc tgcacctctt   59760
gtccattgtg tccgcctttt atctgcttcg tttttgctaa cagggggaaa aaatggtgag   59820
tacaaaaggg gacgtgcaga gttgaaggaa ataactaggt ttcagaggtc aacttggtgc   59880
ccgtttagta ctgtgtgtag cagaggcagt agaatctgag gatgagtttg ttttcacta   59940
gccaagggga agggaggaaa tgatgggagc aggtaggtta ctgggtctgg ttttgttcat   60000
ttgaaaacaa tctgttgttt gaggctgaag gtggcttggg tgatttcttt gcagtgctgg   60060
ttccggaccg ggatgtgagg gtcagcgtga aggccctggc cctcagctgt gtgggagcag   60120
ctgtggctct ccacccagaa tctttcttca gcaaactcta taaagttcct cttgacacca   60180
cagaataccc tggtatgtta aaagttcaca tcttattttc tcagatttaa tcattattgt   60240
aaaaacgatt tcagtattga ctattttagt tttagagcgg tgttttgagt ttatttggga   60300
ttttttttt ttttgagac ggagtctcac gctgttgccc aggctggagt gcagtggcgc   60360
gatctcggct cactgcaagc tccgcctcct gggttcacgc cattctcctg cctcagcctc   60420
ctgagtagct aggactacag gcgcccgcca ctgcgcccgg ctaattttt gtattttag   60480
tagagatggg gtttcactgt ggtctcgatc tcctgacctt gtgatccgcc cgccttggcc   60540
tcccaaagtg ctgggattac aggcttgagc caccgcaccc ggcctatttg ggatatttga   60600
cccgcgttgt agctcttcag aaaacacatg aatagtgaag ttctttgttt catggtttct   60660
ctttagatga aatccgtaga ggaaaaaaat agaaacctca gcacgtaaga gccaacttat   60720
atacgcatcg gatttaaacc taaagcacaa attgtgcatg gtcacggtgg cgctgagtca   60780
cactcagcca ggccaggcat tcacactcag ggtgagtggg caccaggact ggctgaggca   60840
gcagtggacc cgtgtctgca ccctgcccat gcttattgtg gagccttctc gctcgctctc   60900
tttctttggg tgagagggta cacttgtgtt tttgaattta tatgaggtaa gggtttatat   60960
atagggtttt ttctaatctt tttttaagtg gaatctggaa ttttaatcag atttactatc   61020
tgacagccta gaattataat ccagaaagtc tgtggtattg aggacatatt ggcaatatga   61080
tgaatctgta atcctaaat cctgaaactt tttttttttt ttaatcactt agggttatta   61140
tagtgaagtc atttctgaat ttggatcttc tcttcatacc tcttttctc tttcctgaga   61200
attaagcttt tgttttgagt tagaaagttg atagtaggaa attgttccat ggctgggcaa   61260
tttatctcca cagaggaaca atatgtctca gatatcttga actacatcga tcatggagac   61320
ccacaggttc gaggagccac tgccattctc tgtgggaccc tcatctgctc catcctcagc   61380
aggtcccgct tccacgtggg agattggatg gcgccatta gaaccctgac aggtagtggc   61440
cagttttca gctgtgtttt ttctagatat ccttactaag gtttccgttt ccatgacgat   61500
gtttgtttct gttcttctgt caggaaacac attttctttg gcggattgca ttcctttgct   61560
gcggaaaaca ctgaaggacg agtcttctgt cacttgcaag ctggcctgta cagctgtgag   61620
ggtgagcgcg atctctgtgg agccattgct tcacttagtg ggcatttat cattgctgca   61680
attacaattg gagcttaata ggaaatattt ccatacactc taaagctgta accagtaata   61740
tccaccatgt atccatctct tagctttaga aagaaaacat tgccagtaaa gttaatgctt   61800
```

```
cataaacttc agtttaagtt ttaattctca gaatatttgt ttgaaataga cttcttccta    61860
aaggatatat ttagaaataa cctatcatta catgtaaagt ctgttgaata tgctgggcac    61920
ggtgactcat gcctgtaaac tgagcacttt gggaggccaa ggtggaagga ttgcttgagc    61980
ccaggagttc aagactatgg gcaacatggt tgatcctgtc tctacagaaa attaaaaaga    62040
aaaaaaaaaa ttaactgggc gtggtggtgc atacctgtag tctcagctac tcgggaggct    62100
gaggtggggg gattacttga gccccggaga tgaaggctgc agtgaggcat ggctgcatca    62160
ctgccctcta gcctgggcaa cagagtgaga ctgtctcaaa ataatagta ataataatcc     62220 gttgaattaa aaaaaacccc aaaaaccact gtgttaggcc catggtgtag taagagttaa    62280
agtgagcctt agggattatt tactcaacct ctgtgtttgt atgaagtgga atggccccag    62340
ttctttaagt gatagcatgt tgaacctttc cataccagct ggctcgtaag tcacaactgg    62400
ccagtcaaca agagtcaaaa ttaactagta aaaatcaaag caaaaaactt agaattgtcg    62460
aatttgtgcg atacctcccc cttttaaaat gtcatgcctg acagtaattt ttccctagtt    62520
tccaggtttt gtttcagtca attgtgtctg tcttgagcag aaggaagcgt gctaacagct    62580
cagtctcatg gctagctggg ggtctatgtg tcagccatgc atgtgatggt gcccctgggt    62640
gcctgaggct gcaggggagg ggtacagcag taggggcctg ttctgttctc ccgtgccttg    62700
gagtacatag tgatatagtg gggtggtcct tggtgtaggt ccctcgttcc taccctgggt    62760
ctgcgattta tttagaagtg gtgttggagc tgtgcggcag gccccttgt aactgatcaa     62820 tgtttgtgaa gttgccgttt gagaattgaa accatgacat aagcagaaat ggaagaaaag    62880
aaccagttat ttgaaaggga cacattcact tttaagcttg tatttactga gataaaatat    62940
ataccatcag tgttcttgag aggtgtggga aaagtgcaac atcctggttg cagttaaacc    63000
cagaacgttg tgtgttgaag actgacagtt ctcaaaccgt caagacgcgg gtactgagtg    63060
ggactaacct gctgccctct tgcctcggac cttgtgttcc agcattgtgt catgagtctc    63120
tgcagcagca gctacagtga gttaggactg cagctgatca tcgatgtgct gactctgagg    63180
aacagttcct attggctggt gaggacagag cttctggaaa cccttgcgga gattgacttc    63240
aggtaagtga gtcacgtcca ttagatttca tgaactaagc tcaattgaaa gtcctggggt    63300
cacttggtat aaggaatgat gttatcaagt accctgccca tcagaaatct gagcggttta    63360
ggtagatgac agtgattttc tcccccagt ggcttttgc tgaacctcgc cctatgcgtg      63420
gattttattt tattttatta tttatttaga gacatgatct tgctctgttg cccaggcttg    63480
gatgcagtag cacagtcata gctcactgta gctttgaact ccaggactcg agtggtcctc    63540
ctgcctcaga ctcccggtta gctaggacaa taggtgtgtg ccatcacact ggctaatatt    63600 ttatttttg tagaaatggg gtcttgctct gttgcccagg ctagtctcat ctcctgagct      63660
caattgatcc tccaatcatg gcctcccaaa gtgctgggat tacaggcatg agccactgtg    63720
cctggcctag aattttaaaa gataaataga agagtagttt ttttttttt tttgatagt      63780 cctagtcatt taagtgttct ggatagtagg aataaaagag cttagaattt ttcatctttg    63840
tcttaaactt tttaaaaaat gtagcttatg ttaattctgc ttgttttaaa agaatatact    63900
catcattata ctgaacctag gtaagacagc tggtttatat tttgttgcaa ttaaaaaatg    63960
tgagctgtgg ttgcagtgag ccaagatcgt ggccattgca cttcagcctg cgacagagc     64020 gagactccgt ctcaaaaaaa aaacaaacca aaaaacgtga gctgtgttgg aactttcatt    64080
ttctaagagt aaagttttgg caggagaagt tttctgtcag tactttatt tagaagggaa      64140
```

```
attttttataa ttcaggtgtt ttgttttttgt tttgttttt cccccccaagc cacctttat     64200
agagcccttg tgggttattt tatttaatcc ttagaatgtt tataaatctg ggactgttct     64260
cggctccacc cacagatagg ggcgctgagc atgcgtgagt gggcagcaag atagcaggtt     64320
atggagggcc cagctcgccc cttctgtggt ttgagccagt tctgtacggg acttacagag     64380
tgttttgaaa tagtatttat tttgaagaaa aagaaaaaca gtttactgag tgctatctta     64440
ttgagtctgg agttgtgaga ggaatgccac ccctatttgt ttgaagccat cggccttttc     64500
tgttgtcttg agtaagtgct gcccaagggc cttccagggc gcctgactga gcctgctctg     64560
aagcaagctg gcggaaagtg tttactgagt aactaaatga tttcattgtt aaatgtgctc     64620
ttttgttagg ctggtgagct ttttggaggc aaaagcagaa aacttacaca gaggggctca     64680
tcattataca ggggtaagcg gcttattttt gtgagatact gttttacctt aaggaggtga     64740
aagtgaggct ttccttgtgg aatttctcta aatgcattca tcgtatttta gatctgttta     64800
tttcacagtt tatatcatga aagttataat tgtgtcacat ggatttaagt ctagcaatgt     64860
tgagttcttt ctcactagct ttccaaaata tcttacctaa aatttagtca aatacaagat     64920
tatgtttatt tttattatcc ttctctctaa agcttttaaa gctgcaagaa cgagtgctca     64980
ataatgttgt catccatttg cttggggatg aagaccccag ggtgcgacat gttgctgcag     65040
catcattaat taggtatttta ccagtatttt atctctttta cttttttggt tgaagtacta     65100
aaaggtatga acatggaaag agagggaaga attcaaagga tgtagagcag tattcctgaa     65160
tctgagctca tttcagctat tctgttctta aactatcaag aaaaaaaaat ccaaaaaagt     65220
ctaaaattat aattaaaaaa acaaaatact aaccatccat tgtaaaagt aatgcatttt     65280
cattgtaaaa atttggacta tagagaatag cactaagaag aaaaaaaatc accttcaatt     65340
ctgctaccac ctggaagtaa tcgctgttaa tattttgctg tatactttttt atgagtttct     65400
tattcaaaat ggggtcaaaa ttacatgcaa ttgtgtaacc taattttcac tgaatatttt     65460
attagcatttt ttctgttatg aaacagtaat tttagttatg ggtcattgtt ttactatgtg     65520
attgtgataa aattttacat aaatttttttt tggaaattaa ctattgtaca taaatgtgta     65580
taattttctt tttccgagaa ttcctggaag ttgagttagc agcccaggct ttgaattttt     65640
ttttttttttt gagacagagt cttgttcgtt tgcctaagcg cgatctcggc tcactgcaac     65700
ctccgcctcc caagctattc tcctgcctca gccccccgag tagccgggat tacaggtgca     65760
caccaccaca cccagctaat ttttgtattt ttagtagaga cagggtttca ccagattggc     65820
caggctggtc tcaaactcct gaccccatga tccacctgcc tcggcctccc aaagtgctgg     65880
gattacaggt gtgaaccacc atgcctggcc aggctttgaa tttaaaaaaa attttctaat     65940
agctttatgg cggtataatt tacatttctt gaaacctact cgttttgagt gtatagtaaa     66000
cttcaattttt atcacatttc tatcaccccca aaggtccttg ggcccattgc agtaacctcc     66060
ggttcccgcc cccattccta ggcagccact catctatttt ctgtccctta agatttgtgt     66120
tttcgtcagg cacggtggct cacgccttta ctcccaccac tttgggaggc cgaggcaggt     66180
ggatcatggg gtcaggagtt tgagaccnnn nnnnnnnnn nnnnnnnnnn nnnnnnnnnn     66240
nnnnnnnnnn nnnnnnnnnn nnnnnnnnnn nnnnnaccct gtctgtacta acaatacaaa     66300
aattagtcag gtgtggtggc gggcatctgt aatcctagct acttgggagg ctgaggcagg     66360
agaatcgctt gaacgtggga ggcgaagttg acagtgagca gagatcgtgc cactgcattc     66420
cagcctgggc agcagagaga gactctgtct gaaacaaag atttgtattt tctggacatt     66480
ttatagaact ggggtcatag tataaatgga cttttgcatt tggcttcttt cacttaattt     66540
```

```
tgagattggg tcttgtagca tgtatcggta gtttgttcat ttttattggt gagagtatta  66600
tatgaataat accatatttt atctatccat cagatggata ttattgagtt catgttttgg  66660
ccaatttatg aattatggta ctgtgaacat ttgcctacaa gatttgtata ggcatgtttt  66720
catttctctt gagtggataa cctagaagtg gattttttaaa taattttttgg tacttactgt  66780 gaaactgctc ttcagaaaca taccatcgtt tgtccttttct ttcttgtctt tctctttctt  66840
tctttctttc tttctttctt tctttctttc tttctttctt tctttctttc tttctttctt  66900
tctttctaca tagacacatt ttaagaaaaa tttcagtagt ttttggggta caagtggttt  66960
ttggttacat ggctgaattt tggttgcatg gtgaagtctg agattttagt atacttgtca  67020
cccaagtagt gtatcttgta cccaatatgt agttttctgt ccctcacctt cctcccagcc  67080
tcccgccttg tgagtctcca atgtgcatta taccactctg tatgcccttg cgtactcaca  67140
gcccagctcc cacttctgag aacatactgc agaaacatac caaaggatac tcccactgcc  67200
agaatgtgat tgtgcctgat tcttctcacc aataaatatt tcaaaaaaag ttaaatatat  67260
atcagttttt tgggcagaag ttgatacttc tctttatttt ttatttttttt ttgagatagg  67320 gtctcactct atgatgccca gactggagtg cggtggtgcc atctagctta ctgcagtctc  67380
tgcctcccag gttcaagtga ttctcccacc tcagcctccc aagaagctgg aattacaggg  67440
gagagccact actgccagct aattttttgta ttttttggta gagatggggt ttcaccatgt  67500
tggccagact ggtctcaaac tcctgacctc aagtgatcta cctgccttgg ccttccaaag  67560
tgctgggatt acaggcgtga gctaccacac ccggctgata tttctttta aaataactta  67620 ccttcttttg aaagtaatac atgttaaatg aacaaaattt aaggaaaata taaaaaagga  67680 aataatctttt ataatgaaac tactgaaaga aaaccaaaat tacattttgg tgcatattct  67740 tttttcgtttt catcattgta atttgcatttt ctttgattac ttgtgagaca cacttttcat  67800
ttacttaaag gttcgtatga cttgcctgtt cagaaatttt gcagctttac catttctgc  67860 aaatgatagc aacttctttt tattttttta ttttttatttt tattttttatt ttttttttg  67920 agacggagtc tcgctctgtc gcccaggctg gagtgcagtg gctggatctc agctcactgc  67980
aagctccgcc tgctgggttc acgccattct cctgcctcag cctcccgagt agctgggact  68040
acaggcgccg ccacctcgcc cggctagttt ttgtatttttt tagtagagac ggggtttcac  68100
cgtgttagcc aggatggtct cgatctcctg acctcgtgat ccaaccgtct cagcctccca  68160
aagtgctggg attacaggct tgagccaccg cgcccggccg caacttctttt ttatttgttt  68220 gtttgtggtg acagagtctc gctctgtcac ccaggctgga gtgcagtggt ggaatcttgg  68280
ctcattgcaa ctattgcctc ctgggttcaa gcgattttcc tgcctcagcc ccccaggtag  68340
ctgggattac aggaatgtac caccatgccc ggccaatttt tatatcttta gtagagatgg  68400
ggtttcgcca tgttggccag gctggtcttg aactcctggt ctcaagcggt tccctgtct  68460 cggcttccca aagtgctggg attacaggtg tgagccaccc tacccagcca atagttactt  68520
cttatattcc agaaaaaatt gtactcatga tcaagtctcc atgaggaaaa agactttaat  68580
taaagatatt gcagtttgca gaccaatatg ataaaatagt tgattgtttc taaaagtatt  68640
actgagtaat gatggcagat ataagccctt ttgttttttgt aggaaaatgt tacccatgtt  68700
ctgcatttga attcagttta gatttgttag gaatctcagc ttaagctttg ccatctggga  68760
gtgtttggga caattttgca gacagaattg caaaagtgcc taaggggatgc aactggcact  68820 cagacctgct ccttgctcag tactctgtgg acagatgttc agcgcttgtt gatgttgatt  68880
```

```
aaaaggttta gaaagagaac tttcaaagtt ggttttaat taaagcattt aatagtgtga    68940
ataaaaaggg acttaatttt atgacagaca aaagaaagta cagcacctgg cggggcgcgg    69000
gggctcacgc ctgtaatccc agcactttgg gaggctgagg caggtggatc atgaagtcag    69060
gagttcaaga gttcaagacc agcctggcca aggtggtgaa accccgtctc tactaaaact    69120
acaaaaatta gccaggtgcg ttggcaggca cctgtaatcc cgctactcag gaggctgaga    69180
caggagaatc acttgaacct ggatggcaga ggttgcagtg agccaagatt gtgccactgc    69240
actccagcct gggcaacaga gtgagagtct atctcaaaaa aagaaaaaag aaaatacagc    69300
acccagttat gtcagagtgg gtgcatcaga gagtgaccct gagattggag acgatgctgt    69360
cacgtgcttg aagaatgcta cctgagaaag ggggcgagaa gtggtgtttg ctggtaacca    69420
gaggtgttgg cttagccacc tgcagggagg gtggtctatc acaggtgagt ttcatctact    69480
ttcttaagca aatcaacctt acttttgtgt taggcttgtc ccaaagctgt tttataaatg    69540
tgaccaagga caagctgacc cagtagtggc cgtggcaaga gatcaaagca gtgtttacct    69600
gaaacttctc atgcatgaga cgcagcctcc atctcatttc tccgtcagca caataaccag    69660
gtatgctgac ccagtggcgt cctcacattg ttgggaaaat gccctttcct gatgcctttc    69720
tttaggcttt aattgaaaac attttatttt ctagaaaaaa gctttagctc aggatgtttg    69780
agtgtaggtc attcctttga taggatattg tcattctgag gattgaccac accacctctg    69840
tatttaagcc ctgccacaat cacacagctg tgacactata aatcttttaa tcgtttatta    69900
catttaatgt gctgacagtt atattttgt gtgtgacact tacgtattat ctgttaaaaa    69960
attttcactt tagttgtgtt acctttaaag aggattgtat tctatcatgc ctgttgattt    70020
gtaggtgagc gggctattaa agtcagtgtt atttagggct atccactagt tctgtgatt    70080 gcaatgactc tccttcacat ttgttgtgga gcttttgaat atagcgtcaa atggccacat    70140
atatcccatg cttacctgat tcttaggtga gtaggacaga gtgctttaat gaagctataa    70200
tcttcagaat tctagcttgc aaaggagatt gcagaaggat aagacttgtg cttttcaatt    70260
ttgtctttta aatgttattt taaaaattgg cttatatga tactcttttt ctgctgagta    70320
acggtatttt acagaacttg gactagatga cttctaagct taaatgatca cttgatgctt    70380
tttttctgaa ttaggaactc agcttacaca tttcaaagtc ataattcctg aatacataac    70440 atctttttt catgtaaaga ctgctttaaa aaacacatgg aaggtcgggc gtggcggctc    70500
acacctgtaa tcctagcact ttgggaggcc caggcgggca ggttgcctga gttcaagagt    70560
tcaagaccac cctggacaac atggcaaaac ctgcctctac taaaacataa aaaattagcc    70620
gggcgtggtg gtgggcacct gtaatcccag ctacttggga agctggggga tgagaatcac    70680
ttgagccctg gaggcagagg ttgcagtgag ccaagatggt gccattgcac tccagcttgg    70740
gctacagagt gagactgtgt ctcaaaaaaa aaaaaaaaa aaaaaaaag ccacaaaaca    70800 acaacaacaa aaacacacgg aaacatttta tttggccacc ttagtatttc cccttcagat    70860
aattcctttg tttaaactca gaactggcat tttctctctt tgaaaagatt caggacaaat    70920
actcctttaa gataagcaga aacagtgaaa gagtatttga ttatcaggaa tttgataggc    70980
ttagaataaa ttgttgcttc ttaatgtcat ttcagaagat gaatattaat agatgccaac    71040
tgagatatca ttaaaattgg ttactactac tttgaaaagt ttcccagttc caaacttcag    71100
caggcctctt cacaattcaa cagtgcttaa ttgggacttg tgtgatagat acgattccca    71160
attgtgtagc agagtgtgct gcttagctac ctattctgtt agcattcgtg tgttaactta    71220
aaatcataat ctccttagtt ttgttgagtg tctctgtgga tgagacactg tgagggatac    71280
```

```
aaaatcagat tggctttatt caaaccattg gggtattatt tttatttttt gccttttttc    71340
catgtgttct aaaggaatta gagtttgaat ataactataa tgggggatag aaatttacat    71400
gtgccatgaa gggaatgcag aaaagtgcca tgggagctca gaagtggaga aaggaattt     71460
ttttcttgga agcaggagta acttcatgaa gcatttattt caacttagag atagtaggca    71520
atgctgtaag gggagtgtgg ctgcagcgaa agtgtttggg gcagactggg aggaagggag    71580
ggaataaatt cagccattgt tatggcataa tgatcaaaat ttattttcag cccctctttc    71640
acttaaaagt tgagactgct taacttcttt taatctttaa tcttaaactt ttaaatgcca    71700
tttgatcttt aaaaagatat gttttaatag tatattttaa gtctctgtat ttttcttat     71760
agaatataca gaggctataa cctactgcca agcataacag atgtcactat ggaaaataac    71820
ctttcaagag ttattgcagc agtttctcat gaactgatca catcaaccac gagagcactc    71880
actgtaagtc tctttcttga ttggtcttaa tgaaattata ataatttttc gtgacttgta    71940
tggccagtta gttttatggt catcttatgg tgaggtgctt gtattagagc tcttacttat    72000
ctgtggggct tgctaagaaa ttgtgtttct gtgaaaagga tcttagctta ctccaggaat    72060
gtaaataact atttttttct gattattaaa gtaacatatg ccaaaagtta aaaaattcag    72120
ccaatttagg aagacataaa atgaaaata  agccaggcgt ggtggctcac acctgtaatc    72180
ccagcacttt gggaagccga ggtgggggc  tcacttgatg tcaggagttc gagaccagcc    72240
tggccaacat ggtgaaaccc atctctactg aaaatacaaa aattagctgg gcatggtggc    72300
gggcgcctgt aatcccagct actcgggagg ccgaggcagg agaatcactt gaacgtggga    72360
ggcagagctt gcagtgagcc gagatcgagc cactgcactc cagcctgtgc aacagagcga    72420
gactttgttt ccaaaaaaaa aaaagagaaa gaaaactact gtcacctgca tnnnnnnnn     72480
nnnnnnnnnn nnnnnnnnnn nnnnnnnnnn nnnnnnnnnn nnnnnnnnnn nnnnnnnnnn    72540
nnnnnnnnnn nnnnnnnnnn nnnnnnnnnn nnnnnnnnnn nnnnnnnnnn nnnnnnnnnn    72600
nnnnnnnnnn nnnnnnnnnn nnnnnnnnnn nnnnnnnnnn nnnnnnnnnn nnnnnnnnnn    72660
nnnnnnnnnn nnnnnnnnnn nnnnnnnnnn nnnnnnnnnn nnnnnnnnnn nnnnnnnnnn    72720
nnnnnnnnnn nnnnnnnnnn nnnnnnnnnn nnnnnntta  gtagagatgg ggtttctcca    72780
tgttggtcag gctggtctca aactcctgac ctcaggtgat ccaccgcct  tggtcaccca    72840
aagtgctggg attacaggcg tgagccacca cacccgtctt tacatttta  taataataat    72900
ttatgttgct gatattagaa aagaaccata atatccaaga attcaagaac aattaaatta    72960
tgtacatatg ctagtgtata gtgtgatgct ttggagaatt tttaacaatg tggagatata    73020
taatctgaat tgtagtattg agtgaaaaaa ggcagaatac aaacctagta gggggtatag    73080
tcggatttca gttaagaaaa ataatattta catatataca ttcctcacat tggcagataa    73140
tcaccaagat acattttggg attgtggatg attttttgtgt tctttatatt tttcaggtat    73200
tctcaaattt tctaaaatga gcaagtataa cttttgtcat cagaaaaaat aatatgcaaa    73260
agtaatgtta atttgttggt gaccaggtta aacctttta  ttttattat  tatttttga    73320
gatagagtct cgctctgttg cccaggctgg aacgcagtgg tgtgatcttg gctcactgca    73380
gcctctgctt cccgggttca aacgattctc cagcccagc  ctcctgagtg ctggaatta    73440
caggtgcagg gcaccacacc tggctaattt ttgtattttt agtagaggtg ggtttcacc    73500
aggttggtca ggctggcctc gaactcctga cctcgtgatc cacctcctc  ggcctcccaa    73560
agtgctggga ttacaggtgt gagccgctgc acccagccaa accttttta  tttatttgac    73620
```

```
aaaagaaata cttgcatgtt atagaaaact aaatattgtt tgggctgtct gcagtatggt   73680
cttctcttga tttgttcaaa atattgtaaa ctttgatttg ttcaaaatat tgtaaacttt   73740
gcttattttt tttgttcttc ccttgctttg ttcaaaatat tgtaaacttt acttattttt   73800
ttttgttctt cccttggttt gttcaaaata ttgtaaactt tgcttattta tttttattgt   73860
ggctgacatg tgtcagacac tgttgtaggc ctgggatgta aaaacaggat tcctgccctt   73920
acggtctctg gaggctggtc agggagatga tgtggtcagc tggagctccg ctcctaaggt   73980
tgtgcagggg cagttgagag gcggaagggt gggacagcat ttcaaggtgt gggcagcaca   74040
ggagtctctc ttcattggga tataattgcc attccgataa catgtatttg agttgtctaa   74100
agtaggaagt tgtaccatgg tgggacagat atctcatggt tatcatacac agatctcagt   74160
tctcattgtt tgtactttt ataaagggta aaggagata taattcaata aaccttgtg    74220 gtgtttgggt gtgattttat tgtttctttg ttctatagtt tggatgctgt gaagctttgt   74280
gtcttctttc cactgccttc ccagtttgca tttggagttt aggttggcac tgtgggtatg   74340
tattttcctc agtatgtatt aatagttgtc tacaacagta taatataaac gtagttatta   74400
ggatgccctt tttctttctt tttaagtctt ttatcagttt ggcttttgca aaaatatctg   74460
atagaatact tgtttctgct gtattagttg tgtgagacta gtgacaggag ctgtgggaat   74520
tgaatgccaa atgttcttag gcattttttgg gaatttgagg gtgtgatctt caagttcatc   74580 tagggggaatt ttcatatgct ggcaaaatac ttttctcatt agcttgattc tttccagaat   74640
tatttgctgc atattagaag tttaggaacc ttttttcact taaatgtgat ctaacatatg   74700
aaatggtgat gatttaggaa ctactgtact tacattaaca gcttttactt aaaaatgatt   74760 ttccccccagt agatgaccct actcacatct gggaaataat ttcaagtctt ctccagcatt   74820
caggaataag ctttcattct gtgtatcaat tactgagaat gattttggtg actcacatca   74880
catttgagaa gtaaacctgt agatttcttg tgtgtgtcag tgaataacca gctgacattt   74940
gcttgaagtg gattacattc tctgctctag aatgattgct ttcccgcctt cctcacatat   75000
agactgagca actatggttt ctagtcatag gtccggcact agacttgact tctgagcaac   75060
tttggcattg gagtaaaatg tattaattta aagaaagcta aaaattcatt caagtaaaca   75120
tacagttcta atacttttta aagtttaaaa tatagatagg tttaagtgat aaaaaaatat   75180
gagtagacac cataatcctc atttctgtat ctgttcacaa ggggttgata tttatgagtt   75240
ctattctcca tacccattct gtgttctctt aatcctcagt cagcacctca ggtggttggg   75300
attcagttct tggtagtttg acttatactc tcttttctag gggattgagc cctgggtagt   75360
cctccttata tgagattgca atttgtcttc caataacttt tactacaaga tatggggtat   75420
taaaggatgc cattggggaa ccaagataat attagtatca ggaaaactaa ccacgtcaga   75480
cctgccccat tgggtatcaa gtatactatt tttccatagt aataaagagc tcaccccagc   75540
caattctctt ttattttgga cctgtttatt caatggcatt aagatgccca aatgtctggg   75600
tagctatctc atctccaatt cagcagaacc attgtcatat gccctagtgg aagcattcct   75660
tcattggaca cttaggcccc agtacttta ttcagatcta ctacctgatt tcatttctca   75720
aatgattttt atggagcttt aatttatagg aagttgtta gttgattaac agtaaaacag   75780
tttctgagct ggtataaaac atattgtgac acgcttttct cttggaattg caagagaaag   75840
gaagactgtt gtttgcttga aatttttcta taatttgacc ttgcaaatgt ctgcttccag   75900
agtgcctcca ctgagcgcct ccgatgagtc taggaagagc tgtaccgttg ggatggccac   75960
gatgattctg accctgctct cgtcagcttg gttcccattg gatctctcag cccatcaaga   76020
```

```
tgctttgatt ttggccggaa acttgcttgc aggtactgag ttgaagcagg gactccgagg    76080
cttggatttt gatttcctta gggggaatgg gggtggtgag catatgaggg gaaaatacta    76140
aaaggtcatc gccagtgatg gcttgtccct ttagtcaaat ttcagatgtt acctatatgc    76200
acaaacacat gcagctgttc tgtgctgagt attttaaagt ggcctcttcc cagtatggcc    76260
cctcagttaa ctacaaataa actcattttg aatttcatct tagtgggcac catatgccag    76320
tactgcctca ggcactggga tggtaagaaa gtataaagta tggactccat tctcaagttg    76380
gttttagatt agaggggata catgtaaaca gaagtgcagt ggtcacacag agtggccatg    76440
atcactctcc ttgggcagat ttatgggctg ataggaaagg gcacaacagg gagagggtgc    76500
agcaccgtgg cgatgataat ggaggatgtg gccagcaagg aagacgcagt ccattgaaat    76560
tgattttggg agaagttgcc aatctccatg aaagaatcgg gacctgtgtt ctttgcttta    76620
ggaggctata ggagagtttc gtgaaaggga ctaaagatg agtattttaa taagatcatt    76680
cagccaactt gaatgtgggc tggaggagaaa ggtagagaga ctcaggagat taatgttgac    76740
gctaaggcaa gagatgggga gtctaaacca agataatggc tttgggattg tagggaagac    76800
actgatcgta agagaatgaa ggaggcagaa ttgccaggcc tgggtcacca actgaacttc    76860
ggttgtgaag accaagaaac ctgggatgac ttcacatcct gggcaggtgt gtggtagtga    76920
cagtcatgga aattgggaac acagatttgt ggggaagaca tcagtttgag tttgagtttg    76980
agtttgagtt tggcttatcc gttgaatatc agacacagat gtctggccaa ctctcaacat    77040
agattagggt cttaaatgac ttcagttccc caagcaattt gtccttccca tactgttggg    77100
ctagagaggt aatatctatg cccatatcac agccagtgct cctaaatctc tgagaagttc    77160
atgggcctct gaagaagaag ccaacccagc agccaccaag caagaggagg tctggccagc    77220
cctgggggac cgggccttgg tgcccatggt ggagcagctc ttctcccacc tgctgaaggt    77280
gatcaacatt tgtgcacatg tcctggacga cgtggctcct ggaccggcaa taaaggtaat    77340
gtcccactta ggtgctggat taatatagcc ttaatgactg tgggtttcca gactatcttt    77400
atttagtaat ctgtctcttc tttattctct tttacttaa atgaacaaaa ttgctcagat    77460
tgtgacacta aatttaacat caaaatgtga ccatgtggcc gggtgcagtg gctcatgcct    77520
gttattccag tactttggga gactgaggtg ggcagatcac ttgaggccaa gagttcaaga    77580
ccagcctggc caacatcaca aaacccccatc tctactaaaa atacaaaaaa attagttggg    77640
cgtggtggca catgcctgta gtcccagcta cttgggaggc tgaggcaaga gaattgcttg    77700
aacctgagag gtggagtttg cagtgaacct tgattgtgcc actgcattcc agcctggatg    77760
acagagtcag gctctgtctc aaaagaaaaa aaaatgtga ccatgtgttt tacagctcct    77820
ttggtatcat cagtcactgt taccccctaag agggaaatac atagctttag ttttaggttt    77880
ccatcattag ccaagaaagc tcagaattgg ttttcctggc taaagtacct cattgctgtc    77940
tccttaaatc ttagttaatg gctactgtcc tggctagcat agttatagag catgtccatg    78000
gttgtagaat gttctgccaa tctcagggac agttttgctt ttctgtgaag caataaaatc    78060
aacttcaaaa caaatgttaa ctgttttgcac aatggattta agatagacca gttcacatac    78120
tttttttttt ttttgagacg gagtttcact cttgttgcct aggctggagt gcaatggtgc    78180
gatctcaggt cactgcaact tctgcctcct gggttcaaac gattctcctg cctcagtctc    78240
tagagtagct gggattacag gcatgcacca ccacacccag ctaatttttt tgtattttta    78300
gtagagacgg ggtttcacca tgttggtcag gctggtctca aactcctgac ctaaagtgac    78360
```

```
ctacccgcct tggcctccca aagcgttgag attacgggca tgagccacca cgcccagcct   78420
aagatagacc agttcactta ctgttatatc tgtttactct ctctttgctg tgtcttctac   78480
ctttaaaaat ctccccacta acttcccatt ctcctttagc tgccatcagt cacttccctt   78540
ctctgcaaac atctctggag agtctcagcc tcagcccaca gagcttccca ctgctctgag   78600
gtggaccttg tttgtaagac ttcttggccc tcttggcctg gaccctgtct actacttcag   78660
ccatccttcc ttaaccatcg ctagtggttt tgttgccac cctccatagc agcgtttccc   78720
ttccagatca tgtctttaca tctctgggca ctgctctggt cctgcctgcc tttccctctc   78780
tgtaccctgc aggccgctgc cgccatcttg agtgtcctct tcacttggct ttcagagggc   78840
ccacagagtt tcccactgct ctgaggtggg ccttgtttgc aatacttctt ggccctcttg   78900
gattactgca ctagccttt gttttggaaa cagcatttt aaaaaattt aatttattt   78960 ttttgagata ggatgtcact ctgttgccca ggctggagtg cagtgtcatg atcgtagctc   79020
gctgtggcct tgatctccca ggctcaagtg atccttctgc ctcagcctcc tcagtagttg   79080
ggagtacagg tgtgcaccac catgcccagc tagtttttg attttttttc ttttttcttt   79140 tttttgaga cagagtctca cactgtcgcc cggactggca caatcttggc tcactgcaac   79200
aacctccacc tcccaggttc aggtgattct cctgcctcag cctcctgagt agttgggatt   79260
acaggcgcct gccaccacaa ctttttgtat tttaggaga cgggggttt caccatgttg   79320 gccagtctgg tctcgaactc ctgatctcgt gattcgccta cctcagcctc ccaaagtgct   79380
gggattacag gcatgagcca ctgctcccag ccaggaaaca gcattcttga gataattcat   79440
ataattcacc catttaaagt atataattca ttctctttag tatgcccaca gagttgtgca   79500
gccatcacca gaatcagttt tagaacccac aaaggaactc tgtacccttc acccaaaacc   79560
ttccatgccc ccagctgcag gcagccactg acctaccttc tgtctctgtg actctgcatc   79620
ttctggacat tactgtggat gggctcatac agtcagtgag cttgtgactg gtgccttcta   79680
ccaagcaggg ttttcagtgc agtagccttt cttttctttt tttttttta aattgagacg   79740 gagcttctgc ctcccaggtt caagcgattc tcctgcctca gcctcccaag tagctgggac   79800
tacaggccca tgccaccatg cctggctaat tttttttttt tttttgtatt tttagtagag   79860
atggggtttc accatgttag ccaggatggt cttgatctcc tgacctcatg atccgcccac   79920
cttggcctgc caaatgctg gaattacagg cgtgaaccac cacacctggc taacctctca   79980
tgtactgtct gcggttcttc cctgatgcct tccagtccat gcacccgatt gtagccctc   80040 atcctattat ggtttaaggt gactgtctta gtcaccatgg gttgccataa caaaatacca   80100
tagcctgggt ggcttcaaca acagaattta cttctcacag ttctagaggt taggaagttc   80160
aagatctagg actttcacct tgccctcaca tggtgagggg gtgagggagc tctctggtgc   80220
ctcttatatg tggacgctaa tctcattcat gagggtctgc cctcatgccc cagtcacctc   80280
tcaaaggccc cacctcctaa taccatcacc ctggtaatta agtttcagtg tatgaatttg   80340
ggggactata gacattgaaa ccataacaag cacttttcta aaagatcagg gagtgagtaa   80400
gtaccagagc taggacctca attccacctc tcggtcatct tgccttcact ctgctccatg   80460
atggctgcct cctagagtga tgggagcctc catgttttat attctctcat gtgttgtgta   80520
ttggagagag ttcagacttt atgaatacat ctggatttgt tgacttctag ctttgctggt   80580
aaccagctgt gaccttgagt aaattacttc atctctgagc ctgttcctc tttttgaaaa   80640 gggagtttaa aatgctgttt tgggttgggc atggtggctc atgcctgtaa ttccagcact   80700
ttgggaggct gagatgggag gatcacttga gcttggagtt cgagaccagc ctgtgcatca   80760
```

-continued

```
tagtgtgaga tcctgtctcc tcaagaaatt aaaaaattaa ctgggtgagg taacgtgtgc    80820
ctgtgggccc atctactctg gaggctgagg tgggaggatt acttgagcct gggaggttga    80880
ggctgcagtg aactatgatt gcgccccatc ccgggtggcg agtgagaccc tatctcaaaa    80940
aaaagaaaaa aaaatgctgc tttgcacccc tttctcatgt catggtgtca tggctaacat    81000
cgaatgccct ggttgtttgc tgttggaagg cgtgggccta ggggctccct gaggactcct    81060
tccatcttca attcgttctc tgtgtacctg ttagcaagtt gtgggccagt ccctgccatg    81120
taccattgtg tgggtaaaag taaataaaat gtgtacagtg tctgaactgt acatataggg    81180
gtccaagaac aaaatgaatg acatgggtta gctctttcta ataaatggta aaccaaata    81240
ttctaatttt cagttttgtt atacttccat cacatgtttt tgttttttgt ttttgttttt    81300
ctatttagg cagccttgcc ttctctaaca aaccccccctt ctctaagtcc catccgacga    81360
aaggggaagg agaaagaacc aggagagcaa gcatctgtac cgttgagtcc caagaaaggc    81420
agtgaggcca gtgcaggtag gaaacagtgt ggggaaggga gggacaggag tgcagcatct    81480
gtcatgtagc aacataggat ttaagtaact tggtgtttta gagaaatata atacacatca    81540
gtaaagtgag agaaggtttc tccaggtgcg gttcaagata ttagaaacta atgactaata    81600
tacacagacc acctttttggt ctgaagcatc tctaagtgcc acctgctgac acgcagcccc    81660
tgcagcctcc aggcttccag ccccagcacg gagcctcact ctcctgtgct tccctggttg    81720
cgggtgaggg ctggagaggc ctcctgattt tcagtaaggg aagtggtgta gatgcttagg    81780
aatagatata gtgagtgaaa aaattgattc tgatatgtca aaatttctga ttggaaatgg    81840
aatatttaca tttggaagaa ctaaaggaga gagaaagtgg ggataaagtc atctgagttg    81900
gaggagctta aaccatgcac aagtttggag gaccttttt taacccatga aaaggtcaga    81960
acagaagggg ctaggattta gttgtgactg cagttttttcg aattcccatc catactgctc    82020
ttggagggca gtggcagggg caggagagga gcctggcaaa gcatgaagtg actgctgctg    82080
cctctgctat ctgggtcgcc tggctgcctg tctgtacagt ctccctccaa acccattctc    82140
tcgctgtctc ttggtgccca ggggccagtg atggttctcc cgtttgtttt gtgtatatag    82200
catttatatc aaggctattt atttatttag agacagagtc ttgctctgtc gcccaggctg    82260
gagtgtagtg gtgcaatctc ggctcattgc aagctccgcc tcccaggttc aagcaattct    82320
cttgcctcag cctcccaagt agctgggact acaggtgtgc accactacac ctggctaatt    82380
ttttgtattt tttttagtag agacagggtt tcaccatgtt ggccaggatg gtcttgatct    82440
cctgaccttg tgatccacca acctcagcct ctcaaagtgc tggaattaca ggcatgagcc    82500
actgcacctg gcctatttat ttatttttaa ttgacaaaat tgtatatgtc tgtagtatac    82560
aacatgatgt ttgaaatatg tatacattgg ccaggcgcag tggctcannn nnnnnnnnn    82620
nnnnnnnnnn nnnnnnnnnn nnnnnnnnnn nnnnnnnnnn nnnnnnnnnn nnnnnnnnnn    82680
nnnnnnnnnn nnnnnnnnnn nnnnnnnnnn nnnnnnnnnn nnnnnnnnnn nnnnnnnnnn    82740
nnnnnnnnnn nnnnnnnnnn nnnnnnnnnn nnnnnnnnnn nnnnnnnnnn nnnnnnnnnn    82800
nnnnnnnnnn nnnnnnnnnn nnnnnnnnnn nnnnnnnnnn nnnnnnnnnn nnnnnnnnnn    82860
nnnnnnnnnn nnnnnnnnnn nnnnnnnnnn nnnnnnnnnn nnnnnnnnnn nnnnnnnnnn    82920
nnnnnnnnnn nnnnnnnnnn nnnnnnnnnn nnnnnnnnnn nnnnnnnnnn nnnnnnnnnn    82980
nnnnnnnnnn nnnnnnnnnn nnnnnnnnnn nnnnnnnnnn nnnnnnnnnn nnnnnnnnnn    83040
nnnnnnnnnn nnnnnnnnnn nnnnnnnnnn nnnnnnnnnn nnnnnnnnnn nnnnnnnnnn    83100
```

```
nnnnnnnnnn nnnnnnnnnn nnnnnnnnnn nnnnnnnnnn nnnnnnnnnn nnnnnnnnnn    83160
nnnnnnnnnn nnnnnnnnnn nnnnnnnnnn nnnnnnnnnn nnnnnnnnnn nnnnnnnnnn    83220
nnnnnnnnnn nnnnnnnnnn nnnnnnnnnn nnnnnnnnnn nnnnnnnnnn nnnnnnnnnn    83280
nnnnnnnnnn nnnnnnnnnn nnnnnnnnnn nnnngcactt taatatttag tatcggttta    83340
atgataatgt ttgtgcccdt actgtcttta aaacatttt acgtcatccc tgtttgatta    83400
cttggtgtgc tcatgaagtt gttggccact agggaatctt aggctcagag aggttctgga    83460
attggtcagt ggtccttgaa ttagccgctc ctatgattct ctaactgatt tctcaaaaag    83520
caaacaagca accacagcaa aacagctgtg cacaccactc ttcttatttt gttattgttt    83580
tagtacttag gccgtactta tgtttgttag tcagtttctc attacttcta gttaatcaaa    83640
agatcagagg caatatttga gtattttcat actagaatgc tttaaaaaaa gtcattattg    83700
gccgggcgcg gtggctcaag cctgtaatcc cagcactttg ggaggccgag acgggtggat    83760
cacgaggtca ggagatcgag accatcctgg cgaacacggt gaaacccgt ctctactaaa    83820 aaatacaaaa aactagccgg gcgagatggc gggcgcctgt agtcccagtt acttgggagg    83880
ctgaggcagg agaatggcgt aaacccggga ggcggagctt gcagtgagct gagatccggc    83940
cactgcactc cagcccgggc gacagagcga gactccatct caaaaaaaaa aaaaaaaaa    84000 aaaaagtcat tatttccagt aatctcttta aaacttggca agttattttg atctaaaagt    84060
ttatcttttg tgtgcacatt tttaaagctt ctagacaatc tgatacctca ggtcctgtta    84120
caacaagtaa atcctcatca ctggggagtt tctatcatct tccttcatac ctcaaactgc    84180
atgatgtcct gaaagctacg cacgctaact acaaggtatg ggcctctgca tcttttgaaa    84240
atatatatgc ccacatactt atgtctaatg gatcgttgat gttttctta tgatttgtag    84300 gacgtataag ccctttgaga tatgagttac aattcgtgtt ttcaagtttg tctttcagct    84360
ttgtttatga tagcatctgt catacaggtg ttttggattt tcatattgtt tgtactcaca    84420
gctaagattg attacgtgag agagctagga tgtgcagcca ggttattggg ggaagtggcc    84480
tcggtggagt ctggagggat ctgtgtacag gcttccttcc ctcctgtgag gctcacacaa    84540
aaatacagca acctgctggt cctgcaggtc ccctctgcct aacatgagcc acaattccag    84600
actcacagaa gcaggcgttc agcataaacc acgtgtttca aatagtctgg gcgttgtgag    84660
ccacttgtta tcagctaggg aaagttttta tgtcagtgta aggaactgtt gaccagataa    84720
ccccaagagc cggcctttct gtctagggat gttttagttt tctagttcat tttttttttt    84780
ttaactttaa aattttctat tcatctgcaa tttgttagat atgaagtacg catctaattt    84840
aattttggtt ttggttgtcc ccaatgctgt ttacagaaga attttttgc actaattggc    84900 ttaagttact tacattctca tagttctcta gtttcatttg ccattttgtt atatcaatct    84960
atctgtctgc tcatctatta gaagcatcct ttttttcctg ttgtagacag tctcgctctg    85020
tccccaggct ggagtgcagt ggtgcaacca tgcctcactg cagtctcaac ctccagggct    85080
caagtgatcc tcccacctca gctcctgggt acctgggact acaggcatgt gccaccatag    85140
ccagctgctt tttacatttt ttgtagagac agggtctccc taagttgcct gggctggtct    85200
caagttcctg gcttaagtaa tccttcctcc ttggcctccc aaagtgctgg gattacaggc    85260
gtgagcaact gcacctggct agaagtatac ttcttagtta ttatagcttc atggtattta    85320
tgatgggatc agttctcctg ttcttagaa ttttctggat attcttcttt gttgattttg    85380
ggatgtgaac aatagaatca acttctactt gtaggttgat ttagggagaa cttataccte    85440 agatgttaag ttaccctgtc cagaatgtgg gatgctttcc tatttgttca aaacgtttta    85500
```

```
aattacctca gaagcacatg aaatttaaag gattttaaaa aaaactttaa agattatttc   85560
acatagctct tgcacatttc ttggtaaatg aatcctcagg tgttcttctg tttttgttac   85620
taatagatac ttctcatggt tgttttttt tttttttcc tgaaaatcat ttgtcaaact    85680
tatgtggctt cttttctgaa ggatgtttga taattttgga agatataaaa gtcttcatat   85740
tttacaaggt ttggagtctc tttaagctgc gtggttctca cgtcagctcc caaagcagaa   85800
gacggcatgt cgaaaaatgc catagagaag ctacttcttt tccacctgtt ttcagctcat   85860
atcatcttga atttcggggc accctttctat gctcctagtg cttgctgtct gtttattatt   85920
ttccttcctg aataccctga actccagcat gttctgctgt aattctggcc tccctggcgt   85980
cttggactcc tgtttccttt gctctgtcat ccccacggtc agctcctgct gcgcagcttc   86040
tcagctgaac tgtttggagt ggctggcggg tcttgctgga tctttgagta ttgcctctgg   86100
tttccttggt tccttctgct gagttgctca gcgtctccac tccccatttc tcgtgtggcc   86160
cttcctgctc tcctctgatt cctttttgtct tccctggttt cttgctttgg ttttcagtct   86220
ccgcagaact tttgccactc ttctgaaaac ccggaggctt tttcatctta attctcatt    86280 catgacctct tttcccttat ttgagaggta gaccttccca tggtgagctt ctcttttccag   86340 aattccatgt cttcttttcc ctcccactta cctgttgtcc aggagaggtc agattgctgt   86400
gcgcattgga gaagaaccct ttcttccctg ggctcttcat ttcacatgac atcaccacat   86460
cacctcatcc cttggaccct cagtggtggc actgctggat ttttctttcc tttggctggc   86520 cttgggcac  acccaggttg accctagctt agtcatggta tttagatcaa ctcacatttt    86580
cagtttctgt gtctgtctct tgcctgcttc tgactttgcc cagagaaagc ttttcacaa    86640 gggttcttag atttacgagc accttctttc ctgaggcagt gttttgccaa atatttattt    86700
tcctagtcag tctcgcctta cctttcttgt tatacatgat gtctttggtc ctgacccatt   86760
ctctgagtct gtaaaataga attgctgtat aatttaatta catgaaatcc tttagaatct   86820
taatacatct tacaccaggt gtaacatttt atgatatcca aattgaacaa ccctgtgtga   86880
atttgacagt gatttctccc agggatccta atgtataagg aataggactt tgtatttctct   86940 attttttgat ataccacata ccagatactg atcatgatgg acatttaacc cttttttcct   87000
cattaggaaa gaaagttagg aattacatct ttcagtagtg ccagtgtgac ctgaaagatg   87060
cctttgaaag agtagttttt gtatagctat ctgaaaggaa tttctttcca agatatttc    87120 ccagtgctga caacaaacac gcagacacgc cctacaaggt caatgtacag cgccgcacag   87180
tggaggcgtc tgccgcagcc gttaatgttt gtatctttgg ttgtacttta cgagatcttg   87240
acggggccag taaccgtgtg ttctctcctt caccttctca aggtcaccct ggatcttcag   87300
aacagcacgg aaaatttgg agggtttctt cgctcagcct tggacgttct ctctcagatt   87360
ctagagctgg ccacactgca ggacattggg aaggtctgtg tcttgttttg acgtgcgtcc   87420
tctgggctga gttcatctag gatggagtcc ggttctccag ggtgcctccg ggagactcct   87480
ccctgcgcca cggacttgca tcacaggacc cgagtctgac tctgccttag ccatgaagtt   87540 tgggggaag gttctatttg tattctgttt ttgtctgtta tcacgtatta gcttagaccc   87600
agtttagttt agaaaattgg tgggtttaaa aatgtgttta tagagtcctt tatttcttaa   87660
tttgaccttt tcaagtggaa agggggcaaaa cagacagatg aggggggcggg gcgggaggtg   87720 tgacttgctc ttttgtgcct gaggaagtaa cagagctggg gttgacagtt atattctctg   87780
gttttatgtc caggaatttc ccctgccgca cccctagttg atagcgaaaa tgttcaaaac   87840
```

```
tatgagaaag ttagaatgct gtggtaaaca ctctattatg tacacacaac ccagcttctg   87900
cagttgtttg cgtttggcta cgtttccttt ctatgtatat agccatctct ccatttacca   87960
gtacatctta ctttataatg catttttaaaa ggagtgacag atgcctccct ccaccaaatg   88020
tgtgtcttca cgtgaaatac agtatgtctg atgcacttca tttgttctta tgtcttttgaa  88080 tcttttttatc tggacatgga cacaaggtta cctagttta atcgttacat atgttagtgc   88140
ttcttctctg ttattcctca tgttttccc atgtatctat ttagtgtgcg cagttgtcat    88200
ttttaatggc tatctagtgt cctgctgtgt tgatactcca tcgttccctt agagtaaaac   88260
ttgttgagac ttcagtaatg tcacctgctc agtgagactt tcctggccat cctttcaaaa   88320
cttgcttctc tctgtactct ctttccctgt tcattttttct ctttgaccca tagcatcgtc  88380
taacagtcaa ccttaaaata aataaataaa taaagacttc agagaaatgt ccaaatacat   88440
ggagtcagtt tgggaatgag aaatgaggat tataatccgg gatgcacggc atgtccggct   88500
gccagtgcct ctggtgaagg aaggggaagg ggaagctgtt attgtcagaa agggagagaa   88560
tcacataggc tccctggaag cagagttcgt tggctccaga ggctgaaagc cagagttgtc   88620
gtcattcact ggtggaattg taggcaccgg gcaggtgttc agttgagagt attttaactg   88680
aattgctgca gtcctccaga atggctagtg ataaatctgg tcatagaaac atgtattcac   88740
gtggaacatg caagccatgc acagcagata tgtaaaggat gtacgggaag ggtttcttct   88800
agggttgttg gaaagtcttt ggaaacagct ctaacctggg gcacataagc atgaacccca   88860 tctcccttg tgctttccta gtccaattt gtctgggtct gacaaagtga tttgatccct     88920
gtatctgcaa ctttcacaaa acatactatt tatttatttt acttccttgt cttttcagtg   88980
cctatagcag tgcctggaag attgtggaat ttagtgaaca tttgttgaat gaatagatgt   89040
tcttgttaaa aatgagtttt agtgtctcat ttatcttaca tccacactgt ggtggagcca   89100
tattagccca tttcacgcca taactggaag ctgaaagatg tgacattctt ggggccagat   89160
aagtcagtgg cagagcctga gttaagtctc atagattttc tttttctttt tcgttttg     89220 gtggctagct ttggttttat tttatttat ttatttattt ttattatact ttaagttctg    89280
ggttacatgt gcagaacgtg cagttttgtt atataggtat acatgtgcca tgatggtttg   89340
ctgcacccat caacctgtca cctacattag gtatttctcc taatgttatc ccttccctag   89400 tccccctcacc ccgatgggcc ccggtatgtg atgttcccct ccctgtgtcc atgtgctctc  89460
attgttcaac tcccacttgt gagtgacaac atgcagtgtt tggttttctg atcttgtgat   89520
agtttgctga gaatgatggt ttctggcttc atccatatcc ctgcaaagga cattaactca   89580
tcctttttta tggctgtata gtattccatg gtgtatatgt gccacatttc ttaatccagt   89640
ctatcatcga tggacatttg ggttggttcc aagtctttgc tgttgggact agtgccacaa   89700
taaacatacg tgtgcatttg tctttattgt agaatgatat aatcctttgg gtatatgccc   89760
agtaatggga ttgctgggtc aaatggtatt tctagttcta gatctttgag gaattgccac   89820
actatcttcc acaatggttg aactaattta cactcccacc aacagtgtaa agtgttcct    89880 atttttccac aacctctcca gcatctgttg tttcattaat ttttaatgat cgccattcta   89940
gctggtgtga gatggtatct cattgtgatt tgatttgca tttctgtaat gaacagtgac    90000
gatgagcatt tattcatatg tctgttgact gcataagtgt cttcttttga gaagtgtctg   90060
ttcatatcct ttgtccattt ttagatgggg ttgtttgctt tttttttttt tttgtaaatt   90120
tgtttaagtt ctttgtagat tctggatatt agcccttgt cagatggtta gattgcaaaa    90180
attttctccc attctgtaag ttgcctgttt actctgatga tagtttcttt tgctgtgcag   90240
```

```
aagctctttta gtttaattag atcccatttg tcaattttgg cttttgttgc cattgctttt    90300
ggtgttttag acattaagtc tttgcccatg cctatggcct gaatgttatt gcccaggttt    90360
tcttctagga tttttatagt cctaggtctt atgtttaagt ctttgatcca tcttgagttg    90420
atttttgtat aaggtgtaag gaaggggtcc agtttcagtt ttcagcatgt ggctagccag    90480
ttttcccaac actatttatt aaatagggaa tcttttcccc attgcttatg tgtgtcagat    90540
ttgtcaaaga tcagatgctg gtagatgtgt ggtgttattt ctgaagcctc tgttctgttc    90600
cattggtcta tatatctgtt ttggtaccat gctgttttgg ttactgtagc cttgtagtat    90660
agtttgaagt caggtagcgt gatgcctcca gctttgttct tcttgcccag gattgtcttg    90720
gctatgcagg ctcttttttg gttccatatg aagtttaaag tagttttttc caattctgtg    90780
aagaaagtca gtggtagctt gatggggata gcattgaatc tataaattac tttgggtagt    90840
aaggccattt tcacaatatt ggttcttcct atccatgaac atggaatgtt tttccatttg    90900
tttgtgtcct ctcttatttc cttgagcagt ggtttgtagt tctccttgaa gaggtccttc    90960
acatctctta taagttgtat tcccaggtat tttattctct tagtagcaat tgtgaatggg    91020
agttcactca tgatttggca caatctcagc ccactgcaac ctttgcctcc tgggttcaag    91080
gaattctcct gcctcagcct ccagagcagc tgggattaca ggcacctgcc accatacctg    91140
gctaattttt tgtatttta gtggaaacgg ggttttacca cattggccgg ctagtctcg    91200 aactcctgac ctcgtgatcc acccacctca gcctcccaga gtgctgggat tacaggcttc    91260
agcaactgcg cccagccaga ttttcagatc tccctctctt tgccctaaac cactgtgctt    91320
aataagaatt ctttagtggc cagcagtctc catgtgtaac acattgtagc aaaatggaaa    91380
atattacatg ttttaaattt gagtgtgaga tatactgaaa taaaaatcat ctaaatgaga    91440
ttctttaaat aataagattt tcttttttgt atgtgggttt ttttttaaca ttattattat    91500
gactgtcgta tatagaaatg gctgttttca actacagtca gtgaatgtat caaatgctgc    91560
cttatccaaa taataaaagt aaatgattaa caagtcacaa tttagtgaag attgatgtta    91620
gttgatcttt atattcctga attagccaca tggttgtgtg tgtgtatata tgtttagagg    91680
tacatataga taataagctc atctctgaaa attttttcat ttggcataag aataactgga    91740
taattaagca tcttattctc tggcctgtgt ctttacagtt aaaggtagat ttactcacct    91800 ctccttttttt gtttttctca gttcatcttt tttgctattt catgacggag gcccattta    91860 cctttctcgt atatccttttt gtttgtactt tggaagcctc acctgcttaa ttgttgagtt    91920
tttaatctgt ggtcttttag aggaggatgt gtagggtaga agctttcaca ggttcttctt    91980
tgcacttggc ccttggctgt tttgaggaat ctccctcact aactcacagc atagcaaggt    92040
ttgagatctc ttctgccaca cagcagttcc caggcagctg gaaagatatg cagatgctca    92100
gattgtcagg ccagccttga gatatacaaa ctactgagcc ttatctgtga ccttgcttag    92160
gtgaaggcat cagagcccct gcaccgacat gtgtaggcct ctggatgtgt gcggggctgg    92220 gtgttgggt ctgagcacaa gtgtagctgg agaggtgagc ttgttgtggt gacgggtatg    92280
agcaagtttt cttcagactt ctgtgagttt acctcgttcc aggatttaaa ggcacagaga    92340
ccttagaatt aaaatagaat cattttcttt ttctaaatag caacactagg aataaaaaat    92400
aataattcca cattctttac aggtaatgtt ttgttttttct tgtcttctaa tccttattta    92460
ttctgtactt attttttatac gtatttgaaa tgtattatgt gttggagttt cttttttgca    92520
ttatattata cacggttttt catgtaactc cttactgttc cattttatat gttttgtctg    92580
```

```
gtttatttta agactttatc agcaaatcgg gaaaccgtct ctacaaaaac aaaaacaaaa    92640
gcaaaaatag ttggccacag tggcatgcgt ctgtggtccc agctactcgg ggctgaggtg    92700
ggaggattgc ctgagcccgg gaggttgagg ctgcagacaa ccatggtcgt gtcactgcac    92760
tccagcgtgg gtgacagact ttatactgtc tgtttggggt gatttggtaa tgatatgccc    92820
tgatgtagtt tttttatatc ttgtgtttct tgtgcctggg tttattgagc ttgggtctgt    92880
ggcttcatag tattttttaaa gtttggaaaa tttttagggca ttatttcccc aaagattttt   92940
ttctgccctg ttcccctcct ttttttcctc tcttaaaggg gctgtgattt cctgaatgat    93000
tgcttagtgt tgtcccatag cttattgatg ctcttttcag tgttttttgt gttttctgtt    93060
ttctatagtt tctattattg tatttgcaag ttctctaact tttcttctac gatgtctaat    93120
gtgttgttta tctgttaatc tattgttaat cctgtccagt attttttttt tttttttgaa    93180
acagtctcac tctgttgccc atgctggagt ttagtggtac aatctcggct cactgcaacc    93240
tccacctccc aggctcaagc aattgttctg cctcagcctc ccaagtagct gggactacag    93300
gcacgtgcca ccacacctag ctaattttttg tattttttatt agagatgggg tttccccatg   93360
ttggccagac tggccttgaa ctctgatctc aggtgattca tccacctcgg cctcccaaag    93420
tgctgggatt ataggcatga gctaccttga ctggcccctg ttcagtgtat atcactaatt    93480
gtgtttttat ctatataagt ttgatttagg tcttttaaaa atttctccct gtgtctctac    93540
ttagctttgt gaacacagtt gtaataactg ttttaatatc tttctctgct agttctaaga    93600
tcttctaata acttcctggt tctcggtgtt tttgattggt ctattgatgc tccttgttgt    93660
ggattgtgct ttcctgcctc tttgcatcgc tgccaatttt tggttggatg cccaacattg    93720
tgaattttac tttgctggat gctagacatt tttgtgttca cagagatctt cttgagtttt    93780
gctctgaggt tagttgagtt acatgtgat ggtttactct tttgggtctt gctttataat    93840
gagtactcta cctaatgaac cagaaagttc gggttttcca gtctgcctgc tgagaacggt    93900
gactgtttct agcccgtgtgt gagtgcccga gcgccgctcc ctctgatcct ttctgatgct    93960
tccctctgtg gcctcaggga gtttcctcac acacacagtt ctgctgagta ctcgaggggt    94020
ccttccccga tctccaaggc tctctctgtc ttgttctctc ttctctggtg ctctgtccta    94080
taaactgtgg ctatcttggt ctccttagat tctcagcacc tcttcaattc agagggttgc    94140
ctgtccctcc tccttgtgcc acagcctagg aactctctta agaagtgag gtggggcagc    94200 tgtgggctc actttgtctc tcgtctccca gggatcactg tccttcatgg ctgatgtcca    94260
atgtcttaag gactctggat tttgtctgtt ttgttttttg gttggctttg tttgtttcaa    94320
acaggagggt aaacccagtt cctcactctc attgtgctca gtactggaag tctcgctctg    94380
ttatattgga tattagtatt tgtagcagag ccctggttcc ctggtacttg gggagctctt    94440
gaaaggccag aaacagcatg ctttctcacc tttcccaggg cttccgtttc tggtgcacac    94500
aaagcattcc atacacattt gttaaagttc tttgttagac aaatagtgat tcacaggctc    94560
tatttgtaat ttttcagta agcatgtatt agatatctgc tgggagctag tagaaacaaa    94620
aagtgacatg tgacaaattc aattctgaca agaacaacct taaacattta gaatataatt    94680
tgagtaaatc agaatttttaa aaatgtgtgg ccccttgaata tttgaaacca acaagaatct   94740
attgcttatt agtagaggat atttttgttga acaagtggag agagaggcat tttcagtcta    94800
actggtgttg gcttttagca gctgttggaa accggttcat gattagccag gcagtggtga    94860
aacaggctgt gcattctgaa tgcctagatt ggtggcactc ttcgagttag catcttcttc    94920
tttcttcttt tttttgagat ggactttcac tcttgttgcc caggtaacaa ctccagtgca    94980
```

```
atggtgccat ctcggctcac tgcaacctct gcctcccggg ttcaagcgat tctcctgcct   95040
cagcctccca agtagctggg attacaggtg tgcgccacca tgcctgacta attttgtgtt   95100
tttagtagag atggggtttc actatattgg tcagactggt cttgaactcc tgacctcaag   95160
tgatccacct gcctcgacct cccaaaatgc tgggattaca ggtgtgaacc actgctccca   95220
gccccttctt gattcttgta aaggacattg ggtgctgtac accttgttat agatgttgat   95280
aaaaattctt gtgagaatag taacgttaag gtagttgttt ggtcattttt gtctatcagt   95340
ataagataat tctaggactg atttgtggta aatcacacat tgctgtatca tagttgtgtt   95400
cactgaacat attcagggc tttacagatg cagggctctt agctgctttg cgcacttctg   95460
aattcctgcc ctgagaacag gactggatac ctagtagacg ataggtattt gataacagtt   95520
taatgaatta atgagtgaat gaacagatac gtaggtatgt gaaagaatgg ttgtaatgta   95580
tgtaacttgg atttcaagac ttactctgtt caaataagaa atggaaaact ttcctctgat   95640
tttgctctac tatttacact ctttaaatgg aagttatctt gtacctttga tttctgtcta   95700
ggattcgtac aataatgggt catctctgag tcacttacgg tctcactgtt ctttccacag   95760
tgtgttgagg atcctagg ataccctgaaa tcctgcttta gtcgagaacc aatgatggca   95820
actgtttgtg ttcaacaagt aagagcttca ttcttttcct attctgttaa gactttcagg   95880
tatgacgaca aaatgctgct actccttaag cagcaggtgc tggtggcgta atcagctggg   95940
aggattgtgg ggtccagcat agcacttttc ggctcattcc atgattgagc caagaggccg   96000
accttcccgt cattcccag gaggacgagg tctgtcattg tggagagcaa aggacatcag   96060
aagctcccct gcatcctcac tcgttaactt ccagtccctc ggggtttttg tttagcgtgc   96120
tcaatctcat ttagaatcgc aaggaaaccc aaaactctta tttaaggtac aaacagcact   96180
tcatacaata tctcgccgag gtaataatag tgattcacag gaagaatttc acattgtgaa   96240
tctttgctaa tgtatccagt tatttacaga tggatttgat atttgtgtgg gagattctta   96300
aagtgttgtt catgccacgt tgtttgtgct tcaattttt cactatagtt gttgaagact   96360
ctctttggga caaacttggc ctcccagttt gacggcttat catccaaccc cagcaagtca   96420
caaggccgag cacagcgcct tggctcctcc agtgtgaggc caggcttgta ccactactgc   96480
ttcatggccc cgtacaccca cttcacccag gccctcgctg acgccagcct gaggaacatg   96540
gtgcaggcgg agcaggagca cgacacctcg gggtaacagt tgtggcaaga atgctgtcgt   96600
tggtggaagc acaaagagc aagcaggaaa tactttgtaa aagaataaaa acgaaaaatg   96660
ttagccaaca tcttctaata gtctgctgta ttcaaagaac tctaggaaat atggttgatg   96720
caaagatgat ttaaggcata gcccggcctt tcaagaagtg tgtggccagt gagtgagatg   96780
ggcttgggac ttacacatct cagaggtggg ggtagaggag gaggaacact gagtgggctg   96840
agaagcagcc agctttcatt gccaaagtgt gtcagcaaac cagaaggcag ttcataatgt   96900
ccccacccgt tcaaagcaca ggccctgtag agtggtgtgg catgtgttgg tggcacttt   96960 caggcctgta acaaggatga aagaacagct tcattgcagc acagtagtgc tggtattcag   97020
aggtatatga aggtcatgga agcatcttgg atatgttacc ttgtgttttg tcaactttat   97080
gactagaaat ctctttttac ttaaatttat gtttgtgtct ttaatgcctg gaatacagga   97140
cttcttaaat tgccataagt atcaacaggt atttgagtta ctaatctgta tagtagcaat   97200
aatagaatcc cttgttttt cttttataaa tgtaatgatt aaatagctac aattgaaaca   97260
ctagagtcag gagtcaagga aaatacccat gttccaggct gtatgttagt gatgtactca   97320
```

| | |
|---|---|
| ctgtgtattc cagtttcagg aataagtctg tttcaatgct ttctgtaacc atttggggta | 97380 |
| ttaataagca agtgagtgta tgcatgtttg ggttaatttc atatatgtgt cttagaaagg | 97440 |
| atatcattga tgtaaatatt ttcaaggctt atcctccaaa aaaatcctgt gatttcttct | 97500 |
| aaattactga tcttttaaat gaccttcacc tttctctcaa gtctcactta agactgggct | 97560 |
| gagtagtcag tttcctgtag cagtaaaaag ctcagacttg agtagccttc cacaggtgac | 97620 |
| gagacttgat ggctgtcagg cagctgtaaa ctgtaaatag agtgtcatta tctcgagagg | 97680 |
| gtgatgctgc cacactgagt ggcctttcaa gttgtttctc agtctgacat gttctgatcg | 97740 |
| tgtgaatgtg aaattggttt gaacaggagt atatctgagt gcagaggaga ttatttaaag | 97800 |
| atattctcat tgtctgcttc ccttctattc ccatttggca gatggtttga tgtcctccag | 97860 |
| aaagtgtcta cccagttgaa gacgaacctc acaagtgtca caaagaaccg tgcagataag | 97920 |
| gtaaatggtg ccgtttgtgg cgtgtgaact caggcgtgtc agtgctagag atgaaactgg | 97980 |
| agctgagact tcccaggtat tttgcttgaa gcttttggtt gaaggctcac ttacggattc | 98040 |
| tttcttctt tcttttgttt ttttatagaa tgctattcat aatcacattc gtttgtttga | 98100 |
| acctcttgtt ataaaagctt taaaacagta cacgacaaca acatctgtgc agttacagaa | 98160 |
| gcaggtttta gatttgctgg cgcagctggt tcagttacgg gttaattact gtcttctgga | 98220 |
| ttcagatcag gtttgtcgct tttaatcttt catccatcat acctgtacct aatttagtac | 98280 |
| aaattaccct gaaagacact gaaatctact ttaaagaaat gtgaactgtg tttccccacc | 98340 |
| ccccatcaat tgctgctgct tatgtttttc atgcacttag ctagtacaag gcccggggca | 98400 |
| tagccagcct cagcaagtcg gcatccttgc cccagctccc tggactcaag gctaacctgg | 98460 |
| ggttggctgt tagggatttc caaaggtttg tcccatccac tcgcctcccc tccaaaataa | 98520 |
| gtttgaattt aaattgtgag atttaattaa gattttattgt ttggggaaca tttttgcaaa | 98580 |
| atctagagag ttagttaaa tggattatca attatgacta taattgatca tctgcagttt | 98640 |
| caggctatct aacaggttag cttacctctt taaaaaggaa tggaatttag ccggacagta | 98700 |
| actgagaccc acgctcctgg agtccacgtg ggagccgcgt ggctctgcac aaacaagcat | 98760 |
| ttgcactctt cccctcttgg ctgcgttgcc ctcctcctgc agttgctgtg ggcactagat | 98820 |
| tctggctagt catgtcccctt catgatgcac agtttcctca agattcgtgc cagttaaatc | 98880 |
| actgcctttt catagtcaaa atttaactgt catctttgac ccatgatctt gggctacttc | 98940 |
| cttatgtggg gtaggaatat ttttgagata gaaatattac acttctctgt ttccttctag | 99000 |
| acaaaaatct gttaattctg ttagtaccgt gactcatctg aaagggtctg tttccctagg | 99060 |
| agaactgagg gcacgtggtc aacactgatt tcccaccatg ggtattgagg tggggtctgc | 99120 |
| tttttttttgt tttgtctttt ttttttttgag acggagtctt gctctgtcgc ccaggctgga | 99180 |
| gtgcaatagt gccatctcag ctcactgcaa cctccacctc ccgggttcac gccattctcc | 99240 |
| tgcctcagcc tcccaagtag ctgggactac aggcacccac cacttcgcct ggcttatttt | 99300 |
| ttgtagagac cgggtttcac catgttagcc aggatggtct ctatctcctg acctcatgat | 99360 |
| ccacctgcct cggcctccca agtgctagg attacaggcg tgagccaccg tgcccggcct | 99420 |
| ggggtctgct tttaatgaaa gaggcatcta ggggtgggct ttgccttggc ttgatgcttt | 99480 |
| gaacctttgt tcacaaaacc tatctgaaga aaatctgtct cagtgggcca ttgctctcct | 99540 |
| caggaaacat gcattgggaa cttcttttcg tttcctttga cactaggagg ctgcctgggg | 99600 |
| agaagccctg gtctatggct atgggcaagc aggggctgag aggagcaggc tctcagtggg | 99660 |
| gcagggtacc ccaagggaag ccagaaccct gatttgttcc attctagtga gaacaaagac | 99720 |

```
tacagtctac cttttcttca gaatttccca gttctaactg ggcatggtgg cacacctctg   99780
tagtcctagt tactgaggag gctgaggcgg gaggatcact tgagtccagg agtttgagtc   99840
cagcctgcac aacatggcaa ggcctgtctc taaaataata gtaataatca taatctctag   99900
ttctagccgg gcacagtggc tcatgcctgt aatcccagca ctttgagagg ccgaggcagg   99960
taaatcattt gagctcagga gtttgagaac agcctggcca acatgatgaa acccatctt  100020 tactaaaagt acaaaaatat tagctgggtg tggtggcagg tgcctgtaat cccagttact  100080
tgggaggctg aggcaggaga atcacttgaa cccgggagat ggaggttgca gtcagctgag  100140
attgtgccac tgtcctccag cctgggcgag acagagcgag actgtgtctc aaaataataa  100200
taacaacctg tggttctgac tcgtcatggg taggaactga ttttctcatg tggtagttac  100260
agactatggt ctccttgggc ctgtctttag tagggaaaaa aggcaactcc ccactctaac  100320
ataaaatggg tggacttgaa tgttttatca aattctttct ttagtcgttc tactggagct  100380
ttttcttcaa tgtagaatat tctgttgctt tattatattt gtctgcaatc tccatgtgat  100440
atttccatgt tgagggagga cagccttgag ctccccccgt gctgcctgcg gccctgcagg  100500
catgtggaat tcatctttgg cctgtgcttt cttctgggtc ccggtgcccc tgcccgcgag  100560
gctcatgtcc agctgcccct ttgtggtggt gtgaggtcat tcctgctgtg agcgctctgg  100620
tttcatgttt gttccgattg cctttcatca gccgatcccc tttctcccag ttcttaagat  100680
tcaatacagt gacagtttta tgaacaagaa tagaactaga acagacaagc cattgaactc  100740
tatgctgata atgatttacc gagcacctgc tgtatgtttg cattccgcgc agaggctctg  100800
agaaagccgg gccatgtgct ccatgcttta tcggtggaag ctcctcatca ggttgggaaa  100860
gctgacagct gcgtagaata ccagtgtgac acaaagctgg ctcccgtgcg gcccttgcgt  100920
gttgcctctc agatggtggg aggaagaagg tcgactcctt tggggatctt actaccaaac  100980
cagtttcagg gaatctgcta ccctgtctgc cattaatggg aacagatgag tccccaaggt  101040
gtacttctgg gtattgtctg atgtcgcttg gaatttatta cttgttttc caatgaggtt   101100 tcacctcagt gtgtagtaaa gttgttgagg ggattcctgg aggtgttcta cagttatcta  101160
ggctgatttc agaatagagt tatgcttata gtccaattta tcagctgtca agaaattcat  101220
ttaaaatttg tgcagataag caggaggaaa agaaacctgg tttttacgtt ttaatcctat  101280
tattgatgta aaattttact ttccttcccg taggtgttta ttggctttgt attgaaacag  101340
ttcgaataca ttgaagtggg ccagttcagg taatagcatt tgttatttt agagttttt    101400 ctccttcttg tgtacttaca tgtaatttag gttattaaga tgaatgttta aactactgtt  101460
aggcattttt gctgttttct ttaaatggaa atctgattaa catgctgtgc attttgctt   101520 ctcttaaaaa ttaatgtata tctcaagact tgtttggaag tagttacata tctgaaaatt  101580
ccatatgttg tcagttttca ttgcacattt caaagcattt aattatgttg acagatggcg  101640
gaatgaaatc ttgtggtgga gcactagttt ttaaatcttc ttagagaaag cagttttat   101700 ataaggttgt ctttagtaat tattatgcac ttgtattctc tgcagctttt ttttgctaga  101760
tgttgaggtt ttaatacttc ttgctagtcc attacaggtt tataatgatt gaaagttaaa  101820
attctttagt acctgaaata cttaataaat actgtagtta ggaaaactta gtgcagaagg  101880
aaagtgttcc cagattccct ggggtctgga agcatagcgt tgttctaat cacgtgacac   101940 ctccactgtg ttttggggca agttactttt tctcttttga gtttcaattt ctacaagagc  102000
aaaggggcag agagagctag ggagattgta gctgctgtgc ctctgtgccg tcaggtgcct  102060
```

```
tctacctgct ccctctgaac ctttacacct gtcccggctc tgcacaaggg cacagatggg   102120
atgcactgtg gcagggatgg gcttagagta gatcactgac acctgttagc ttcatgtgcc   102180
ctcatgaatt attttatgtt gcttatattg atatgtatct taattttaaa agaaaggtct   102240
aaatggatgt ttttgtttct agggaatcag aggcaatcat tccaaacatc ttttcttct   102300
tggtattact gtcttatgaa cgctatcatt caaaacagat cattggaatt cctaaaatca   102360
ttcagctctg tgatggcatc atggccagtg aaggaaggc tgtgacacac ggtaatggga   102420
cacatctttc actgtcgtct tcagtgtcac gatgtgcttg gcagtgttcg ttttcttttt   102480
tttgttgttg ttgtttttttt tttttgaga cggagtctcg ctgtgtctcc caggctggag   102540
tgcagtggcg tgatctcggc tcactgcaag ctccgcctcc cgggttcacg ccattctccc   102600
gcctcagcct cccaagtagc tgagactaca ggcgcccgcc accacgcccg ctagttttt   102660
tgtattttta gtagagacgg ggtttcacca tgttagccag gatagtctcg atctcctgac   102720
ctcgtgatcc acccgcctcg gcctcccaaa gtgctgggat tacaggcttg agccaccgcg   102780
cccggccggc agtgttcgtt ttcatacacc cactttcaac tttgtcagtg gcggccgtgt   102840
gcgtctcagg ctctgcatat gtgtctgtgt gtctgtgtat gtgaatgtac tggttagaga   102900
cgtttcaaaa gagaagagag catattcttt actctcagca atttgtaatc ttctcaggga   102960
aaaaagttc aagaaacagt aagatagcct aaggtacaga tagattctga atataaagtt   103020
cctgttcatt cacacgaaac actaaaagtt cttcacctga tcttagccca aaggccgaga   103080
agcgatgaaa cactaaaat tcttcagtcg aacttgctgt gaattaaatt ttgatctctc   103140
atccaggtgg tattggagat acagtttgac ttgggttcag ggctttctgt tttgcctgat   103200
gattattttg ctggagctta aataaagaca gggctccagg agatggccag ctgtgcaagc   103260
ccccagcctg tggaaggagc tagcctggtt ttatgaatga gctgtaaatc tttctttgag   103320
cttttgaac tggtcttcca gcattgccct attgacccct ccctgactcc tttgctggaa   103380
tccgtaggct tttgaacttt gacagggaca catcctaaga cccttgcaaa ccctagatg   103440
tgagaatggc actactacat agagtctttt ccactcagcg tgtgtgcaga agaacatcaa   103500
ccatgctgtg tggcgaggca gggccttggc tgacctctca gtcaaggcct tagctttaca   103560
gagctaagcc agttagtctt tgccatggct tcacaatggc ttcaggttca cactgccaaa   103620
gtatagatta ttaaaggcat aggtgtttgg tttcctgcac ttggagggtc tttggacaga   103680
aaatcagtag gcagccaaag ccagtacttt gcgctgggaa gcttggtcgt ctgtgagagg   103740
gtcagagagg atacccatgt gtgcgcacca ccgaagggtc agtgagtctc agggctctgc   103800
gtgcatgtct cagggctgga gagagtgtgt cactgagagg tcagagtgtt tgtgcgtgtg   103860
tgtcaaagag ggttgcagtg tgcccttcac tgaggggtca gagggtgcct cacgtgtgtg   103920
tatgtgtgtg tgtcactggg tcagtgagtg ttcttgtgtg tgcatgtcac tgagaggtca   103980
gagggtgcct ttgtgtgtgt gtgctcatgt gtgtgtgcgt gtcactgagg ggtcagtgtt   104040
cctgtgtgca catgacattg agggtcagag tgtgcctctg tgtgcgtgtg ctcgtgtgtg   104100
catgcgtgac acctccactg tgttttgggg caagttactt tttctctttc tcttttactt   104160
ggtcatctgt gagagggtca gagaggatat ggtcctgtgt gcgcatgaca ctggggcaga   104220
gtgtgcctct gtgtgtgtgt gtgctcctgt gtgtgtacgt gtcactgagg ggtcagtgtt   104280
cctgtgtgcg cgtgacactg aggggcagag tgtgcctctg tgtgtgtgtg tgtgctcctg   104340
tgtgtgtacg tgtcactgag gggtcagtgt tcctgtgtgc gcgtgacact gaggggcaga   104400
gtgtacccgt gtgccaatga aaggcatttc ttatttttt ttatatgtgg tcacagtaga   104460
```

```
ccaattaatt tattttgact cctgttttag accaaaataa gacctggggg aaagtccctt   104520
atctatctaa tgagagagtg agtttactta aaaaagcata ataatccagt ggctttgact   104580
aaatgtatta cgtggaagtt tttattgtct tttcagatga atcaaataga ttattctcga   104640
gaccaggaat ggtgctgttt tggttatttg ggaagtttta tcattttcaa attgaccttt   104700
gaatttgagt cacctttttt cagaagtggt gttaaattac aggagcccta ggttttttt    104760 ccttttttag aagccatcac aaaatgatcg gtgttcagag gaaaagcttt gatcttccac   104820
aatggtataa tgattgataa ccttaattca tctcttacca taaaccaagt atgtgtaagg   104880
gttttcttta tttcttgata tcattttgta gatgttgaga gcagttttcc aaatgtaatt   104940
tccatgaaat gcctgatgag ggtacccttt tgtccccaca gccataccgg ctctgcagcc   105000
catagtccat gacctttttg tattaagagg aacaaataaa gctgatgcag gaaaagagct   105060
tgaaacccaa aaagaagtgg tggtatcaat gttactgaga ctcatccagt accatcaggt   105120
aagaggaatg tgtgttggaa ctgtcgtgga tactttattg acccgtacag atggaaggaa   105180
gtgccatgtg gtaacactca ctgttaaccg tgctactttg aactaggttt gagctttctg   105240
aggcctgggg agatgctggg gcagcggcgg gtgcagggg  aggtgggggc ggggacagg    105300 cgtggtggca ggaggtatca ttggtgttta tccttccttt ttttttttt tttttgagat    105360 ggagtctcac tccgttgccc aggctggagt gcggtggcat gatcttggct cactgtaagc   105420
tccatctccc gggtttaagc gattctcctg cctccacctc ccgagtagct gggattacag   105480
acatgcacca ccatgcccag ctaatttttt tttttttttt tttgtatttt tagtagagat   105540
ggggtttcac catgatggcc aagctggttt caaactcctg acctcaagtg atccgcctgc   105600
ctcggcctcc caaagtgctg ggattacagg cgtgagccac cgcgcccggc ctggtgttta   105660
tctttaaagt gggtacagcc acaggggttc acctgactcc tggtctgaga gtcacaagat   105720
cgttcaagat agtgaggccc tcttttccaa aacaaggacc aaaaatcagt tgacagtgtt   105780
ggtcaagatg gtagaaacct aaaatgatag aaatctcaac tctgaaataa aactttatt    105840 tgcatatta tttaccacta tttttgacata gggctaaggt cttttctttt gagctagttt    105900
ctggttttgt tttcttaagg tggcataaga attcaaagac attttgagga aaactgagtg   105960
tagaaatctc tctttttaa tgacttctct tttctttcag cttgtactgt tgtgtagccc    106020
tcgcttattt tgtcaattct ttttagctgt ttgtctttga atcttatga agccatagct    106080 tttctcataa gaagcagcac tttctttgtt cattcatatt ttaattaact cctgtagtat   106140
ttaaatactt aatgcctaat taaatcacat aattgcaatg caaaagtaca tgtatcataa   106200
agaggtctga aaatgagcaa ctggcaagca ggtggctgca ggcagagctg ctgggtggg    106260 tgggtgtcct ggagaagagc tcatcagctg catgttcagt gagctctgga tatctctgtg   106320
taaaaatgat cactaataaa cttgtgctca actgtgcaca cttccggaaa ggagatgctg   106380
ttcagtagat tgcctctgca gagaacacag aattgaaggg aatttccaca aaggcggtga   106440
gccgcctgca gaatagttta gtcaaggctg tgtttgaatt ttgccaaaga ttaatataca   106500 tttattttt tcatgctgtg cctttttctct gattgtgaaa tattataaat tctatccaaa   106560
taacaatgat ggcaagtcct cctgagcaaa gtgtgcagct tgcatgtgtc ctagaggaac   106620
tcgtgtttcg ttctgattcc cctgcatttc tcatgtcata gagtggggat tgcatccgtg   106680 tcccctgtc ctcgtgggga tcacatctgt ttggatccta gagtcttcaa gctgagctgg   106740
gacaagtgta acagatggac acatgggggt ggaaaggcgc ctctaggcag cagactctct   106800
```

```
aattgtgcac actcttatag gtgttggaga tgttcattct cgtcctgcag cagtgccaca    106860
aggagaatga agacaagtgg aagcgactgt ctcgacagat agctgacatc atcctcccaa    106920
tgttagccaa acagcaggtt tgtccccgca gccttggctc gttgttgcat agtgatggta    106980
gcttaaggtc cttgtgaaag gtgggtggct ggaatcagct cttccttcaa tcctaatctg    107040
tgctttgata gcagttctcc atgctagtca tggggcaact gacttcattt cttctcataa    107100
tgccatctca ggttggtatt gcccacctcc tttacggggg gaactcatga ctcagagagg    107160
ttatggaggc gatcaggcag cacacagctt tagagtgctg gggtgagggc gggccaagtc    107220
tgactctaaa gcccgaaccc ttacctccta tactgcctcc tgcattctgg tcaacgcagt    107280
gttttatttg gtggttacat ttttgttttt gttaccttac tacttgtaat ttagcagttt    107340 tccttttcctt tccttttccct tccttttcctt tttccttctt tctttccttt ctgacagggt    107400
ctcgctctgt cactcaggct agagtgcagt cgtgtaatct cactgcaact tccgcctccc    107460
aggttcaagc aattctccca cctcagtctc ccgagtagca aggaccacag gtgtgcacca    107520
ctacacctgg ctagtttttt gtattttttag tagaggcgag gtcttgctgt gttgcccagg    107580
ctggttttag actcctgggt gcaagtgatc caccaacctt ggcctcccaa agtgctggca    107640
ttacaggtgt gagccacctc acctggccta ttcatcacta atcagaattt ctatgatcaa    107700
atgacatgaa ttgttgtttc cacaaatgca gtggaaggaa atggcctggc agtaccaatt    107760
ttggaagcaa caggccccca gtcaggcaca ggacactgtg cccccagtgt agcagcatct    107820
ctatctcaca gagaaggtgg tgcgtcctcc tcaaggcagc tccgccagaa aatctcatga    107880
gcggcctggc acggcttgag gttgccttttt aaatggactc agcaaataca tgtttgttca    107940
tcttgattat acacaataaa caactactct gtatagtaca agtagtccgt ggttttttgc    108000
atttgattta aaccagagac atgtgatatt gatggttact gccttcatga ctgcaccccc    108060
atcctgattt cataatagaa tgttatcctg agaccagtta gacaatggaa cagggatctt    108120
ggcttctggt gagactgaca gcagttttag cgtggtcagg gtctccctgc ccacagatgg    108180
tgttagaatg gtgctctgga agctttattc cattatcttc tgtgcataat ctgagtagag    108240
tggagattga aggcctgaat gcatagtaaa tatctgactt aatttctgcc gcaatggaaa    108300
ttgtgcgata aaacatttat gaaatgcgta gcacagcccc ggccaggtag ctcagcacag    108360
gagcctgttg cattcagaag tagtgctaga tactatcctg ttactggcag tacatacatc    108420
agtgatcaga gcagattcaa gaaagacccc ctgccttctt ggagtgaagg ttttgttggg    108480
atggggtgag gggacagaca atagaaaaac cagtgagtga agtctctacc atggcagctg    108540
atcagggacg ctgtacagaa gaatcccgga gggaagagag ttaggtggtt tcggcggcgg    108600
agtggcattg ttcagttggt gatgagaaac gttgtggtga tctggtgaca tttgagtgaa    108660
tttgcagaaa ggaaagatac aagcctagga gatacctggg ggaggagcat tccaagaaga    108720
gcaaacagct gcaaaggccc tgggggggaac gtgctgttag ggtaaaagca atggggtgg    108780 aggagtgggg cagctatgcg gagggaaggg agcgaggcct ggtggggtga ggccagcatg    108840
gaggagcctg agaggnnnnn nnnnnnnnnn nnnnctccc aaagtgctgg gattacaggt    108900
gtgagccact gcaccccggc ctgttttttt tagagacgga gtcttgctct gtcgcccagg    108960
ctggagtata gtggtgcgat ctcggctcac tgcagcctcc gcctccggga ttcaagcgat    109020
tctcctgcct cagcctcctg agtagctggg actacaggcg tgtgccactg tgcctggcta    109080
attttttgta gagacggagt ttcaccgtgt tagccaggat ggtctcaatc tcctgacctt    109140
gtgatccgcc cgtctcagcc tcccaaagtt tacaggtgga ttacaggtgg ctcccacacc    109200
```

```
gagccaagag tttgcatttt taacaaattc ccaggtgata ctaatgctgc ttttctggga 109260
ccacactttg agactcagtg atagaaagat ttattggtag gatagtaaaa taggagtaat 109320
tttttttttc cacaaaattg gcaattgggg gaaatttaat cttcctttt tctttagcta 109380 tgacttattt attctgttta ttttaggcat ctgtgagcac tgttcaactg tggatatcag 109440
gaattctggc cattttgagg gttctgattt cccagtcaac tgaagatatt gttctttctc 109500
gtattcagga gctctctttc tctccatatt taatctcctg tccagtaatt aataggctaa 109560
gagatgggga cagtaattca gcactagaag aacacagtga agggaaacaa ataaagaatt 109620
tgccagaaga aacattttca aggtatgctt tctatctgag cctgtaacta acccatgcct 109680
tttgggaagt cacttggtat ttcatgatca gttaagtctg gaataacacc tggtctcgct 109740
tcagttctga gctgggtaaa gaagtctgta tcagtgtaat tttctaatcc atcctggctt 109800
atctgtggct cctgtttcat acctctcttg aggttctgtc atgttctgtc tcttgtcctc 109860
agcagagatg ctacagcagt ggcttgctca ggtaggacag ggcagtgggg tggctgtcct 109920
gggggcaggc agtaggcgtg cattgccttc agggaagtta aacccaaga gaagccacag 109980 aaagtgaatc ttatattctc accatgtgcc ggcagtttta cacgctgtca gtaataaaat 110040
acttctccct gcaaggcaga ctgcctccag taaatacctg tagtatcaaa tcctgtcttc 110100
cctcataaat tgttgggaag ctccctcagg acagtggtca ggcactcgta aatgcttgct 110160
gcctagatgg gtccctctcc acctctgctg gattctgagc attcactgag ttagagctgc 110220
tgctgcaaat gtgctacttc tgcctgagtg gctgtgactt catgcagccg tcatttggtt 110280
tgtcgtcagt gaagatgccc tgtgttgtcg atggagataa gcccagtaag cctgctgggc 110340 accttttgt ttgcgggttc agcaggcagc ccgtggcttt ccctctgttg cattgaagca 110400
gctggctaaa actgatggta cattaaattc ctatgacaga tgatcagctt gtatttgtgt 110460
aatggtgtac agtttacaaa gcttaaaaaa atactacctg ccatttcatc ctcagcgagg 110520
aaggtgatac acagagagga aaagtgactg tatccaaggc gatggtgtta cgcgtttcac 110580
tttaacggtt taatgtactt tacttctatt tttactttat atttaccaca tatattttca 110640
tatatacttg gcataagtgc tttatagtag tcacctaatt cactgtcacc cttttgttt 110700 cttggaaggt ttctattaca actggtgggt attcttttag aagacattgt tacaaaacag 110760
ctgaaggtgg aaatgagtga gcagcaacat actttctatt gccaagaact aggcactctg 110820
ctaatgtgtc tgatccacat cttcaagtct ggtaggtaaa tcacattagt cttcctcgag 110880
tatctcaatt ccccattctg cactgtacgc tcttagagtg taggagctat gctgcccggt 110940
agaaactctg tcttgcccag agtgccagtt gaaaatgttt gttgctataa gagtcagcct 111000
gatccatatg acccagcagt tctactcttg ggtatgtacc caaaagaatg gaacgcaggg 111060
tggtgaaaag atgtttgcat gccagcgttc atagcagcgt tattcacagc agctaaaatg 111120
tggaagcaac tgaagtgtcc attgatggac gaatggataa gcaaatctg gtgtatactt 111180 agagtggaat attattgaac cttaatattc aataaccttaa aggacattc tgacacgtgc 111240 tacaacatgg gtgaccccta aggacattat gctaaatgaa ataagccagt cacaaaagga 111300
caaatactat gtgattcctc ttatatgagg gacctggagt acttaattca tagatacgga 111360
cagtagagtg gtggttgcca ggggctgcgg gggaggggag ttgttttac aagatgaaaa 111420 gagttattct agaaacgaat ggtggggatg gttgtataac agtgtgaatg tatttaatgc 111480
tactgaactc tacagttaaa aatagttaag atgagccagg tgtaatggct catgcctgta 111540
```

```
atccaagcac tttgagaggc caaggcagga ggactgcttg agccaaggag tttgagacca 111600
gcctcagcaa catggcaaga ccccatctgt acaaacagac tagccaggga tagtggtgtg 111660
cctgtggtcc caactactca ggacactgag gctggtggac cgcttgagct caggaggtca 111720
aggctctagt gaagtatgtt catgcctctg cactccagcc tcgactacag agtaagaccc 111780
tgcctcaaaa aaacaaagca agacaagacc caaaaatggt taagacgggc caatcacact 111840
ggcttactcc tgtaatccca acacttcggg gggtcaaggt ggaaggatca cttgaagcca 111900
ggagcttgaa accagcctga gcaacatagt gagacccta tctctacaaa gaaaataaaa 111960
aactagctag gtatggtagg cacatgcctg tagtcccagc tacttgggag gccgaggcgg 112020
gatgatcgct tgagcttgag accagcctgg aaaacatagg aagagactcc atctccacaa 112080
aaataaaaaa aataaaaaaa ttatccaggg gtagtgacgt gagcctgagc ccaggaggtc 112140
aagctgtagt gagccacgat cgtgccactg cactccaacc tgggcgagag atcgagacca 112200
tgtctctaaa gaaagaaaat tacaaggaca gtgaacccaa gaaagtcagt tgtgcagcaa 112260
gcatagaaag caaccagtcc aaattaggac agtgtgtttt ccaagaagaa cgatcatttg 112320
tcatgagaat gctttgcttt aaataaatga gtaaataggt agaagactag ttctagggga 112380
taggcacgtc tttcttctct caacaagaaa aagaaaggc aattctaatc tctaggaaaa 112440
gcaaatagca ttaagtcatg gtccaaatat gaggcaaacc aaaatatggc ttgattttc 112500
agcagttgat ctgttggaag cccttgatat taaaaaggtt ctcctttaag cagtttaggg 112560
gtcatgatca aagacccata gaaagagatg ccatcctttt aggatccttg gctctcttgg 112620
gaactgtatt cacgtagtca taatgtaagt attgcttgag ctttcatttt tggaatcaat 112680
atgtgactga aacactgaag acttactgac ttaattatgg tttcagaaca gaatgaaaat 112740
gtcttcagtt ctgatgaata taaaaggaaa actaaccaag ttaatttggc aagtagatgg 112800
tagagatggg gtgggaatgg aagggcact aaaatcctta cctagcattg ttggagttac 112860
atgattacat catctgaagt tgacagacca aaatatagag gcttcaaagg tatccagata 112920
gagctaaaca tgtaactcag attgttagga ggtagtataa atgagccaaa tctcctcttt 112980
attaccgtag agttaatggg taatgtctaa agttgtctga agtctgtaaa tcatgacaaa 113040
ttatgatgtg gtgattgtat tcaacagtct ttcagttgca gggataaaac cccaatttaa 113100
actagagtaa gagaaagaat ttgttggttt gagctcctgg aaagtgcagg caagggtagt 113160
tggtaggact gcatctagtg ttataattct atggtctgca ttgtatattt atgcatatca 113220
gctctgcttt cttctcttaa tttgtatact tttaaaattt tattttaaag atagggtctc 113280
actttgtcgg ctacgctgaa gtgcagtggt gtgaagtgca gtgcgaggct cgctctagcc 113340
tcgaactcct gggctctaga gttcttcctg cctcagcctt ctaaggagct gagacaatag 113400
gcattcacca ccatggctgg ataggtttta aaattctttt gtagaaatgg aggccttgtt 113460
atgttgccca ggctggtctt taactcctag cttcaggcga tcctcctgcc tctgcttccc 113520
aaaatgctga ggttataggt gtgagccacc gcgcccagtc tcatctctgc ttcctgtctt 113580
agcccctcaa gtaggcatgt gattggcctt gcataagtca tatgggtgac cataaccgc 113640
tgaatgctct ggtccacctg gccaaatgg gagactggac agcattccat tgacgaggag 113700
gtggggcttg tctccgggag taagggagag gagcgcatgc agtaactgat ggtctgctgc 113760
acgggatagc ggcgcatcag ttagaatttt gaaggtaact accagaactg aaaacagaaa 113820
agataacaag tagttgcctt aaaaagggat ggggcagggt gcttttgtga tcagaaactc 113880
cttttctctta ttggattttt gtacacattt tgcggacata cccttagagt aaagataatt 113940
```

```
agcattttca gccttggtcc atttgaggag tggcccgcct ccctgctagc aggctctggg   114000
tctgctaggt tcagttgagc atcctggctc ttgcctgcat ggaacttaca gtcagtgcgt   114060
cagtatcaca agtcttaata tttcctatga aggaaaacaa tagtgcagtg acagacaaaa   114120
tgggtgggcg ggcagaggca ggatttccga ggggagaag tagctagctt tttgcagaga    114180
aatgttccgg cacccgagag agcagctgag agtgcaggca ggcaggaggc gagtggggcc   114240
tggccgcaca gcgtcacaga gtcccagaga aaggggcctc ttcatggcca ctgcattcag   114300
ctgctgtcac cctccacaca agccatggcc aaaatttaat tttgataatg gactctagtt   114360
tttgagcctt acttgctatt attgaaagaa ttttcttgtt tcttttttaaa gatcttcaga   114420 ttatgcttca ctgaccactg taataagttt aaagttgaga aaatatgcct tgttaatgaa   114480
tgataggtca attttagtat attggtcatt ttaatatttt gccaccagtt ggtttgaatc   114540
tgatgccagg aggagacagc ctcatttctt ttttttttt tgagacggag tctcgctctg    114600
ccgcccaggc tggagtgcag gggccggatc tcagctcact gcaagctccg cctcccgggt   114660
tcacgccgtt ctcctgcctc agccgcccga gtagatggga ctgcaggtgc ccaccatctc   114720
gcccggctag ttttttgtat ttttcagta gagacggggt ttcaccgtgt tcgccaggat    114780
ggtctcgatc tcctgacctc gtgatgcgcc cgtctcggcc tcccaaagtg ctgggattac   114840
agacttgagc taccgcgccc ggccgagaca gcctcatttc taaggactag tcttgccttt   114900
gtgggataag ggtggtgtgt tctgtgtctt tctacatgtc cgagcgatct ctgcagctca   114960
aaggtgttca ctgtcttatt gtgctgattt cctcttcttc catctcaaaa ttgaggcaaa   115020
atactttcac tattgaagtg ttgtccagta gaacttccag cagagacggg atgtctgcac   115080
tgtctaattt agttgccttt agccacgtgt ggtgttccat acctgaaatg tggctggtct   115140
gattgggtag cttaatttat aatttattt aattttaatt aagtttgaac agctctgtgt    115200
ggatagtggc tcctgtatga aactgcaggt ctgttgagaa gcatctttac tggagagagt   115260
ggagggcttg gaggggcac atgggtttcc tgctgctatc tttgaccta tttaattggc     115320 ccaacatttg caagtaagtt gtctgtgcgt gtatatataa atgtctgttt ctgtcttctt   115380
gtttcgtttg actgcattta tttgaaagac actaggtggc agaattactg tatttggttg   115440
gtttaaagat aagagttgaa gtaatccgtc ttgtgttttt atatcggtaa ggtgtgttta   115500
gcatgtaaaa ttggtaattc gtattcacgt actgcttaaa caaaggctaa gaattccacc   115560
catacactga aaatggagac ctttgaattt gtccatttca ggcattactt cttaaacaat   115620
acctggttca ggaactagtc agaatggcac ccttgacttt tagtttcctg ctttttcctt   115680
tgttggggga ggagggtatt tagctcaaag gtgtgtgcct atttcagatt ccatctagga   115740
gaagcagaat agccaagaca gatacctgtc ctcctgttta caacatttgg ggtaaccagc   115800
atccctctcc tttggtccaa gatagacggg tttagaaaca gatgatggta ccagaggccc   115860 cggggggtgga agcatcagct ttgtttgttg tccatgtggc tggattagag ctgtctggct  115920
ttgtagcctc aacacggccg tccagctttg ctcagtatga ttttcaagga cacatcttgt   115980
gcccttccct gcctgccatc cagaccatac ccagtcaggg tggcaggaac tgctgcccct   116040 tcctcccctga gtcctggtcg tgggtggtgg agaggtacca tgaccctcac ggaggcctgc  116100
tcacccttcc tctgcggcag aggcgatggc tgcacgacag ctctttccct gtcctttcca   116160
aagcgtccat ggttccactt gatggggcaa agcaggaata ctggaagaga aagtggtcct   116220
ttctatagta ataaagttga cattgattca agttcaccct tggggaaagg acagggccac   116280
```

```
taacaattat aatgctggaa gcagtggaat tttctcatgg gtatatagta ggtttaattt   116340
taattatccc agttaattct tagaacagct ctgtgaagta tttccccctt tctgcttgag   116400
ttctaaaaga tcctatgcca aaaccaagaa tgaaaaccca agcattcttt cttgctcatc   116460
gatctttctc tcatcgggcc acttcttggg ttgttagtgg tgaatgtagc cgctggcaat   116520
tgcagaatac ccaccatggg ccccagtcac tgtgtggcgt ggattagagg tggttctctc   116580
catgtcatag ccgaacaagc ccagcccaga gaggtttctg ccctaggagc tcttgatggt   116640
ggaattggga tgcgatccca catcctgcct gtgttttgaa agcagcattc ttcatttcca   116700
gttcctgctt ccgttgttcc ttttagtatt tctttgttta actcacgaaa tcaggacttg   116760
gggagctgct gcgtgcagct gtagctgttt ctctgggtgc agcctgcatc caccttcctg   116820 ccccctcct tactgccatc gtggtctctg ggcacttggt ccctttctct tcccccgagt    116880 cccctttggct ccctgtgcc acccttgtga tccacaggct ctgccttctt tctgtctgag   116940
actgctgctc atcactaccc gggacccttag gaagggaggt tcctccgaga agcatcttct  117000
aatctcagcc acgttctcaa tgccgctgtt ggctttgtta aataatggta gctactgtaa   117060
caaataaacc aacatttcca tggcttcaca ccagagaagg ttgtttcttg gttttatgac   117120
aatgtgttga gggtgtttct ggttcacgga tggttttcct ccatgtggga attcgggac    117180 ccaggctcct ttccttcttt tggttctctt ctctgggcct ccacatcctc tgtgtctagt   117240
tggggacaag gagagggaag gtagagaaga aggctctgtg gccttggaca agtgacatgc   117300
atgcctttgc tggtgttctc tgctggtggt gggtcacagc cccacccccgt acgaggggac 117360 tgggagacgt cgtcctgctg cctcccagca gcaagcagca ctgtggtctc tgatgtgttt   117420
tctatgagga taaaaacagg cgattccagg atgagtaaag tcagggaaac ccttggaagg   117480
aggtgaccag gcaggtgtca ccatgggatt agtggtggct tcagaatgag ccgccaagag  117540
tgcagtgcct tctaaagctt ttgctattct gatatgccca caccatgccc agcaggtgtc   117600
tgccttgctc tccgcagaga gagtgatgaa tccttctcgt gaacctctgt cccgttcttc   117660
ctccctccac ctggaaggga ccctgggttc cttgaaacat cccggtggaa caggggacct  117720
tctgtcctgt ccctaagctc agcctcatcc tcctgccagc ttcccaaccc ctcttatgtc   117780
tgcttcctca cgccacatcc ttctggattc tctggaattg aattttgcct ttgatgctta   117840
tttaaaaata tccattgcag gccaggtatg gtggctcaca cctgtaatcc tgtgcacttt   117900
gggaagccaa ggcgggcaga ttgcttgaac ccaggagtct gagattagcc tgagcaacat   117960
ggtgaaatcc tgtttataga gaatacaaac agggcatggt ggcgcacacc tatactccca   118020
gctagacagg atcgactgag ccctggaggc cctggaggcc gaagctgcag tgggctgtga   118080
tcgtgccact gtattcccgt ctgggcaaca gagtgagacc ctgtctttaa aaaaaaaaa    118140 aaatccattg catacttcac cacagtgaaa cgtgtgtctt atctttcctt tccggcctgt   118200
agctgctctt ttgcacttat agccgcacta agtcaacctt aaattaaaag caaaccagca   118260
cttcctgtgc tcttctgctt ccttcatgag ggtccctccc tctgtgtacg ctccattctc   118320
attgccccgg tggtttgttt ccctcttggt tctcaagctg tggcagcctg cctcttatca   118380
tctttactga aaagtccttt gcagaggctg cctgtgttct ttctttctcg gtccctctca   118440
tcctgggccc cccagcttga tgctgtgggg ctgccctctc ctcactcagt agcttgcagg   118500
gtcttctctg tctagccact taattggttg tgttccccga gttgctgtcc gtggtctctc   118560
gtcactgttt tctctgtgtc tctgcctctc tcctcggcct tggtaggtct ctccctttg    118620 tgaccctggc tgttgctctc gtggacaact ttctcttgct ggtccgcgta gtcctggcat   118680
```

-continued

```
ccagcttctc aacatgggac ttgtcctgcc agtacctcag acttacgctg aaaattgaac  118740
tagcaccact gtcactctcc aggacctctt cttgttaatt aggtcattag ggatgttcga  118800
aatcccagca tcattgtcca ttcctcctcc tgccagccca gggaccctga ccttacctcc  118860
tcctctccat ctaccgggag gtggctctca gagtccgtct catcttccac ccgaacttcc  118920
ctacagactc cccgctgccg ccccaggggc tgagcacttc ctccgtgcct cgtgcagcgc  118980
tgagcccttt acctgggttc tcctgttttgc tccttattgc aacccgtgtgg acagatactg  119040
ctcttaattc catcttaaac ctgaggaagc tgaggcccca ggtaaggtgc atccaaggtc  119100
actcaggtag taaactgtag agccacgatc cgaaccaggc agtctgattc ggagcctgtg  119160
ttgacactca gccacctaga acacagctca gattgtgggt ttctattacg tgttcaaaac  119220
cgccacatcc cgggtctgtc cctgcacgtg ccctgtggcc tggctgcatc ttcttgaagg  119280
cagcgcatgc gtcttcactc aaggggccca tgcaggaaag agggccccac agaaggacga  119340
ggccagtgca gaatgggctg gaggggacga tgctgactgt gaagcaagtg tagagaaatc  119400
ccaggaaacc tggaggaacc agagacaggg cattagaact catcgttgtg acctggtctg  119460
tattctctga gtgtgctgct gcttttagct cgcttcctta gtctcaggtt gtagtttaag  119520
gcattgtgga gccctaaaaa gcctctactc tgttttgcc tgtttcggga ccctttcact  119580
tcggggatgt gttgaatttt ttgttttttgt tttttaattt tttgagatag agtcttgctc  119640
cattgcctag gctggagtgc aatggcacaa tcttggccca ctgcagcccc tgcctcctgg  119700
gttcaagcga ttcttgtgcc tctgcctccc aagtacctgg gattacaggc gcccgccacc  119760
acgcctgacc aatttttata ttttttagtgg agacagagtt ttgccatgtt ggccaagctg  119820
gtctcgaact cctgacctca agtgatccac ccacctcggc ctcccaaagt gctgggatta  119880
taggcatgag ccaccatgcc cggcctgaaa tttaatcaga aataaaattt tgaccccaac  119940
aatgatgcta ggaggcccag atctggggga gagggcaacc ttggccagat gggcctgtct  120000
ctgtttccca agtcttgctg cctctccctg ctgtgctttg cagcctgtgc atgtctctgt  120060
gcctctgatc ttgttcatcc agaggagagg atagaatcaa gtcatgattc ctggagccct  120120
gagaagaatg ctgtggagaa acttgcaggt agactctaac tgagtgtgtg gctgaggtgc  120180
cagcattgtg tgtggggagg ctgaccgctt ggcctgccca ggcccaggat gctccatggc  120240
cgggcacaga ggcaacttgg ctgtcaggtg tcaggagcct gcagagagca cacagcctgg  120300
accgcagggc gctgcccatg ttcttccagc acctgtcctg cttgctcacc tggcctctta  120360
cagcatttct gtccctcagt tcttagcaag cccaggagct gttcaggttg caggtgccg  120420
agtgctgttc ctgcctgtgt agctgtggct cagtcctgtg ggggccccg ctgtggcctg  120480
agtgcagtga ttcgaggtgc cgagtgttcc ctgactcgtt ctgcaggagc tgtgttcaga  120540
cttttcacagc tcttggcttg gagcttctgg agggcttggc attgccaacc agtgcagggg  120600
tggacagtgg gagaggagga atgctagctt tcttgaccag tccattaaat aaatgggata  120660
ttggccgggc acggtggctc acgcctgaat cccagcactt gggaggctg aggcgggtgg  120720
atcacgaagt caggagttcg agaccagcct ggccaacatg gggaaacccc ctctattcta  120780
aaaatacaaa aattagctgg gcgtggtggc agacacctgt aatcctagct actcgggaga  120840
ctgaggcagg agaataggtt gaaaccagaa ggcggaggtt gcagtgagcc aagatcatgc  120900
cactgtactc ccacctgggc aacaagagtg aaactccatc tcacaaaaaa aaagcagaa  120960
tgtctgtttc tgcttagaaa aatcagaatt ttctaaatgc caggtgcttt gaatatgtaa  121020
```

```
gtatgggaaa caactcagcc tgtttcattt ttatgtaaaa tctccacgta gccatgtggc   121080
actggaccga gatgaaagca aagacatttc tccttctgaa ctttgtttct aggaatgttc   121140
cggagaatca cagcagctgc cactagactg ttccgcagtg atggctgtgg cggcagtttc   121200
tacaccctgg acagcttgaa tttgcgggct cgttccatga tcaccaccca cccggccctg   121260
gtgctgctct ggtgtcagat cctgctgctt gtcaaccaca ccgactaccg ctggtgggca   121320
gaagtgcagc agaccccgaa gtaggttcat aatgcccaca gcccagggcg ctggcccagc   121380
actctgtcct gagactccca gtaacctgag attgggccac cgttacagca ttttcatttt   121440 ccatttttg tgagggcttg taaaatttct gctgcatatt aatattcctt tcatggacag   121500
catattgtag agacaaacat gcggtccagc caaaggcatt cagaatagca attgcttcct   121560
aaatgtgatt ttctttggca agttctttga caccattcca tcttgtggat tatgcttgtc   121620
atgctgtgtg gctcctacta agttctagtc cttcagttgg ttccatagcc agacatgttg   121680
caatgtctta acttcattat aaattaaatg tggttctggt tattcttaga taatggagta   121740
acgatttagc aaatttcaaa acctcttgga aatattattt gaccattcaa aaagacttac   121800
taagtctctc attatgggtg cccctctttt tgtaaaaggt tttcaggctt aagctccatt   121860
tctaggtgct ccaacactct gttatttgta tacacgtgga aataaaagct gtgacatccc   121920
cgccctagct gaatcctcag cacagtgttt ctggaaggct caagatccca cactggggaa   121980
aagaagttcc agagagaaaa gagggcaggt gctgccgtgc ctctctgctc agtatggata   122040
ctgggccatg tgcggccagg gcttgcagta gggccagttc atggcactca gctggaaagt   122100
ccactgttgg cgggcattcg taaccatcca ctctgtgccg tatgtagtgg ggtgtggcat   122160
ccaagtattt gaaatcagcc gcgtgcagag aaatcagccg cggatgcagc agatcactct   122220
ttttctgaca ggcctgctca ctctgatgtt atatcagaaa gctctgaatc tgggaattgt   122280
gttccctgaa ttggaataac agaaatgctt agatgatcag tgtttaaaag aaataaacca   122340
aaggtaaatt tagtttggaa ttcagcaagc gtcttcattc agccctctga gggcaaacta   122400
cagcttttca taaatgtagg taaattctct gtttcttgac cccttctgac ccagttttcc   122460
tttataacct tctgtattgt tccattatcc tgaaataaca ttaatagatt aggctgggtg   122520
tggtggctca tgcctataat cccagcacct tgggaggcca aggcgggagg atcacctgag   122580
gccaggactt cgagaccagc ccagcctggc aacatggtg aaaccctgtc tctactgaaa   122640
ataacaaaaa ttagccaagc gtggtgacag gtgcctgtag tcccagctac tcagaaggct   122700
gaggcaggag aattgcttga acccaggagg caaaggttgc agcgagctga gatcacgcca   122760
ctgcactcta ggctgggtga cagagtgaga ctccatctca aaaaaaaaa aaaaaattaa   122820 tggatcaatg gattttttaac ctaatagtta aattaaaaaa atatcattct ttaatggtaa   122880
tgtaaaggta aaattaagag aagataatat gtaacaagca ttttagtatg tgagtgtcca   122940
aggtctccct gtggtggaag gaaaaaataa atccccataa gtgtccacga tgctcataga   123000
gagcagagct gttccggttt aaaccgctgc tcttaggact gtgttttcc agctatgggt   123060 ggtgggggat gagtaccttt ttatttccat gagatgagaa aaatgaatta ctagaagtat   123120
gaagcacaaa acacagctgc tctttttta tctggactca gcagctataa aattgctcta   123180
tccagttgca gaagttcctg ctgcttaccc ttgatgcccc ctcggttagt gtgcatctcc   123240
tttcaggctg gctcccagat gggagctggc tccaggcgac actgggtgct ctgctccagg   123300
aggtccttgt gtgggcccta ccccggccta gcccctctct tatggactct gtcaccatgg   123360
gtttgattca ctcaatctgt cttaccttt ggtgagctgt tagagtcctg cctatacttc   123420
```

```
agcacttgtg ggtgtgttgt ggtacacatg acatgttggt cacttcccag ctcatcttgt 123480
tctgagtcac cctggatttg gtacgttcat tcgccactag tagctggcgg tatatggcct 123540
gcgatttgga ggacttgtgc tgctacaaat tggggctgaa tttgagttga cactggccct 123600
tctttatgtc tactgctaat atttgaattg caaatgctgc ctcttctctt tcagaggctc 123660
attaccctat agctgtatta ttgcaaagta cataattaca gcttgagtgt aagtcacgct 123720
gggctggcag gacagccaac tgagaaaggg caagtttcct gttagttttc acattgacac 123780
ataatttaca atacagtaga atgtactttt gtatcaactg tagtcagtaa cagcccctc 123840
ccccaaccac ataagatata gagcagtgct gtcgcttcac atagttccct cttcctctgc 123900
catgtcccgc cctccccagg tctaaccacc aatccgtgct ctattcagcc cattgcagag 123960
ggtcatagaa atagaatcta caggctgggt gtggtggctc atgcctgtaa tcccagtgct 124020
ttgagaggct gaagtggaag gatcacttga ggctaggagt tcgagactag cctgggctac 124080
ctagcaagac cccatctcca gaaaaaaaaa atttgaaaat tacaagcatg tccctgtagt 124140
tccagctgct tgggaagctg aggcgggagg atctcttgtt gaggttacag tgagctatga 124200
tcgtgccact gtgctccagc ctgggtgaca cagcaagacc ttgtctttgg gaaaaaatt 124260
aagaaagaga tggaaccaca cagtgtgcag ccttttgagt ctggccccctt gcagtgagcg 124320
gtgtctaccg tcatgcgttg cacacgtgtt ggtggctggc ttcttgtgac tgctgagcat 124380
tatatggctg ggctgtagat tgctttcact tcaccagttg ggaaacagag aaaaggcagt 124440
ttttaaaaag tttaaatctg tagaattttg gttttttacca gttctcttct aaatcctgag 124500
ggattacagg aaaagttgtt gtatttcaga atattcttag cttgatgtga cctctctccc 124560
tgttaaggcc ctttgctgca atgggaagga cgtcgtcctc ggtcagaccc tgaaggtcag 124620
aggggcactt tgggagtgtg tcaacatttt aactgtatgg actagagcca agagtctcaa 124680
gatttataat tcccacctat tcaaaaagaa aaaataataa taataaagtg agaagaagtc 124740
aatgtaaagt gaaataaacct gtgttggtgg ggaagaagtg ttttttaaaca gaatttccat 124800
aatgtatacc ctgaacgtgt ttagagtggt gatgtttcat tgggaaacga acagtaaaac 124860
atgaaagcag ggagattttc tttctggcag ttggcaactt tcatggcaga tggggaattt 124920
gaaaagcaat tgctcaatta tcaaacatag ccagtgtgag ttctgaaata aaggtgctga 124980
ttgaatgtgc agctttatgg tggatttgt cattcaggca agcattttaa ttttctgcct 125040
gttaaattct gttttctta gttttttcata tgtggtttat tgtagcttgg aatagataa 125100
ctgagagtat atattacaca tacaacattc tgatatggca atatttaaac caacttgtct 125160
gttttagaac tagaattaaa cataatcatc ttcagtattt tgcaaataag ctcactgcca 125220
tccagaaaca ttgtcaatgc atctgttgct ccttctagaa gacacagtct gtccagcaca 125280
aagttactta gtccccagat gtctggagaa gaggaggatt ctgacttggc agccaaactt 125340
ggaatgtgca atagagaaat agtacgaaga ggggctctca ttctcttctg tgattatgtc 125400
gtaagtttga aatgcctgta aacggggttg agggaggtgg ggaccgggag aacatcctga 125460
gtagatgaca cttgcctgga ccctctggaa cccagactgc ccagtgtcct gccagctcca 125520
tcaaaactaa atctggaatg aatgtttact tctgctctga catataattg gagaccgggc 125580
ctggccttcc agtcactgga ttctaagctg gactgtgaga gttgatgcag ctgactcatt 125640
tatcaaatgc ccagctattg gcttcacgcc tacacgatgc tgggcatatt tgttaattca 125700
agggaagcaa tggaataata ataactaatg atttgaaaaa caagataagt gcattgacta 125760
```

```
tagtggggtt ctgattttaa attttttaaa aaagtaatac caggagcagt ggcttacgcc    125820
taaattctag caactcgaga ggctgaggtg gaaagatcac ttgagcccag gagtttgaga    125880
caagcctggg ctacggtgta agaccccat ctctaaaaaa ataaaaaatg aaaaattatc    125940
caagtgtggt ggctcgtgcc tgcaatcaca gcttcttgag aagctgaggc cagaggatgg    126000
ctagagcgtg ggagttcgag accagcctgg caacacagag aaaccctgcc cctaccgaaa    126060
gaaagaaaaa ttagcctgat ggtggtgcgt gcctgtggtc ccagctacct gagagactga    126120
gaagggagga ttgcttgagc ccagaagttt gaggctgcgg tgagccgtga ctgtgtcact    126180
gcactttagc ctgggtgaca aggcgagacc cctgctctaa aaaacaattt ttttaagtta    126240
atttgtagaa aaggtgttag atgttcattg ccgtatttta tgatggattc ctgtttaaat    126300
gccattctct taaaaaaaaa aaaataactt gtaggagttt ttaaccgtaa aattagcatc    126360
acatgtttac catggagaat ttacaaaaaa caaacagagg aaaataaaac ctctgtaatc    126420
atactactca gagataactt gctgttagat ttcggtgtag atctaatact ttttctgtat    126480
ttatattaaa aatacttaaa acatatacat ttctttgtta caaacatggt atcttataga    126540
tagtgctgtc acatagcaaa acagtgttaa atattctgaa tcagaaaagg aagccgactc    126600
tccaactgaa agaggtgtta tcctagagac ttttttctggt gatggcaatt tgttaatatt    126660
cactttttgc tttacattct gtattgaaat agttttttctg ttttgttcta cttttaagga    126720
taatataatt gtatcatgct gttttttcaca gaaatgtaag aaaaaaagat attaattttg    126780
taagttaata gaggttgagc atcccaaatc caaaaatctg aaatcccaga tgctccaaat    126840
tctgaagctt tttgagtgct gacattatgt tcaaaggaaa tgttcattgg aagatttcag    126900 atttttgat ttagggagct caacaaataa gtataatgca catattccaa aacctgaaaa    126960
aaatcctaca ttcagaatac ttctgatccc aaacatttca gataagggtt attcaaccct    127020
tactgtcaga tgatcccaaa tgaaaaatat taatcgttaa ccaaatgtca aggaattgat    127080 cacatttac agtttctgcc taggattatg aatcaagatg aaaaggctct gcgtgtttaa    127140
aaatatatat atttttattt tcttataaat cttaaatgta tcaacactta agatgtattt    127200
gatatgtgga atccattcat atttttggatt aaacaattct gtcaagaccg tggcagtgat    127260
agaggatttt ttttttcccac tgaactatca caaaattgga aaaagagtaa ttggagaacc    127320
ccactggctt ggccagctcg aagccccgga gggggcaggc agtgctgtgg atgggagcgt    127380
cgcagtacca cgctgcccct cctgcccatg gatctctgag gcctgccttt gtcctttgac    127440
ccttggccat ttgttagtgt ctctgagagc tggactgctg tacccctactt ccccagggg    127500 gcctgacttc acacagcctc tgctgcagtg cgtggttgga ggtgacggcc ttggtaaatc    127560
cagtttcctg cctcctcaat tatttgtgct catacactgt atatttttta gtgaggttta    127620
tatttgagat gtgttttctc cttcttaccc tttctggcct ttctatggat taatacctgg    127680
tctcttcttg tgtacttgaa agtgaatctc tcatcgtatt tttccttagt gtcagaacct    127740
ccatgactcc gagcacttaa cgtggctcat tgtaaatcac attcaagatc tgatcagcct    127800
ttcccacgag cctccagtac aggacttcat cagtgctgtt catcggaact ccgctgccag    127860
cggcctcttc atccaggcaa ttcagtctcg ttgtgaaaac cttcaactg tacgtcttca    127920 tcctgccaac aattgccagt tgcagttttc tctgccttaa aaatggagta ttgaaatttt    127980
taactttaat ttctgactgg caaaatagtc atctttttgtt cttttccttc tcgctgttag    128040
ccaaccactg tgaagaaaac tcttcagtgc ttggagggga tccatctcag ccagtcggga    128100
gctgtgctca cgttgtatgt ggacaggctg ctgtgcaccc ctttccgtgt gctggctcgc    128160
```

```
atggtcgaca tccttgcttg tcgccgggta gaaatgcttc tggctgcaaa tttacaggta 128220
ttgggaaaag aaaccctgat attgatttat attgaaaatt tagcaggcca agcaaaacag 128280
gtggctgcct ttttcctcca taggtgtggt cttgacacgg tcaccaatag aaacatggaa 128340
atatctgcaa acttgccatt cctcgtgtgt ctgatctgtt tcttgaactt ttttctagtc 128400
tgtccttact aggatgaact gtacacatca gtttatcctt tttaaatgag catgaggtta 128460 ttttggggttg tacagtgtca caaacacact aatgtgtttt tgtctattag agcagcatgg 128520
cccagttgcc aatggaagaa ctcaacagaa tccaggaata ccttcagagc agcgggctcg 128580
ctcagaggta atgctggaaa cacaggtcat ccttgtgtta ggagaaccca ggatataaaa 128640
gatatagatt tgtgcgggaa taaattcaca ggacaagaaa ttgatgtgcg ttataggtgg 128700
gtttgctgca gaagtgccat aatagaaagc ttcctacttt taaaacaacc agatctcact 128760
ttatatggag taaaggacaa ccagcaggat cacgtctatg acatgagtgg aggcagtttg 128820
cactcctttt ggctgtttga gaggtagtat ttagaatgcc tgtattcact gtcctgtgat 128880
gagtgggaaa ataggttatc agctttatct tagcaaaatc aaagcatatc atctaattgc 128940
taaacaagag ttggcaaatc tgaaagacat tactgaatcc ttggcatgca ggacttacat 129000
ctgcatcccg ttgccatttt ttctcttcaa agcatttaat cacttagttg tgtttgcaaa 129060
gtcttttaga agcctttatc agaaatcctt acatctccta tgtgagtgta tttccatgac 129120
tgcaaaataa gttaaacttt taccttttt cttcccttgg tgggggcgga aattgtgtgt 129180
gtgaaaggga aagagagaca gcagagaagg agaatataat tatcatgctg tgtcctttga 129240
gctgaaattg caaaaaagaa aacacacaca cacatgcttt gatttcagtc ttaagagtac 129300
cttgttgatg gtgttttttaa atgggattgg gcacaattag gtggacagtt tggggcgatt 129360
tttcggtctg tagggccaag ctgttttgta atttgcttta taaagttgtc actctcatag 129420
catatggtgg cagataaact attattactt tttgaccata gacttagtct tcagtccaga 129480
tgagggagat taaaagatta taaatatctt gtgccagatg aggtgatttt attttgaaat 129540
gaccataaat tcctatcagt tgtcttactg ggatatttga tagtggagtt tgtgcatttg 129600
agtcttagat gatctgtttt acgtttatta agaaagcctt tattagcttt tataccatgt 129660
atggactgtt gcaatgtttg agtataaatg aaatttctgg acaatattaa tggagtacaa 129720
actgtgatac cttagaagta aactagggcc tgcgtttata tcatgacctg tttgagtgtt 129780
gatgagaaaa tagctgtgaa gaaaaagttt taaacaagtt tcattttcct ttaagaagcc 129840
actaatagtg catccttagg gtgtatattt ctagaatcct agtgtgcaga gtttagacta 129900
agactaaaaa aaaaattgca ctgtaatttc ctttttgttt gtattttaga caccagaggc 129960
tctattccct gctggacagg tttcgtctct ccaccatgca agactcactt agtccctctc 130020
ccccagtctc ttcccacccg ctggacgggg atgggcacgt gtcactggaa acagtgagtc 130080
cggacaaagt aagtgtccag cgtgtctgca tgcgaggcac agggcagagt gcctctgtca 130140
cctgaggcag atacagagag tgcagaggag gtgcggtgga cccaaggagt gctggcgctc 130200
tgctcggctc aatgaagccg tggttagaga cctgggggga ccatcaatgt ccgagggagc 130260
aaagcagtgc tgatgtggga ccgtttcggt aggagtgcga ggtgagtcgt tagtgggtga 130320
ctcaagggaa agtcaattgt ggcctgcagg cccctgactg cacaggcctt caagcacatg 130380
tcagtgcatt tagcctccct ccatcgcctc ataccttctg gccacctgtg agttgcactg 130440
ccactgccag ccatactggt atgttgtcag cacctccact gctcatacct caccgttagg 130500
```

```
gaccacttgg ggccttggta gagccttggt actctacttt cctggagaga gttcagctta   130560
tgaatatgaa tttagatttc aaaaaccagc agcccaagta taagaaagcg aaggttcagt   130620
cctgccgcct taggctctat ttgctaagca tctgccctgc cctgccctgg ttgctgggaa   130680
gagatgagca aagcagacag cccaggagag gatggcaaag gggccgctaa cccttagtag   130740
tttagctata tttggaagga ctattagaaa ttcaccaggt gaaggggggag gccgtgagag   130800
tacccaggta ggtaacagaa gtccaaagag gaagacctgt ggtgtggtga gctgtatagc   130860
cacaacatgc cggccggagg ccctctcagt tagcctagtg cagtgttccc aagcactggc   130920
ctaggcctgt agctccaggg atgtgaagtc cccttgaacg ccacccatca tgttcccctt   130980
attcatcttt ttcttcccag gactggtaca ttcatcttgt caaatcccag tgttggacca   131040
ggtcagattc tgccgctgctg gaaggtgcag agctggtgaa tcggattcct gctgaagata   131100
tgagtgcctt catgatgaac tcggtacggg gggagcagcg gaagcaagga atcctcagct   131160
tttcttgtga cttccaagtg ggatttgtct cctcatgtga cccacttgtt gacaacacat   131220
gttgaggact ccactctgga tggggacggg atgacggaga gactccactc tgaatggggc   131280
tgggaactgg ggaggactcc atttcagggg gccgggacat gggggatatg ctgatcgaga   131340
ttgtttcagc cacattagaa tccaaggagg caagtcgatt tcactcaacc tttcatgcat   131400
ttaaagaaaa tggaggtggt cttagattac agtcatttca ctggtttgtt ctcatggcag   131460
tgaggaaggg tattgggatt ggtgtctgtc ttaattcagg atctttgaga agatggagag   131520
cactccctca gggattagga gagactcgag atggaaatga agattttact acttacaggt   131580
cctggcgggt acatggcatg cccagaggcc cctcacacgt ggaagttggg ggcatgtgag   131640
ggaatgaagt gtggtcctgg gcactagggt gggggacctg agcggnnnnn nnnnnnnnnn   131700
nnnnnnnnnn nnnnnnnnnn nnnnnnnnnn nnnnnnnnnn nnnnnnnnnn nnnnnnnnnn   131760
nnnnnnnnnn nnnnnnnnnn nnnnnnnnnn nnnnnnnnnn nnnnnnnnnn nnnnnnnnnn   131820
nnnnnnnnnn nnnnnnnnnn nnnnnnnnnn nnnnnnnnnn nnnnnnnnnn nnnnnnnnnn   131880
nnnnnnnnnn nnnnnnnnnn nnnnnnnnnn nnnnnnnnnn nnnnnnnnnn nnnnnnnnnn   131940
nnnnnnnnnn nnnnnnnnnn nnnnnnnnnn nnnnnnnnnn nnnnnnnnnn nnnnnnnnnn   132000
nnnnnnnnnn nnnnnnnnnn nnnnnnnnnn nnnnnnnnnn nnnnnnnnnn nnnnnnnnnn   132060
nnnnnnnnnn nnnnnnnnnn nnnnnnnnnn nnnnnnnnnn nnnnnnnnnn nnnnnnnnnn   132120
nnnnnnnnnn nnnnnnnnnn nnnnnnnnnn nnnnnnnnnn nnnnnnnnnn nnnnnnnnnn   132180
nnnnnnnnnn nnnnnnnnnn nnnnnnnnnn nnnnnnnnnn nnnnnnnnnn nnnnnnnnnn   132240
nnnnnnnnnn nnnnnnnnnn nnnnnnnnnn nnnnngagaa acctcctggt gctttagccg   132300
tgcgttgata cacagcagat gggagggaag tgggcacccg ggaggacaaa tgcatgtaga   132360
ggctggggt ggaggcaggt gttcatgaaa agagacctta cagggagggc aacacaacag   132420
tgtgttctga tgtactgaag agctagactg aaaagaacag gagaattcac ccaaaatcca   132480
tttactaaaa ttgtttatcc tttttttttt tgagacgaag tctcgctctt gtcccccagg   132540
ctggagtgcg atggtagatc ttggctcact gcaacctctg cctcctggat ttaaacaatt   132600
ctcctgcctc agcctcccga gtacaggcat gcgcccacca cgcccggcta attttttgtat   132660
ttttagtaga cacgcggttt caccgtgttg gccaggcttg tcttaaactc ctgacctcag   132720
gtgatctccc tgcctcagcc tcccaaagtg ctgggattac aggcctgagc cactgcgccc   132780
ggcctaaaat tgtttatctt aagattcatg cagtgaaaac taacttactg agtgataaat   132840
ttgcttagtg atctgtttat taggttttct aaatttgcta attgggcttt gaacagctgt   132900
```

```
aaaagttctg actgtaaaag aaagctgcaa cttttggcat tcatgatgct tttctgaata 132960
ttaaactaag atagatgttt tacctgaaga attggccccc aatcttataa atggctaaac 133020
aaaaaaggtt gctaaaacat aatccaaatt gtcataggaa ataccatttt tccaaccaaa 133080
attttgtcat tcatatggct acttttactt atttcagctg catttgacca tcttttcaa  133140 acttcaggga tggctggtgt atcaccgaga tcttggatga cactttagct ttgattttct 133200 gttttttatga attaaaattg tcataccaaa attttttactt caagcaaatc caagagcata 133260
aaaaattaaa atatcactta aagtaccaag agagaacaga aatatatttt actaagcgta 133320
cgttgaatga agttgttcaa atatttgtaa caggcataga gtagaatttt cttaaaaaca 133380
tttttgatgg tataccaatc tgtgttttct cagaaacatt tgccttattc tttttctgt  133440 tgtgtttttc ttacctgatt gaaagctcct aatctgttgt tattgtttgt ttaacccttta 133500 atgctctgat ttcaggagtt caacctaagc ctgctagctc catgcttaag cctagggatg 133560
agtgaaattt ctggtggcca gaagagtccg cttttttgaag cagcctgtga ggtgactctg 133620
gcccgcgtga gcagcaccgt gcagcagctc cctgctgtcc accacgtctt ccagtccgac 133680
ctgcctgcag agccggcggc ctactggagc aagttgaatg atctatttgg taattaaaat 133740
taaaatttat cttattttta gaaaggttcc agggccagta tagtactttg caccaagtaa 133800
atatacaata aaggcggtgg atctaataca gcgaaagcgt ttacagaggc agctaaagag 133860
cagcactggt ggcctcagcg cagaatttct tcctgcgtgt ttgccacttt gccgttcatt 133920
gacgtggtca cggacatagg gctctaagcc cttgaggaag gctgggccag acctcagggg 133980
agatgcagcc ccaaactaca tgcagtcatg tggatggatg cgtagatgtg ccattgagga 134040
gcaatgtctt gtgctttcat cagattctca aagaattgct tgactgcctt tcgaaggtgt 134100
tgcatctgtg ctcatgtttg cacccaccca cgagggcctt ctgtttcagg ggatgctgcg 134160
ctgtatcagt ccctgaccac tctggcccgg gccctggcac agtacctggt ggcggtctcc 134220
aaactgccca gtcacttgca ccttcctcct gagaaagaga aggacaccat gaaattcgtg 134280
gtggcaaccc ttgaggtaag aggcagctcc ggagctcatt gttgctgtgg gaggggacac 134340
ggggctgaca ctggagaggg taaagcagtt ttatttgaaa agcaagagct ctgaccaatc 134400
cagtcactat tctgtctcag cctggcagta agtcttgtca ccgtcaagtt attgtagcca 134460
gccttcaccc ttgcctcgcc actcctcacg gtggcctgtg aggtcagcca ggtcccttc  134520 tcatctgcac ctccagtgtt atgtggatcg taattttaga gacttgaaaa ataaccatct 134580
gtaggtactt tgtgtcttaa gttggcctgg acatgtcagc caaggaatac ttggtttgtg 134640
ttagtgcttg taattagccc ccaaaacatg tacacattct ggatgcatta aactcaggcc 134700
tgtatcctta aagggccatc tctgtgctgc ctgccctcag cagggacaca ctttgcagac 134760
ccacagaggc tccgcctcca cctcacacca aagaaaggga ggagtccaaa gggcatcagt 134820
gccgttactc acaaaatgat aaatacaccc ttattctgaa ccaggtggag tcagatggtt 134880
tgtgatccct gtcctttagg tttcagctta gtggggaagt gggaaagcca gcgtgtgatc 134940
acagcacagg gtgattgctg ccgattatat tatgtgcctg ctgtgtgcag gacaacatac 135000
tttacacgca tcatccttatt tgactctcac aactccctgt gagataggct ctgttactcc 135060
catttgacag gtgaggagag caaggcttag agaatttcag tgacttgccc aggtccactg 135120
agctaggaag tagccattct ggcgtttgaa ctcaaggcct gctatcccta gaacccacgc 135180
tctcaaattc aacctctgag gctatgccag aggcaagccc cagtgctgtg ggcgccccag 135240
```

```
ggaagaacct ctggcctggt ggccacgtag cccaggagag atgtctacag gagcccacag   135300
cgctgaagga gagaagggca gcagagttaa gggggcattc tggcagagag gggactggca   135360
ccttggggaa tagctgggtc aggactgaat gtcatggagt caggtcagag ctgtccttct   135420
ggagggcaag gcatctgga cctgcttccc ctcaatgctt tggacggttc caccacaact    135480
gattcacacg gcctcccaa atgaaggtac acgagcgggc attctgtgac ttggtacttc    135540
cctttaggcc ctgtcctggc atttgatcca tgagcagatt ccgctgagtc tggatctcca   135600
ggcagggctg gactgctgct gcctggccct gcagctgcct ggcctctgga gcgtggtctc    135660
ctccgcagag tttgtgaccc acgcctgctc cctcatccac tgtgtgcact tcatcctgga   135720
ggccggtgag tccccatccg tgaacaatgg gttcctatcc tagttcctgt ctagttcacc    135780
atgtttatat tttgtgctgc ctgttttgcca ggtactaagc taggaattgg ggatggagag  135840
gtagataaaa tacgcattag gaagggctgg gctccatctc tttttttttt ttttttttt    135900 tgagacggag tctcgctctg tcgcccaggc tggagtgcag tggccagatc tcagctcact   135960
gcaagctccg cctcccgggt tcacgccatt ctcttgcctc agcctcccga gtagctggga   136020
ctacaggtgc ccgccacctc gcccagctag ttttttcgtat tttttagtag acgggggtt   136080 tcaccgtgtt agccaggatg gtctcgatct cctgacctcg tgatccgccc gtctcggcct   136140
cccaaagtgc tgggattaca ggcttgagcc accgcgcccg gccggctcca tctcttactc   136200
tccaatatat tggagtctac actggaattt aacttgaatt tgcttttta gtcatttat    136260 ttagattttg gaatttcagc tttcatcaaa attacttcta aatttatgt ctctgtgatc    136320 tttggtctta gctgactgtt ttatgcattt agtcttatat gatcgaaagg ttagtaagat   136380
tacgttcaga agattgtttt ctgttcaaat gcttgtttct atactgcact ataatattaa   136440
cgtactgtaa aataaaagtg gcttattctt ttcaaggaac agtatcctca acaagggtta   136500
ttagccacaa ttttttaaaaa attggacatc atggtttaca tgttggaggg catttgaag   136560 cttttgtattt tcaaattaaa cattatagag tgatgttttg atgtttcata attgttttca   136620
tctgtgcatt tgtggccagc ttgaaaacaa agatccaggg attaatactt aaaagccaga   136680
cttcttgggg gttatagaga tgattttggt agtaatgaat cttgagccgt ctgataataa   136740
cctcggggtg agagatggcc aacaggagag agtcgaggga cttacaaatc tgaatgaaat   136800
ctgaagtaca aatcttcaga catatgccac taaccaagag attggtacct cagtctaata   136860
ttgtctgttt gtctaaaatt ggttctaaga aatctaggct catctgtcta tccctttgaa   136920
cttttgtgag gctgcacaaa tgtaaaattt tgaatgaaaa gcactgatgg aagtctgtgg   136980
aaattcttct gtttgttctg ttgtaatttt agttgcagtg cagcctggag agcagcttct   137040
tagtccagaa agaaggacaa ataccccaaa agtcatcaga gaggaggagg aggaaataga   137100
tcctaacaca cagagtaagt ctcaggaccc attctttctt acatgtggtt cctccaagac   137160
ttaaaagtca ttcacagaga cgtgcgccgt ggtgagtgtg cactcctgga agcgcaccgt   137220
agctcggctg tgtcctgctg ctcctcctc gccgtgggag gctttagtcc attgctttgc   137280
cacactcttt tgtttcaccg tatccctgtg catgcggctg tttctgaccc tacagagcag   137340
ctgggatgcc tctgggggag ccttccccg ctccagcact tccacatgcg gttactctgg   137400
gctcctggag ggcagggagc aggtttgtct tctctgtgtt ctcagaaatt aatgcttggc   137460
ccctggtcag caagcagcaa cctttttgttg agtgatactg aataaataca tgtttcccac   137520
atgagtattc agtaacctca gtgtcaggtt caggcatctg ttttggtgga tatttaaaag   137580
aaaattccac ttttcctaca gaaaaaaaaa aataaataaa tctaaatccc agtgatttaa   137640
```

```
gccagttata gacttagaca tatactacgg cttttcatgc cctttcctcc cagttctaga    137700
gtagtatttt actaggaaaa tggtggcaat gcctgttgag aggaaaagtt tttggccaag    137760
tgtctttcgt tcttgccagg ggccctaggc tgctggggct acttcagttt ctttagccca    137820
gtgtctggca gggaatgctc cctgtagcct gtcccacaga ggcaggggtg cctcacctgg    137880
ggcctgtcca cgcattttac acagcaccct tacttggagc atcaggcatc ttttccgcgt    137940
tccgtggctc aggaaacaca cctttttcaat catgagttcg ccagtgcttt tgggcttttt    138000
ctcccagctt ttgtgcaatc ctagttatgg atggagtttt cctgccttta gtcttctgca    138060
tagtactttt ttcttctggt tcccggttcg aggttttgta attaaagaat gacccagaag    138120
cagtggcatt ttcttttctt ttctttcttt ttttttttg agacagagtc tggctctgtc    138180
gtccaggctg gagtgcagtg gccggatctc agctcactgc aagctccgcc tcccgggttc    138240
acgccattct cccgcctcag cctcccgagt agctgggact acaggcgccc gccacctcgc    138300
ccggctagtt ttttgtattt tttagtagag acggggtttc accgtgttag ccaggatggt    138360
ctcgatctcc tgacctcgtg attcacccgt cttggcctcc caaagtgctg ggattacagg    138420
cttgagccac cacgcctggc cagcagtggc attttcatac acagccaagg tcttctctga    138480
atttttatct cgaacctctg tgggtccttc aggcttcagt ttgtgatttc atgatttctt    138540
gttgctacct aaggaatatg aaaacaccca cctccctact ctgcgtcttc cagccgatgg    138600
cacctcaggc tcttggtcct gtgcttctgt ggcgaggata agaatagtgc caaccatgtg    138660
gattgagata gatcagttag tccatccatg tcaagcacct ggaatggatg acagtcttgt    138720
tgtgaatact caacagatgc taccatgact ttagttagat ttccattgct ttgaaacagt    138780
tgagacatct cagagctttg agccagagca gtgggccctg atgcaggttc tgtttggttg    138840
aagatgattg tgcttattcc ctgtggccct tgtagaccgg agtgggaagc ttgcttgatt    138900
ttaatcacct cgataggatc ttacttctta aaggtcatcc aataaataat gagccaactc    138960
attagcctgg ggcttaattg cttaagtcca atgagaagtc attctctatc ctaggaagtt    139020
gcccaaactg tagaatctcg tggcctgtgg gtagtagcca cttactacac attcactgac    139080
tcaacgaatc atatttttag tagatacaat attctagact caagacacca tgatgtggat    139140
cttcccaggg gtgtgacgtg ttcctcggcg tctgccttgg gagtttccat ttccatcaga    139200
accatgcccc agggccctca aacactctga tctaggaaag ccagtgaagc aaggatgaca    139260
gcgtggccct ttgataccag ctgagggaca gacacaggtc ctgggagacc agagaaagac    139320
aaggggcaga ggaagtgtcc tagagggtgg gccagaggge tgggaacgaa ggccagagct    139380
caggttcagg accattccag caatcccagc agaaaatggg gaggattgta tggtataggc    139440
ggatatgaag gaggtagact ctgcaagctt tcagtggcca actcattcta ggtgattcca    139500
caattacagc ttgagcagct gcttgtcggt catgcttctt acactgggca agtagaatgt    139560 gtttttaaa aagtcttctc ttaaccattg cttgtttaga tccgaagtat atcaccgcag    139620
cctgtgagat ggtggcagaa atggtggagt ctctgcagtc ggtgttggct ttgggtcata    139680
aaaggaatag tggcgtgccg gcgtttctca cgtcagtgct caggaacatc gtcgtcagcc    139740
tggcccgcct gcccccttgtc aacagctaca cacgtgtgcc cccactggtg agtctggtcg    139800
ttccgtgtag aagaccaagt acggtgaaac gcatgggtaa gccctgggct gggcacaccg    139860
gagagggcag ggcagagtcc ccgcggccca gaggctgcca gctgtggttc tggtgccagc    139920
tgtggttctg gtgccagctg tggttctggt gccagctgtg gttctcgtgc caggctgctt    139980
```

```
tcctcaggca ccgtatgtgg aggtcgctag tagaaatact gggttttcta aaatgaagtg 140040
aggccccaca tccctaagag attagtgtta gacttgattc taaagcaact agaccacttt 140100
gcttactggt agaccagaaa ccacactccc tcgagtgagt gagattttcc tttggaaata 140160
attcatgttt ttctacacaa ttttgctgtt gtcttcagaa tcggtttaaa gtaggtgtta 140220
ttgctgggca cagtaactca tgcctgtaat cccagcactt gggaagccaa aggcgggcag 140280
atcacttgag gtcaggagtt tgagaccagc ctggccaaca tggtgaaacc ccgtctctac 140340
taaaaataca aaaattagcc aggtgtggtg gtgtgcacct gtaatcccag ctactcagga 140400
gactgagaca ggagaatggc ttgaacccag gaggcggagg ttgcagtgag ccagatcac 140460
gctactgcac tccagcctgg gcaacagagc aatattttgt ttcaaaaaaa aaaaaaaaaa 140520
aaaaaaaaaa aaagtaggtg ttattgatca ggatgcttgt ttcagataac gaaagagctta 140580
gcttgaggag agtgagggtt gatggaaggg gactggcttc tgctcagtga aatggcatca 140640
tccccccacca gcctgctgaa gtaagatgat gggacctgtt ccttagggac tgcagcatcc 140700
tcaggcaaga aagaaaggcc gaccggcagg gtgtgagcca gcaggtatag gtcagtgaca 140760
atggagctgg gtcccaggga agaggcttgt ggctgcttga aagggcgcg tgcccgtctg 140820
cgtgcgcgtg tgtgtatgta cgctggagag tctggggagg cttgctccaa ggacacagta 140880
tttgatcctg agacatgagg agggttctgc cgcaggcgat gaaggtattc agatggagag 140940
ctcattcgga agaagaggcc agggcctggt ggtgctggaa gcagttgcag aacagggagt 141000
tgtaagcttt cctaggaaga gcagcaggag tgctggagaa gcaggccacc cttgctgcat 141060
gggggttgct cttggccca ctcttggtgc acggcgagtc actgtgagtt cgttagcatc 141120
tggttctgaa acagtaactg ctcctttgga ggggctcggg gagaccatgt aggagggcac 141180
agtcaagagg tcatgctatc tggaacacac ttgaggatat gccaggacgg actgcatgct 141240
gtagataaaa ttcctctagc aagctcttaa ccggcattga ggagttccct gagtgcggtc 141300
atctggaagg cagctgtgaa aggcactgca gtctccccc gggcaggtac caggagcaca 141360
ggggagcaga actgatttaa agagagggct ttcctgtggt gaggtgagag atgagctggt 141420
cattatcata gaacccctct gcctgtgtgc agatgcgctg tgggaatcct ggggttccgt 141480
tgggtcctct gtcacctcac tgaaggcatg tcagctgagc tggccagacc ttcagctgat 141540
cctgccactt gaacagcatc aagcctgcct ctggattctt ctgtgcacgg tgcttgtcta 141600
atcacctcat gcacagagaa ctgtacttca gagtttacag aaataagctg tatggttcat 141660
tttcgtgcct gcttgccaac aaacatatct gagctgaact tcattgaacg cctgcccttta 141720
ttctaacaca ccatctgctg tttgtgggcg aggggtgctg tctctaactc ctgcctgcct 141780
ctcccagcat ccctgagtgg ggtgtgccag cagcctcagg gtgaggacag gaagtgggag 141840
ggcagagcag atttggaagg gccacttgat ggggaaggaa gtcccaggaa gcagttggag 141900
ctgttttctg ggggagaagg tgccagcttg ggacagtgt tgtagtgagg aggaagccca 141960
gtggagagaa gtgggcttc ctgcttcctc acagtgtgtc tgtcctgact cagctcgggt 142020
gatgtcactt ccttttcatc ttctcaggtg tggaagcttg gatggtcacc caaaccggga 142080
ggggattttg gcacagcatt ccctgagatc ccgtgtgagt tcctccagga aaaggaagtc 142140
tttaaggagt tcatctaccg catcaacacg ctaggtactc ttggggcctc tttcaggtca 142200
ccatcgtcgg gcatgtaccg ggaggaaatc cagagcccca gtactgggat cttctcattt 142260
gactccagaa aagatttaag catgataata atacaaacct gtgtgaatac attttgcagt 142320
gtcagcaaaa ctccttttac tgagaaaata gatcccagtt cctgtgtttt gtggcttgaa 142380
```

```
tcccagcttt ttatattctg ggcttgtttg aagtcaggaa agattcatgt gtaacagaca    142440
acgtgaggcc aaattctgcc ttcgattttg catttaggct caacagtggc agcgcttgtc    142500
tcggagtgtg ttctcgtgtt caccagtctg atcctgttgt gtctcactgg tgcgttttct    142560
cacatgggaa caagcagacg ggagcagatg gagtcaagtc tcttagcact cgccttcctc    142620
agagcctaga ggcagcatgg ggagaaagcg ggcttggggc tcagacagtc ctggtctgct    142680
tccagccctc tgtagctgag cagcgcggaa caagtccttc taacctctag agaccctcag    142740
ttttgtcaaa tgtaaaatgg gagtcacgtc tatttcatag aattgttgca gatttagaaa    142800
ttacatttct ttttttttt tgagacggag tctcggctct gtcacccagg ctggagtgca    142860
gtggcgcgat ctcggctcac tccaaactcc gcctcctggg ttcacgccat tctcctgcct    142920
cagcctcccg agtagctggg actacaggcg cccgctgcca cgcctggcta atttttgta    142980
ttttagtag agacagggt tcattgtatt aaccaggatg gtctcgatct cctgacctcg    143040
tgatccgccc acctcggtct cccaaagtgc tgggattaca ggagtgagcc accgtgcctg    143100
gcctagaaat tgcatttcta aacaagtgtt agcccttatt tctaaataag tgtcgaaatg    143160
aataagtcac cactttcgcc cctatttgat ggcaagaggt gtgatcttgt ggtgggattg    143220
taatcagtca gtcctcagtg actgtgccct gctgtggtgt ttcctggaaa gttcttgtct    143280
tgtcctagaa agtctggcag gggcaccctg tctccactgt ccagtcttct ccccaggccc    143340
ttcaggcttc tgcaaatttg aggcttgttt tcatcccaga aggttctggc agcagacgcc    143400
ttgcgtctac tgtcccctt agttaattag ataattcaat gtccaaaggg aaccctgagc    143460
aggaacctca agccagctgc ctcacggagc tcctcctctt cctcactgtg aagattggtg    143520
tcagtggcct cctggtctcc cccttgccta acacgagctc cttgcttac ttgggtgccc    143580
ttgcccttga actccccggc agacgtgcgt gacccaagac tgtgctacag tccttgtttt    143640
tgttcatgct catcttcttc ttggttcatt gttttccctg taatgtcaat tgttttattt    143700
gtctgtatct gtgtctgaat cagtcctgca cgctctcctt ctctctgtct tttgttcttt    143760
ctttacccag tttatcacag gaccccga tgtccatttc tctagttctc ctgtcctaag    143820
caccccatcc tgtctttctg gccttatcac aagtggcgtg tctgcctcag acatcatgat    143880
gggggcatga agcacagctg tcagaaacaa ctgttcgtta ggtacactcg aattcagctc    143940
atcaatagga atggagggtc tatcagatgt gttttcactg aatccctgtt cnnnnnnnnn    144000
nnnnnnnnnn nnnnnnnnnn nnnnnnnnnn nnnnnnnnnn nnnnnnnnnn nnnnnnnnnn    144060
nnnnnnnnnn nnnnnnnnnn nnnnnnnnnn nnnnnnnnnn nnnnnnnnnn nnnnnnnnnn    144120
nnnnnnnnnn nnnnnnnnnn nnnnnnnnnn nnnnnnnnnn nnnnnnnnnn nnnnnnnnnn    144180
nnnnnnnnnn nnnnnnnnnn nnnnnnnnnn nnnnnnnnnn nnnnnnnnnn nnnnnnnnnn    144240
nnnnnnnnnn nnnnnnnnnn nnnnnnnnnn nnnnnnnnnn nnnnnnnnnn nnnnnnnnnn    144300
nnnnnnnnnn nnnnnnnnnn nnnnnnnnnn nnnnnnnnnn nnnnnnnnnn nnnnnnnnnn    144360
nnnnnnnnnn nnnnnnnnnn nnnnnnnnnn nnnnnnnnnn nnnnnnnnnn nnnnnnnnnn    144420
nnnnnnnnnn nnnnnnnnnn nnnnnnnnnn nnnnnnnnnn nnnnnnnnnn nnnnnnnnnn    144480
nnnnnnnnnn nnnnnnnnnn nnnnnnnnnn nnnnnnnnnn nnnnnnnnnn nnnnnnnnnn    144540
nnnnnnnnnn nnnnnnnnnn nnnnnnnnnn nnnnnnnnnn nnnnnnnnnn nnnnnnnnnn    144600
nnnnnnnnnn nnnnnnnnnn nnnnnnnnnn nnnnnnnnnn nnnnnnnnnn nnnnnnnnnn    144660
nnnnnnnnnn nnnnnnnnnn nnnnnnnnnn nnnnnnnnnn nnnnnnnnnn nnnnnnnnnn    144720
```

```
nnnnnnnnnn nnnnnnnnnn nnnnnnnnnn nnnnnnnnnn nnnnnnnnnn nnnnnnnnnn  144780
nnnnnnnnnn nnnnnnnnnn nnnnnnnnnn nnnnnnnnnn nnnnnnnnnn nnnnnnnnnn  144840
nnnnnnnnnn nnnnnnnnnn nnnnnnnnnn nnnnnnnnnn nnnnnnnnnn nnnnnnnnnn  144900
nnnnnnnnnn nnnnnnnnnn nnnnnnnnnn nnnnnnnnnn nnnnnnnnnn nnnnnnnnnn  144960
nnnnnnnnnn nnnnnnnnnn nnnnnnnnnn nnnnnnnnnn nnnnnnnnnn nnnnnnnnnn  145020
nnnnnnnnnn nnnnnnnnnn nnnnnnnnnn nnnnnnnnnn nnnnnnnnnn nnnnnnnnnn  145080
nnnnnnnnnn nnnnnnnnnn nnnnnnnnnn nnnnnnnnnn nnnnnnnnnn nnnnnnnnnn  145140
nnnnnnnnnn nnnnnnnnnn nnnagaaaat aaggcagcag actggtgttt ctttcttttt  145200 ttttttctc ctaccttatt ttgagagagt agccagatgg tgtcttgact gatattccag  145260
agcagggaca aagcccactg aggtttgggg gctgcaatta ccaatggctg gaatgcattt  145320
gattacggtg cgttccatgt taaggatcaa taagattgtg ctcttctgg aaagtatctt  145380 ttagttttat ttattggtat tcagaggagt gtaggttgaa ttaaaatgaa aaggcatttt  145440
ataaaggccg tgagtagtac atggtttcat ttttctaatg tcttgcagag attttattag  145500
gcttctcgaa gtgttcacgt acattacgtt aatgtgatac taagagtaac tgtactctgg  145560
cacagcgaag ccagcagaat gggaagttgt ggaatgcagg cccttgattc tgatagaagg  145620
tgtggtatga actcgcagaa atgacagttt ggagggtaga catatgtcac aagtcatcaa  145680
gattgtcttt aaattcatcc atagaagcta acaggttgtc ataagcaaag cctctaaaat  145740
gtatgaggga attcaaggat aatttatcaa aaagtaattc atgtttggag ttttgtgccc  145800
aaaggagtcc ttgatttgaa aaatgggtgt ttgcccatca gattgtttca gggtccgtat  145860
gtgcagaggc cgtgcctcgt gccccgtgag ctcagcctga cagaagtccc ttggtagcac  145920
ttagggactt ggttagcact tcttcccttt gaggcagggt ggactctggg ttctgcattc  145980
agagctggct gtgggtgtct tgctgttctt gttgacctgt gggctctcct tccaggaaga  146040
cacagagagg acgcagatca acgtcctggc cgtgcaggcc atcacctcac tggtgctcag  146100
tgcaatgacc gtgcctgtgg ccggcaaccc agctgtgagc tgcttggagc agcagcctcg  146160
gaacaagcct ctgaaagctc tggacaccag gtttgcctga attcccacgt gtctccagga  146220
catcatgggt gctgcggaca gtggggtccc cgctgaagca tccagcagct tccccaggc  146280 tgttttcctt tgttgctaga attgaaaacg ctgtccatgt ggcctgtgca ggaggtgcag  146340
acccaaaggt ggcctcttgg ccattgagga gctggaaacg cgacgggaac tgacatgggg  146400
ttattgggca tttaggggta aacattagca gagcaagaat gagcgggcaa gtggtagaac  146460
acccacctaa gggctcatgg acaggtgctc acttaggaag tgagtttcgt ttggtattac  146520
accaggttcc tttaggcagg gcggagggaa agttctggcg tttttcactt gtaagatttt  146580
gaaggaaaca aaacactctt tacctttttt ctgaaatgta ggtttgggag gaagctgagc  146640
attatcagag ggattgtaga gcaagagatt caagcaatgg tttcaaagag agaacatc  146700 gccacccatc atttatacca ggcgtgggat cctgtccctt ctctgtcccc ggctaccaca  146760
ggtacctgag ggagagggtg gggggtggct gtacttgggc tgggatgaga aaagactggc  146820
gtgctcacca caccagttat gcaggaagac ctgagtgtgg tttgagttgg aggctgtggt  146880
gctaaatagc tgccccattc ataagcagga gtcttattca ggcccaggga ggaaataaaa  146940
tctggaaatg aattaggagc attatctcct gccagtcaat tctcacgggc tgtaagaaca  147000
gcaggattta aaagttgaat gagttcctta tgttaagaac tcaaccgagt tcatctcacac  147060 aagctgaatc tccagctttt cctaagaaac caggtgtggc agtggctgca gggcggggca  147120
```

```
cagctgggcc tgagcacccc gctccctgca cctctcccct ccctgggccc tgtctgtcgg  147180
tgcccactct cccaccaagc ctgccagttg tgtgcctgcc ctatcacagg catcagagtt  147240
tgtcacctgg tttaaaagaa gggagttgtg tagggatctg gggatgcaca ttttcactg   147300 aacagtattt tagcatagag gtttgtgatt ccctggttat ttaggagttt aagcaccta   147360 aaggctttaa ttgcagaaag gtctatgtgg acatgcaatg tgttatacgc agtgtctatg  147420
accctcaaat gtttattagg gtattgaaat aaactgagca cttggagggc catggatcca  147480
gcttcaagga gttcataggt caggaggacc caggagcaat gacctgtcgt agacggcaga  147540
aaagaggggc acagaggtgg gttgggggca tacacaggca gctcctggag ctccaaggag  147600
agcaagtgct tccagggaag ggggtgtgga ggctccttgg gaggaggcga gttgatgctg  147660
gggtctggca gagggttagc tgggacatt cggctggagg ctgttgtctg ggaattgggg    147720
ggatgcccag cagaaagaca tgcggaggtt gtttggcctg gggcgtgggg ggtgtgagag  147780
gtcgagtggg ggcattatcc tgctcccgct cctgctggct gtatctggtc agcctgggca  147840
ccgaggcggg ttctggaaag cactgttcac agatgcttat ctgagtcccc cagannnnnn  147900
nnnnnnnnnn nnnnnnnnnn nnnnnnnnnn nnnnnnnnnn nnnnnnnnnn nnnnnnnnnn  147960
nnnnnnnnnn nnnnnnnnnn nnnnnnnnnn nnnnnnnnnn nnnnnnnnnn nnnnnnnnnn  148020
nnnnnnnnnn nnnnnnnnnn nnnnnnnnnn nnnnnnnnnn nnnnnnnnnn nnnnnnnnnn  148080
nnnnnnnnnn nnnnnnnnnn nnnnnnnnnn nnnnnnnnnn nnnnnnnnnn nnnnnnnnnn  148140
nnnnnnnnnn nnnnnnnnnn nnnnnnnnnn nnnnnnnnnn nnnnnnnnnn nnnnnnnnnn  148200
nnnnnnnnnn nnnnnnnnnn nnnnnnnnnn nnnnnnnnnn nnnnnnnnnn nnnnnnnnnn  148260
nnnnnnnnnn nnnnnnnnnn nnnnnnnnnn nnnnnnnnnn nnnnnnnnnn nnnnnnnnnn  148320
nnnnnnnnnn nnnnnnnnnn nnnnnnnnnn nnnnnnnnnn nnnnnnnnnn nnnnnnnnnn  148380
nnnnnnnntt gcagtgagcc aagatcacgc cattgcactc cagcctgggc ggcagagcga  148440
gactctgttt caaaaaaaaa aaaaaaaaaa aaaaatctt taatgttcat tgtttttgtc    148500
ctttttattc ctaggtccca caagcagaga aaatattact tttgttttta tttatgttct   148560
ttattctaga aagtagttaa gagacctcac atgtagtgat agagatgtat ataagagaca   148620
gtgagagggc ctgagctgga cttaagcaag gaccgtgaga caccaaaagg ggtgaggaca   148680
gagtggagtt agctgagatg ctcaggagga agtagatgcc atgaagggct ctgttgtggg   148740
gggctgcagg cttggccctg agtgtccctg tggccagttg ttgggggggg cccagtgtgc   148800
aggcagacag ctcggccact ttgtggcagg tcacgttggt ctgtgcttct gtttcctcct   148860
caggtaagtg aagggattta agggtccagg tgtggtggct cacacctgta atgtataaca   148920
ttttaggagg ctgaggccgg aggctcacct gagctcaggc ggttgaggct gcagtgagcc   148980
atgattgcac cactgcactc cagcctgggc aacagaccaa tactctgtca cttaaaaaaa   149040
gtgtaaacag aaacacaggg ccatttacat atgatgcac atggcaggag ccccacaggt    149100
gtatgctcag gggagggccc agctttgctg gctgacttgc acctatccct ccaccctgtg   149160
ctgtgtcttt cgctcactgg gttcctggtt tagtgaaacc agttgtgcag gacggttccc   149220
ttggtagctt ttgttgcagt ggaaatgggt caggatatgg tgtgtagaag cacttatgag   149280
ctctgagagt ttcctcttat gacttcctgg cctgcagcct tcacagcaga aaccccatga   149340
tgtcacacgc ctgtttctgt tccctgctct gtgccctgta ctgtcctgtt ctgtgcctgc   149400
tggtttcagt gacaggaggc agggagctgc tggaccagcc tgtattttc tagacatagt    149460
```

```
tggaaaaaga agtcacgctc ttctgtcctc tcacctttga cagatgtttc cacctcaaga   149520
taagtggaca tggccaatag gacgcactgt acttttcctg gatgtgtttc tgaagggcag   149580
gctgagagtg agaggcctgg agctcactgg gtgcctgtgg ccttgtcctg ccccggga    149640 cactggtctg tgcccgagat actccctatt ccccacgccc cactgcattt gcccacatcc   149700
ttcgatgttt gccctgtgtc caatgtctgc aaaccgactg tcatgggatt atactgggc    149760 tgaagtatag tgccacccct gccctgtcgg ggacgttcag ccccagatgc cactggactg   149820
agccactgct tgcttttagg aaaggggtg ggggttatgg gtctgggctt ggggagcaca    149880
ggggctgctc cttggcctga gaattgttca tacagactcc ctgcccactc cctgcagggg   149940
tgctgggtcc caggggggaa atggcccttg gtgccaagaa cgtgagttgg gcctagggcc   150000
agtgatgatg gagaacagct ttttatgggc acacagccca tagcactgtg ccaagtgctc   150060
gaggctccca gagaagcagg cagaaaggag gacagtcgag gtgtgctgag cacgtggtgg   150120
ctgtgtgatc tggagcgcgg gtcacagagg cgcgggacg ctctggcctg gggtttacca    150180
caatgactgc cagtggcgga gatcggaaaa gaaatctcac gcgttggttc cgtgttttgg   150240
ggggttccgt gttttggggg gttccgtgtt ttgggggt ccgtgttttg gggactgcat     150300
tgagatctca cttacgagtg agagcgtccc cttcgtagag cctcttctg tgtcgcctcc    150360 tcagccgctc ctggggctgg ctgactcctg atccaggccc ttagcgtgtg ctggagcttc   150420
ccagcagcag tccagccccc accccaccct ctctgtggac tcccttgcct gtaagctggg   150480
gtgtctgaac gacccttgca aagggcaga ctgttcaacg gtaggcatgt gctgagtccc     150540
ggcggccgca cccgcccacc aggagcctgg cactgtggct gcagcgctga gcagcaccct   150600
gtttctgtgg caggtgtcca tacactctgt gtggctgggg aacagcatca cccccctaag   150660
ggaggaggaa tgggacgagg aggaggagga ggaggccgac gcccctgcac cttcatcacc   150720
acccacgtct ccagtcaact ccaggttttc caatggcctt tttctttct acagaaattt     150780 gaaatttctt atcagtcatt tgatttgttt gaggtgcttc ttgaaatgag cctctcatct   150840
tctgtaccca gaaaacaccc atcttgcata ttctacagga acaccgggc tggagttgac     150900 atccattcct gttcgcagtt tttactcgag ttgtacagcc gctggatcct gccatccaac   150960
tcagccagga ggaccccggc atcctgatc agtgaggtgg ttcgatccgt aagtgagcct     151020
tcccattccc ctcacactgg cacatgccac acgcaccaca cacgctgcac acacagacac    151080
gccacaccac acgtaccaca tgcaccacac acgtcaca tcacacatac cccacatgca      151140
cggaacacac acacgccaca tgcacacgta cccacatgc atgcaccaca cacacacacc     151200
acatgcacac gtaccccaaa tgcacgcccc atacacctca catgcacaca taccccacat    151260
gcacacaaca cacacatgcc acatgcacac gtaccccgca tgcacacaac acacacatgc    151320
cacatgcaca cataccccac atgcacacaa cacacacacg ccacacgtgc acacacatac    151380
accacatgca ccacgcacag cacacatgcc acacgcacac acaccaca cacccccac       151440 acagcccata caccactttc atgcaacaca caccacacac aatgccacac tcgccacatg    151500
cacacacacc acatgtacat accacacaca tgccacacgc accacacaca tgccacatgc    151560
accacacaca tgccacacca cacacaccac acacaatgcc acactcacca catgcacaca    151620
caccacatgt acataccaca catgccacat gcaccaca catgccacat gcaccacaca      151680
cacaccacac acatcacata catgcaccac gtgtactatg tacacacaca gacacaccac    151740
acgcgtacac cacacacaga cgcacacacg cgtcccgcgc agtcatgtct cttaggtgta   151800
agaacacgac ttgccagtag cggcgttctg gatgtgttgc ctggattcta actgcgctac   151860
```

```
tctcccttg ctttcctggt gttccacatc tccagcttct ggtggtctca gacttgttca 151920
ctgagcgcaa ccagtttgag ctgatgtatg tgacgctgac agaactgcga agggtgcatc 151980
cttcagaaga cgagatcctc gctcagtacc tggtgcccgc cacctgcaag gcagctgccg 152040
tccttgggat ggtaagtgac aggtggtaca gaggttcctg tcctgaagcc atgtgggccc 152100
atctgccttg ggacctggtg ttggccagag gtgccaggtg cggctgcctc cttccaagag 152160
ttgacccgag ccggactcca cagcccacgt gagctgcagt gcttctcagc tggagggggt 152220
tcagcgacgg tcagtgccat ccacaggcca ccgtgatgtg ggtcgtggcg gccaagccat 152280
ggtttggggt cccgtgtccc tgggcttgtg acatcattgt agtagcccat ccccacagaa 152340
ccatggtgtg tggtagcact gaagcatcgt agatggtgga aacgcgactg gcttccccat 152400
gctctgccct gaggcctgac tgcctcactc cccctcagtt atgttccagg cccccgaac 152460
ttcctgactg dacagcttct ctcctggggg ccattttgtc acagtgaccc tgcgtttcca 152520
gtcccaagtc tgggtgctat agtgtcttct tagcatggtg tttctcttag tctatttcgg 152580
ctgctaccac aaggtacctt agactgggtg atttataaac agtggaaatt cacttctcat 152640
agttctgggg gctggaagtt catggtcaag gtgccaacag atttggtgtt tggtgagggc 152700
tgctctctgc ttcatagatg gcatgttctc actgggtcct cacggtgaaa ggagtgaaca 152760
agctccctca ggcctttcaa aagggcccca atccacaagg gctcacccct catgacttca 152820
tcaccacccg aggccccacc ttctagtact gtggcactgc aaattagttg tcagtgtaag 152880
agtttcgggg gggatacatt cattcagacc atcccaaggg tcaagtgttc atcctcttga 152940
gctcctcctt attctgcttc tggtttatca ggattcagcc cgtgcagcac ggtacctgtg 153000
ttctgtgggc acatcaccac atggcatttc ccaagcatcc atcagctgta cacatgaaat 153060
cgctacctgt gggccccgac tgctggcaaa gcctattcaa ggatgtcaga actgtcagag 153120
ctggagcctc tgggtctttg tcatgtggca ttacctagta atccatttta tgatagcaat 153180
agaaacgcgt gtcttcaaca acacctcag tggctgccgt gtgccagccg tctggagccc 153240
ttggtgagaa tggcatggta gtgcccatca gggcctgctt accccatgct ctggatgggc 153300
tcctgtcagt aacaacgctg tcgtgacagt gatgatgttt ttttgccgtc actccagctg 153360
ctaacatttg cggagctctt cctcctgcac cccacctgac aaaggcaccc taggcggcca 153420
gcgtcagagg ttagctggct tgtctgggtc acacaaaatg cggcagaggt gggactgagc 153480
ccatgtctgt gacctgaagc ctgactccct gcgagtcttg actactcttg cctggactct 153540
gtcctccccg agcccaaact ccagtcatct tcccttgtgg gtggccgtca gcctggtgcc 153600
gtgctggtga cttggcagcc atccaggagg tggaaacaat gaacgcgtgg gctccctgtg 153660
tgggcatctc tcttcactgc gagcaccctc tgggtgttgc ccacatgatg tcaaagcggc 153720
tctcggaagg ggtccttctc ctttatgggg agtttcagct gctgggctaa cttgaattgt 153780
aatgtggttt tgtgctcagg cccagagctc cttaggcaag tgttgtgcca tcagtaatca 153840
aatgagaaat aatcattttg aaaagcagat cctaaggcag gatggtcatg ggcactaatt 153900
cccagctctg tgcatctttc ttgaagacgg tgatcctctg tgaaggtttt cagcatgtca 153960
tgcttggtac cagcgtatcc agagcatgtc attttgaggt atttgcctcc tgttgtgaaa 154020
tccgtgccac ctgagagcag gtcctgatgt gggactttca gaggtgggac caggggccgt 154080
gggagcgcag tccttaggga ggtgccgcgt ggcgttgtgt gtatgagggg atagcacagg 154140
gtgaggtggg ggcccaagaa ggaagtgatc caccaaagaa cagcctcttt cggtcctcat 154200
```

```
tcctgggatg ggtgggagcg gcttctgtgt cttccggtca tttcccctgc ggagaagctc   154260
ctgccactgc caagaacctc atcttgttcc acaacaagaa gaggctgcct ggccatccag   154320
cgctccatgg gaattctgtg tccccatagt cttgggctga agagagcga catacctggg     154380 tgacttctgc aggggtctcc tcactgttaa agagcagatt gaaagtgaag aatgtgggct   154440
aagtgtttag gtcgatattt aaccccatta ggttttggat actaagtgaa attgaggcca   154500
ttttggttga aggttggcat aaactactat cagggatccc caagactacc cccaggcttt   154560
tctagaagga ctctcagcta agatgtaata cagtaaaagc acacaaaaca caatcagcaa   154620
accaaatcag caagggcaga ggcccatggg gcggtgtccc gaggaaacca ggcccgagct   154680
tccagaatcc tctcccggcg gggtcgtgca ggacacactg agctccccca gagtgagccg   154740
tgacagcgtg tgcagtgtcg tcaccaggct caagcttcca gaatcctctc ccagtggggt   154800
cgtgcaggac gcactgagct cccccagagt gagctgtgac agtgtgtgca gtgttgtcac   154860
cagggaagcc cactagagac tcggtgccag ggttttgact gcgggctggg cacgtgggca   154920
ccttctgcct gcttcgtgcc catactctgg actcccagag ggaaggcaga ttctcagcac   154980
aaacaccgtt gcccacacaa gcagctgagc acagagagcc cctcctcagt gaggatggtg   155040
ggcaccgtcc cgacaccagc caggggccag ccttgcacac agacctctca ggatggtctt   155100
gggccgtgca cacaagcatg agggcagcgc accgcccccg ccctccttg gctgtgggga     155160 ggagccactg ggcgtgagc tctggtggca tcagcagctt ttgtctgtgt gtgtctagga     155220
caaggtcgtg gcggagcctg tcagccgcct gctggagagc acactcagga gcagccacct   155280
gcccagcagg gtcggagccc tgcacggcat cctctatgtg ctggagtgcg acctgctgga   155340
cgatactgcc aagcagctca tcccagtcat cagtgactat ctcctctcca acctgaaagg   155400
gatcgcccag tgagtgggag cctggctggg gctaggacgg gggtctcgga atgagctgcg   155460
aaggaagcag catcaccctc tccaagtgcc caggtccctg gccagatggc aggcaggtgt   155520
cagtgggaac ccaggtgggc gccatggctg aggttggtga gacgcaaggg cacaggtgtg   155580
tcctagaggc ttcctcgggc accccagtg agctagagct cctgcctctg ctgctgtctc     155640
atgtggcgct gagcacattt ccccatgtgc ccattcctga ctctgctcgc gaggccagcg   155700
gttctcattc tctgctctca gaaccctctc ctcattaccc aggccagcct cctctctgca   155760
ccttccccgc cctggcccag cacctccctc ctgtttccac tgtgactccg acctcacttt   155820
atcttaaagc tgctgggcgg caggttctgc acagatgtgt ccttgacaaa gcacggctgg   155880
tgccacaacc ccttaacgag caagtcaagc tcttcacaac gatgtcttgt gagtgcggag   155940
ggctctgtga caccctggtc tcacctccgc tctcccgaag tcgcagaggc tttagcagag   156000
atgggcccag cctctctgag tcacaggctt tagagctgtc tgtagaggga gggtagaatt   156060
tcatcagcca cccacatggg ggagttgagg gcaagaattt ggagcaaaga tgggaaaggg   156120
gctgggaaga atggccagtg atcccctttg acaagtgggc aggagatggg ggccgggtca   156180
aagttgagtg gaagacttgg agggagatgg gaagatctct gtaggcacag ttcagacagg   156240
agggaggtgt gagccagggc actggctggt ggctgtctgg caggatttgg gacatcctgg   156300
agcagggaca gtggctcaac aggggccatt gccctcatcc aggccagagt ggcacaagct   156360
tgtggggagg cccttctcgt ctgtcatcct tgctgggcgg tgggtgctgt gctagcagga   156420
cgcaggacag gcggacagct ggcaactgtc tctgcatccc tggagcctgg catagggcaa   156480
gtcacacggg ggacacaggc ctgcaaatca ggcacatgcg ttggtgcagc gaggtgattt   156540
tggggggcag ccccacaaca ggccccaggc acaggccaaa gccctggctg tgctggcgtg   156600
```

```
ttgggccgtc tatggctctt gctgtgggca tggaggactc aggaaaggag agttgaggtg   156660
gcccaggagt tgcgtttggg atgcagagag cttgtggcat ccaggtagaa atggtgtgtg   156720
gggctggcct cagtgccatg ggcacgggct gtgtcacatg cctccgaggt agaggtggga   156780
ccacgtggtg atggatataa gcatcactgg gcacatttct gtgggtggag gggggcatct   156840
tactggctcc tctgttcaca gtggccactc attcagtccc tggctaccgg gtccccattg   156900
tgccatgggg aaggcaggtg ctgtcggggg atcacacaag gcagcacgtc atggtggaat   156960
gtgccacgaa ggaaaagcac agggcactca ggaagtagag gggactggcc tggggtgtgg   157020
gaatccaggg cctctttgag ggacagagag aggaagtctg tggtggccag tatggaggtg   157080
gccacagggg aggctgggcc aggccgagag ggcagggcgt ggaggaggta gacgggctca   157140
gctatccagg gaggggtcga gcagaggctg aagggtcagg ccaggttaca ggggcctggg   157200
gagccacaca gggtaggtgc ttccgggagc cagcctggcc cgcagctctt cactcccgcg   157260
tggggccgga catgctgcga agccctctct acgttggatg gggcggctg agcctggctg    157320 ctgtctcccg ttttcagctg cgtgaacatt cacagccagc agcacgtact ggtcatgtgt   157380
gccactgcgt tttacctgat tgagaactat cctctggacg tagggccaga attttcagca   157440
tcaataatac aggtgagtgg gccctggctg tcttcctctg cacacgggga gtgggcttcc   157500
cttctctttt ccttgcggga tcataccagt gggccagttt tgacttggtg gggaggaggc   157560
atgaacacct gagaccatgc agcgacagaa acctttctcc ctgtgcagat gtgtggggtg   157620
atgctgtccg gaagtgagga gtccaccccc tctatcattt accactgtgc cctcagaggc   157680
ctggagcgcc tcctgctctc tgagcagctc tcccgcctgg atgcagaatc cctggtcaag   157740
ctgagtgtgg acagagtgaa cgtgcacagc ccgcaccgcg ccatggcggc tctgggcttg   157800
atgctcacct gcatgtacac aggtgagcag gtacacagtg cccgcaaggc cagcccaagt   157860
cctgttcaag ggagacagga gcatgctcgc tcaaggaacc tagactaggt gtcctctgat   157920
ttgacacttt tagtgttgcc ccaagctggc cccatcacct gcaagagag gctctggagc    157980 ccccagggct ggagtacctg gtcagggttg accacccctc tggtcactca tcccatgtgg   158040
ctgagctgtg ctgggtcctg ggctagcgag gggctcacat cacctgctgt caggtcttct   158100
ccagtgattc attggactcc tgtgtacaaa gcactatcta cagagcctgt tgggttgtat   158160
agatgtaacc ttcgtactga acactttat tacaggaaag gagaaagtca gtccgggtag     158220
aacttcagac cctaatcctg cagccccaga cagcgagtcg gtgattgttg ctatggagcg   158280
ggtgtctgtt cttttgata ggtaagaaac gaagccccat ccctcagccg ttagcttccc     158340
tagaattttg gcctgaagct gagcgtttgt gtgtgttggc tgatcccctg gcgctgttgc   158400
tggagtcccg ccagtgattc ctgaccacag cctgaccgtg ggctgccttg gctcaggttt   158460
ccactggcga gctggtggtc cttggacccc agcgctcagg tgtagtgttg accagttcca   158520
aggttgtccc agcgcctgcc catctctcct gagggctcag gcaccgcacc tggccgtgtg   158580
gggtatggca gggggcagga atgaccagtc tctgggaggg tgcggcagaa gcctgcgcag   158640
tgatgaggag ttggctcagc ctggctgcct gtcgtgagag gggagcccac gggggtctgt   158700
gggagggggt ccatggtgcc tgtgagcagg gtgaggggca gcagcaggag gaggaaggtg   158760
aaacccacac atgcatcttt gagacccgtg tggtcagtgg cttctcctcg ctacccctcc   158820
gccccactgc tgtgcgtgaa ttggtgttga gaattggctt cgctcccctg ctctggaagt   158880
gggttaggag cttcgtaggg cttttctca aggacaaggc tccctgattg ctctcaggcc      158940
```

```
tcagtcctgg cgacatggcg gatctggggc gttgttgtgc tgccttgcct gtgctctcca 159000
atcagggtgt cccagtcctg gcgacatggc ggatctgggg cgttgttgca ctgccttgcc 159060
tgtgctctcc aatcagggtg tccagtgggg agccatttgg cttttctcaa gagcatactc 159120
aggtggactt tgctctattc tttggccaga tgaggtgttc tgaacagctg agcctgtgct 159180
tgtctgtttt catgttttt tttttttttg agatggagtt ttgcccttgt cacccaggct 159240
ggagtgcaat ggcgcgatct cggctcactg caacctccac ctcccgggtt caagcgattc 159300
tcctgcctca gcctcccaag tagctgggat tacaggcacg tgccaccacg cccagctaat 159360 tttgtgttt ttagtagaga cagtgcttca ccgtgttggc cgaactggtc tcgaacttct 159420
gaactcaagt gatccaccct cctcggcctc ccaaagtgct gggattgcag gcatgagcca 159480
ccgtgcctgg ccccatgtc gattttaaaa cgcacctctg catcattctt cagttcccac 159540
atgctcactg agcaccacca cagctggcag acggacacag ggaggcgcca cgaccagtcc 159600
tggccttcaa ggggcttgtg gtctagtgga cccagtgcta ggtggcgagt gctccagaga 159660
gcgtggtgta tgccttccgc tctaccgccc tccagacgcc gcaggaggc accttggagc 159720 tgaccacaga tctccctccg tggagcactg tcttcagcgc agccgccatg ccactgctgg 159780
gcgagggtct gcgggcgggt agagccagga gcacctctga aaagtgcac tgccgtttct 159840 tggctgcttc ctgtgcatct cagttacaca cagctggcat gtgtgcactg atgagacagg 159900
aacatgatgg ttgcttttca gcactaaaaa ggatactgct caggggcgt gtttcaggat 159960 ctggttaggg aaaaagcagc gagagcacag atggggccct gtttggtaac aagaaaaaag 160020
tcccggttga caacagtgct acaaagtgtt agaacacata gaaatgttta tggagcattt 160080
ggatgtggaa agcagcaaaa acataatgag aaggggttct tttgttagga tttttaaaaa 160140
tctcttttgt aacatcctc cggctgcacc atttctgcat attctttat gtagctttca 160200 gactcttagg atttctggtc actgcagggc gtgggagcca gacagagcct atgcctagca 160260
gcctgtcttc acgagctgga cagaggagga gctgggtttt gccttttta gcctcaaatt 160320 tcatactcca gttgcttagg ctctgacttt ccccacttgg aaagtccctc acggccaagg 160380
gtacctccca gccctgattt cacatcagca ttttccccag agccaaggcc ctccgcgggc 160440
aggtggggca gctgtgggag ctggtgccag gctctgacct gtgtccctcc tcccaggatc 160500
aggaaaggct ttccttgtga agccagagtg gtggcgagga tcctgcccca gtttctagac 160560
gacttcttcc cacccaggga catcatgaac aaagtcatcg gagagtttct gtccaaccag 160620
cagccatacc cccagttcat ggccaccgtg gtgtataagg tgaggttgca tgtgggatgg 160680
ggatggagtg gggaagcctg gaggtggaat tgaccccgac ttgccagcag attcgccaga 160740
agaacccagc cctccccctt taaagcagca atgcctctgg cccccacccc accccaccca 160800
cccgggcaca gcaggtgctt cccgcccccc agccctgaca ctcaggcgcc cgcttgctcc 160860
tggcaggtgt ttcagactct gcacagcacc gggcagtcat ccatggtccg ggactgggtc 160920
atgctgtccc tctccaactt cacacagagg acccccagtcg ccatgccac atggagcctc 160980 tcctgcttct tcgtcagcgc gtccaccagc ccatgggttg cggcgatgta tcctctctgg 161040
gtccctggtg ctggccccgt ttccctcgtc aacaccgagg ctcatgtttc atgataaagt 161100
tttgaaacct aacctttgca aaagccccac agatgccaag gtgacaggcc ctcagcccca 161160
gggaagtaca atgctgacag ggatacagaa aggagcacat ccagacattt gctgaccagg 161220
gcctctcaga ggggcccgtg tatggcagaa gggtcgaagc tgctaagggg cccttctgtg 161280
gagggcctgg gtgaggggag cgagggtggg cggcggtctc tgcagacctc ccgcccactc 161340
```

```
gcgggctctg tgtggctggg cttctcctga cactgcttct cattagctttt ggtcattgtg   161400 cctcgatcac cctctcgggg aaaggcttaa gtaaagatcc agttcccacc cccagatgct   161460
ggctgccagg agtttccctt tccacagccc tcccccaaga cagaccacaa gagcctccga   161520
gcagcacggt tgtcctggtg ctgacagcac agcctcgccc agtgtgcctg gcgtggtctct  161580 gcccgcactg tactggagca gggctcgtgg gggccagcag gacagcagga gcatcggcca   161640
ccagcgctac acaggagcca ggccaggtga gtgctgccga gtgggtgcct gcctgcaggc   161700
ctcctgcttc cttggccagc tctgcccagc tcacttctgc cctgctggcc ttccagcagg   161760
gtgtccagcc agccaagggt tgcaggaatg aaggtggagg cgctgctgca gctggagcca   161820
tccaggtagc ccttccgggg ctctgctggc tctccaggct ccctgggccc cttcgtaggc   161880
tgtttcagga gaggagctcc caggtgagga cagggaggca gcattcccct catttgccgg   161940 ccttttttcct taactcctgc accagcctcc cacatgtcat cagcaggatg ggaaagctgg   162000
agcaggtgga cgtcaacctt ttctgcctgg ttgccacaga cttttacaga caccagatag   162060
aggaggagct cgaccgcagg gccttccagt ctgtgtttga ggtggttgca gctccaggaa   162120
gcccatatca ccggctgctg acttgtttac gaaatgtcca caaggtcacc acctgctgag   162180
cgccatggtg ggagagactg tgaggcggca gctggggctg gagcctccag aaatctgcgc   162240
cctgtgccct gcctccaccg agccagcttg gtccctgtgg gcttccgcac atgccgcggg   162300
cggccaggca acgtgcgtgt ctctgccata tggcagaagt gctctttgtg gtacagtggc   162360
caggcaagga gtatctgcag tcccgtgggg gctgagcctg aggccttccg gagagcagga   162420
gcagctgtgc tgcacgccat gtgggtgacc aggtcctttc cctgatgct cacctgttgg    162480 gtgttgccag gctgcagctg ctcttgcatc tgggccggaa gtcctccctc ctgcaggctg   162540
gctgtgggcc cctctgctgt cctgcagtag aaggtgccgt gagcaggctt tgggaacact   162600
ggcctgtgtc ttcctggtgg ggtgtgcatg ccacgccctg tgtctgtatg cacagatgcc   162660
atggcatgtg ctgggccagt ggctggggt gctagacacc cagcaccatt ctcccttctc    162720
tcttttcttc tcaggattta aaatttaatt atatcagtaa agagattaat tttaacgtaa   162780
ctctttctat gcccgtgtaa agtatgtgaa ttgcaaggcc tgtgctgcat gcgacagtgt   162840
tcggggaggt gggcagggcc cctggccacg ctccctctcc tgtagccact ggcatagcct   162900
tcctgagcac ccgctgacat ttccgttgta catgttcctg tttatgcatt cacaaggtga   162960
ctgggatgta gagaggcgct agtgtgcagg tggccacagc aggactaagg acaggccccc   163020
actgtcctag gggcatgctc gcctgcagcc cctccttctt gggcacagac aactgttgtt   163080
ctccacccac attagggaca gcagcctccc tatcagctga gaaggccagc cctccctggc   163140
tgtgagcagc ctccgctgtg tccagagaca tgggcctccc actcctgttc cttgctagcc   163200
ctggggcggt gtctgcccag gagctggctg gccggtgatg ggatctgccg ttccatggat   163260
gcatgcccca agggtgtcac tgagctgtgt tttgtctgag cctctcttgg tcaacagcaa   163320
agcttggcgt cttggcactg ttagtgacag agcctggcat cccttctgcc cccgttccag   163380
ctgacatctt gcacggggac cccttttagt caggagagtg cagatctgtg ctcattggag   163440
actgccccac tgccctgtca gagccgccac tcctatcccc aggccaggtc cctgaccag    163500 cctcttgttt gcaggcccag aggagccaag tcattaaaat ggaagtggat tctggatggc   163560
cggctgctgc tgcacatagga gctggatttg ggagctctga gatggggcag gagctctgct   163620
tcctcagccc ttgaggcgag ccaggcgagg ttggcgactg tcatgtggct tggtttgctc   163680
```

```
atgcctgttg atgttttggg tattgaatat ggtaagtgga ggaaatgctt ttctggagtc   163740
tgtgcaggtg ctgccttgag accctcaagc ttccacctgt ccctctccta tgtggcagct   163800
gaggagcagc tgacatgtgg acttgtgtgc tgcccacata catgaggggg cgctgaaagg   163860
gagcccctgc tcaaagggag cccctcctct gagcagcctt tgacaggcct gtatgaggct   163920
tttcccacca gctcccaaca gaggcctccc ccagccagga ccacctcgtc ctcgtggcag   163980
ggcagcagga gcggtagaaa gggtctgat gtttgaggag gcccttaagg gaagctactg   164040
aattttaaca agaaagccac cattcttccg tattggttgg gggctcctgt ttctcatcct   164100
agcttcttcc tggaaagcct gctagaagct ttgggaatga ggggaaagtt ctcagaaccg   164160
ttgctgctcc ccacccacct cccctgcagt aagttatgtc aacagctcgg agacagaagt   164220
atcacaggcc agatgttgtt ctgctagatg tttacatttg taagaaataa cactgtgaat   164280
gtaaaacgga gccattcccc ttggaatgca tatcgctggg ctcaacacag agtttgtctt   164340
ccttttgttt acgacgtgat ctaaaacagt ccttagcaag gggctcagaa caccccgctc   164400
tggcagtggg tgtcccccac tcccaaaggc ctgcctgtgt gctccagaga tgaatatgag   164460
ctcattagta aaatgacttt acccatgcgt aagtcaagta cacgtgcacg tgcatatgga   164520
cacatctgta gttttataca cgcacatctc aagacagaga tgcatggcct ccaagagtgc   164580
ccgtgtcggt tcttcctgga agttgacttt cctcagacct gccaggtaaa gttagctgtg   164640
tgacgggcgt ccaggcgcgg ggcttggtca gagcagggct cattcatggc tcactaggat   164700
cccaccggag aaaacggtct ccatatcaac tctgccgaag ggaggaagac tttgtcgcgt   164760
tcctaaaaaa cctatggcaa gcaccaatca tattatccaa attgtgttga aaatgtgatt   164820
aatttggttg tcaagttttg ggggtgagct gcggggagac tgcttttgtt ttgctgctgg   164880
taatatcagg aaagacttta atgaaaccag ggtagaattg tttggcaatg cactgaagcg   164940
cgtttctgtc ccaaaacgtg cctcccttcc gctgcgggcc cagctgagtc tgtgtaggtg   165000
acgtttccgc tgccaagcg ctctttgtta ctgtccaccc ccatttctgc cagcacacgt   165060
gtcctttcag gaggaaaatg tgaagctgaa acccctccag acacccagaa tgtagcatct   165120
gagaaggccc tgtgccctaa aggacacccc cgccccccacc ttcatggagg ggtcattcca   165180
gagccctcgg agccgatgaa cagctcgtcc tcttggagct gagctgagcc cccacggag   165240
ctcgggacga atagtaaaca gcaataactc ggtctgtggc tgcctggcag gtggaagttc   165300
ctcccccctga ggggcggagt gaggttagtt ctgtgtgtct gtggggtgga gtcagcctgc   165360
tcctgctacc tgtgagcatc ctgcccagca gacatcctca cccggctttg tccctcccca   165420
cttcctccct ctgcggggag gacccaggac cacagctgct ggcagggta ggcttggagc   165480
tgtgctccgg aggggccacc tgtgggagcg agaagaagga agatcttgag agctgccgag   165540
gcaccctgga gagctcagga tggtccaggc gagaagagga cactcgctcg ccaggcctgg   165600
gcctcctggg aaggagggag ccgctcagag cgccgcatga caactgaagg caacctggaa   165660
ggttcagagg ccactcttcc cccgtgtgcc tgtcacgctc tggtgcagtc caaggaacgc   165720
cttcccctca gttgtttcca aaagcagagt ctcccgctgc aatctgggtg gtgattgcca   165780
gccttggagg attgtggcca acgtggacct gcctacggag ggtgggctct gacccacgtg   165840
gggcctcctt gtccaggtct cattgctttg tgctgtggtc agagggactg tcagctgagc   165900
ctgagctccc ctggagccag cagggctgtg atgggcgagt cccggagccc cacccagacc   165960
tgactgcttc tgagagcaaa gggaaggact gacgagagat gtatatttaa ttttttaac    166020
tgctgcaaac attgtacatc caaattaaag gaaaaacatt gaaaccatca gttgttgctg   166080
```

```
tgtgaggctt gctttacttc atgagaacct agaccttgct gagctggagt cttaggaaac    166140
tgtctcctaa gtgcttatcc agcaggggca gaaactgtcc caccagctaa catctgacat    166200
tacggagggt cccgcaggca gctgccagca aggacaagcc ctgtgttttc tgtagccagg    166260
gatgaggaag tggccccagg ggcctggctg ggtgctgctt caagggcctt cgcaaaccac    166320
agtacaggtg gtcttcctgc actgcagatg ggagctgtgg gagctgctgg atccttcatg    166380
gtcaagtgac atcataagct tatatgacac acacaagcct caggacttgg cccatggcac    166440
tggagcaggt catcaggccc agcagactag agctgtgttc tcacagggcc catgaccctt    166500
ctagctcctt ggccattgaa acctgtgtcc ctgacccagc tgctcccagg tacccccaa    166560 agcagctggc acatcccacc tctggtgtgg cctgggctgc tgtgtgtccg cagggcctgc    166620
cccgtctgtt ctagcttgtt tctcctgtct gaaccagcgc ctactccaag aaggctctgc    166680
tcagcccagc ggggatgctt ctaagctcgg cccagcctct gggaagcctt ggtggtcggt    166740
ggtgtagtca tcctgggatg cagaacgaaa acctgcaaga acaaaactgt ggcttcgtct    166800
ggtgcagggt atttagttac tgtttgctga ggtcctgtct ggttctggcg aatgggcagg    166860
ggtcgcccac ccattctttc cctgctctgc tgtccgtgcc aggagagacg ggggcctgtt    166920
ggccaagggg gcagctcctg ctgcctgctg tccttaggca cgtgcaggga ccccctttct    166980
ctgagcagga tggggatcag tctgccagag ggatgtggtg gacaggccca gccgggtaaa    167040
aaattccccc agttgctcaa agcatttggg gcggggcatg ccacttgagc tccttaaatc    167100
tgtctcatag gtgacaccgc tccagggcgc cccaggggct ctccccttca gagctaccaa    167160
agttctggtc acttcagaaa aatggagcac cccttctcc ctggtccaga tgtggacagc    167220
cagacccttg gcacacctag cacacctggc atggctggta atttcagaaa gaaaaggggc    167280
cggggtccag tgggaagcag tggcgaaccc ctcatgcgtg ggctttgcga tccctccccc    167340
tgccacggca gagctgccct cagcacagcc ttcctcttcc tcatcggaga gcacaccctg    167400
tccccttgcc ggggctgtgc tctgtgcctg cagtggtatt tggttttggc tgctactggc    167460
tttgttccaa agaggatctg gaagtcgctt cccctgtgtg gagcgtggag cactgtgagt    167520
cagatgaggg aagtagccag ggggaggtga gtacccggcg gagccgccac agaaaggact    167580
gggtaggggg ccttgcctcc acgtgatgtg acacggccag ccgaggacag aggaagcccc    167640
gttcctgggg gtgtgggggtg cacccctcag ggaagcctgc agtggggccc aaggaaaggc    167700
gttctctgcg agcccacgag tctgctctgt gggcaccgtg acaatgcccg tgggcagagg    167760
tgggcccggc cttgtgtcgt caccaggacc tcttttggga aaccatgtgg gcatcccttg    167820
cgggtccccc aggttctgca gtcccagcgg cctggctgcc tgttgggcac atggcttgag    167880
ccgcccagag ggcccagccc tgttggcagc cacatcctct ggaggccctg ccggtggggc    167940
tggctttctc taccccacac caggcctcca agtatactgg tcggggtgt ctgggccctg    168000 gg                                                                  168002

<210> SEQ ID NO 5
<211> LENGTH: 10295
<212> TYPE: DNA
<213> ORGANISM: Rattus norvegicus

<400> SEQUENCE: 5
gcactcgccg cgagggttgc cgggacgggc ccaagatggc tgggagcttt ggttccgctt     60
cggtctacct cgtagagccc cattcattac cttgctgcta agtggcgctg cgtagtgcga    120
```

-continued

| | |
|---|---|
| ataggctcca agccttcagg gtctgtcctg tcgggcagga ggccgtcatg gcaaccctgg | 180 |
| aaaaactgat gaaggctttc gagtcgctca agtcgttcca gcagcaacag cagcagcagc | 240 |
| agccgccgcc gcaggcgccg ccaccaccgc cgccgccgcc gcctcaaccc cctcagccgc | 300 |
| cgcctcaggg gcagccgccg ccaccaccgc cgctgccagg tccggccgag gagccgctgc | 360 |
| accgaccaaa gaaggaactc tcagccacca agaaggaccg tgtgaatcac tgtctaacaa | 420 |
| tatgtgaaaa cattgtggca cagtctctca gaaattctcc agaatttcag aaactcttgg | 480 |
| gcattgctat ggaactgttt ctgctgtgca gcgacgatgc ggagtcagac gtcagaatgg | 540 |
| tggctgatga gtgcctcaac aaagtcatca aagctttgat ggactctaat cttccaaggc | 600 |
| tacagttaga actctataag gaaattaaaa agaatggtgc tcctcgaagt ttgcgtgcag | 660 |
| ctctgtggag gtttgctgag ctggctcacc tggttcgacc tcagaagtgc aggccttatc | 720 |
| tggtgaatct tcttccatgt ttgacccgaa caagcaaacg accggaggag tcagttcagg | 780 |
| agactttggc tgcagctgtt cctaaaatta tggcctcttt tggcaatttc gcgaatgaca | 840 |
| atgaaattaa ggttctattg aaagctttca tagcaaatct gaagtcaagc tctcccactg | 900 |
| tgcggcggac agcagctggg tcagcagtga gtatctgcca gcactctagg aggacacagt | 960 |
| acttctacaa ctggctcctg aatgtgctcc taggtttgct ggttcccatg gaggaagacc | 1020 |
| accccactct cctgatcctt ggtgtgttgc tcacactgag gtgtctagtg cccttgctcc | 1080 |
| agcagcaggt caaggacaca agtctaaagg gcagctttgg ggtaacacgg aaagaaatgg | 1140 |
| aagtctctcc ttctgcagag cagcttgtcc aggtttatga actgactttg catcacacac | 1200 |
| agcaccaaga ccataatgtg gtgacagggg cattggagct cctgcagcag ctcttccgta | 1260 |
| cccctccacc tgagctgctg caagcactga ccacaccagg agggctcggg cagctcactc | 1320 |
| tggttcgaga ggaagccggg ggccgaggcc gcagcgggga tatcgtggag cttttagctg | 1380 |
| gagggggttc ctcatgcagc cctgttctct caagaaagca aaaaggcaaa gtgctcttag | 1440 |
| gagaggaaga agccttggag gatgactcgg agtccaggtc agatgtcagc agctcagcct | 1500 |
| ttgcagcctc tgtgaagagt gagattggtg agagctcgc tgcttcttct tcgggtgtct | 1560 |
| ccactcccgg ttctgtaggt cacgacatca tcactgagca gcctcgatcc cagcacacac | 1620 |
| ttcaagcaga ctctgtggat ttgtcaggct gtgacttgac cagtgctgct actgatggag | 1680 |
| atgaggaaga catcttgagc cacagctcca gccagttcag tgctgttcca tccgaccctg | 1740 |
| ccatggacct gaatgatggg acccaggcct cctcacccat cagtgacagt tctcagacca | 1800 |
| ccactgaagg acctgattca gctgtgactc cttctgacag ttctgaaatt gtcttagatg | 1860 |
| gtgctgacag ccagtattta ggcgtgcaga taggacagcc acaggaggaa gacgaggagg | 1920 |
| aagctgcagg tgttctttct ggtgaagtct cagacgtttt cagaaactct tctctggccc | 1980 |
| ttcagcaggc acacttgttg gaaagaatgg gtcatagccg gcagccttct gacagcagtg | 2040 |
| ttgataagtt tgtttcaaaa gatgaggttg ctgaagctgg ggacccagaa agcaagcctt | 2100 |
| gccgaatcaa aggtgacata ggacagccta atgatgatga ttctgctcct ctggtacatt | 2160 |
| gtgtccgtct tttatccgct tccttttgt taactggcga aaagaaagca ctggttccag | 2220 |
| acagagatgt gagagtcagt gtgaaggcc tggccctcag ctgtattggt gcagctgtgg | 2280 |
| cccttcatcc agagtcgttc ttcagcaaac tctacaaagt acctctcagt accatggaaa | 2340 |
| gtactgagga acagtatgtc tctgacatcc tgaactacat cgatcatgga gaccctcagg | 2400 |
| tgcgaggagc tactgccatt ctctgtggga cccttgtcta ctccatcctc agcaggtccc | 2460 |
| gtctccgtgt tggtgactgg ctgggcacca tcagggccct gacaggaaat acattttctc | 2520 |

| | |
|---|---|
| tggtggactg cattccttta ctgcagaaaa ctttgaagga tgaatcttct gttacttgca | 2580 |
| agttggcttg tacagctgtg aggcactgtg tcctgagtct ttgcagcagc agctacagtg | 2640 |
| acttgggatt acaactgctt attgacatgc tgcctctgaa gaacagctcc tactggctgg | 2700 |
| tgaggactga actgctggaa actcttgcag agattgattt caggctggtg agttttttgg | 2760 |
| aggcaaaagc agaaagttta caccgagggg ctcatcatta tacagggttt ctaaaactac | 2820 |
| aagaacgagt actcaataat gtggtcattt atttgcttgg agatgaagac cccagggttc | 2880 |
| gacatgttgc tgcgacgaca ttgacaagac ttgtcccaaa gctgttttat aagtgtgacc | 2940 |
| aaggacaggc tgacccagtc gtggctgtag caagagatca aagtagtgtt tacctgaagc | 3000 |
| tcctcatgca tgagacccag ccaccatccc acttctccgt cagcaccata accagaatct | 3060 |
| atagaggcta cagcttacta ccaagtgtaa cagatgtcac catggaaaac aacctctcaa | 3120 |
| gagtcgttgc cgcagtttct catgaactca ttacgtcaac tacacgggca ctcacatttg | 3180 |
| ggtgctgtga agccttgtgt gttctttcag ccgccttttcc agtttgcact ggagtctag | 3240 |
| gatggcactg tggagtgccc ccactgagtg cctctgatga gtccaggaag agctgcactg | 3300 |
| ttgggatggc ctccatgatt ctcaccttgc tttcatcagc ttggttccca ctggatctct | 3360 |
| cagcccatca ggatgccttg attttggctg gaaacttgct agcagcgagt gcccccaagt | 3420 |
| ctctgagaag ctcatgggcc tcggaagaag aaggcagctc agcagccacc agacaggagg | 3480 |
| agatctggcc tgccctgggg gatcggactc tggtgcccat ggtggagcag cttttctccc | 3540 |
| acctgctgaa ggtgatcaat atctgtgctc atgtcttgga tgacgtgact cctggaccag | 3600 |
| caatcaaggc agctttgcct tctctcacaa acccccttc tctaagtcct attcgacgga | 3660 |
| aagggaagga gaaagagccc ggagaacaaa catccactcc gatgagtccc aagaaaggtg | 3720 |
| gagaggccag tacagcctct cgacagtcag acacctcagg acctgtcaca gcgagtaaat | 3780 |
| catcttcact tgggagtttc taccatctcc cttcctacct cagactgcat gatgtcctga | 3840 |
| aagccactca cgccaactat aaggtcacct tagatcttca gaacagcact gaaaagtttg | 3900 |
| gggggttcct gcgctctgcc ttggacgtcc tttctcagat tctagagctg gcgacactgc | 3960 |
| aggacattgg aaagtgtgtt gaagaggtcc ttggatactt gaaatcctgc tttagtcgag | 4020 |
| aaccaatgat ggcgactgtc tgtgttcagc agctattgaa gactctcttt gggacaaact | 4080 |
| tagcctcaca gtttgatggc ttatcttcca accccagcaa gtctcagtgc cgagcacagc | 4140 |
| gccttggctc ttccagtgtg aggcccggct tatatcacta ctgcttcatg gcaccataca | 4200 |
| cgcacttcac gcaggctttg gctgatgcca gcctgaggaa catggtacag gcggaccagg | 4260 |
| agcacgatgc ctcagggtgg tttgatgtac tccagaaagt gtctgctcag ttgaagacga | 4320 |
| accttacaag tgtcacaaag aaccgtgcag ataagaacgc tattcataac acattaggt | 4380 |
| tatttgagcc tcttgttata aaagcattga agcagtacac cacgacaaca tcagtacaac | 4440 |
| tgcagaagca ggttttggat ttgctggcac agctggttca gctacgggtc aattactgtc | 4500 |
| tactggattc agatcaggtg ttcatcgggt ttgtgctgaa gcagtttgag tacattgaag | 4560 |
| tgggccagtt cagggaatca gaggcaatta ttccaaatat attttttcttc ctggtactat | 4620 |
| tatcttatga gcgctaccat tcaaaacaga tcattggaat tcctaaaatc atccagctgt | 4680 |
| gtgatggcat catggccagt ggaaggaagg ctgtcacaca tgctattcct gcgctgcagc | 4740 |
| ccattgtcca tgacctcttt gtgttaagag gaacaaataa agctgatgca gggaagagc | 4800 |
| ttgaaaccca gaaggaggtg gtggtctcaa tgctgttacg actcatccag taccatcagg | 4860 |

```
tgctagagat gttcatcctc gtcctgcagc agtgccacaa agagaatgag gacaagtgga      4920
aacggctctc tcggcaggtc gcagacatca tcctgcccat gttagccaag cagcagatgc      4980
atattgactc tcatgaagcc cttggagtat taaataccct gtttgagatt ttggctcctt      5040
cctccctacg tcctgtggac atgcttttgc ggagtatgtt catcactcca agcacaatgg      5100
catctgtaag cactgtgcag ctgtggatat ctggaatcct agccattctg agggttctca      5160
tttcccagtc aaccgaagac attgttcttt ctcgtattca ggagctctcc ttctctccat      5220
atttaatttc ctgtccagta attaacaggt taagggatgg agacagtaat ccaacactag      5280
gagaacgcag tgaagggaaa caagtaaaga atttgccaga agatacattc tcaaggtttc      5340
tcttacagct ggttggtatt cttctggaag acattgttac aaaacagctc aaagtggaca      5400
tgagtgaaca gcagcataca ttctattgcc aagagctcgg cacactgctc atgtgtctga      5460
tccacatatt caaatctgga atgttccgga gaatcacagc cgctgccact agactcttca      5520
ccagtgatgg ctgtgaaggc agcttctata ctctagatag cctgaatgca cgggtgcgag      5580
ccatggtgcc cacacaccca gctctggtac tgctctggtg tcagatccta ctgctcatca      5640
accacactga ccaccgatgg tgggccgagg tgcagcagac gcccaagaga cacagtctgt      5700
cctgcacgaa gtcactaaac ccccagatat ctgctgaaga ggattctggc tcagcagctc      5760
agcttggaat gtgcaataga gaaatagtac gaagaggggc ccttattctc ttctgtgatt      5820
atgtctgtca gaatctccat gactcagaac acttaacatg gctcattgtg aatcacattc      5880
aagatctgat cagcttgtcc cacgagcctc cagttcaaga cttttattagt gccattcatc      5940 gtaattctgc agctagtggt cttttatcc aggcaattca gtctcgctgt gaaaatcttt      6000
caactccaac cactctgaag aaaacacttc agtgcttgga aggcatccat ctcagccagt      6060
ctggtgctgt gctcacactg tatgtggaca ggctactggg caccccttc cgtgcgctgg      6120 ctcgcatggt cgacacccctg gcctgtcgcc gagtagaaat gcttttggct gcaaatttac      6180
agagcagcat ggcccagttg ccagaggagg aactgaacag aatccaggaa cacctccaga      6240
acactgggct tgcacaaaga caccaaaggc tctattcact gctggacaga ttccgactct      6300
ctactgtgca ggactcactt agcccctttgc ccccagtcac tccccacccct ctggatgggg      6360 atgggcacac atccctggaa acagtgaatc cggacaaaga ctggtacctc cagcttgtca      6420
gatcccagtg ttggaccagg tcagattctg cactgctgga aggtgcagag ctggtgaacc      6480
gtatccctgc tgaagatatg agtgacttca tgatgagctc ggagttcaac ctaagccttt      6540 tggctcctg cttaagcctt ggcatgagcg agattgctaa tggccaaaag agtccccttt      6600
ttgaagcggc tcgtagggtg actctggacc gggtgaccaa tgtggttcag cagctgcctg      6660
cagtccatca agtcttccag cctttcctgc ctacagaacc cacagcctac tggagcaagc      6720
tgaatgatct ctttggtgat accacatcat accagtctct gaccacactt gcccgtgccc      6780
tggcacagta cctggtggtg ctctccaaag tgcctgctcc tttgcacctt cctcctgaga      6840 aggagggggca cacggtgaag tttgtggtaa tgacacttga ggccctgtca tggcatttga      6900
tccatgagca gatcccactg agtctggacc tccaagccgg cctagactgc tgctgcctgg      6960
cactgcaggt gcctggcctc tggggggtgc tgtcctcccc agagtacgtg actcatactt      7020
gctcccttat ccactgtgtg cgattcatcc tggaagccat tgcagtacaa cctggagacc      7080
aacttcttgg tccggaaagc aggtcacata ctccaaggcc tgtcagaaag gaggaagtag      7140
actcagatat acaaaacctc agtcacatca cttcggcctg cgagatggtg gcagacatgg      7200
tggaatccct gcagtcggtg ctggccctgg gccacaagag gaacagcacc ctaccttcat      7260
```

```
ttctcacagc tgtgctgaag aacattgttg tcagtctggc ccgcctcccc ctcgttaaca    7320
gctatactcg tgtgcctcct ctggtatgga aactcgggtg gtcacccaag cctggagggg    7380
atttcggcac agtgtttcct gagatccctg tagagttcct ccaggagaag gaggtcctca    7440
aggagttcat ctaccgcatc aacaccctag ggtggaccag tcgtactcaa ttcgaagaaa    7500
cttgggccac cctccttggt gtcctggtga ctcagccctt ggtgatggaa caggaagaga    7560
gcccaccaga ggaagacacc gaaaggaccc agatccacgt cctggctgta caggccatca    7620
cctctctagt gctcagcgca atggctgtgc ctgtggctgg caatccagct gtaagctgct    7680
tggagcaaca gccccggaac aagccactga aggctctcga taccagattt ggaagaaagt    7740
tgagcatgat cagagggatt gtagaacaag aaatccaaga gatggttttcc caaagagaga    7800 atactgccac tcatcattct caccaggcat gggatcctgt cccttctctg ttaccagcta    7860
ctacaggtgc tcttatcagc catgacaagc tgctgctgca gatcaactca gagcgggagc    7920
caggcaacat gagctacaag ctgggccagg tgtccataca ctccgtgtgg ctggggaaca    7980
acatcacacc cctgagagag gaggaatggg atgaggagga ggaggaagaa gcggatgccc    8040
ctgcgccaac atcaccacct gtgtctccag tcaattccag aaaacaccgt gctgggttg     8100 atattcactc ctgttcgcag tttctgcttg aattatacag ccgttggatc ctgccatcca    8160
gtgcagccag aaggacccct gtcatcctga tcagtgaagt ggttcgatct cttcttgtgg    8220
tgtcagactt attcactgaa cgtacccagt ttgaaatgat gtatctgacg ctgacagaac    8280
tacggagagt gcaccettca gaagatgaga tcctcattca atacctggtg cctgccacct    8340
gtaaggcagc tgctgttctt ggaatggaca aaactgtggc agagccggtc agccgcctac    8400
tggagagcac actcaggagc acccacctgc ccagccagat cggagccctg catggcatcc    8460
tctatgtgtt ggagtgtgac ctcttggatg acactgtaaa gcagctcatt ccagttgtta    8520
gtgactatct gctgtccaac ctcaaaggaa tagcccactg cgtgaacatt cacagccagc    8580
agcatgtgct ggtgatgtgt gccactgcat tctacctgat ggaaaactac cctctggatg    8640
tggggccaga attctcagca tctgtgatac agatgtgtgg agtaatgctg tctggaagtg    8700
aggagtccac cccctccatc atttaccact gtgccctccg gggtctggaa cggctcctgc    8760
tgtctgagca gctctctcgg ctagacacgg agtccttggt caagctaagt gtggacagag    8820
tgaatgtaca aagcccacac agggccatgg cagccctagg cctgatgctt acctgcatgt    8880
acacaggaaa ggaaaaagcc agtccaggca gagcttctga ccccagccct gctaccctg    8940 acagcgagtc tgtgattgta gctatggagc gagtgtctgt gctcttgac aggatccgca    9000 agggatttcc ctgtgaagcc agggtcgtgg caaggatcct gcctcagttt ctagatgact    9060
tctttccacc tcaagatgtc atgaacaaag tcattggaga gttcctgtcc aaccagcagc    9120
catacccaca gttcatggcc actgtagtat acaaggtttt tcagactctg cacagtgctg    9180
ggcagtcatc catggtccgg gactgggtta tgctgtctct gtccaacttc acacaaagaa    9240
ctccagttgc catggccatg tggagcctct cctgcttcct tgtcagtgca tctaccagcc    9300
catgggtttc tgcaatcctt ccacacgtca tcagcaggat gggcaaactg gagcaggtgg    9360
atgtgaacct tttctgcctg gttgccacag acttctacag acaccagata gaggaggaat    9420
tcgaccgcag ggctttccag tctgtgtttg aggtggtggc agcaccagga agtccatacc    9480
acaggctgct tgcttgtttg caaaatgttc acaaggtcac cgcctgctga gtagtacctg    9540
tggaacaaga ggctgagagg aggcaactgc tgtggctaca gcctccaggg gcctgcacca    9600
```

-continued

| | | | | |
|---|---|---|---|---|
| agcttctgct | aaggctgcct | tggacgtgca | ggcttccact | tgtgtcaagt | ggacagccag | 9660 |
| gcaatggcag | gagtgctttg | caatgagagc | tatgcaggga | acatgcacta | tgttggggtt | 9720 |
| gagcctgagt | cctgggtcct | ggcatcactg | cagctggtgg | cagtgctagg | ttgaccaggt | 9780 |
| gtttgtcttt | ttcttagtgt | tgccctggcc | atagttgcca | ggttgcagct | gccctggtat | 9840 |
| gtggaacaga | atccgagctc | ttgtaagatg | gttctgagcc | ccctgtccc | actgggctgg | 9900 |
| agagctccct | cccacattta | cccagcaggt | gtacctgcca | caccagtgtc | tggacacaaa | 9960 |
| gtgaatggtg | tgggggctgg | gaactgggac | tgccaggtgt | ccagcatcat | tttcccttc | 10020 |
| tctgtttct | tctcaggagt | taaaatttaa | ttatatcagt | aaagagatta | attttaatgt | 10080 |
| aactcttcct | atgcccgtgt | aaagtgtgtg | acttggcaag | gcctgtgctg | catgtgacaa | 10140 |
| agtttatgga | agtggatgcg | ccttctggcc | accactctct | ctcctgtagc | tactcagtct | 10200 |
| agtcgggcag | gtccctcatg | tagccctccc | aacaccctat | ggcacttgca | cttcacacgg | 10260 |
| ctccttttc | ttatgcattc | catttgacta | gcaca | | | 10295 |

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tagcattctt atctgcacgg                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
acccgtaact gaaccagctg                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ttccctgaac tggcccactt                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctctgattcc ctgaactggc                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 10
gcctctgatt ccctgaactg                                           20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tgcctctgat tccctgaact                                           20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ttgcctctga ttccctgaac                                           20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
attgcctctg attccctgaa                                           20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tggaatgatt gcctctgatt                                           20

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gtttggaatg attgcctc                                             18

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ccaatgatct gttttgaatg                                           20

<210> SEQ ID NO 17
```

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gccttccttc cactggccat                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgcatcagc tttatttgtt                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cctgcatcag ctttatttgt                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agctcttttc ctgcatcagc                                              20

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
gtaacattga caccacca                                                18

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ctcagtaaca ttgacaccac                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
```
atgagtctca gtaacattga                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tccttgtggc actgctgcag                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttctccttgt ggcactgctg                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tcattctcct tgtggcactg                                              20

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
attctccttg tggcactg                                                18

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cgagacagtc gcttccactt                                              20

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
tgtcgagaca gtcgcttc                                                18

<210> SEQ ID NO 30
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 30
ttgcacattc caagtttggc                                                    20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tctctattgc acattccaag                                                    20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tttctctatt gcacattcca                                                    20

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
tctctattgc acattcca                                                      18

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcagggttac cgccatcccc                                                    20

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
accttatctg cacggttc                                                      18

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ctctctgtgt atcaccttcc                                                    20
```

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
ctccgtccgg tagacatgct                                                   20

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
ggaaatcaga accctcaaaa tgg                                               23

<210> SEQ ID NO 39
<211> LENGTH: 29
<212> TYPE: DNA
<213> ORGANISM: Artificial sequence
<220> FEATURE:
<223> OTHER INFORMATION: Probe

<400> SEQUENCE: 39
tgagcactgt tcaactgtgg atatcggga                                         29

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gtctgagcct ctctcggtca a                                                 21

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
aagggatgct gggctctgt                                                    19

<210> SEQ ID NO 42
<211> LENGTH: 30
<212> TYPE: DNA
<213> ORGANISM: Artificial sequence
<220> FEATURE:
<223> OTHER INFORMATION: Probe

<400> SEQUENCE: 42
agcaaagctt ggtgtcttgg cactgttagt                                        30

<210> SEQ ID NO 43
<211> LENGTH: 21
<212> TYPE: DNA
<213> ORGANISM: Artificial sequence
<220> FEATURE:

<223> OTHER INFORMATION: Primer

<400> SEQUENCE: 43
cagagctggt caaccgtatc c                                                    21

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
ggcttaaaca gggagccaaa a                                                    21

<210> SEQ ID NO 45
<211> LENGTH: 26
<212> TYPE: DNA
<213> ORGANISM: Artificial sequence
<220> FEATURE:
<223> OTHER INFORMATION: Probe

<400> SEQUENCE: 45
acttcatgat gagctcggag ttcaac                                               26

<210> SEQ ID NO 46
<211> LENGTH: 25
<212> TYPE: DNA
<213> ORGANISM: Artificial sequence
<220> FEATURE:
<223> OTHER INFORMATION: Primer

<400> SEQUENCE: 46
aggagaaaaa caaagaacac cagaa                                                25

<210> SEQ ID NO 47
<211> LENGTH: 25
<212> TYPE: DNA
<213> ORGANISM: Artificial sequence
<220> FEATURE:
<223> OTHER INFORMATION: Primer

<400> SEQUENCE: 47
caattagggc aactcagaaa tagct                                                25

<210> SEQ ID NO 48
<211> LENGTH: 22
<212> TYPE: DNA
<213> ORGANISM: Artificial sequence
<220> FEATURE:
<223> OTHER INFORMATION: Probe

<400> SEQUENCE: 48
ccaactggtc ccccagccaa ga                                                   22

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
cagagctggt gaaccgtatc c                                                    21

```
<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ggcttaagca gggagccaaa a                                              21

<210> SEQ ID NO 51
<211> LENGTH: 26
<212> TYPE: DNA
<213> ORGANISM: Artificial sequence
<220> FEATURE:
<223> OTHER INFORMATION: Probe

<400> SEQUENCE: 51
acttcatgat gagctcggag ttcaac                                         26

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcctagtgtt acattaccgc                                                20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ctcgactaaa gcaggatttc                                                20

<210> SEQ ID NO 54
<211> LENGTH: 17
<212> TYPE: DNA
<213> ORGANISM: Artificial sequence
<220> FEATURE:
<223> OTHER INFORMATION: Primer

<400> SEQUENCE: 54
tggtccccca gccaaga                                                   17

<210> SEQ ID NO 55
<211> LENGTH: 18
<212> TYPE: DNA
<213> ORGANISM: Artificial sequence
<220> FEATURE:
<223> OTHER INFORMATION: Primer

<400> SEQUENCE: 55
cccaccgtgt gacatcca                                                  18

<210> SEQ ID NO 56
<211> LENGTH: 26
<212> TYPE: DNA
<213> ORGANISM: Artificial sequence
<220> FEATURE:
<223> OTHER INFORMATION: Probe
```

```
<400> SEQUENCE: 56
agctatctcc gagctgccct gattgg                                            26
```